United States Patent
Van Zandt et al.

(10) Patent No.: US 11,389,464 B2
(45) Date of Patent: *Jul. 19, 2022

(54) ARGINASE INHIBITORS AS THERAPEUTICS

(71) Applicant: Mars, Incorporated, McLean, VA (US)

(72) Inventors: Michael Van Zandt, Guilford, CT (US); Gunnar E. Jagdmann, Branford, CT (US)

(73) Assignee: Mars, Incorporated, McLean, VA (US)

( * ) Notice: Subject to any disclaimer, the term of this patent is extended or adjusted under 35 U.S.C. 154(b) by 123 days.

This patent is subject to a terminal disclaimer.

(21) Appl. No.: 16/794,905

(22) Filed: Feb. 19, 2020

(65) Prior Publication Data

US 2020/0246362 A1 Aug. 6, 2020

Related U.S. Application Data

(60) Continuation of application No. 16/107,087, filed on Aug. 21, 2018, now Pat. No. 10,603,330, which is a continuation of application No. 15/207,902, filed on Jul. 12, 2016, now Pat. No. 10,098,902, which is a division of application No. 14/614,115, filed on Feb. 4, 2015, now Pat. No. 9,440,995, which is a continuation of application No. 13/276,806, filed on Oct. 19, 2011, now Pat. No. 9,233,985.

(60) Provisional application No. 61/406,760, filed on Oct. 26, 2010.

(51) Int. Cl.
*A61K 31/69* (2006.01)
*C07F 5/02* (2006.01)

(52) U.S. Cl.
CPC .............. *A61K 31/69* (2013.01); *C07F 5/025* (2013.01)

(58) Field of Classification Search
CPC ........... A61K 31/69; C07F 5/025; A61P 35/00
See application file for complete search history.

(56) References Cited

U.S. PATENT DOCUMENTS

| | | | |
|---|---|---|---|
| 4,172,896 A | 10/1979 | Uno et al. | |
| 5,358,970 A | 10/1994 | Ruff et al. | |
| 5,427,798 A | 6/1995 | Ludwig et al. | |
| 5,763,493 A | 6/1998 | Ruff et al. | |
| 6,583,124 B2 | 6/2003 | Asgharian | |
| 6,723,710 B2 | 4/2004 | Christianson et al. | |
| 8,894,970 B2 | 11/2014 | Tomczuk et al. | |
| 9,200,011 B2 | 12/2015 | Van Zandt et al. | |
| 9,233,985 B2 | 1/2016 | Van Zandt et al. | |
| 9,266,908 B2 | 2/2016 | Van Zandt et al. | |
| 9,440,995 B2 | 9/2016 | Van Zandt et al. | |
| 9,994,594 B2 | 6/2018 | Van Zandt et al. | |
| 10,065,974 B2 | 9/2018 | Sjogren et al. | |
| 10,098,902 B2 | 10/2018 | Van Zandt et al. | |
| 10,143,699 B2 | 12/2018 | Gross et al. | |
| 10,287,303 B2 | 5/2019 | Sjogren et al. | |
| 10,391,077 B2 | 8/2019 | Blaszczyk et al. | |
| 10,398,714 B2 | 9/2019 | Gross et al. | |
| 10,494,339 B2 | 12/2019 | Van Zandt et al. | |
| 10,538,537 B2 | 1/2020 | Van Zandt et al. | |
| 10,597,411 B2 | 3/2020 | Sjogren et al. | |
| 10,603,330 B2 | 3/2020 | Van Zandt et al. | |
| 10,844,080 B2 | 11/2020 | Sjogren et al. | |
| 10,851,118 B2 | 12/2020 | Sjogren et al. | |
| 11,021,495 B2 | 6/2021 | Sjogren et al. | |
| 2002/0081626 A1 | 6/2002 | Kaddurah-Daouk et al. | |
| 2004/0063666 A1 | 4/2004 | Christianson et al. | |
| 2005/0004074 A1 | 1/2005 | Lyons et al. | |
| 2009/0118243 A1 | 5/2009 | Gjorstrup | |
| 2010/0056480 A1 | 3/2010 | Meurs et al. | |
| 2010/0189544 A1 | 7/2010 | Nakamura et al. | |
| 2010/0189644 A1 | 7/2010 | Christianson et al. | |
| 2012/0083469 A1 | 4/2012 | Van Zandt et al. | |
| 2012/0129806 A1 | 5/2012 | Van Zandt et al. | |
| 2014/0371175 A1 | 12/2014 | Van Zandt et al. | |
| 2015/0080341 A1 | 3/2015 | Van Zandt et al. | |
| 2015/0191492 A1 | 7/2015 | Van Zandt et al. | |
| 2016/0137595 A1 | 5/2016 | Markwalder et al. | |

(Continued)

FOREIGN PATENT DOCUMENTS

CA 2431080 A1 12/2004
CN 103068830 A 4/2013

(Continued)

OTHER PUBLICATIONS

Ajinomoto Amino Acids Link News Aug. 2005 vol. 11: 3-4.
Arina et al., "Adoptively Transferred Immune T Cells Eradicate Established Tumors Despite Cancer-Induced Immune Suppression," J Immunol, 193: 1286-1293 (2014).
Baggio, et al., "Inhibition of Mn2+ 2-Arginase by Borate Leads to the Design of a Transition State Analogue Inhibitor, 2(S)-Amino-6-boronohexanoic Acid," J Am Chem Soc, 119(34): 8107-8108 (1997).
Barbul, "Arginine and Immune Function," Nutrition, 6(1): 53-58 (1990).

(Continued)

*Primary Examiner* — Sahar Javanmard
(74) *Attorney, Agent, or Firm* — Foley Hoag LLP; David P. Halstead

(57) ABSTRACT

Compounds according to Formula I are potent inhibitors of Arginase I and II activity:

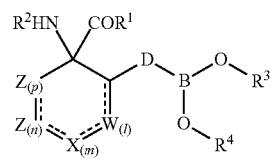

where $R^1$, $R^2$, $R^3$, $R^4$, D, W, X, Y, and Z are defined in the specification. The invention also provides pharmaceutical compositions of the compounds and methods of their use in treating or preventing a disease or a condition associated with arginase activity.

9 Claims, No Drawings

(56) References Cited

U.S. PATENT DOCUMENTS

| | | | |
|---|---|---|---|
| 2016/0137652 | A1 | 5/2016 | Beck et al. |
| 2016/0375044 | A1 | 12/2016 | Gross et al. |
| 2018/0251479 | A1 | 9/2018 | Van Zandt et al. |
| 2020/0223872 | A1 | 7/2020 | Sjogren et al. |
| 2020/0246362 | A1 | 8/2020 | Van Zandt et al. |
| 2020/0339607 | A1 | 10/2020 | Sjogren et al. |
| 2021/0261573 | A1 | 8/2021 | Sjogren et al. |

FOREIGN PATENT DOCUMENTS

| | | |
|---|---|---|
| CN | 103249737 A | 8/2013 |
| CN | 103402549 A | 11/2013 |
| CN | 103249737 B | 6/2016 |
| CN | 105879030 A | 8/2016 |
| JP | 2011/519868 A | 7/2011 |
| JP | 2012/515799 A | 7/2012 |
| JP | 2013/525364 A | 6/2013 |
| JP | 2013/542223 A | 11/2013 |
| JP | 2015/516397 A | 6/2015 |
| WO | WO-1999/019295 A1 | 4/1999 |
| WO | WO-2007/005620 A2 | 1/2007 |
| WO | WO-2010/085797 A2 | 7/2010 |
| WO | WO-2011/133653 A1 | 10/2011 |
| WO | WO-2012/058065 A1 | 5/2012 |
| WO | WO-2012/091757 A1 | 7/2012 |
| WO | WO-2013/059437 A1 | 4/2013 |
| WO | WO-2013/059587 A1 | 4/2013 |
| WO | WO-2013/158262 A1 | 10/2013 |
| WO | WO-2014/071231 A1 | 5/2014 |
| WO | WO-2015/061752 A1 | 4/2015 |
| WO | WO-2016/153078 A1 | 9/2016 |
| WO | WO-2016/210106 A1 | 12/2016 |
| WO | WO-2017/075363 A1 | 5/2017 |
| WO | WO-2018/119440 A1 | 6/2018 |

OTHER PUBLICATIONS

Bartolucci et al., "Direct, Regioselective and Chemoselective Preparation of Novel Boronated Tryptophans by Friedel-Crafts Alkylation," Organic Letters, 14(2): 600-603 (2012).
Busnel, et al., "Synthesis and evaluation of new ω-borono-α-amino acids as rat liver arginase inhibitors," Bioorg Med Chem, 13(7): 2373-2379 (2005).
Calithera Biosciences, Inc. Poster, EORTC-NCI-AACR; Nov. 29-Dec. 2, 2016; Munich, Germany.
Calithera Biosciences, Inc. Poster, SITC Conference; Nov. 9-13, 2016; National Harbor, MD.
CAS Registry No. 1374395-07-9. CA Index Name: "3-Pyrrolidinecarboxylic acid, 3-amino-4-(3-boronopropyl)-1-[(5,7-dichloro-1,2,3,4-tetrahydro-3-isoquinolinyl)carbonyl]-,(3R,4S)-rel-". STN Entry Date: May 24, 2012 (Last update: May 28, 2012).
Colleluori, et al., "Classical and Slow-Binding Inhibitors of Human Type II Arginase," Biochem, 40(31): 9356-9362 (2001).
Curtis et al., "Secondary Amines Containing One Aromatic Nitro Group: Preparation, Nitrosation, Sustained Nitric Oxide Release, and the Synergistic Effects of Released Nitric Oxide and an Arginase Inhibitor on Vascular Smooth Muscle Cell Proliferation," Bioorg Med Chem, 21(5): 1123-1135 (2013).
Ellyard et al., "Alternatively Activated Macrophage Possess Antitumor Cytotoxicity That Is Induced by IL-4 and Mediated by Arginase-1," J Immunother, 33: 443-452 (2012).
Extended European Search Report for EP Application No. 16815284.1 dated Dec. 3, 2018.
Extended European Search Report issued by the European Patent Office in corresponding Application No. EP 16860883 dated Jun. 19, 2019.
Geiger et al., "L-Arginine Modulates T Cell Metabolism and Enhances Survival and Anti-tumor Activity," Cell, Cell Press, 167(3): 829ff (2016).
Gritli-Linde et al., "Opposing Effects of Suramin and DL-Alpha-Difluromethylornithine on Polyamine Metabolism Contribute to a Synergistic Action on B16 Melanoma Cell Growth in Vitro," Anticancer Res, 18(2A): 863-870 (1998).
Horig, et al., "From bench to clinic and back: Perspective on the 1st IQPC Translational Research conference," J Transl Med, 2(1): 44 (2004).
Illies, et al., "Binding of alpha,alpha-Disubstituted Amino Acids to Arginase Suggests New Avenues for Inhibitor Design1," J Med Chem, 54(15): 5432-5443 (2011).
International Preliminary Report on Patentability for International Application No. PCT/US2011/033223 dated Oct. 23, 2012.
International Preliminary Report on Patentability for International Application No. PCT/US2013/030930 dated Oct. 30, 2014.
International Preliminary Report on Patentability for International Application No. PCT/US2016/038983 dated Jan. 4, 2018.
International Preliminary Report on Patentability for International Application No. PCT/US2016/059342 dated May 1, 2018.
International Preliminary Report on Patentability for PCT/US2017/068307 dated Jun. 25, 2019.
International Search Report and Written Opinion for International Application No. PCT/US2011/033223 dated Jul. 14, 2011.
International Search Report and Written Opinion for International Application No. PCT/US2011/056844 dated Dec. 14, 2011.
International Search Report and Written Opinion for International Application No. PCT/US2012/060789 dated Dec. 19, 2012.
International Search Report and Written Opinion for International Application No. PCT/US2013/030930 dated May 23, 2013.
International Search Report and Written Opinion for International Application No. PCT/US2017/068307 dated Mar. 26, 2018.
Ivanenkov et al., "Small-molecule Arginase Inhibitors," Pharm Pat Anal, 3(1): 65-85 (2014).
Jung, M.E.; Gervay, J., J Am Chem Soc, 1991, 113, 224; slide excerpt.
Kabalka et al., "Synthesis of novel boron containing unnatural cyclic amino acids as potential therapeutic agents," Tetrahedron Lett, 42(41):7145-7146 (2001).
Kabalka, et al., "Synthesis of a series of boronated unnatural cyclic amino acids as potential boro neutron capture therapy agents," Appl Organomet Chem, 22(9): 516-522 (2008).
Koziara et al., "Paclitaxel nanoparticles for the potential treatment of brain tumors," J Control Release, 99(2): 259-269 (2004).
Lei, et al., "Progress of Boronic Acids as Enzyme Inhibitors" Chinese J Pharm, 40(3): 213-219 (2009). (English Abstract only).
Li et al., "An Engineered Arginase FC Protein Inhibits Tumor Growth In Vitro and In Vivo," Evidence-Based Complementary and Alternative Medicine, vol. 2013, Article ID 243129: 1-9.
Lorvik et al., "Adoptive Transfer of Tumor-Specific Th2Cells Eradicates Tumors by Triggering an in Situ Inflammatory Immune Response," Cancer Research, 76(23): 6864-6876 (2016).
Peggs et al., "Blockade of CTLA-4 on both effector and regulatory T cell compartments contributes to the antitumor activity of anti-CTLA-4 antibodies," JEM 206(8):1717-1725 (2009).
Raber et al., "Metabolism of L-Arginine by Myeloid-Derived Suppressor Cells in Cancer: Mechanisms of T Cell Suppression and Therapetuic Perspectives," Immunol Invest, 41(6-7): 614-634 (2012).
Raber et al., "T Cells Conditioned with MDSC Show an Increased Anti-Tumor Activity After Adoptive T Cell Base Immunotherapy," Oncotarget, 7(14): 17565-17578 (2016).
Rodriguez et al., "Arginase I Production in the Tumor Microenvironment by Mature Myeloid Cells Inhibits T-Cell Receptor Expression and Antigen-Specific T-Cell Responses," Cancer Research, 64: 5839-5849 (2004).
Rodriguez et al., "L-Arginine Consumption by Macrophages Modulates the Expression of CD3κ Chain in T Lymphocytes," J Immunol, 171:1232-1239 (2003).
Rodriguez et t al., "Arginine Regulation by Myeloid Derived suppressor Cells and Tolerance in Cancer: Mechanisms and Therapeutic Perspectives," Immunol Rev, 222: 180-191 (2008).
Rossnagl et al., "EDA-Fibronectin Originating from Osteoblasts Inhibits the Immune Response against Cancer," PLOS Biology, 14(9):1-32 (2016).
Sandgren et al., "Suramin Selectively Inhibits Carcinoma Cell Growth that is Dependent on Extracellular Polyamines," Anticancer Res, 23(2B): 1223-1228 (2003).

(56) References Cited

OTHER PUBLICATIONS

Scheit et al., "Synergistic Effects Between Catalase Inhibitors and Modulators of Nitric Oxide Metabolism on Tumor Cell Apoptosis," Anticancer Res, 34(10): 5337-5350 (2014).

Schäfer, et al., "Failure is an option: learning from unsuccessful proof-of-concept trials," Drug Discov Today, 13(21): 913-916 (2008).

Segal, et al., "Chronic Oral Administration of the Arginase Inhibitors 2(S)-amino-6-boronohexanoic Acid (ABH) Improves Erectile Function in Aged Rates," J Androl, 33(6): 1169-1175 (2012).

Seiamnia et al., "Alpha-Difluoromethylornithine (DFMO) as a Potent Arginase Activity Inhibitor in Human Colon Carcinoma Cells," Biochem Pharmacol, 55(8): 1241-1245 (1998).

Singh et al., "Arginase Activity in Human Breast Cancer Cell Lines: $N^{\omega}$Hydroxy-L-arginine Selectively Inhibits Cell Proliferation and Induces Apoptosis in MDA-MB-468 Cells," Cancer Research, 60: 3305-3312 (2000).

Steggerda et al., "Abstract B045: Arginase Inhibitor CB-1158 Elicits Immune-Mediated Antitumor Responses as a Single Agent and in Combination with Other Immunotherapies," Second CRI-CIMT-EATI-AACR International Cancer Immunotherapy Conference: Translating Science into Survival (2016).

Steggerda et al., "Inhibition of Arginase by CB-1158 Blocks Myeloid Cell-Mediated Immune Suppression in the Tumor Microenvironment," Journal for Immuno Therapy of Cancer, 5(101):1-18 (2017).

Steppan, et al., "Development of novel arginase inhibitors for therapy of endothelial dysfunction," Front Immunol, 51(4): 5905-5908 (2013).

Table of A-Values: CHEM 330 handout.

Tate, et al., "Effect of arginase II on L-arginine depletion and cell growth in murine cell lines of renal cell carcinoma," J Hematol Oncol, 1(14): 1-10 (2008).

Vissers et al., "Plasma arginine concentrations are reduced in cancer patients: evidence for arginine deficiency?" Am J Clin Nutr, 81(5):1142-1146 (2005).

Works et al., "Immuno-Oncology Agent CB-1158 is a Potent and Selective Arginase Inhibitor and Causes an Immune-Mediated Anti-Tumor Response," Cancer Research, 76(14): Abstract 552 (2016).

Yang et al., "Ipilimumab (Anti-CTLA4 Antibody) Causes Regression of Metastatic Renal Cell Cancer Associated With Enteritis and Hypophysitis," J Immunother 30(8):825-830 (2007).

Extended European Search Report for EP Application No. 20165627.9 dated May 26, 2020.

Extended European Search Report for EP Application No. EP 20162218 dated Sep. 7, 2020.

Spranger et al., "Mechanism of tumor rejection with doublets of CTLA-4, PD-1/PD-L1, or IDO blockade involves restored IL-2 production and proliferation of $CD8^{+}T$ cells directly within the tumor microenvironment," Journal for ImmunoTherapy of Cancer, 2(3):1-14 (2014).

Extended European Search Report for EP Application No. EP 21158664 dated Mar. 26, 2021.

Scorei et al., "Boron-Containing Compounds as Preventive and Chemotherapeutic Agents for Cancer," Anti-Cancer Agents in Medicinal Chemistry, 10: 346-351 (2010).

Smoum et al., "Boron Containing Compounds as Protease Inhibitors," Chem. Rev., 112: 4156-4220 (2012).

ARGINASE INHIBITORS AS THERAPEUTICS

CROSS REFERENCE TO RELATED PATENT APPLICATIONS

This application is a continuation application of U.S. application Ser. No. 16/107,087 filed Aug. 21, 2018, which is a continuation of Ser. No. 15/207,902 filed Jul. 12, 2016 now U.S. Pat. No. 10,098,902 issued Oct. 16, 2018, which is a divisional application of U.S. application Ser. No. 14/614,115 filed Feb. 4, 2015 now U.S. Pat. No. 9,440,995 issued Sep. 13, 2016, which is a continuation of U.S. application Ser. No. 13/276,806 filed Oct. 19, 2011 now U.S. Pat. No. 9,233,985 issued Jan. 12, 2016, which claims the benefit of priority to U.S. Provisional Application No. 61/406,760, filed Oct. 26, 2010, the contents of each of which are hereby incorporated by reference in their entireties as if fully set forth herein.

BACKGROUND OF THE INVENTION

The present invention relates generally to inhibitors of arginase and their use for the treatment of pathological states. Two isoforms of arginase have been identified to date. Arginase I (ARG I), which is expressed in the cytosole, and Arginase II (ARG II), which is expressed in mitochondria. The arginase enzymes together with the NOS enzymes play an important role in regulating the levels of free arginine in cells.

The arginases are implicated to play a role in various pathological states. These include, for example, erectile dysfunction, pulmonary hypertension, hypertension, atherosclerosis, renal disease, asthma, T-cell dysfunction, ischemia reperfusion injury, neurodegenerative diseases, wound healing, and fibrotic diseases. Although, the mechanism of action of arginase enzymes in these disease states is still a subject of ongoing research, several studies implicate that the arginase enzymes are often upregulated during pathological disease states.

For example, it is postulated that upregulation of arginase activity results in reduced levels of arginine, which in turn reduces the level of NO a physiologically important signaling molecule that is required for cell division, stimulating enhanced blood flow and for controlling muscular and neurological signal transduction.

In addition to its role in regulating NO levels, arginase also effects production of critical polyamines such as putrescine, spermidine and spermine. As arginase consumes arginine it produces ornithine. Ornithine is subsequently converted to putrescine, spermidine and spermine via ornithine decarboxylase, spermidine synthase and spermine synthase respectively. Thus, the arginase enzymes control physiological signaling events by controlling the intracellular levels of polyamine signal transducers. See Wang, J-Y; and Casero, Jr., R. A., Ed; Humana Press, Totowa, N.J., 2006.

These results implicate, therefore, a role for inhibitors of arginaseas candidate therapeutics for the treatment of various disease states. The present invention provides Formula I compounds as inhibitors of arginase activity, as well as methods for using the inventive compounds in treatment.

SUMMARY OF THE INVENTION

The present invention provides compounds that inhibit arginase activity and pharmaceutically acceptable formulations of such compounds, as therapeutic agents for treating various diseases states associated with an imbalance or dysfunction of the arginase enzymes. Specifically, the present invention provides compounds that conform to Formula I.

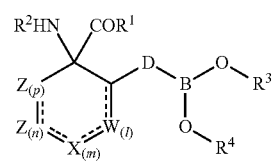

For Formula T compounds, $R^1$ is selected from the group consisting of —OH, $OR^a$, and $NR^bR^c$.

Substituent $R^a$ is selected from the group consisting of hydrogen, straight or branched chain $(C_1-C_6)$alkyl, $(C_3-C_8)$cycloalkyl, $(C_3-C_{14})$aryl, $(C_3-C_{14})$heterocycloalkyl-$(C_1-C_6)$alkylene-, $(C_3-C_{14})$heteroaryl-$(C_1-C_6)$alkylene-, and $(C_3-C_{14})$aryl$(C_1-C_6)$alkylene-.

Each of $R^b$ and $R^e$ are independently selected from the group consisting of H, —OH, straight or branched $(C_1-C_6)$alkyl, —$SO_2$—$(C_1-C_6)$alkyl, —$SO_2$—$(C_3-C_{14})$aryl, $(C_3-C_{14})$heterocycloalkyl-$(C_1-C_6)$alkylene-, and $(C_3-C_{14})$heteroaryl-$(C_1-C_6)$alkylene-.

Substituent $R^2$ is selected from the group consisting of H, straight or branched $(C_1-C_6)$ alkyl, and $(C_1-C_6)$alkyl-C(O)—.

Variables W, X, Y, and Z are each independently selected from the group consisting of a bond, —C(R''')$_2$—, —CR'''—, —NR'''—, —N—, —O—, —C(O)—, and —S—. Alternatively, variables W, X, Y, and Z are each independently —C(R')(R''')—. Moreover, no more than three of W, X, Y, and Z can simultaneously represent a bond and no two adjacent members of W, X, Y, and Z are simultaneously —O—, —S—, —N—, or —NR''—.

Subscripts l, m, n and p in Formula I are each independently integers between 0 and 2 inclusive such that at least one of l, m, n, or p is not 0. In addition, the dashed line

in Formula I indicates the option of having one or more double bonds.

Substituents $R^3$ and $R^4$ in Formula I are each independently selected from hydrogen, straight or branched $(C_1-C_6)$ alkyl, and C(O)—R'. Alternatively, $R^3$ and $R^4$ together with the boron atom to which they are bound form a 5- or 6-membered ring that is either fully saturated or partially saturated.

For compounds that conform to Formula I, D is selected from the group consisting of straight or branched $(C_3-C_8)$ alkylene, straight or branched $(C_2-C_8)$alkenylene, straight or branched $(C_2-C_8)$alkynylene, $(C_3-C_{14})$arylene, and $(C_3-C_{14})$ cycloalkylene. In some embodiments, one or more —$CH_2$— groups in D are optionally and independently replaced with a moiety selected from group the consisting of O, NR', S, SO, $SO_2$, and CR'R. However, no two adjacent —$CH_2$— groups in D are simultaneously O, NR', S, SO, or $SO_2$.

For certain Formula I compounds, D conforms to one of formulae -$L^1$-$L^2$-$CH_2$—$CH_2$—, —$CH_2$-$L^1$-$L^2$-$CH_2$—, —$CH_2$—$CH_2$-$L^1$-$L^2$-, -L-$CH_2$—$CH_2$-$L^2$-, -$L^1$-$CH_2$-$L^2$-

$CH_2$—, or —$CH_2$-$L^1$-$CH_2$-$L^2$-. The variables $L^1$ and $L^2$ are independently selected from the group consisting of O, NR', S, SO, $SO_2$, and CR'R", wherein R' and R" are as defined below. In embodiments when -$L^1$ and -$L^2$ are adjacent to each other, however, $L^1$ and $L^2$ are not simultaneously O, NR', S, SO or a $SO_2$ group. In another embodiment, $L^1$ and $L^2$ are not simultaneously present. According to this aspect of the invention, linker D is selected from the group consisting of -$L^1$-$CH_2$—$CH_2$—, —$CH_2$-$L^1$-$CH_2$—, —$CH_2$—$CH_2$-$L^1$-, $L^2$-$CH_2$—$CH_2$—, —$CH_2$-$L^2$-$CH_2$—, —$CH_2$—$CH_2$-$L^2$-.

In yet another embodiment, any two adjacent —$CH_2$— groups of D optionally represent two members of a ($C_3$-$C_{14}$)-cycloalkylenyl group.

Substituents R', R" and R'" are each independently selected from the group consisting of H, OH, $S(O)R^d$, $S(O)_2R^d$, ($C_1$-$C_8$)alkyl, ($C_3$-$C_6$)aryl, —$NH_2$, —NH($C_1$-$C_6$)alkyl, —N[($C_1$-$C_6$)alkyl]$_2$, —C(O)NR$^d$R$^e$, —C(O)($C_1$-$C_6$)alkyl, —C(O)($C_3$-$C_{14}$)aryl, —C(O)O($C_1$-$C_6$)alkyl, —C(O)O($C_3$-$C_{14}$)aryl, ($C_3$-$C_6$)cycloalkyl, ($C_3$-$C_{14}$)heterocycloalkyl, —C(O)($C_3$—$C_{14}$)heterocycloalkyl, ($C_3$-$C_{14}$)heteroaryl, ($C_3$-$C_{14}$)aryl-($C_1$-$C_6$)alkylene-, —C(O) ($C_3$-$C_{14}$)aryl-($C_1$-$C_6$)alkylene-, —C(O)($C_3$-$C_{14}$)aryl, ($C_3$-$C_6$)cycloalkyl-($C_1$-$C_6$)alkylene-, ($C_3$-$C_{14}$)heteroaryl-($C_1$-$C_6$)alkylene-, ($C_3$-$C_{14}$)heterocycle-($C_1$-$C_6$)alkylene-.

Any alkyl, alkylene, aryl, heteroaryl, cycloalkyl, or heterocycloalkyl is optionally substituted with one or more members selected from the group consisting of halogen, oxo, —COOH, —CN, —$NO_2$, —OH, —NR$^d$R$^e$, —NR$^g$S(O)$_2$R$^h$, ($C_1$-$C_6$)alkoxy, ($C_3$-$C_{14}$)aryl, ($C_1$-$C_6$)haloalkyl and ($C_3$-$C_{14}$)aryloxy.

For Formula I compounds, $R^d$, $R^e$, $R^g$, and $R^h$ are each independently selected from the group consisting of —H, straight or branched ($C_1$-$C_6$)alkyl, optionally substituted ($C_3$-$C_{14}$)aryl($C_1$-$C_6$)alkylene-, optionally substituted ($C_3$-$C_{14}$)aryl, ($C_1$-$C_6$)hydroxyalkyl, ($C_1$-$C_6$)aminoalkyl, $H_2$N($C_1$-$C_6$)alkylene-, optionally substituted ($C_3$-$C_6$)cycloalkyl, optionally substituted ($C_3$-$C_{14}$)heterocycloalkyl, optionally substituted ($C_3$-$C_{14}$)heteroaryl, optionally substituted ($C_3$-$C_{14}$)aryl-($C_1$-$C_6$)alkylene-, NR'R"C(O)—, and ($C_3$-$C_6$)aryl-($C_3$-$C_{14}$)-cycloalkylene-.

It should be understood that, notwithstanding the description of Formula I given herein, Formula I does not include 1-amino-2-(3-boronopropyl)cyclohexane carboxylic acid, more specifically (1S,2S)- or (1S,2R)-1-amino-2-(3-boronopropyl)cyclohexane carboxylic acid.

The present invention also provides pharmaceutically acceptable salts, stereoisomers, tautomers, and prodrug forms of Formula I compounds.

Compounds and pharmaceutical formulations in accordance with this invention are useful for treating a number of diseases and conditions, including but not limited to pulmonary hypertension, erectile dysfunction (ED), hypertension, atherosclerosis, renal disease, asthma, T-cell dysfunction, ischemia reperfusion injury, neurodegenerative diseases, wound healing, and fibrotic diseases.

One embodiment of the present invention, therefore, is a pharmaceutical composition that comprises a therapeutically effective amount of at least one of the compounds according to Formula I, its pharmaceutically acceptable salt, stereoisomer, tautomer, or prodrug and a pharmaceutically acceptable carrier.

The invention also provides in another embodiment a method for inhibiting Arginase I, Arginase II, or a combination thereof in a cell comprising contacting the cell with at least one compound according to Formula I.

Pursuant to another embodiment, the invention provides a method for treating or preventing a disease or a condition associated with expression or activity of Arginase I, Arginase II, or a combination thereof in a subject, comprising administering to the subject a therapeutically effective amount of at least one compound of Formula I.

According to another embodiment and as noted above, the invention provides a compound of Formula I for the treatment or prevention of a disease or condition associated with expression or activity of Arginase I, Arginase II, or a combination thereof in a subject. Also described is the use of a Formula I compound for the same purpose, as well as the use of Formula I compounds in the manufacture of a medicament for treatment or prevention of a disease or condition associated with expression or activity of Arginase I, Arginase II, or a combination of both enzymes in cells.

DETAILED DESCRIPTION

The inventive compounds are inhibitors of arginase. Specifically, inventive compounds that conform to Formula I are cyclic analogs of α-amino acids that contain at least one boron-containing group. The present invention also encompasses formulations of Formula I compounds as well as formulations comprising prodrug forms of the compounds, such as esters, amides and dioxaborolanes, which upon administration are cleaved through metabolic processes to give free compounds of Formula I.

The inventive compounds and their pharmaceutical compositions are useful in treating or preventing diseases or conditions that are associated with the expression or activity of arginase. Examples of disease states for which compositions of the inventive compounds find therapeutic applications include without limitation pulmonary hypertension, erectile dysfunction (ED), hypertension, atherosclerosis, renal disease, asthma, T-cell dysfunction, ischemia reperfusion injury, neurodegenerative diseases, wound healing, and fibrotic diseases.

Definitions

"Alkyl" refers to straight, branched chain, or cyclic hydrocarbyl groups including from 1 to about 20 carbon atoms. For instance, an alkyl can have from 1 to 10 carbon atoms or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2$CH($CH_3$)$_2$, —$CH_2$CH($CH_3$)($CH_2CH_3$), —$CH_2$CH($CH_2CH_3$)$_2$, —$CH_2$C($CH_3$)$_3$, —$CH_2$C($CH_2CH_3$)$_3$, —CH($CH_3$)CH($CH_3$)($CH_2CH_3$), —$CH_2CH_2$CH($CH_3$)$_2$, —$CH_2CH_2$CH($CH_3$)($CH_2CH_3$), —$CH_2CH_2$CH($CH_2CH_3$)$_2$, —$CH_2CH_2$C($CH_3$)$_3$, —$CH_2CH_2$C($CH_2CH_3$)$_3$, —CH($CH_3$)$CH_2$CH($CH_3$)$_2$, —CH($CH_3$)CH($CH_3$)CH($CH_3$)$_2$, and the like. Thus, alkyl groups include primary alkyl groups, secondary alkyl groups, and tertiary alkyl groups.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The terms "alkylene" and "substituted alkylene" refer to divalent alkyl and divalent substituted alkyl, respectively. Examples of alkylene include without limitation, ethylene (—CH$_2$—CH$_2$—). "Optionally substituted alkylene" refers to alkylene or substituted alkylene.

"Alkene" refers to straight, branched chain, or cyclic hydrocarbyl groups including from 2 to about 20 carbon atoms having 1-3, 1-2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a (C$_1$-C$_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl," alone or in combination refers to an aromatic monocyclic or bicyclic ring system such as phenyl or naphthyl. "Aryl" also includes aromatic ring systems that are optionally fused with a cycloalkyl ring, as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

The term "heteroatom" refers to N, O, and S. Inventive compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heteroarylene" refers to divalent heteroaryl, and "substituted heteroarylene" refers to divalent substituted heteroaryl. "Optionally substituted heteroarylene" refers to heteroarylene or substituted heteroarylene.

"Heterocycloalkyl" means a saturated or unsaturated non-aromatic monocyclic, bicyclic, tricyclic or polycyclic ring system that has from 5 to 14 atoms in which from 1 to 3 carbon atoms in the ring are replaced by heteroatoms of O, S or N. A heterocycloalkyl is optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

"Heteroalkyl" means a saturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N. Heteroalkyl is also intended to include oxidized S or N, such as sulfinyl, sulfonyl and N-oxide of a tertiary ring nitrogen. The point of attachment of the heteroalkyl substituent is at an atom such that a stable compound is formed. Examples of heteroalkyl groups include, but are not limited to, N-alkylaminoalkyl (e.g., CH$_3$NHCH$_2$—), N,N-dialkylaminoalkyl (e.g., (CH$_3$)$_2$NCH$_2$—), and the like.

"Heteroalkylene" refers to divalent heteroalkyl. The term "optionally substituted heteroalkylene" refers to heteroalkylene that is substituted with 1 to 3 substituents, e.g., 1, 2 or 3 substituents, attached at any available atom to produce a stable compound, wherein the substituents are as described herein.

"Heteroalkene" means a unsaturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N, and having 1-3, 1-2, or at least one carbon to carbon double bond or carbon to heteroatom double bond.

"Heteroalkenylene" refers to divalent heteroalkene. The term "optionally substituted heteroalkenylene" refers to heteroalkenylene that is substituted with 1 to 3 substituents, e.g., 1, 2 or 3 substituents, attached at any available atom to produce a stable compound, wherein the substituents are as described herein.

The term "cycloalkyl" refer to monocyclic, bicyclic, tricyclic, or polycyclic, 3- to 14-membered ring systems, which are either saturated, unsaturated or aromatic. The heterocycle may be attached via any atom. Cycloalkyl also contemplates fused rings wherein the cycloalkyl is fused to an aryl or hetroaryl ring as defined above. Representative examples of cycloalkyl include, but are not limited to cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "cycloalkylene" refers to divalent cycloalkylene. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term "nitrile or cyano" can be used interchangeably and refer to a —CN group which is bound to a carbon atom of a heteroaryl ring, aryl ring and a heterocycloalkyl ring.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "amine or amino" refers to an —$NR^dR^e$ group wherein $R^d$ and $R^e$ each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "amide" refers to a —NR'R"C(O)— group wherein R' and R" each independently refer to a hydrogen, ($C_1$-$C_8$)alkyl, or ($C_3$-$C_6$)aryl.

The term "carboxamido" refers to a —C(O)NR'R" group wherein R and R each independently refer to a hydrogen, ($C_1$-$C_8$)alkyl, or ($C_3$-$C_6$)aryl.

The term "aryloxy" refers to an —O-aryl group having the indicated number of carbon atoms. Examples of aryloxy groups include, but are not limited to, phenoxy, napthoxy and cyclopropeneoxy.

The term "haloalkoxy," refers to an —O—($C_1$-$C_6$)alkyl group wherein one or more hydrogen atoms in the $C_1$-$C_8$ alkyl group is replaced with a halogen atom, which can be the same or different. Examples of haloalkoxy groups include, but are not limited to, difluoromethoxy, trifluoromethoxy, 2,2,2-trifluoroethoxy, 4-chlorobutoxy, 3-bromopropyloxy, pentachloroethoxy, and 1,1,1-trifluoro-2-bromo-2-chloroethoxy.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "alkylsulfonyl" refers to a ($C_1$-$C_6$)alkyl group wherein one or more hydrogen atoms in the $C_1$-$C_6$ alkyl group is replaced with a —$S(O)_a$ group. Subscript "a" can either be 1 or 2, so as to give an alkyl sulfoxide (sulfinyl group), or an alkyl sulfone respectively. Examples of alkylsulfonyl groups include, but are not limited to dimethylsulfoxide, ethylmethyl sulfoxide, and methylvinylsulfone.

The term "haloalkyl," refers to an ($C_1$-$C_6$)alkyl group wherein one or more hydrogen atoms in the $C_1$-$C_6$ alkyl group is replaced with a halogen atom, which can be the same or different. Examples of haloalkyl groups include, but are not limited to, difluoromethyl, trifluoromethyl, 2,2,2-trifluoroethyl, 4-chlorobutyl, 3-bromopropylyl, pentachloroethyl, and 1,1,1-trifluoro-2-bromo-2-chloroethyl.

The term "aminoalkyl," refers to an ($C_1$-$C_6$)alkyl group wherein one or more hydrogen atoms in the $C_1$-$C_6$ alkyl group is replaced with a —$NR^dR^e$ group, where $R^d$ and $R^e$ can be the same or different, for example, $R^d$ and $R^e$ each independently refer to a hydrogen, ($C_1$-$C_8$)alkyl, aryl, heteroaryl, heterocycloalkyl, ($C_1$-$C_8$)haloalkyl, ($C_3$-$C_6$)cycloalkyl and ($C_1$-$C_6$)hydroxyalkyl group. Examples of aminoalkyl groups include, but are not limited to, aminomethyl, aminoethyl, 4-aminobutyl and 3-aminobutylyl.

The term "thioalkyl" or "alkylthio" refers to a ($C_1$-$C_6$) alkyl group wherein one or more hydrogen atoms in the $C_1$-$C_6$ alkyl group is replaced with a —SR group, wherein $R^J$ is selected from the group consisting of hydrogen, ($C_1$-$C_6$)alkyl and ($C_3$-$C_{14}$)aryl.

"Amino ($C_1$-$C_6$)alkylene" refers to a divalent alkylene wherein one or more hydrogen atoms in the $C_1$-$C_6$ alkylene group is replaced with a —$NR^dR^e$ group. Examples of amino ($C_1$-$C_6$)alkylene include, but are not limited to, aminomethylene, aminoethylene, 4-aminobutylene and 3-aminobutylylene.

The term "sulfonamide" refers to an —$NR^gS(O)_2R^h$ group where $R^g$ and $R^h$ are each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "sulfoxide" refers to a —S(O)— group in which the sulfur atom is covalently attached to two carbon atoms.

The term "sulfone" refers to a chemical compound containing a sulfonyl ($S(O)_2$) functional group attached to two carbon atoms. The central hexavalent sulfur atom is double bonded to each of two oxygen atoms and is covalently attached through single bonds to each of two carbon atoms.

A "hydroxyl" or "hydroxy" refers to an —OH group.

The term "($C_3$-$C_{14}$)aryl-($C_1$-$C_6$)alkylene" refers to a divalent alkylene wherein one or more hydrogen atoms in the $C_1$-$C_6$ alkylene group is replaced by a ($C_3$-$C_{14}$)aryl group. Examples of ($C_3$-$C_{14}$)aryl-($C_1$-$C_6$)alkylene groups include without limitation 1-phenylbutylene, phenyl-2-butylene, 1-phenyl-2-methylpropylene, phenylmethylene, phenylpropylene, and naphthylethylene.

The term "($C_3$-$C_{14}$)heteroaryl-($C_1$-$C_6$)alkylene" refers to a divalent alkylene wherein one or more hydrogen atoms in the $C_1$-$C_6$ alkylene group is replaced a ($C_3$-$C_{14}$)heteroaryl group. Examples of ($C_3$-$C_{14}$)heteroaryl-($C_1$-$C_6$)alkylene groups include without limitation 1-pyridylbutylene, quinolinyl-2-butylene and 1-pyridyl-2-methylpropylene.

The term "($C_3$-$C_{14}$)heterocycloalkyl-($C_1$-$C_6$)alkylene" refers to a divalent alkylene wherein one or more hydrogen atoms in the $C_1$-$C_6$ alkylene group is replaced by a ($C_3$-$C_{14}$) heterocycloalkyl group. Examples of ($C_3$-$C_{14}$)heterocycloalkyl-($C_1$-$C_6$)alkylene groups include without limitation 1-morpholinopropylene, azetidinyl-2-butylene and 1-tetrahydrofuranyl-2-methylpropylene.

The term "($C_3$-$C_{14}$)heteroaryl-($C_1$-$C_{14}$)hetercycloalkylene" refers to a divalent heterocycloalkylene wherein one or more hydrogen atoms in the $C_1$-$C_6$ heterocycloalkylene group is replaced by a ($C_3$-$C_{14}$)heteroaryl group. Examples of ($C_3$-$C_{14}$)heteroaryl-($C_1$-$C_6$)heterocycloalkylene groups include without limitation pyridylazetidinylene and 4-quinolino-1-piperazinylene.

The term "($C_3$-$C_{14}$)aryl-($C_1$-$C_{14}$)heterocycloalkylene" refers to a divalent heterocycloalkylene wherein one or more hydrogen atoms in the $C_1$-$C_{14}$ heterocycloalkylene group is replaced by a ($C_3$-$C_{14}$)aryl group. Examples of ($C_3$-$C_{14}$)

aryl-$(C_1-C_{14})$ heterocycloalkylene groups include without limitation 1-naphthyl-piperazinylene, phenylazetidinylene, and phenylpiperidinylene.

The term "$(C_3-C_{14})$aryl-$(C_1-C_6)$alkyl-$(C_1-C_{14})$heterocycloalkylene" refers to a divalent heterocycloalkylene wherein one or more hydrogen atoms in the $C_1-C_{14}$ heterocycloalkylene group is replaced by a $(C_1-C_6)$ alkyl group that is further substituted by replacing one or more hydrogen atoms of the $(C_1-C_6)$ alkyl group with a $(C_3-C_{14})$aryl group.

The term "$(C_3-C_{14})$heteroaryl-$(C_1-C_6)$alkyl-$(C_1-C_{14})$heterocycloalkylene" refers to a divalent heterocycloalkylene wherein one or more hydrogen atoms in the $C_1-C_{14}$ heterocycloalkylene group is replaced by a $(C_1-C_6)$ alkyl group that is further substituted by replacing one or more hydrogen atoms of the $(C_1-C_6)$ alkyl group with a $(C_3-C_{14})$heteroaryl group.

The term "$(C_3-C_{14})$heterocycloalkyl-$(C_1-C_6)$alkyl-$(C_1-C_{14})$heterocycloalkylene" refers to a divalent heterocycloalkylene wherein one or more hydrogen atoms in the $C_1-C_{14}$ heterocycloalkylene group is replaced by a $(C_1-C_6)$ alkyl group that is further substituted by replacing one or more hydrogen atoms of the $(C_1-C_6)$ alkyl group with a $(C_3-C_{14})$ heterocycloalkyl group.

The term "$(C_3-C_{14})$aryl-$(C_1-C_{14})$cycloalkylene" refers to a divalent cycloalkylene that is monocyclic, bicyclic or polycyclic and wherein one or more hydrogen atoms in the $(C_1-C_{14})$cycloalkylene group is replaced by a $(C_3-C_{14})$aryl group. Examples of $(C_3-C_{14})$aryl-$(C_1-C_{14})$cycloalkylene groups include without limitation phenylcyclobutylene, phenyl-cyclopropylene and 3-phenyl-2-methylbutylene-1-one.

The substituent —$CO_2H$, may be replaced with bioisosteric replacements such as:

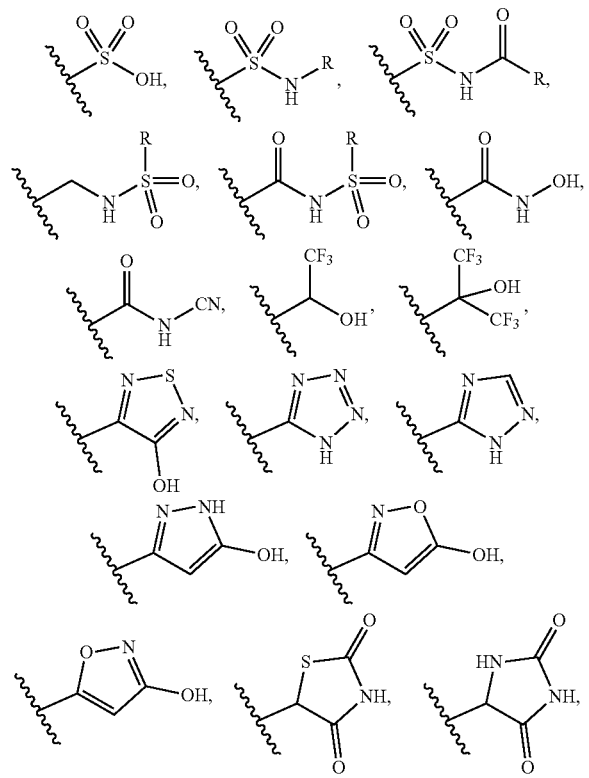

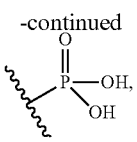

and the like, wherein R has the same definition as R' and R" as defined herein. See, e.g., THE PRACTICE OF MEDICINAL CHEMISTRY (Academic Press: New York, 1996), at page 203.

The compound of the invention can exist in various isomeric forms, including configurational, geometric, and conformational isomers, including, for example, cis- or trans-conformations. Compounds of the present invention may also exist in one or more tautomeric forms, including both single tautomers and mixtures of tautomers. The term "isomer" is intended to encompass all isomeric forms of a compound of this invention, including tautomeric forms of the compound. The compounds of the present invention may also exist in open-chain or cyclized forms. In some cases one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the invention.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, cinbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of a compound to increase or decrease the function, or activity of, for example, Arginase I or Arginase II. "Modulation", in its various forms, is intended to encompass inhibition, antagonism, partial antagonism, activation, agonism and/or partial agonism of the activity associated with arginae. Arginase inhibitors are compounds that, e.g., bind to, partially or totally block stimulation, decrease, prevent, delay activation, inactivate, desensitize, or down regulate signal transduction. The ability of a compound to modulate arginase activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, that is a compound which upon administration to a patient, must undergo chemical conversion by metabolic processes before becoming an active pharmacological agent. Exemplary prodrugs of compounds in accordance with Formula I are esters, dioxaborolanes, and amides.

Compounds

The present invention is directed to cyclic analogs of α-amino acids. More particularly, the inventive compounds contain at lease one boron-containing group as shown in Formula I:

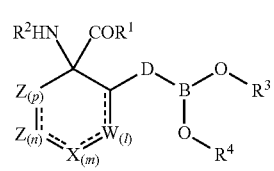

For Formula I compounds D is selected from the group consisting of straight or branched $(C_3-C_5)$alkylene, straight or branched $(C_2-C_8)$alkenylene, straight or branched $(C_2-C_8)$alkynylene, $(C_3-C_{14})$arylene, and $(C_3-C_{14})$cycloalkylene. In one embodiment, one or more —CH$_2$— groups in D are optionally and independently replaced with a moiety selected from group the consisting of O, NR', S, SO, SO$_2$, and CR'R". For compounds in accordance with Formula I, however, no two adjacent —CH$_2$— groups in D can simultaneously be O, NR', S, SO, or SO$_2$.

According to one embodiment, D has the formula $-L^1-L^2-CH_2—CH_2—$, $—CH_2-L^1-L^2-CH_2—$, $—CH_2—CH_2-L^1-L^2-$, $-L^1-CH_2—CH_2-L^2-$, $-L^1-CH_2-L^2-CH_2—$, or $—CH_2-L^1-CH_2-L^2-$. The variables $L^1$ and $L^2$ are independently selected from the group consisting of O, NR', S, SO, SO$_2$, and CR'R", wherein R' and R" are as defined below. In embodiments wherein $-L^1$ and $-L^2$ are adjacent to each other, $-L^1$ and $-L^2$ are not simultaneously O, NR', S, SO or an SO$_2$ group.

In another embodiment, $L^1$ and $L^2$ are not simultaneously present. According to this aspect of the invention, linker D is elected from the group consisting of $-L^1-CH_2—CH_2—$, $—CH_2-L^1-CH_2—$, $—CH_2—CH_2-L^1-$, $L^2-CH_2—CH_2—$, $—CH_2-L^2-CH_2—$, $—CH_2—CH_2-L^2-$.

In another embodiment, D contains a $(C_3-C_{14})$-cycloalkylenyl ring, in which two ring members constitute two adjacent —CH$_2$— groups in D, each having a hydrogen atom removed. Thus, for instance, when D is propylene the C$_2$ and C$_3$ atoms can each omit a hydrogen atom so as to couple a —CH$_2$— group to form a cyclopropyl ring as illustrated by the following moiety

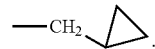

For Formula I compounds, R$^1$ can be —OH, OR$^a$, or NR$^b$R$^c$, R$^2$ is selected from the group consisting of H, straight or branched (C$_1$-C$_6$) alkyl, and (C$_1$-C$_6$)alkyl-C(O)— and W, X, Y, and Z are each independently selected from the group consisting of a bond, —C(R')(R''')—, —C(R''')$_2$—, —CR'''—, —NR'''—, —N—, —O—, —C(O)—, and —S—.

In one embodiment, the invention provides Formula I compounds in which D is propylene, R$^1$ is —OH, each of R$^2$, R$^3$ and R$^4$ are hydrogen, each of W, Y and Z are each —CH$_2$ and l+m+n+p=3. Alternatively, any one of W, Y or Z is —O—, —S—, or —NH— and the remaining two groups are each independently —CH$_2$. As prescribed, therefore, compounds that conform to Formula I include analogs of tetrahydrofuran, tetrahydro thiophene and pyrrolidine respectively.

In another embodiment, are provided Formula I compounds in which D is propylene, R$^1$ is —OH, each of R$^2$, R$^3$ and R$^4$ are hydrogen, each of W, Y and Z are —CH$_2$ groups, X is —NH and l+m+n+p=4. Alternatively, W, X, Y and Z are each —CH$_2$ groups to provide Formula I compounds that are analogs of 1-aminocyclohexane carboxylic acid.

Also contemplated are Formula I compounds in which R$^1$ is —OR$^a$ or NR$^b$R$^c$, R$^2$ is selected from the group consisting of a straight or branched (C$_1$-C$_6$) alkyl, (C$_3$-C$_6$)cycloalkyl-C(O)—, (C$_3$-C$_6$)cycloalkyl and (C$_1$-C$_6$)alkyl-C(O)— group, and each of R$^3$ and R$^4$ are independently selected from straight or branched (C$_1$-C$_6$)alkyl, or C(O)—R', or R$^3$ and R$^4$ together with the boron atom to which they are bound form a 5- or 6-membered ring that is fully saturated, or partially saturated, where substituents R$^a$, R$^b$ and R$^c$ are as defined.

Thus, for certain Formula I compounds, substituent R$^a$ is be selected from the group consisting of hydrogen, straight or branched chain (C$_1$-C$_6$)alkyl, (C$_3$-C$_8$)cycloalkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, and (C$_3$-C$_{14}$)aryl(C$_1$-C$_6$) alkylene-, and each of R$^b$ and R$^e$ are independently selected from the group consisting of H, —OH, straight or branched (C$_1$-C$_6$)alkyl, —SO$_2$—(C$_1$-C$_6$)alkyl, (C$_3$-C$_{14}$)aryl-SO$_2$—, (C$_3$-C$_{14}$)heterocycloalkyl-(C$_1$-C$_6$)alkylene-, and (C$_3$-C$_{14}$) heteroaryl-(C$_1$-C$_6$)alkylene-.

In one embodiment, W, X, Y and Z together with the carbon atoms to which they are bonded to form a ring. The ring can contain one or more double bonds that are represented by a dashed line

Substituents R', R'' and R''' for Formula I compounds are each independently selected from the group consisting of H, OH, —S(O) R$^d$, —S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —C(O)(C$_1$-C$_6$)alkyl, —C(O)(C$_3$-C$_{14}$)aryl, —C(O)O(C$_1$-C$_6$)alkyl, —C(O)O(C$_3$-C$_{14}$)aryl, (C$_3$-C$_6$)cycloalkyl, (C$_3$-C$_{14}$)heterocycloalkyl, (C$_3$-C$_{14}$)heteroaryl, (C$_3$-C$_{14}$)aryl-(C$_1$-C$_6$)alkylene-, (C$_3$-C$_6$)cycloalkyl-(C$_1$-C$_6$)alkylene-, (C$_3$-C$_{14}$)heteroaryl-(C$_1$-C$_6$)alkylene-, and (C$_3$-C$_{14}$)heterocycle-(C$_1$-C$_6$) alkylene-.

Furthermore, for compounds that conform to Formula I, any alkyl, alkylene, aryl, heteroaryl, cycloalkyl, or heterocycloalkyl are optionally substituted with one or more members selected from the group consisting of halogen, oxo, —COOH, —CN, —NO$_2$, —OH, —NR$^d$R$^e$, —NR$^g$S(O)$_2$R$^h$, (C$_1$-C$_6$)alkoxy, and (C$_3$-C$_{14}$)aryloxy, with each of R$^d$, R$^e$, R$^g$, and R$^h$ being independently selected from the group consisting of —H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene-, NR'R''C(O)—, and (C$_3$-C$_6$)aryl-(C$_3$-C$_{14}$)-cycloalkylene-.

It should be understood that notwithstanding the provisions above, Formula I does not include 1-amino-2-(3-boronopropyl)cyclohexane carboxylic acid, such as (1S,2S)-1-amino-2-(3-boronopropyl)cyclohexane carboxylic acid and (1S,2R)-1-amino-2-(3-boronopropyl)cyclohexane carboxylic acid.

Exemplary Formula I compounds include without limitation those shown below in Table 1.

TABLE 1

| Ex. # | Structure* | Name |
|---|---|---|
| 1 | H$_2$N, CO$_2$H / cyclopentane / B(OH)$_2$ | (1S,2S)-1-amino-2-(3-boronopropyl)cyclopentanecarboxylic acid |
| 2 | H$_2$N, CO$_2$H / cyclopentane / B(OH)$_2$ | (1S,2R)-1-amino-2-(3-boronopropyl)cyclopentanecarboxylic acid |
| 3 | H$_2$N, CO$_2$H / tetrahydrofuran / B(OH)$_2$ | (2R,3S)-3-amino-2-(3-boronopropyl)tetrahydrofuran-3-carboxylic acid |
| 4 | H$_2$N, CO$_2$H / tetrahydrofuran / B(OH)$_2$ | (2S,3S)-3-amino-2-(3-boronopropyl)tetrahydrofuran-3-carboxylic acid |

TABLE 1-continued

| Ex. # | Structure* | Name |
|---|---|---|
| 5 | 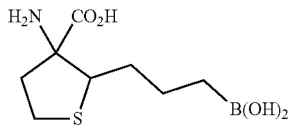 [SMILES: NC1(C(=O)O)CCSC1CCCB(O)O] | 3-amino-2-(3-boronopropyl)tetrahydrothiophene-3-carboxylic acid |
| 6 | 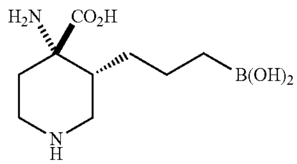 [SMILES: N[C@@]1(C(=O)O)CCNC[C@H]1CCCB(O)O] | (3R,4S)-4-amino-3-(3-boronopropyl)piperidine-4-carboxylic acid |
| 7 | 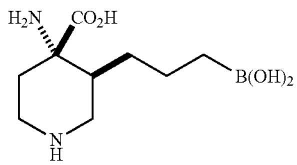 [SMILES: N[C@@]1(C(=O)O)CCNC[C@@H]1CCCB(O)O] | (3S,4S)-4-amino-3-(3-boronopropyl)piperidine-4-carboxylic acid |
| 8 | 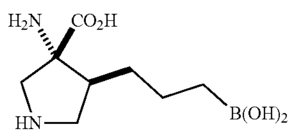 [SMILES: N[C@@]1(C(=O)O)CNC[C@@H]1CCCB(O)O] | (3R,4S)-3-amino-4-(3-boronopropyl)pyrrolidine-3-carboxylic acid |
| 9 | 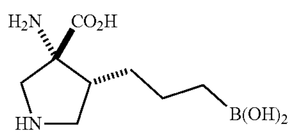 [SMILES: N[C@@]1(C(=O)O)CNC[C@H]1CCCB(O)O] | (3R,4R)-3-amino-4-(3-boronopropyl)pyrrolidine-3-carboxylic acid |
| 10 | 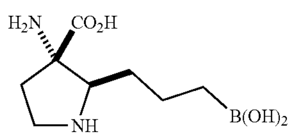 [SMILES: N[C@@]1(C(=O)O)CCN[C@@H]1CCCB(O)O] | (2R,3S)-3-amino-2-(3-boronopropyl)pyrrolidine-3-carboxylic acid |
| 11 | 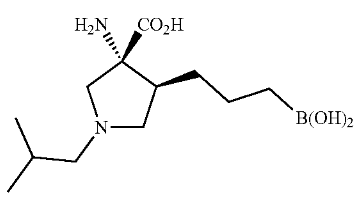 [SMILES: CC(C)CN1C[C@H](CCCB(O)O)[C@](N)(C(=O)O)C1] | (3R,4S)-3-amino-4-(3-boronopropyl)-1-isobutylpyrrolidine-3-carboxylic acid |
| 12 | 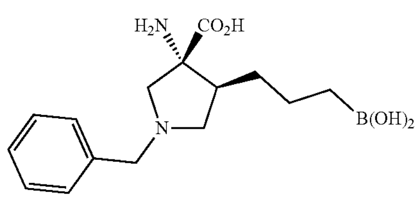 [SMILES: N[C@@]1(C(=O)O)CN(Cc2ccccc2)C[C@@H]1CCCB(O)O] | (3R,4S)-3-amino-1-benzyl-4-(3-boronopropyl)pyrrolidine-3-carboxylic acid |
| 13 | 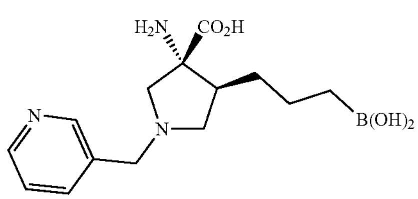 | (3R,4S)-3-amino-4-(3-boronopropyl)-1-(pyridin-3-ylmethyl)pyrrolidine-3-carboxylic acid |

TABLE 1-continued

| Ex. # | Structure* | Name |
|---|---|---|
| 14 | 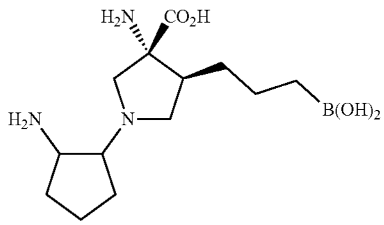 [SMILES: NC1CCCC1N1C[C@H](CCCB(O)O)[C@](N)(C(=O)O)C1] | (3R,4S)-3-amino-1-(2-aminocyclopentyl)-4-(3-boronopropyl)pyrrolidine-3-carboxylic acid |
| 15 | 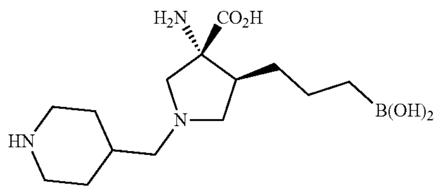 [SMILES: N[C@@]1(C(=O)O)CN(CC2CCNCC2)C[C@@H]1CCCB(O)O] | (3R,4S)-3-amino-4-(3-boronopropyl)-1-(piperidin-4-ylmethyl)pyrrolidine-3-carboxylic acid |
| 16 | 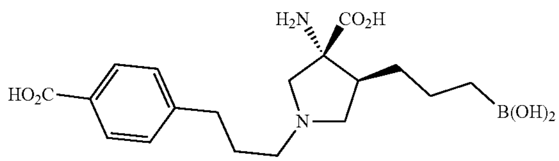 [SMILES: N[C@@]1(C(=O)O)CN(CCCc2ccc(C(=O)O)cc2)C[C@@H]1CCCB(O)O] | (3R,4S)-3-amino-4-(3-boronopropyl)-1-(3-(4-carboxyphenyl)propyl)pyrrolidine-3-carboxylic acid |
| 17 | 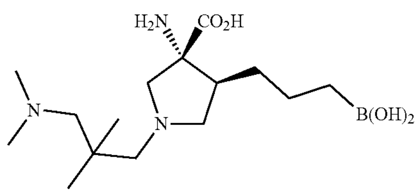 [SMILES: CN(C)CC(C)(C)CN1C[C@H](CCCB(O)O)[C@](N)(C(=O)O)C1] | (3R,4S)-3-amino-4-(3-boronopropyl)-1-(3-(dimethylamino)-2,2-dimethylpropyl)pyrrolidine-3-carboxylic acid |
| 18 | 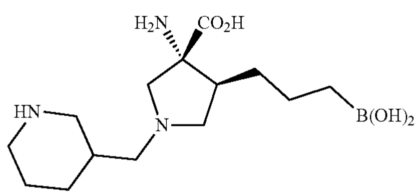 [SMILES: N[C@@]1(C(=O)O)CN(CC2CCCNC2)C[C@@H]1CCCB(O)O] | (3R,4S)-3-amino-4-(3-boronopropyl)-1-(piperidin-3-ylmethyl)pyrrolidine-3-carboxylic acid |
| 19 | 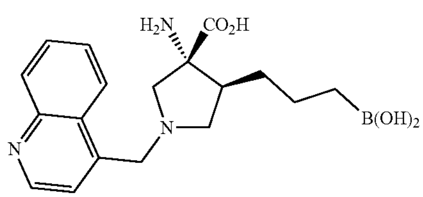 [SMILES: N[C@@]1(C(=O)O)CN(Cc2ccnc3ccccc23)C[C@@H]1CCCB(O)O] | (3R,4S)-3-amino-4-(3-boronopropyl)-1-(quinolin-4-ylmethyl)pyrrolidine-3-carboxylic acid |
| 20 | 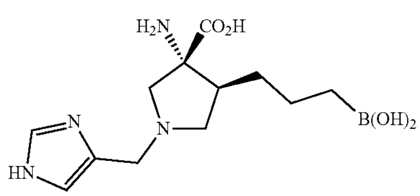 [SMILES: N[C@@]1(C(=O)O)CN(Cc2c[nH]cn2)C[C@@H]1CCCB(O)O] | (3R,4S)-1-((1H-imidazol-4-yl)methyl)-3-amino-4-(3-boronopropyl)pyrrolidine-3-carboxylic acid |
| 21 | 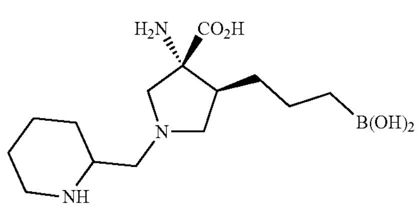 [SMILES: N[C@@]1(C(=O)O)CN(CC2CCCCN2)C[C@@H]1CCCB(O)O] | (3R,4S)-3-amino-4-(3-boronopropyl)-1-(piperidin-2-ylmethyl)pyrrolidine-3-carboxylic acid |

TABLE 1-continued

| Ex. # | Structure* | Name |
|---|---|---|
| 22 | 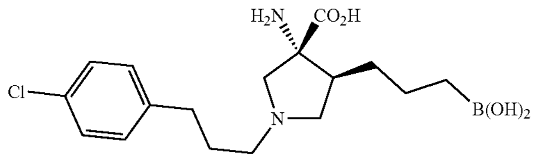 [SMILES: N[C@@]1(C(=O)O)CN(CCCc2ccc(Cl)cc2)C[C@@H]1CCCB(O)O] | (3R,4S)-3-amino-4-(3-boronopropyl)-1-(3-(4-chlorophenyl)propyl)pyrrolidine-3-carboxylic acid |
| 23 | 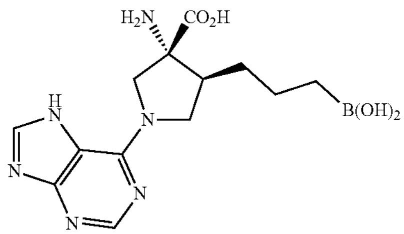 [SMILES: N[C@@]1(C(=O)O)CN(c2ncnc3nc[nH]c23)C[C@@H]1CCCB(O)O] | (3R,4S)-3-amino-4-(3-boronopropyl)-1-(7H-purin-6-yl)pyrrolidine-3-carboxylic acid |
| 24 | 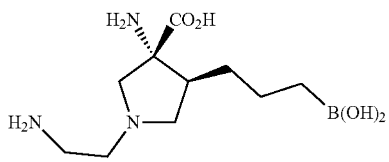 [SMILES: NCCN1C[C@H](CCCB(O)O)[C@](N)(C(=O)O)C1] | (3R,4S)-3-amino-1-(2-aminoethyl)-4-(3-boronopropyl)pyrrolidine-3-carboxylic acid |
| 25 | 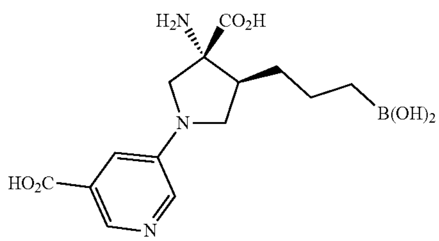 [SMILES: N[C@@]1(C(=O)O)CN(c2cncc(C(=O)O)c2)C[C@@H]1CCCB(O)O] | 5-((3R,4S)-3-amino-4-(3-boronopropyl)-3-carboxypyrrolidin-1-yl)nicotinic acid |
| 26 | 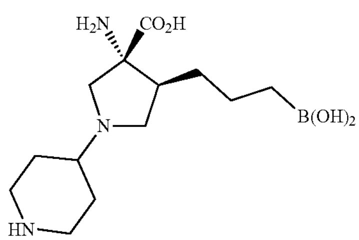 [SMILES: N[C@@]1(C(=O)O)CN(C2CCNCC2)C[C@@H]1CCCB(O)O] | (3R,4S)-3-amino-4-(3-boronopropyl)-1-(piperidin-4-yl)pyrrolidine-3-carboxylic acid |
| 27 | 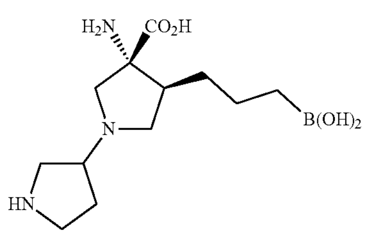 [SMILES: N[C@@]1(C(=O)O)CN(C2CCNC2)C[C@@H]1CCCB(O)O] | (3R,4S)-3-amino-4-(3-boronopropyl)-1,3'-bipyrrolidine-3-carboxylic acid |
| 28 | 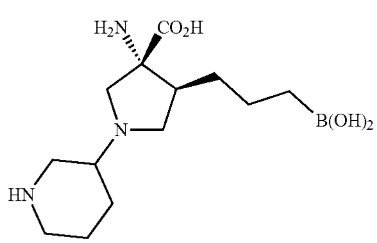 [SMILES: N[C@@]1(C(=O)O)CN(C2CCCNC2)C[C@@H]1CCCB(O)O] | (3R,4S)-3-amino-4-(3-boronopropyl)-1-(piperidin-3-yl)pyrrolidine-3-carboxylic acid |

TABLE 1-continued

| Ex. # | Structure* | Name |
|---|---|---|
| 29 | 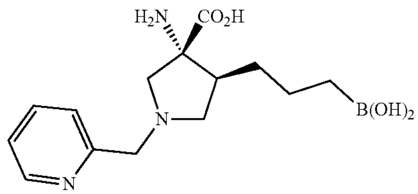 [SMILES: N[C@@]1(C(=O)O)CN(Cc2ccccn2)C[C@@H]1CCCB(O)O] | (3R,4S)-3-amino-4-(3-boronopropyl)-1-(pyridin-2-ylmethyl)pyrrolidine-3-carboxylic acid |
| 30 | 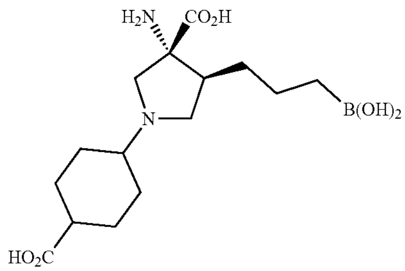 [SMILES: N[C@@]1(C(=O)O)CN(C2CCC(C(=O)O)CC2)C[C@@H]1CCCB(O)O] | (3R,4S)-3-amino-4-(3-boronopropyl)-1-(4-carboxycyclohexyl)pyrrolidine-3-carboxylic acid |
| 31 | 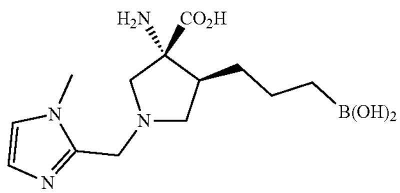 [SMILES: Cn1ccnc1CN1C[C@H](CCCB(O)O)[C@](N)(C(=O)O)C1] | (3R,4S)-3-amino-4-(3-boronopropyl)-1-((1-methyl-1H-imidazol-2-yl)methyl)pyrrolidine-3-carboxylic acid |
| 32 | 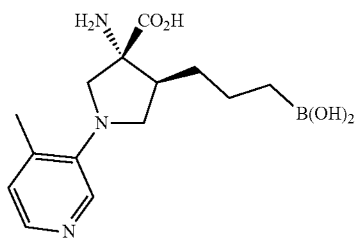 [SMILES: Cc1ccncc1N1C[C@H](CCCB(O)O)[C@](N)(C(=O)O)C1] | (3R,4S)-3-amino-4-(3-boronopropyl)-1-(4-methylpyridin-3-yl)pyrrolidine-3-carboxylic acid |
| 33 | 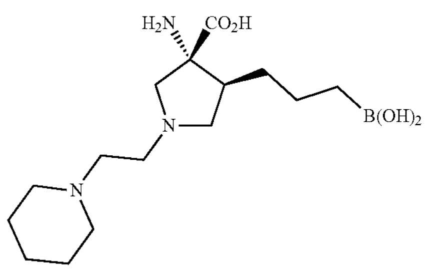 [SMILES: N[C@@]1(C(=O)O)CN(CCN2CCCCC2)C[C@@H]1CCCB(O)O] | (3R,4S)-3-amino-4-(3-boronopropyl)-1-(2-(piperidin-1-yl)ethyl)pyrrolidine-3-carboxylic acid |
| 34 | 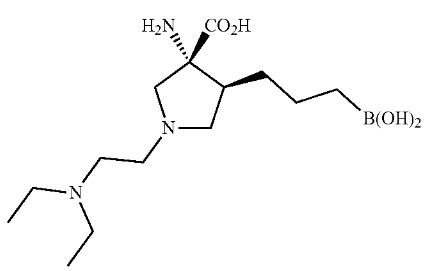 [SMILES: CCN(CC)CCN1C[C@H](CCCB(O)O)[C@](N)(C(=O)O)C1] | (3R,4S)-3-amino-4-(3-boronopropyl)-1-(2-(diethylamino)ethyl)pyrrolidine-3-carboxylic acid |
| 35 | 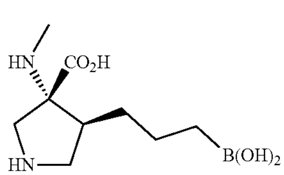 [SMILES: CN[C@@]1(C(=O)O)CNC[C@@H]1CCCB(O)O] | (3R,4S)-4-(3-boronopropyl)-3-(methylamino)pyrrolidine-3-carboxylic acid |

TABLE 1-continued

| Ex. # | Structure* | Name |
|---|---|---|
| 36 | 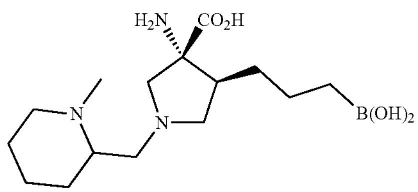 [SMILES: CN1CCCCC1CN1C[C@H](CCCB(O)O)[C@](N)(C(=O)O)C1] | (3R,4S)-3-amino-4-(3-boronopropyl)-1-((1-methylpiperidin-2-yl)methyl)pyrrolidine-3-carboxylic acid |
| 37 | 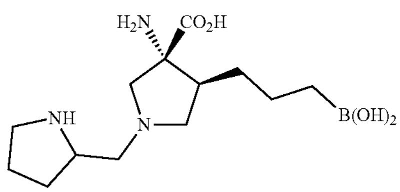 [SMILES: N[C@@]1(C(=O)O)CN(CC2CCCN2)C[C@@H]1CCCB(O)O] | (3R,4S)-3-amino-4-(3-boronopropyl)-1-(pyrrolidin-2-ylmethyl)pyrrolidine-3-carboxylic acid |
| 38 | 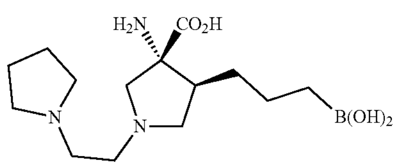 [SMILES: N[C@@]1(C(=O)O)CN(CCN2CCCC2)C[C@@H]1CCCB(O)O] | (3R,4S)-3-amino-4-(3-boronopropyl)-1-(2-(pyrrolidin-1-yl)ethyl)pyrrolidine-3-carboxylic acid |
| 39 | 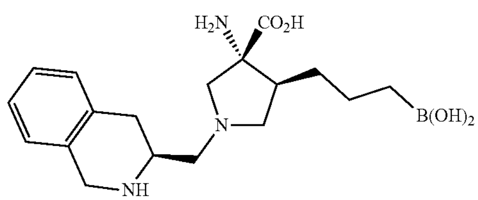 [SMILES: N[C@@]1(C(=O)O)CN(C[C@@H]2Cc3ccccc3CN2)C[C@@H]1CCCB(O)O] | (3R,4S)-3-amino-4-(3-boronopropyl)-1-(((S)-1,2,3,4-tetrahydroisoquinolin-3-yl)methyl)pyrrolidine-3-carboxylic acid |
| 40 | 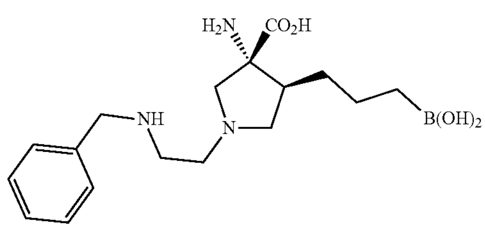 [SMILES: N[C@@]1(C(=O)O)CN(CCNCc2ccccc2)C[C@@H]1CCCB(O)O] | (3R,4S)-3-amino-1-(2-(benzylamino)ethyl)-4-(3-boronopropyl)pyrrolidine-3-carboxylic acid |
| 41 | 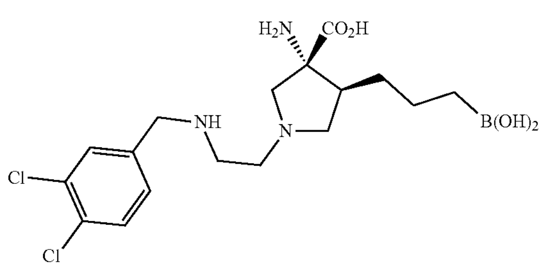 [SMILES: N[C@@]1(C(=O)O)CN(CCNCc2ccc(Cl)c(Cl)c2)C[C@@H]1CCCB(O)O] | (3R,4S)-3-amino-4-(3-boronopropyl)-1-(2-(3,4-dichlorobenzylamino)ethyl)pyrrolidine-3-carboxylic acid |
| 42 | 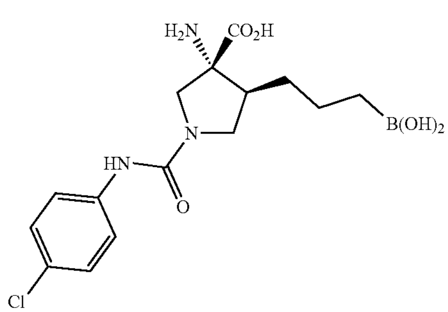 [SMILES: N[C@@]1(C(=O)O)CN(C(=O)Nc2ccc(Cl)cc2)C[C@@H]1CCCB(O)O] | (3R,4S)-3-amino-4-(3-boronopropyl)-1-(4-chlorophenylcarbamoyl)pyrrolidine-3-carboxylic acid |

TABLE 1-continued

| Ex. # | Structure* | Name |
|---|---|---|
| 43 | 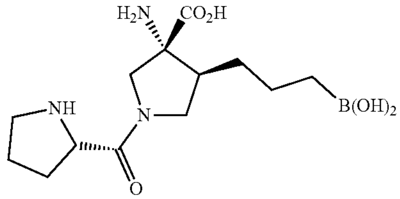 | (3R,4S)-3-amino-4-(3-boronopropyl)-1-((S)-pyrrolidine-2-carbonyl)pyrrolidine-3-carboxylic acid |
| 44 | 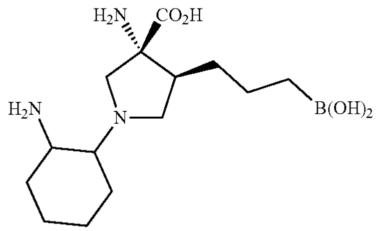 [SMILES: NC1CCCCC1N1C[C@H](CCCB(O)O)[C@](N)(C(=O)O)C1] | (3R,4S)-3-amino-1-(2-aminocyclohexyl)-4-(3-boronopropyl)pyrrolidine-3-carboxylic acid |
| 45 | 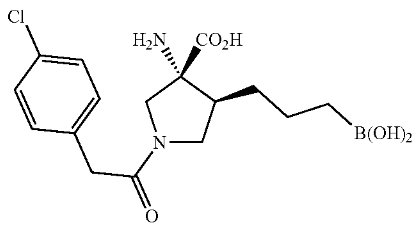 [SMILES: N[C@@]1(C(=O)O)CN(C(=O)Cc2ccc(Cl)cc2)C[C@@H]1CCCB(O)O] | (3R,4S)-3-amino-4-(3-boronopropyl)-1-(2-(4-chlorophenyl)acetyl)pyrrolidine-3-carboxylic acid |
| 46 | 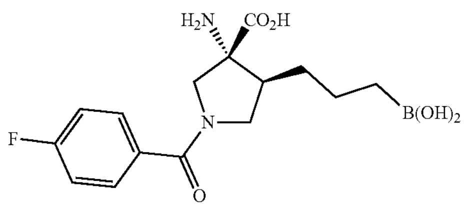 [SMILES: N[C@@]1(C(=O)O)CN(C(=O)c2ccc(F)cc2)C[C@@H]1CCCB(O)O] | (3R,4S)-3-amino-4-(3-boronopropyl)-1-(4-fluorobenzoyl)pyrrolidine-3-carboxylic acid |
| 47 | 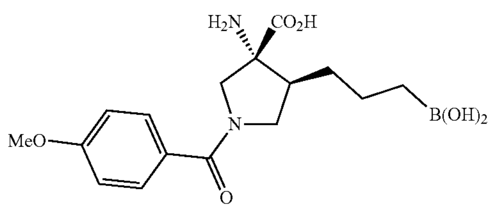 [SMILES: COc1ccc(C(=O)N2C[C@H](CCCB(O)O)[C@](N)(C(=O)O)C2)cc1] | (3R,4S)-3-amino-4-(3-boronopropyl)-1-(4-methoxybenzoyl)pyrrolidine-3-carboxylic acid |
| 48 | 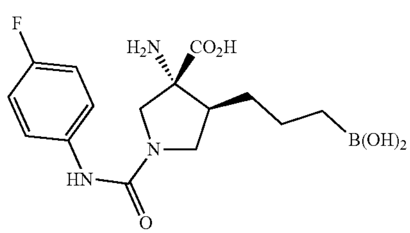 [SMILES: N[C@@]1(C(=O)O)CN(C(=O)Nc2ccc(F)cc2)C[C@@H]1CCCB(O)O] | (3R,4S)-3-amino-4-(3-boronopropyl)-1-(4-fluorophenylcarbamoyl)pyrrolidine-3-carboxylic acid |
| 49 | 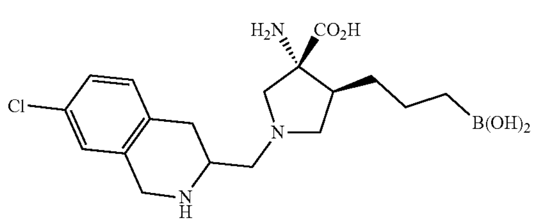 [SMILES: N[C@@]1(C(=O)O)CN(CC2Cc3ccc(Cl)cc3CN2)C[C@@H]1CCCB(O)O] | (3R,4S)-3-amino-4-(3-boronopropyl)-1-((7-chloro-1,2,3,4-tetrahydroisoquinolin-3-yl)methyl)pyrrolidine-3-carboxylic acid |

TABLE 1-continued

| Ex. # | Structure* | Name |
|---|---|---|
| 50 | 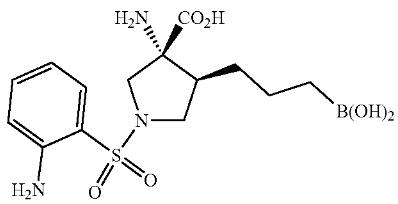 [SMILES: Nc1ccccc1S(=O)(=O)N1C[C@H](CCCB(O)O)[C@](N)(C(=O)O)C1] | (3R,4S)-3-amino-1-(2-aminophenylsulfonyl)-4-(3-boronopropyl)pyrrolidine-3-carboxylic acid |
| 51 | 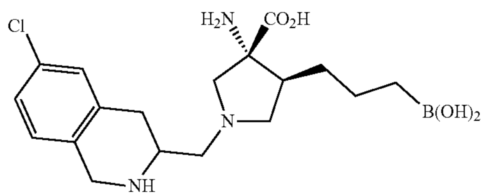 [SMILES: N[C@@]1(C(=O)O)CN(CC2Cc3cc(Cl)ccc3CN2)C[C@@H]1CCCB(O)O] | (3R,4S)-3-amino-4-(3-boronopropyl)-1-((6-chloro-1,2,3,4-tetrahydroisoquinolin-3-yl)methyl)pyrrolidine-3-carboxylic acid |
| 52 | 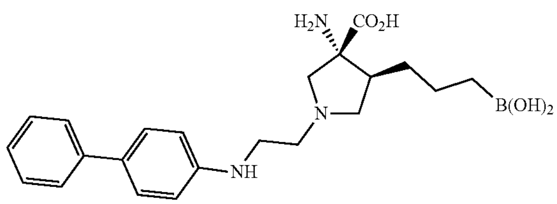 [SMILES: N[C@@]1(C(=O)O)CN(CCNc2ccc(-c3ccccc3)cc2)C[C@@H]1CCCB(O)O] | (3R,4S)-3-amino-1-(2-(biphenyl-4-ylamino)ethyl)-4-(3-boronopropyl)pyrrolidine-3-carboxylic acid |
| 53 | 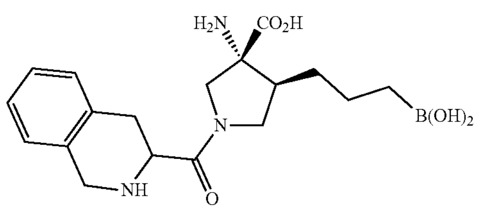 [SMILES: N[C@@]1(C(=O)O)CN(C(=O)C2Cc3ccccc3CN2)C[C@@H]1CCCB(O)O] | (3R,4S)-3-amino-4-(3-boronopropyl)-1-(1,2,3,4-tetrahydroisoquinoline-3-carbonyl)pyrrolidine-3-carboxylic acid |
| 54 | 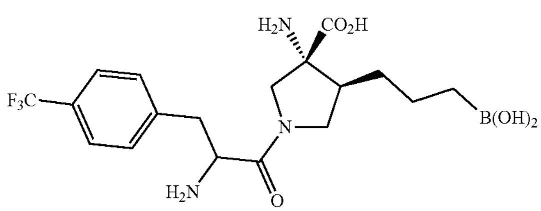 [SMILES: NC(Cc1ccc(C(F)(F)F)cc1)C(=O)N1C[C@H](CCCB(O)O)[C@](N)(C(=O)O)C1] | (3R,4S)-3-amino-1-(2-amino-3-(4-(trifluoromethyl)phenyl)propanoyl)-4-(3-boronopropyl)pyrrolidine-3-carboxylic acid |
| 55 | 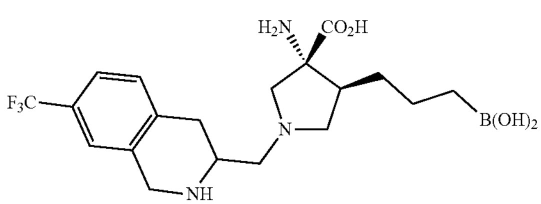 [SMILES: N[C@@]1(C(=O)O)CN(CC2Cc3ccc(C(F)(F)F)cc3CN2)C[C@@H]1CCCB(O)O] | (3R,4S)-3-amino-4-(3-boronopropyl)-1-((7-(trifluoromethyl)-1,2,3,4-tetrahydroisoquinolin-3-yl)methyl)pyrrolidine-3-carboxylic acid |
| 56 | 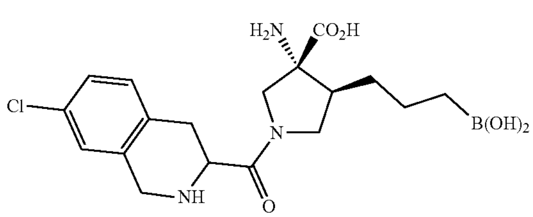 [SMILES: N[C@@]1(C(=O)O)CN(C(=O)C2Cc3ccc(Cl)cc3CN2)C[C@@H]1CCCB(O)O] | (3R,4S)-3-amino-4-(3-boronopropyl)-1-(7-chloro-1,2,3,4-tetrahydroisoquinoline-3-carbonyl)pyrrolidine-3-carboxylic acid |

TABLE 1-continued

| Ex. # | Structure* | Name |
|---|---|---|
| 57 | 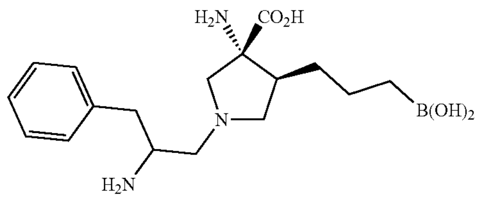 [SMILES: NC(Cc1ccccc1)CN1C[C@H](CCCB(O)O)[C@](N)(C(=O)O)C1] | (3R,4S)-3-amino-1-(2-amino-3-phenylpropyl)-4-(3-boronopropyl)pyrrolidine-3-carboxylic acid |
| 58 | 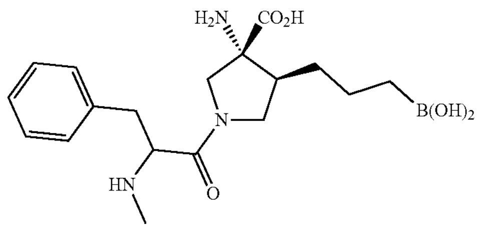 [SMILES: CNC(Cc1ccccc1)C(=O)N1C[C@H](CCCB(O)O)[C@](N)(C(=O)O)C1] | (3R,4S)-3-amino-4-(3-boronopropyl)-1-(2-(methylamino)-3-phenylpropanoyl)pyrrolidine-3-carboxylic acid |
| 59 | 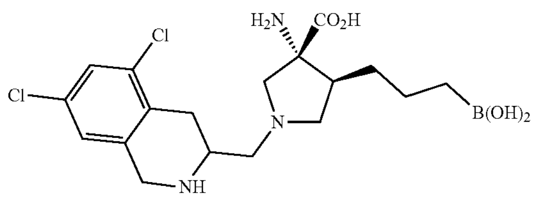 [SMILES: N[C@@]1(C(=O)O)CN(CC2Cc3c(Cl)cc(Cl)cc3CN2)C[C@@H]1CCCB(O)O] | (3R,4S)-3-amino-4-(3-boronopropyl)-1-((5,7-dichloro-1,2,3,4-tetrahydroisoquinolin-3-yl)methyl)pyrrolidine-3-carboxylic acid |
| 60 | 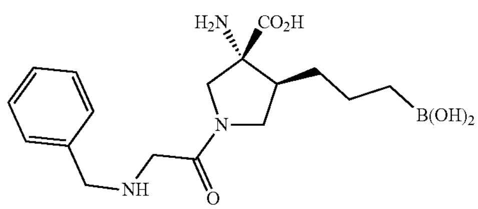 [SMILES: N[C@@]1(C(=O)O)CN(C(=O)CNCc2ccccc2)C[C@@H]1CCCB(O)O] | (3R,4S)-3-amino-1-(2-(benzylamino)acetyl)-4-(3-boronopropyl)pyrrolidine-3-carboxylic acid |
| 61 | 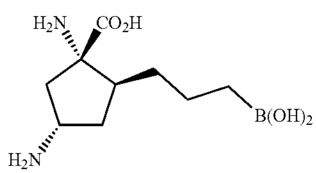 [SMILES: N[C@H]1C[C@H](CCCB(O)O)[C@](N)(C(=O)O)C1] | (1S,2S,4S)-1,4-diamino-2-(3-boronopropyl)cyclopentanecarboxylic acid |
| 62 | 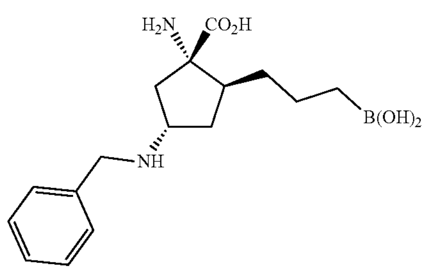 [SMILES: N[C@@]1(C(=O)O)C[C@@H](NCc2ccccc2)C[C@@H]1CCCB(O)O] | (1S,2S,4S)-1-amino-4-(benzylamino)-2-(3-boronopropyl)cyclopentanecarboxylic acid |
| 63 | 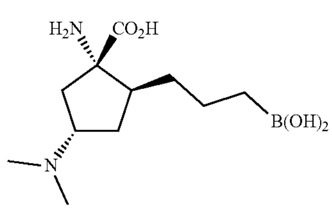 [SMILES: CN(C)[C@H]1C[C@H](CCCB(O)O)[C@](N)(C(=O)O)C1] | (1S,2S,4S)-1-amino-2-(3-boronopropyl)-4-(dimethylamino)cyclopentanecarboxylic acid |

TABLE 1-continued

| Ex. # | Structure* | Name |
|---|---|---|
| 64 | 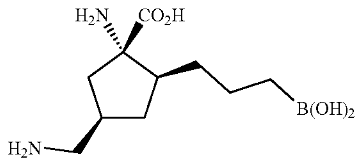 [SMILES: NC[C@@H]1C[C@H](CCCB(O)O)[C@](N)(C(=O)O)C1] | (1S,2S,4R)-1-amino-4-(aminomethyl)-2-(3-boronopropyl)cyclopentanecarboxylic acid |
| 65 | 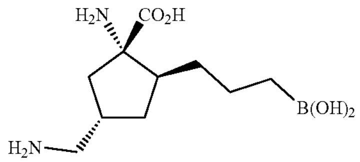 [SMILES: NC[C@H]1C[C@H](CCCB(O)O)[C@](N)(C(=O)O)C1] | (1S,2S,4S)-1-amino-4-(aminomethyl)-2-(3-boronopropyl)cyclopentanecarboxylic acid |
| 66 | 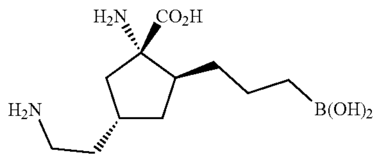 [SMILES: NCC[C@H]1C[C@H](CCCB(O)O)[C@](N)(C(=O)O)C1] | (1S,2S,4R)-1-amino-4-(2-aminoethyl)-2-(3-boronopropyl)cyclopentanecarboxylic acid |

Pharmaceutical Compositions and Dosages

The compounds of Formula I are administered to a patient or subject in need of treatment either alone or in combination with other compounds having similar or different biological activities. For example, the compounds and compositions of the invention may be administered in a combination therapy, i.e., either simultaneously in single or separate dosage forms or in separate dosage forms within hours or days of each other. Examples of such combination therapies include administering the compositions and compounds of Formula I with other agents used to treat erectile dysfunction, pulmonary hypertension, hypertension, asthma, inflammation, ischaemia reperfusion, myocardial infarction, artherosclerosis, immune response, psoriasis and wound healing. Suitable compounds for use in combination therapy include but are not limite to:

Erectile Dysfunction: sildenafil, vardenafil, tadalafil and alprostadil.

Pulmonary Hypertension/Hypertension: epoprostenol, iloprost, bosentan, amlodipine, diltiazem, nifedipine, ambrisentan and warfarin.

Asthma: fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn.

Artherosclerosis: atorvastatin, lovastatin, simvastatin, pravastatin, fluvastatin, rosuvastatin, gemfibrozil, fenofibrate, nicotinic acid, clopidogrel.

The invention also provides a pharmaceutical composition comprising one or more compounds according to Formula I or a pharmaceutically acceptable salt, solvate, stereoisomer, tautomer, or prodrug, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises a compound selected from those illustrated in Table 1 or a pharmaceutically acceptable salt, solvate, stereoisomer, tautomer, or prodrug thereof, and a pharmaceutically acceptable carrier.

The inventive compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise a compound of the invention its pharmaceutically acceptable stereoisomer, prodrug, salt, solvate, hydrate, or tautomer and a pharmaceutically acceptable carrier.

Inventive compositions suitable for oral use may be prepared according to any method known to the art for the manufacture of pharmaceutical compositions. For instance, liquid formulations of the inventive compounds contain one or more agents selected from the group consisting of sweetening agents, flavoring agents, coloring agents and preserving agents in order to provide pharmaceutically elegant and palatable preparations of the arginase inhibitor.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensaturatedion products of an alkylene oxide with fatty acids, for example polyoxyethylene stearate, or condensaturatedion products of ethylene oxide with long chain aliphatic alcohols, for example, heptadecaethyleneoxycetanol, or condensaturatedion products of ethylene oxide with partial esters derived from fatty acids and a hexitol such as polyoxyethylene sorbitol monooleate, or condensaturatedion products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensaturatedion products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Synthesis of Compounds

Compounds of the invention are prepared using general synthetic methods as further described below. The choice of an appropriate synthetic methodology is guided by the choice of Formula I compound desired and the nature of functional groups present in the intermediate and final product. Thus, selective protection/deprotection protocols may be necessary during synthesis depending on the specific functional groups desired and protecting groups being used. A description of such protecting groups and how to introduce and remove them is found in PROTECTIVE GROUPS IN ORGANIC SYNTHESIS Third Edition, T. W. Green and P. G. M. Wuts, John Wiley and Sons, New York 1999.

Exemplary general synthetic methodologies for making Formula I compounds are provided below. More specific syntheses of illustrative Formula I compounds are also provided.

Scheme A below illustrates a general method for synthesizing the cyclic scaffold of many compounds according to Formula I. According to this method, the α-allyl ketone A-3 is prepared from readily available starting materials using different methods. For example, A-3 is obtained via a sequence of reaction steps from the corresponding α-carboxylic acid ester A-1. Thus, when the α-carboxylic acid ester A-1 is commercially available or can be readily prepared, A-3 is synthesized by transesterification of the ester to allyl ester A-2, which undergoes a decarboxylative rearrangement in the presence of palladium catalyst to give the target intermediate A-3.

Scheme A

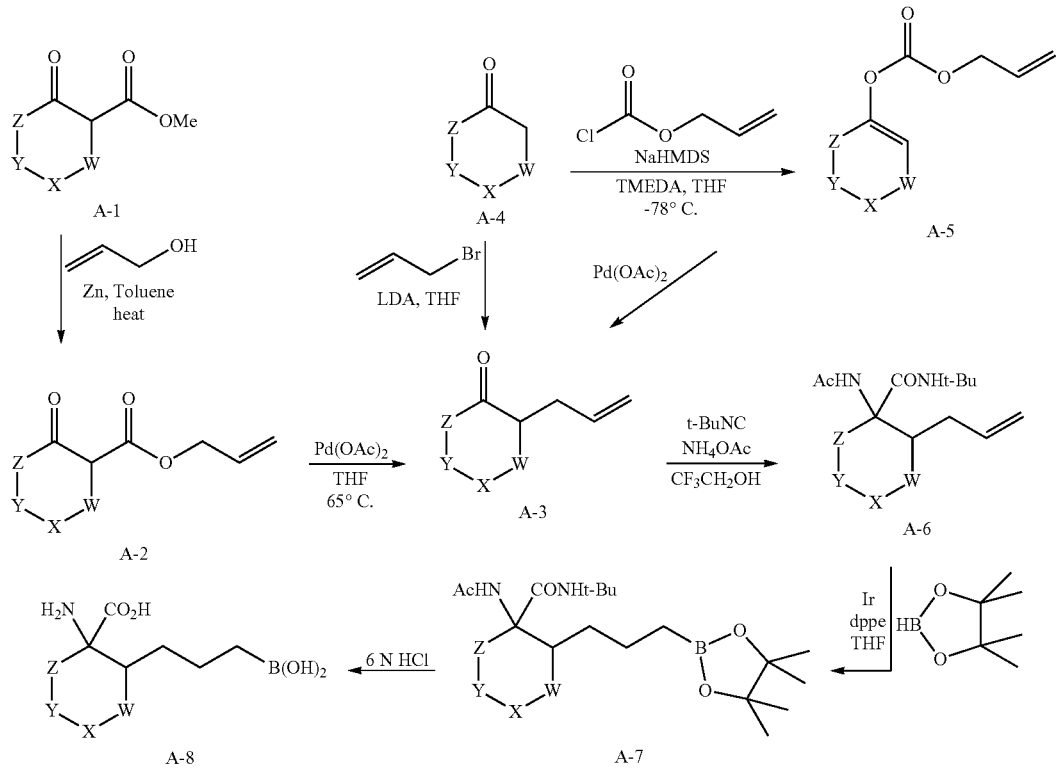

Alternatively, if the carboxylic acid is available it can be converted to a simple ester or an allyl ester directly using a wide variety on known methods. One such method uses allyl bromide in acetone with aqueous potassium carbonate to directly synthesize the allyl ester A-2.

According to an alternate approach, the α-allyl ketone A-3 is prepared directly from the cyclic ketone A-4 using allyl bromide and a base like lithium diisopropylamide (LDA), or sodium hydride. In some cases one prepares α-allyl ketone A-3 from ketone A-4 via the corresponding allyl carbonate A-5. Thus, reaction of the cyclic ketone A-4 with allyl chloroformate in the presence of a base like NaHMDS in a polar aprotic solvent like THF at −78° C. results in the corresponding allyl carbonate A-5 which is then converted to α-allyl ketone A-3 in the presence of a metal reagent such as palladium acetate or tetrakis(triphenylphosphine)palladium.

Often additives like tetramethylethylene diamine (TMEDA), are used to facilitate the formation of the allyl carbonate. This synthetic methodology is versatile and is suitable for the enentioselectively preparation ketone A-3 using certain chiral ligands. A description of this approach can be found in Trost, B. M et al., *J. Am. Chem. Soc.* 2009, 131, 18343-18357.

The α-allyl ketone A-3 thus is readily conveted to the protected cyclic amino acid A-6 using an Ugi reaction, by treating A-3 with tert-butylisocyanate (t-BuNC) and NH4OAc using trifluoroethanol as a solvent. For a review of the Ugi reaction see Doemling, A., *Chem. Rev.* 2006, 106, 17-89. Alternative solvents as well as other isocyante, amine sources and carboxylic acid sources may be used. The choice of amine, isocyanate and carboxylic acid used, moreover, governs the nature of the protecting group present on the resulting amino acid. In some embodiments, enantioselectivity is achieved by using an optically active amine or carboxylic acid.

As an alternative to the Ugi reaction, the α-substituted cyclic amino acid A-6 is synthesized from the corresponding keton A-3 using the Strecker reaction. Many examples of the Strecker reaction and modified Strecker reaction are available in the literature (Ma, D., Tian, H., Zou, G., *J. Org. Chem.* 1999, 64, 120-125; Murata, Y., Statake, K., *Synthetic Communications*, 2008, 38, 1485-1490). The final product containing a boronic acid group is obtained by reacting the protected amino acid A-6 with a borane source such as pinacol borane in the presence of iridium or rhodium as catalyst. The resulting borane intermediate A-7 is hydrolyzed using aqueous acid to give target compounds A-8.

Another convenient method to prepare the allyl ketone intermediate relies on the reaction of carboxylic acid B-1 with oxalyl chloride and (N-isocyanimino) triphenylphosphorane (CNNPh3), followed by quenching of the reaction mixture to give the corresponding chlorohydrozone B-2 as illustrated in Scheme B.

Scheme B

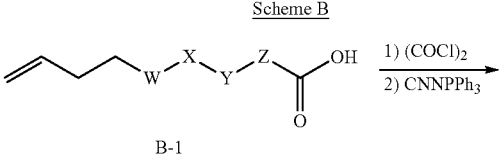

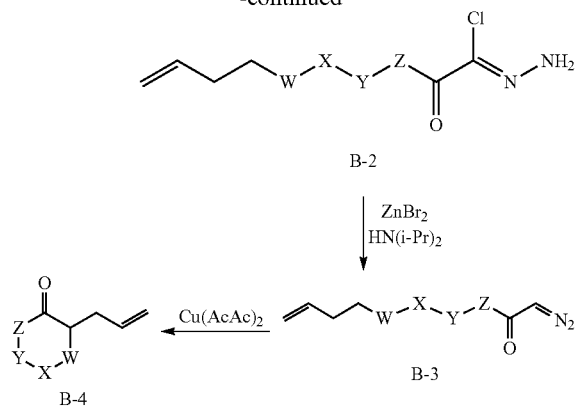

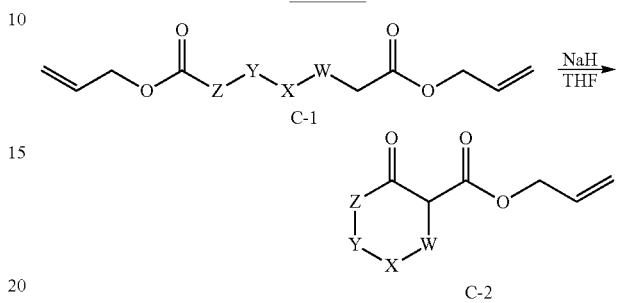

Treatment of intermediate B-2 with ZnBr₃ and a base (e.g., diisopropylamine), results in the formation of a diazoketone B-3, which is subjected to cyclization using Cu(AcAc) to afford the desired allyl ketone intermediate B-4.

Intermediate B-4 is then converted to the target compound using an Ugi reaction followed by hydroboration and deprotection as outlined in Scheme A. See Padwa, A.; Weingarten, D. *Chem. Rev.* 1996, 96, 223-269 for a general review of carbine mediated cyclization reactions.

Alternatively, the allyl ketone intermediate is obtained using the Dieckmann condensation as shown in Scheme C below. According to this method, allyl diester C-1 is cyclized with a base such as sodium hydride or LDA to form the desired allyl ketone C-2 which is converted to the target boronic acid compound using methodologies illustrated in Scheme A. When the starting diallylester C-1 is not commercially available, it is readily prepared from the corresponding diacid using known methods.

Enantioselective synthesis of compounds that conform to Formula I is readily achieved using a variety of methods that prescribe the use of chiral auxiliaries. According to one such method for synthesizing many Formula I compounds, (R)-(+)-1-amino-2-(methoxy)pyrrolidine is used as the chiral auxiliary. See Scheme D and the procedures disclosed by Enders, D. et al., *Organic Synthesis* 1987, 67 and Enders, D. et al., *Synthesis* 2005, 20, 3517-3530.

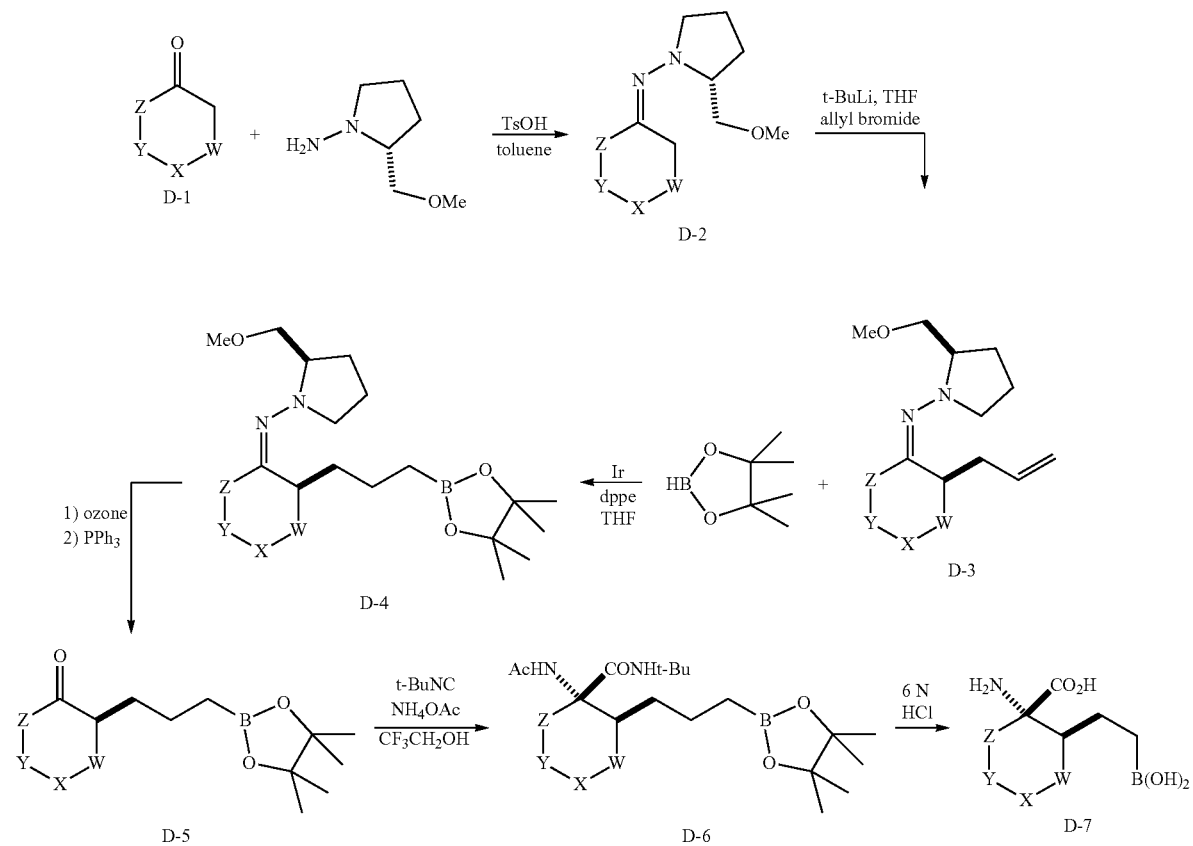

Accordingly, ketone D-1 is condensed with the hydrazine auxiliary in the presence of toluenesulfonic acid in toluene to form hydrazone D-2. Often the condensation reaction is carried out in the presence of molecular sieves or by using of a Dean-Stark apparatus to remove water. Ring substituents on the carbon adjacent to the hydrazone D-2 are enantioselectively introduced under basic conditions. For example, when the desired substituent is a —$CH_2$—$CH_2$—$CH_2$—$B(OH)_2$ group, it is readily introduced by reacting the hydrazone with allyl bromide to give the substituted hydrazone D-3 which is hydroborated to give the dioxaborolane compound D-4. Alternatively, hydrazone D-2 can be directly alkylated using 2-(4-bromobutyl)-4,4,5,5-tetramethyl-1,3,2-dioxaborolane (not shown), to give D-4.

Following the enantioselective incorporation of the side chain, hydrazone D-4 is treated with ozone followed by reduction of the ozonide with triphenylphosphine or dimethyl sulfide to give optically active ketone D-5. Ketone D-5 is converted to the corresponding cyclic amino acid using the Ugi or Strecker reaction as described above. Deprotection of the boron-containing cyclic amino acid D-6 with an aqueous mineral acid provides a Formula I compound D-7.

For some examples hydrazone intermediates D-3 or D-4 are used to introduce a ring substituent where Z is CRR' and R and/or R' are introduced via a second and possibly third alkylations. The synthetic methodology illustrated in Scheme D, also permits the enantioselective introduction of substituent groups R and R' at position Z.

In one embodiment, Formula I compounds having substituent groups at Z are obtained by using the appropriately substituted ketone D-1. Based on the general method illustrated in Scheme D, it is apparent to persons of skill in the chemical art that the illustrative synthetic methodology can be readily practiced by varying the starting materials and reaction conditions to arrive at compounds encompassed by the present invention. In some cases, protection of certain reactive functionalities may be necessary to achieve some of the above transformations. In general, the need for such protecting groups as well as the conditions necessary to attach and remove such groups will be apparent to those skilled in the art of organic synthesis.

Another useful approach for preparing inventive compounds utilizes the Corey-Link amino acid synthesis. See Corey et al., *J. Am. Chem. Soc.*, 114, (1992), pp 1906-1908. In this approach the amino acid is formed from a ketone using a carboxylic acid equivalent like chloroform and an amine source such as sodium azide. When an optically pure amine source like methyl benzylamine is used, diasteromers are formed in the reaction and final products as single enantiomers can often be obtained. As illustrated in Scheme E, intermediate allyl ketone E-1 is treated with the anion of chloroform generated using a base like LiHMDS in THF to form the corresponding carbinol E-2. Subsequent treatment with sodium hydroxide produces the dichloroepoxide which is opened up with an amine source like sodium azide to give the derivatized amino acid E-3. The carboxcylic acid can be protected as an ester (E-4) or amide before hydroboration of the double bond to give intermediate E-5. Reduction of the azido grop and hydrolysis give target compounds E-6. Depending on the functionality required, additional steps or alternative procedures may be required or preferred.

Scheme E

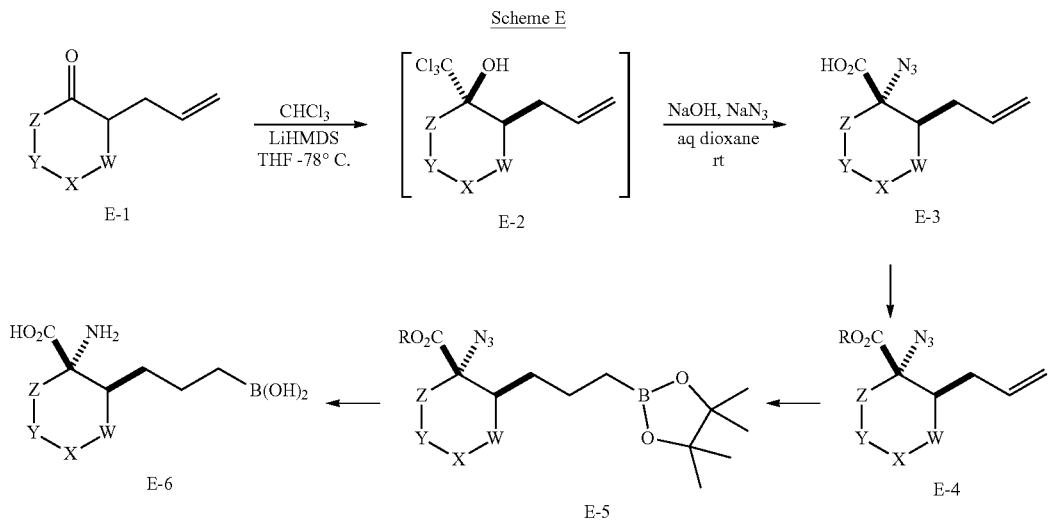

The disclosures of all articles and references mentioned in this application, including patents, are incorporated herein by reference. The preparation of compounds of the present invention is illustrated further by the following examples, which are not to be construed as limiting the invention in scope or spirit to the specific procedures and compounds described in them.

EXAMPLES

In general, intermediates and target compounds containing chiral centers are designated stereospecifically. This designation is used primarily to distinguish relative stereochemistry and does not indicate optical purity. It will be obvious to those skilled in organic synthesis which compounds are optically pure by the methods used to prepare them. The compounds described in the methods and examples sections may also be isolated as hydrates or salts (e.g. hydrochloric acid salts) but are not necessarily designated as such. The compounds described in this invention are generally named using common names, IUPAC names, or names generated using the naming algorithm in ChemDraw 10.0.

Example 1. Preparation of (1S,2S)-1-amino-2-(3-boronopropyl)cyclopentanecarboxylic acid (Anti-Isomer, Racemic)

Example 1 describes the multistep synthetic protocol used to make an illustrative Formula I compound.

Step 1. Method A: Allyl 2-oxocyclopentanecarboxylate (Transesterification)

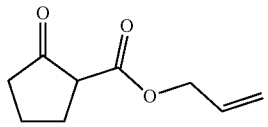

A stirred solution of methyl 2-oxocyclopentanecarboxylate (4.26 g, 30 mmol) and allyl alcohol (10.2 mL, 150 mmol) in anhydrous toluene (25 mL) was treated with powdered zinc (0.40 g, 6 mmol), refluxed for 48 h, and cooled to room temperature. The suspension was filtered, the filter cake rinsed with toluene, and the filtrate concentrated to afford allyl 2-oxocyclopentanecarboxylate (5.01 g, 99%) as a colorless oil. $^1$H NMR (CDCl$_3$, 300 MHz) δ 5.89 (ddt, $J_1$=15.9 Hz, $J_2$=10.5 Hz, $J_3$=4.8 Hz, 1H), 5.33 (dtd, $J_1$=15.9 Hz, $J_2$=2.7 Hz, $J_3$=1.4 Hz, 1H), 5.23 (dtd, $J_1$=10.5 Hz, $J_2$=2.7 Hz, $J_3$=1.4 Hz, 1H), 4.83-4.75 (m, 1H), 3.18 (t, J=9.0 Hz, 1H), 2.41-2.23 (m, 4H), 2.22-2.07 (m, 1H), 1.94-1.80 (m, 1H); MS (+CI): m/z for C$_9$H$_{12}$O$_3$: expected 168.1; found 169.1 (M+H)$^+$.

Step 1. Method B: Allyl 2-oxocyclopentanecarboxylate (Dieckman)

A stirred solution of diallyl adipate (4.53 g, 20 mmol) in anhydrous tetrahydrofuran (100 mL) was cooled to 0° C. and treated with lithium bis(trimethylsilyl)amide (40 mL, 1.0 N in THF, 40 mmol). After the addition was complete, the solution was warmed to room temperature and stirred for 2 h. The solution was then recooled to 0° C. and treated with acetic acid (2.53 mL, 44 mmol) in a dropwise manner. The turbid mixture was warmed to room temperature and filtered. The filtrate was concentrated, dissolved in minimal dichloromethane and purified by flash column chromatography (silica gel, dichloromethane) to afford allyl 2-oxocyclopentanecarboxylate (2.62 g, 78%) as a colorless oil. Characterization data is same as that observed from method A.

Step 2: Synthesis of 2-Allylcyclopentanone

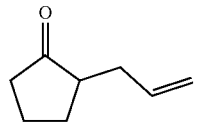

A stirring solution of palladium(II) acetate (51 mg, 0.23 mmol) and triphenylphosphine (0.24 g, 0.9 mmol) in anhydrous THF (20 mL) was heated under an atmosphere of nitrogen to 65° C. To the hot solution is added a solution of allyl 2-oxocyclopentanecarboxylate (2.52 g, 15 mmol) in anhydrous THF (rapid bubbling upon addition). After 45 minutes at 65° C., the reaction mixture is cooled and concentrated. The resulting residual yellow oil was dissolved in minimal dichloromethane and purified by flash column chromatography (silica gel, dichloromethane) to afford 2-allylcyclopentanone (1.32 g, 71%) as a colorless oil. $^1$H NMR (CDCl$_3$, 300 MHz) δ 5.72 (ddt, $J_1$=17.1 Hz, $J_2$=10.2 Hz, $J_3$=7.2 Hz, 1H), 5.09-4.98 (m, 2H), 2.55-2.46 (m, 1H), 2.35-2.22 (m, 1H), 2.22-1.91 (m, 5H), 1.87-1.70 (m, 1H), 1.63-1.48 (m, 1H).

Step 3: (1S,2S)-1-acetamido-2-allyl-N-tert-butylcyclopentanecarboxamide (Anti-Isomer, Racemic)

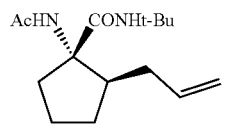

A stirring mixture of 2-allylcyclopentanone (0.993 g, 8 mmol) and ammonium acetate (1.54 g, 20 mmol) in 2,2,2-trifluoroethanol (2.5 mL) was treated with t-butyl isocyanide (1.81 mL, 16 mmol). The reaction mixture was stirred at room temperature for 4 days, following which the mixture was dissolved in a minimum amount of dichloromethane and purified by flash column chromatography (silica gel, 60% ethyl acetate in heptane) to afford the anti-isomer of (1S,2S)-1-acetamido-2-allyl-N-tert-butylcyclopentanecarboxamide (0.771 g, 36%) as a white solid. The later migrating syn-isomer is obtained as a white solid (0.851 g, 40%), by increasing the concentration of the polar solvent ethyl acetate to 80%. Anti-isomer: $^1$H NMR (CDCl$_3$, 300 MHz) δ 7.26 (br s, NH, 1H), 6.82 (br s, NH, 1H), 5.88-5.72 (m, 1H), 5.07 (br d, J=17 Hz, 1H), 5.00 (br d, 0.1=12 Hz, 1H), 2.56-2.41 (m, 1H), 2.36-2.17 (m, 3H), 2.01 (s, 3H), 1.97-1.81 (m, 2H), 1.72-1.60 (m, 2H), 1.32 (s, 9H); MS (+CI): m/z for C$_{15}$H$_{26}$N$_2$O$_2$: expected 266.2; found 266.2 (M+H)$^+$

Step 4: (1S,2R)-1-acetamido-N-tert-butyl-2-(3-(4,4,5,5-tetramethyl-1,3,2-dioxaborolan-2-yl)propyl)cyclopentanecarboxamide (Anti-Isomer, Racemic)

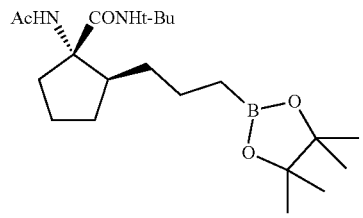

A stirred solution of (1 S,2R)-1-acetamido-2-allyl-N-tert-butylcyclopentanecarboxamide (0.599 g, 2.25 mmol) in anhydrous methylene chloride (9 mL) under nitrogen was treated with Ir$_2$Cl$_2$(COD)$_2$ (45 mg, 0.07 mmol) and DiPhos (54 mg, 0.136 mmol) and stirred at room temperature for 30 min. 4,4,5,5-tetramethyl-[1,3,2]dioxaborolane (0.65 mL, 4.48 mmol) was added dropwise and the solution stirred at room temperature for 20 h. The reaction mixture was poured into water (20 mL) and extracted with ethyl acetate (40 mL, then 2×15 mL), and the combined organic solution was washed with saturate aqueous sodium chloride (30 mL), dried over MgSO$_4$, and concentrated. The residue was dissolved in minimal dichloromethane and purified by flash column chromatography (silica gel, 40-50% ethyl acetate in heptane) to afford (1S,2S)-1-acetamido-N-tert-butyl-2-(3-(4,4,5,5-tetramethyl-1,3,2-dioxaborolan-2-yl)propyl) cyclopentanecarboxamide (0.695 g, 78%) as a white solid. $^1$H NMR (CDCl$_3$, 300 MHz) δ 6.72 (br s, NH, 1H), 5.68 (br s, NH, 1H), 2.46-2.29 (m, 2H), 2.10-2.19 (m, 1H), 2.02 (s, 3H), 2.00-1.88 (m, 1H), 1.75-1.60 (m, 3H), 1.52-1.38 (4H), 1.32 (s, 9H), 1.31 (s, 12H), 0.81-0.70 (m, 2H); MS (+CI): m/z for C$_{21}$H$_{39}$BN$_2$O$_4$: expected 394.3; found 395.2 (M+H)$^+$.

Step 5: (1S,2R)-1-amino-2-(3-boronopropyl)cyclopentanecarboxylic acid (Anti-Isomer, Racemic)

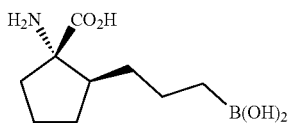 [SMILES: N[C@@]1(C(=O)O)CCC[C@@H]1CCCB(O)O]

A stirred mixture of (1S,2R)-1-acetamido-N-tert-butyl-2-(3-(4,4,5,5-tetramethyl-1,3,2-dioxaborolan-2-yl)propyl)cyclopentanecarboxamide (0.627 g, 1.59 mmol) in 6 N HCl (15 mL) was heated to 90° C. for 20 h, cooled to room temperature, and diluted with water (15 mL). The mixture was extracted with dichloromethane (2×15 mL) and concentrated. Water (20 mL) was then added to the concentrated crude mixture and the aqueous solution is re-cocentrated in vacuo (2×) to remove excess HCl. The resulting residue was dissolved in methanol (5 mL) and diluted to a volume of 40 mL with ether and stirred for 1 hour, to remove solid tertbutylamine hydrochloride by filtration. The resultant filtrate, upon concentration was treated with a solution of concentrated ammonium hydroxide (15 mL), followed by removal of the excess ammonium hydroxide under vacuum (3×). The resulting solid white residue was triturated using acetonitrile and dried to afford the target compound (1 S,2R)-1-amino-2-(3-boronopropyl) cyclopentanecarboxylic acid (0.397 g, 93%) as a white powder that exists as a 1:1 mixture of the cyclized and uncyclized forms. 1H NMR (DMSO, 300 MHz) δ 6.38 (br d, J=11.4 Hz, NH, 0.5H), 5.97 (br d, J=12 Hz, NH, 0.5H), 2.22-2.05 (m, 1H), 1.98-1.42 (m, 6H), 1.43-1.00 (m, 3H), 0.95-0.88 (m, 1H), 0.60-0.42 (m, 1H), 0.38-0.20 (m, 1H); MS (+CI): m/z for C$_9$H$_{18}$BNO$_4$: expected 215.1; found 215.3 (M+H)$^+$.

Example 2. Preparation of (1S,2S)-1-amino-2-(3-boronopropyl) cyclopentanecarboxylic acid (Syn-Isomer, Racemic)

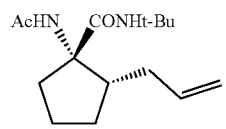

Step 1: (1S,2S)-1-acetamido-2-allyl-N-tert-butylcyclopentanecarboxamide

The target intermediate (1S,2S)-1-acetamido-2-allyl-N-tert-butylcyclopentanecarboxamide was also characterized using $^1$H NMR spectroscopy and represents the other isomer that is formed using stereoselective synthetic method described in step 3 of Example 1. $^1$H NMR spectroscopy (CDCl$_3$, 300 MHz) δ 6.44 (br s, NH, 1H), 6.06 (br s, NH, 1H), 5.80-5.65 (m, 1H), 5.05-4.96 (m, 2H), 2.54-2.56 (m, 2H), 2.30-2.18 (m, 1H), 2.10-1.95 (m, 1H), 1.99 (s, 3H), 1.91-1.72 (m, 5H), 1.58-1.43 (m, 1H), 1.32 (s, 9H); MS (+CI): m/z for C$_{15}$H$_{26}$N$_2$O$_2$: expected 266.2; found 267.2 (M+H)$^+$.

Step 2: (1S,2S)-1-acetamido-N-tert-butyl-2-(3-((4,4,5,5-tetramethyl-1,3,2-dioxaborolan-2-yl)propopycyclopentanecarboxamide (Syn-Isomer)

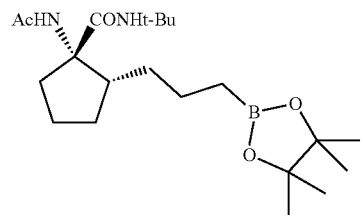

A stirred solution of syn-(1S,2S)-1-acetamido-2-allyl-N-tert-butylcyclopentanecarboxamide (0.600 g, 2.25 mmol) in anhydrous methylene chloride (9 mL) under nitrogen was treated with Ir$_2$Cl$_2$(COD)$_2$ (45 mg, 0.07 mmol) and DiPhos (54 mg, 0.136 mmol) and the resultant mixture was stirred at room temperature for 30 min. 4,4,5,5-tetramethyl-[1,3,2] dioxaborolane (0.65 mL, 4.48 mmol) was then added dropwise and the solution stirred at room temperature for an additional 20 h. The reaction mixture was poured into water (20 mL), extracted with ethyl acetate (40 mL, then 2×15 mL), and the combined organic layers were washed with saturated aqueous sodium chloride (30 mL), and dried using anhydrous MgSO$_4$, prior to concentration. The residue obtained was dissolved in a minimum volume of dichloromethane and purified using flash column chromatography (silica gel, 40-80% ethyl acetate in heptane) to afford syn-(1 S,2S)-1-acetamido-N-tert-butyl-2-(3-(4,4,5,5-tetramethyl-1, 3,2-dioxaborolan-2-yl)propyl)cyclopentanecarboxamide as a white solid (0.710 g, 80%). $^1$H NMR (CDCl$_3$, 300 MHz) δ 6.21 (br s, NH, 1H), 6.06 (br s, NH, 1H), 2.40-2.31 (m, 2H), 2.09-1.99 (m, 1H), 1.98 (s, 3H), 1.98-1.41 (m, 1H), 1.86-1.73 (m, 2H), 1.58-1.48 (m, 3H), 1.32 (s, 9H), 1.35-1.16 (m, 2H), 1.23 (s, 12H), 0.80-0.71 (m, 2H); MS (+CI): m/z for C$_{21}$H$_{39}$BN$_2$O$_4$: expected 394.4; found 395.2 (M+H)$^+$.

Step 3: (1S,2S)-1-amino-2-(3-boronopropyl)cyclopentanecarboxylic acid (Syn-Isomer)

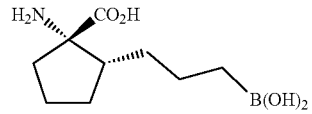 [SMILES: N[C@@]1(C(=O)O)CCC[C@H]1CCCB(O)O]

A stirred mixture of syn-(1S,2S)-1-acctamido-N-tert-butyl-2-(3-(4,4,5,5-tetramethyl-1,3,2-dioxaborolan-2-yl) propyl)cyclopentanecarboxamide (0.641 g, 1.625 mmol) in 6 N HCl (15 mL) was heated to 90° C. for 20 h, cooled to room temperature, and diluted with water (15 mL). The mixture was extracted with methylene chloride (2×15 mL) and concentrated. Water (20 mL) was twice added, and twice removed in vacuo to remove excess HCl. The residue obtained after concentration was dissolved in methanol (5 mL) and diluted to a volume of 40 mL with ether, and stirred for 1 h to remove solid tertbutylamine hydrochloride which is filtered off. The resultant filtrate was concentrated and treated with concentrated ammonium hydroxide (15 mL, 3×). Removal of the excess ammonium hydroxide in vacuo gave a solid white residue which was triturated using acetonitrile and dried to give (1S,2S)-1-amino-2-(3-boronopropyl)cyclopentanecarboxylic acid as a white powder containing a 1:1 mixture of cyclized and uncyclized forms (0.276 g, 63%). $^1$H NMR (DMSO, 300 MHz) δ 6.49-6.37 (m, NH, 2H), 0.2.0-1.85 (m, 2H), 1.83-1.58 (m, 6H), 1.53-1.25 (m, 3H), 1.00-0.80 (m, 1H), 0.49-0.40 (m, 1H), 0.40-0.31 (m, 1H); MS (+CI): m/z for $C_9H_{18}BNO_4$: expected 215.1; found 215.3 (M+H)$^+$.

Example 3: Preparation of (2R,3S)-3-amino-2-(3-boronopropyl)tetrahydrofuran-3-carboxylic acid Step 1: 4-(Allyloxy)-2-oxobutanehydrazonoyl chloride

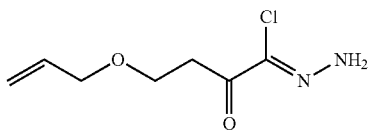

To a solution of 3-(propen-3-yloxy)propionic acid (0.976 g, 7.5 mmol) and anhydrous N,N-dimethylform-amide (0.1 mL) in anhydrous 1,2-dichloroethane (40 mL) under an atmosphere of nitrogen was added oxalyl chloride (5.5 mL, 2.0 N in dichloromethane, 11 mmol). The reaction mixture was stirred for 1 h at room temperature, then concentrated at 40° C. under vacuum to achieve a final volume of 5 mL. Anhydrous dichloroethane (20 mL; 3×) was added and the reaction mixture was concentrated after each 20 mL addition of dichloromethane. The residual solution obtained after the final reconcentration was diluted with anhydrous dichloroethane (20 mL) and added dropwise to a stirred 4° C. cold solution of N-isocyanoimino-triphenylphosphophorane (3.33 g, 11 mmol) in a anhydrous dichloroethane (20 mL). After stirring at 4° C. for 1 h, the reaction is warmed to room temperature and allowed to stir for an additional 3 h. The reaction is stopped by quenching with water (10 mL) and allowing the water-dichloromethane mix stir for an additional 16 h at room temperature.

To the quenched reaction mixture is added water (25 mL), so as to separate the aqueous layer from the organic layer. The aqueous layer was extracted with methylene chloride (2×15 mL) and the combined organic layer were dried over anhydrous Na$_2$SO$_4$, prior to concentration and purification by flash column chromatography (silica gel, 5% ethyl acetate in dichloromethane) to afford 1-chloro-1,2-diketo-4-(propen-3-yloxy)butane-1-hydrazone as a pale yellow oil (1.05 g, 74%). $^1$H NMR (CDCl$_3$, 300 MHz) δ 6.64 (br s, 2H), 5.87 (ddt J$_1$=17 Hz, J$_2$=10 Hz, J$_3$=5.4 Hz, 1H), 5.30-5.14 (m, 2H), 4.00-3.93 (m, 2H), 3.78 (t, J=6.5 Hz, 2H), 3.12 (t, J=6.5 Hz, 2H); MS (+CI): m/z for $C_7H_{11}C_1N_2O_2$: expected 190.1; found 191.2 (M+H)$^+$.

Step 2: 4-(Allyloxy)-1-diazobutan-2-one

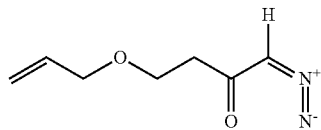

While under an atmosphere of nitrogen, To a stirred solution of 1-chloro-1,2-diketo-4-(propen-3-yloxy)butane-1-hydrazone (2.10 g, 11 mmol) in anhydrous methylene chloride (40 mL) was added anhydrous zinc bromide (0.563 g, 2.5 mmol), followed by the dropwise addition of anhydrous N,N-diisopro-pylamine (2.1 mL, 15 mmol). The reaction mixture was stirred for 1 h, then treated with 1% aqueous ethyl enediaminetetraacetic acid (EDTA) tetrasodium salt (30 mL), and stirred an additional 15 min. The aqueous and organic layers formed upon the addition of aqueous EDTA were separated and the aqueous layer was extracted with methylene chloride (2×15 mL). The combined organic layers were dried over anhydrous Na$_2$SO$_4$, and concentrated prior to purification using flash column chromatography (silica gel, 10% ethyl acetate in dichloromethane), to afford 1-diazo-2-keto-4-(propen-3-yloxy)butane (1.42 g, 84%) as a yellow oil. $^1$H NMR (CDCl$_3$, 300 MHz) δ 5.95-5.80 (m, 1H), 5.36 (s, 1H), 5.28 (dq, J$_1$=15.6 Hz, J$_2$=1.6 Hz, 1H), 5.19 (dq, J$_1$=11.7 Hz, J$_2$=1.6 Hz, 1H), 5.36 (br s, 1H), 5.15-5.30 (m, 2H), 3.98 (dt, J$_1$=5.5 Hz, J$_2$=1.5 Hz, 2H), 3.71 (t, J=6.5 Hz, 2H), 2.57 (br s, 2H); MS (+CI): m/z for $C_7H_{10}N_2O_2$: expected 154.1; found 155.1 (M+H)$^+$.

Step 3: 2-allyldihydrofuran-3(2H)-one

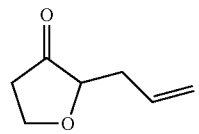

A solution of 4-(allyloxy)-1-diazobutan-2-one (1.505 g, 9.76 mmol) in anhydrous methylene chloride (150 mL) was added dropwise to a refluxing solution of copper(II) acetylacetonate (0.13 g, 0.50 mmol) in anhydrous methylene chloride (150 mL). After refluxing the resultant mixture for 2 hours, the solution was concentrated and purified using flash column chromatography (silica gel, dichloromethane) to afford 2-allyldihydrofuran-3(2H)-one (1.147 g, 93%) as a colorless oil. $^1$H NMR (CDCl$_3$, 300 MHz) δ 5.90-5.75 (m, 1H), 5.20-5.05 (m, 2H), 4.33-4.29 (m, 1H), 4.07 (q, J=9 Hz, 1H), 3.79 (dd, J$_1$=7.5 Hz, J$_2$=4.5 Hz, 1H), 2.60-2.45 (m, 3H), 2.34 (q, J=7.5 Hz, 1H); MS (+CI): m/z for $C_7H_{10}O_2$: expected 126.1; found 127.2 (M+H)$^+$, 149.1 (M+Na).

Step 4: (2R,3S)-3-acetamido-2-allyl-N-tert-butyltetrahydrofuran-3-carboxamide (Racemic)

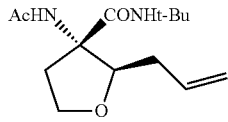

A solution of 2-allyldihydrofuran-3(2H)-one (1.2 g, 9.5 mmol) and ammonium acetate (4.39 g, 57.0 mmol) in 2,2,2-trifluoroethanol (5 mL) was treated with tert-butyl isocyanide (2.37 g, 3.23 mL, 28.5 mmol). After stirring at room temperature for 5 days, the reaction mixture diluted with water (50 mL) and extracted using ethyl acetate (2×50 mL). The combined organic layers were washed with saturated aqueous sodium chloride, dried over MgSO$_4$, filtered and concentrated. Purification by flash column chromatography (silica gel, 50% ethyl acetate in methylene chloride) gave (2R 3S)-3-acetamido-2-allyl-N-tert-butyltetrahydrofuran-3-carboxamide as a colorless oil (930 mg, 36%) and (2S,3S)-3-acetylamido-2-allyl-N-tert-butyltetrahydrofuran-3-carboxamide as a colorless oil (650 mg, 26%). Analytical data for (2R,3S)-3-acetylamido-2-allyl-N-tert-butyltetrahydrofuran-3-carboxamide: $^1$H NMR (CDCl$_3$, 300 MHz) δ 6.65 (s, NH, 1H), 6.06 (s, NH, 1H), 5.86 (m, 1H), 5.16 (m, 2H), 4.20 (dd, J$_1$=9 Hz, J$_2$=4 Hz, 1H), 3.82 (m, 2H), 2.54 (m, 2H), 2.20-2.40 (m, 2H), 2.03 (s, 3H), 1.32 (s, 9H); MS (+CI): m/z for C$_{14}$H$_{24}$N$_2$O$_3$: expected 268.2; found 269.2 (M+H)$^+$.

Step 5: (2R,3S)-3-acetamido-N-tert-butyl-2-(3-(4,4,5,5-tetramethyl-1,3,2-dioxaborolan-2-yl)propyl)tetrahydrofuran-3-carboxamide

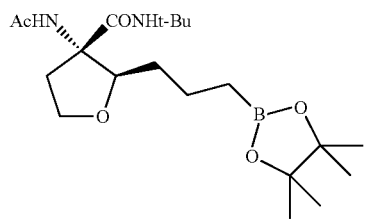

A solution of (2R,3S)-3-acetamido-2-allyl-N-tert-butyltetrahydrofuran-3-carboxamide (930 mg, 3.47 mmol) in dichloromethane (20 mL), was treated with chloro-1,5-cyclooctadiene iridium(I) dimer (70 mg, 3 mol %) and 1,2-bis(diphenylphosphino)-ethane (83 mg, 6 mol %). The solution was stirred at room temperature for 30 minutes and then 4,4,5,5-tetramethyl-[1,3,2]dioxaborolane (1.01 mL, 6.94 mmol) was added dropwise, and the reaction was stirred overnight at room temperature. The next day, the reaction mixture was poured into water and the aqueous solution was extracted using ethyl acetate (3×). The combined organic layers were washed with saturated aqueous sodium chloride, dried over anhydrous magnesium sulfate, filtered and concentrated. Purification by flash column chromatography (silica gel, 50-80% ethyl acetate in dichloromethane) gave (2R,3S)-3-acetamido-N-tert-butyl-2-(3-(4,4,5,5-tetramethyl-1,3,2-dioxaborolan-2-yl)propyl)tetrahydrofuran-3-carboxamide as a colorless oil (864 mg, 63%). $^1$H NMR (CDCl$_3$, 300 MHz) δ 7.01 (s, NH, 1H), 6.10 (s, NH, 1H), 4.38 (m, 1H), 4.12 (m, 1H), 4.00 (m, 1H), 2.96 (m, 1H), 2.02-2.18 (m, 2H), 1.99 (s, 3H), 1.42-1.62 (m, 3H), 1.36 (s, 9H), 1.22 (s, 12H), 0.76 (m, 2H); MS (+CI): m/z for C$_{20}$H$_{37}$BN$_2$O$_5$: expected 396.3; found 397.4 (M+H)$^+$.

Step 6: (2R,3S)-3-amino-2-(3-boronopropyl)tetrahydrofuran-3-carboxylic acid

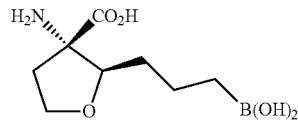 [SMILES: N[C@@]1(C(=O)O)CCO[C@@H]1CCCB(O)O]

A solution of (2R,3S)-3-acctamido-N-tert-butyl-2-(3-(4,4,5,5-tetramethyl-1,3,2-dioxaborolan-2-yl)propyl)tetrahydrofuran-3-carboxamide (860 mg) in 6 N HCl (15 mL) was stirred at 90° C. for 1 day. After cooling to room temperature, the reaction mixture was transferred to a separatory funnel, diluted with deionized water (10 mL) and washed with dichloromethane (3×). The aqueous solution was concentrated. Purification by RP-HPLC (10-100% acetonitrile in water) gave (2R,3S)-3-amino-2-(3-boronopropyl)tetrahydrofuran-3-carboxylic acid, as a white solid (269 mg). $^1$H NMR (D$_2$O, 300 MHz) δ 3.97 (m, 2H), 3.82 (m, 1H), 2.66 (ddd, J$_1$=15 Hz, J$_2$=9.5 Hz, J$_3$=5.5 Hz, 1H), 2.14 (ddd, J$_1$=15 Hz, J$_2$=9 Hz, J$_3$=6.5 Hz, 1H), 1.22-1.49 (m, 4H), 0.67 (m, 2H); MS (+CI): m/z for C$_8$H$_{16}$BlNO$_5$: expected 217.1; found 435.3 (2M+H)$^+$, 417.2 (2M+H-H$_2$O)$^+$, 217.7 (M+H)$^+$, 200.0 (M+H−2H$_2$O)$^+$.

Example 4: Preparation of (2S,3S)-3-amino-2-(3-boronopropyl)tetrahydrofuran-3-carboxylic acid Step 1: (2S,3S)-3-acetamido-2-allyl-N-tert-butyltetrahydrofuran-3-carboxamide

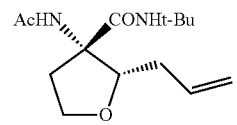

(2S,3S)-3-acetamido-2-allyl-N-tert-butyltetrahydrofuran-3-carboxamide was obtained along with its isomer in step 4 of Example 3. $^1$H NMR (CDCl$_3$, 300 MHz) δ δ 6.99 (s, NH, 1H), 6.09 (s, NH, 1H), 5.78 (m, 1H), 5.08 (m, 2H), 4.49 (dd, J$_1$=9 Hz, J$_2$=5 Hz, 1H), 4.17 (q, J=9 Hz, 1H), 4.04 (td, J$_1$=9 Hz, J$_2$=3.5 Hz, 1H), 2.97 (ddd, J$_1$=12.5 Hz, J$_2$=9 Hz, J$_3$=3.5 Hz, 1H), 2.04-2.36 (m, 3H), 1.99 (s, 3H), 1.38 (s, 9H); MS (+CI): m/z for C$_{14}$H$_{24}$N$_2$O$_3$: expected 268.2; found 269.2 (M+H)$^+$.

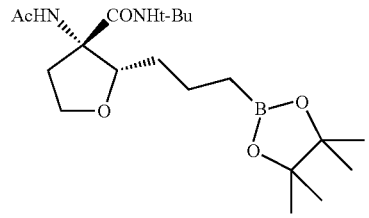

Step 2: (2S,3S)-3-acetamido-N-tert-butyl-2-(3-(4,4,5,5-tetramethyl-1,3,2-dioxaborolan-2-yl)propyl)tetrahydrofuran-3-carboxamide (2S,3S)-3-acetamido-N-tert-butyl-2-(3-(4,4,5,5-tetramethyl-1,3,2-dioxaborolan-2-yl)propyl)tetrahydrofuran-3- carboxamide was prepared using the method described in step 5 of example 3. The title compound as isolated as a colorless oil (496 mg), $^1$H NMR (CDCl$_3$, 300 MHz) δ 6.57 (s, NH, 1H), 5.83 (s, NH, 1H), 4.04 (m, 1H), 3.88 (m, 2H), 2.62 (m, 1H), 2.48 (m, 1H), 2.05 (s, 3H), 1.40-1.58 (m, 4H), 1.33 (s, 9H), 1.24 (s, 12H), 0.83 (t, J=6.5 Hz, 2H); MS (+CI): m/z for C$_{20}$H$_{37}$BN$_2$O$_5$: expected 396.3; found 397.3 (M+H)$^+$.

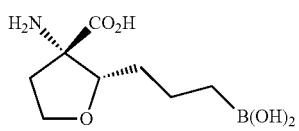

Step 3: (2S,3S)-3-amino-2-(3-boronopropyl)tetrahydrofuran-3-carboxylic acid (2S,3S)-3-amino-2-(3-boronopropyl)tetrahydrofuran-3-carboxylic acid was prepared using the method described in step 6 of example 3. The title compound was isolated as a white solid (91 mg); $^1$H NMR (D$_2$O, 300 MHz) δ 4.00 (m, 1H), 3.80 (m, 1H), 3.73 (m, 1H), 2.58 (m, 1H), 2.04 (ddd, J$_1$=13.5 Hz, J$_2$=8 Hz, J$_3$=4 Hz, 1H), 1.34-1.49 (m, 3H), 1.28 (m, 1H), 0.66 (m, 2H); MS (+CI): m/z for C$_8$H$_{16}$BlNO$_5$: expected 217.1; found 417.1 (2M+H-H$_2$O)$^-$, 399.3 (2M+H−2H$_2$O)$^-$, 217.7 (M+H)$^-$, 200.0 (M+H−2H$_2$O)$^-$.

Example 5: Preparation of 3-amino-2-(3-boronopropyl)tetrahydrothiophene-3-carboxylic acid

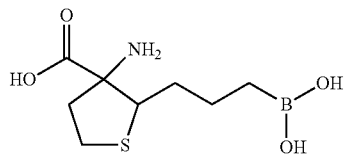 [SMILES: NC1(C(=O)O)CCSC1CCCB(O)O]

3-Amino-2-(3-boronopropyl)tetrahydrothiophene-3-carboxylic acid was prepared in a manner analogous to that set forth in Example 3, except 3-(allylthio)propanoic acid was used instead of 3-(propen-3-yloxy)propionic acid in step 1 of Example 3. The title compound was isolated as a white solid as an inseparable (~1:1) mixture of diastereoisomers (51 mg); $^1$H NMR (D$_2$O, 300 MHz) δ 3.91 (m, 0.5H), 3.70 (m, 0.5H), 3.05 (m, 1H), 2.80 (m, 1H), 2.50 (m, 1H), 2.38 (m, 1H), 1.52 (m, 1H), 1.16-1.42 (m, 3H), 0.64 (m, 2H); MS (+CI): m/z for C$_8$H$_{16}$BlNO$_4$S: expected 233.1; found 234.0 (M+H)$^+$, 216.1 (M+H-H$_2$O)$^+$.

Example 6: Preparation of (3R,4S)-4-amino-3-(3-boronopropyl)piperidine-4-carboxylic acid

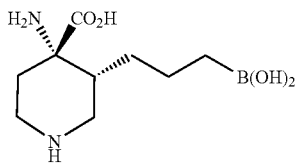 [SMILES: N[C@@]1(C(=O)O)CCNC[C@H]1CCCB(O)O]

(3R,4S)-4-amino-3-(3-boronopropyl)piperidine-4-carboxylic acid was prepared in a manner analogous to that set forth in Example 1 except 1-tert-butyl 3-methyl 4-oxopiperidine-1,3-dicarboxylate was used instead of methyl 2-oxocyclopentanecarboxylate in step 1 of Example 1. Analysis of the reaction mixture indicates that the presence of three isomeric products. $^1$H NMR (DMSO, 300 MHz) δ 3.40-3.17 (m, 3H), 3.04 (t, J=12.9 Hz, 1H), 2.22-2.18 (m, 1H), 2.01-1.68 (m, 2H), 1.45-0.83 (m, 4H), 0.75-0.40 (m, 2H); MS (+CI): m/z for C$_9$H$_{19}$BN$_2$O$_4$: expected 230.1; found 231.0 (M+H)$^+$.

Example 7: Preparation of (3S,4S)-4-amino-3-(3-boronopropyl)piperidine-4-carboxylic acid

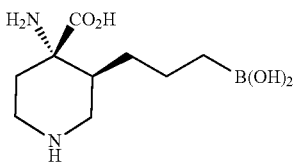 [SMILES: N[C@@]1(C(=O)O)CCNC[C@@H]1CCCB(O)O]

(3S,4S)-4-amino-3-(3-boronopropyl)piperidine-4-carboxylic acid was prepared in a manner analogous to that set forth in Example 1 except 1-tert-butyl 3-methyl 4-oxopiperidine-1,3-dicarboxylate was used instead of methyl 2-oxocyclopentanecarboxylate in step 1 of Example 1. Analysis of the reaction mixture indicates that the presence of three isomeric products. 1H NMR (DMSO, 300 MHz) δ 3.40-3.20 (m, 2H), 2.90-2.61 (m, 2H), 2.28-2.19 (m, 2H), 2.01-1.91 (m, 1H), 1.27-0.95 (m, 4H), 0.75-0.40 (m, 2H); MS (+CI): m/z for C$_9$H$_{19}$BN$_2$O$_4$: expected 230.1; found 231.0 (M+H)$^+$.

Example 8: Preparation of (3R,4S)-3-amino-4-(3-boronopropyl)pyrrolidine-3-carboxylic acid

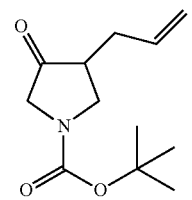 [SMILES: C=CCC1CN(C(=O)OC(C)(C)C)CC1=O]

Step 1, Method A: tert-butyl 3-allyl-4-oxopyrrolidine-1-carboxylate

An ice-cooled (3° C.) stirred solution of N-boc-glycine, allyl ester (6.46 g, 30 mmol) in anhydrous tetrahydrofuran (60 mL) under nitrogen was treated with 1N lithium bis(trimethylsilylamide)/tetrahydrofuran (33 mL, 33 mmol) at a rate to keep pot temperature below 10° C., then stirred at 3° C. for 15 min and cooled (−40° C.). A solution of allyl acrylate (4.45 mL, 35 mmol) in anhydrous tetrahydrofuran (25 mL) was added dropwise, and the mixture allowed to reach room temperature, stirred 1 h, and refluxed for 2 h. The mixture was cooled to room temperature, quenched with glacial acetic acid (2.5 mL), and concentrated. The residual oil was dissolved in methylene chloride (300 mL) and the solution washed with water and saturated sodium bicarbonate (150 mL each), dried (Na$_2$SO$_4$), and concentrated. The residue was dissolved in minimum methylene chloride and loaded onto a silica gel column (350 mL volume) and eluted with 55:30:15 heptane/methylene chloride/ethyl acetate to afford 3-allyl 1-tert-butyl 4-oxopyrrolidine-1,3-dicarboxylate (5.07 g, 63%) as a colorless oil. NMR (CDCl$_3$): δ 5.85-6.00 (m, 1H), 5.20-5.40 (m, 2H), 4.60-4.75 (m, 2H), 4.20 (m, 1H), 3.95-4.10 (m, 1H), 3.87 (d J=6.5 Hz, 1H), 3.62 (t, J=8 Hz, 1H), 1.48 (s, 9H). MS (m+1): 270.4; MS (m-bu-+1): 214.2.

This compound (4.12 g, 15.3 mmol) was dissolved in anhydrous tetrahydrofuran (25 mL) and added to a stirred solution of Pd(PPh$_3$)$_4$(0.36 g, 0.31 mmol) in anhydrous tetrahydrofuran (40 mL) under nitrogen, stirred for 4 h, and concentrated. The residue was dissolved in minimum methylene chloride and loaded onto a silica gel column (350 mL volume) and eluted with 60:35:5 heptane/methylene chloride/ethyl acetate to afford tert-butyl 3-allyl-4-oxopyrrolidine-1-carboxylate (4.16 g, 60%) as a very pale yellow oil. NMR (CDCl$_3$): δ 5.65-5.80 (m, 1H), 5.05-5.15 (m, 2H), 4.02 (m, 1H), 3.89 (br d, J=20 Hz, 1H), 3.67 (br d, J=20 Hz, 1H), 3.31 (dd, J$_1$=11 Hz, J$_2$=8.5 Hz, 1H), 2.60-2.70 (m, 1H), 2.50-2.60 (m, 1H), 2.10-2.30 (m, 1H), 1.48 (s, 9H). MS (m+1): 226.1; MS (m-bu+1): 170.1.

Step 1, Method B: tert-butyl
3-allyl-4-oxopyrrolidine-1-carboxylate

A solution of 1-tert-butyl 3-methyl 4-oxopyrrolidine-1,3-dicarboxylate (48.65 g, 0.20 mol), allyl alcohol (300 mL), and dibutyltin oxide (5.0 g, 20 mmol) in anhydrous toluene (800 mL) was refluxed for 20 h under a Dean-Stark trap with portionwise removal of solvent (total of 200 mL) over the first 6 hours, followed by addition of more allyl alcohol (75 mL) at the end of the first 6 hours. The reaction mixture was concentrated, dissolved in minimal methylene chloride, and loaded onto a silica gel column (700 mL volume) and eluted with methylene chloride, 10%, then 15%, then 20% ethyl acetate/methylene chloride to afford 3-allyl 1-tert-butyl 4-oxopyrrolidine-1,3-dicarboxylate (48.6 g, 90%) as a pale pink oil (NMR and MS as above). This compound (48.47 g, 0.18 mol) was dissolved in anhydrous tetrahydrofuran (200 mL) and added to a stirred solution of Pd(PPh$_3$)$_4$(4.16 g, 3.6 mmol) in anhydrous tetrahydrofuran (400 mL) under nitrogen, stirred for 4 h, and concentrated. The residue was dissolved in heptane and loaded onto a silica gel column (1000 mL volume) and eluted with 60:35:5 heptane/methylene chloride/ethyl acetate to afford tert-butyl 3-allyl-4-oxopyrrolidine-1-carboxylate (27.93, 69%) as a pale yellow oil (NMR and MS as above).

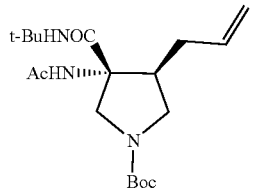

Step 2: (3R,4S)-tert-butyl 3-acetamido-4-allyl-3-(tert-butylcarbamoyl)pyrrolidine-1-carboxylate A stirred mixture of tert-butyl 3-allyl-4-oxopyrrolidine-1-carboxylate (13.23 g, 58.7 mmol) and ammonium acetate (11.95 g, 155 mmol) in 2,2,2-trifluoroethanol (25 mL) under nitrogen was treated with t-butylisonitrile (12.25 mL, 106 mmol), then stirred at room temperature for 4 days and concentrated. The residue was partitioned between water (100 mL) and methylene chloride (200 mL), and the aqueous layer was extracted with methylene chloride (2×75 mL). The combined organic solution was washed with water and saturated aqueous sodium chloride (100 mL each), dried (Na$_2$SO$_4$), and concentrated to an off-white solid. This was recrystallized twice with ethyl acetate (150 mL each) to afford a portion of the title product (8.36 g) as a white solid. The combined mother liquors were concentrated, dissolved in minimum methylene chloride, and loaded onto a silica gel column (650 mL volume). This was eluted with 60%, then 70%, then 90% ethyl acetate/heptane to afford additional product (3.84 g). Total yield of (3R,4S)-tert-butyl 3-acetamido-4-allyl-3-(tert-butylcarbamoyl)pyrrolidine-1-carboxylate was 12.22 g (57%) as a white solid. NMR (CDCl$_3$) δ 6.30-6.70 (m, 2H), 5.60-5.75 (m, 1H), 4.95-5.10 (m, 2H), 3.94 (d, J=11.5 Hz, 1H), 3.75 (d, J=11.5 Hz, 1H), 3.60 (m, 1H), 3.00-3.20 (m, 2H), 2.20-2.30 (m, 1H), 2.00 (s, 3H), 1.80-1.90 (m, 1H), 1.44 (s, 9H), 1.33 (s, 9H). MS (m+1): 368.3; MS (m-bu+1): 312.1; MS (m-boc+1): 268.3.

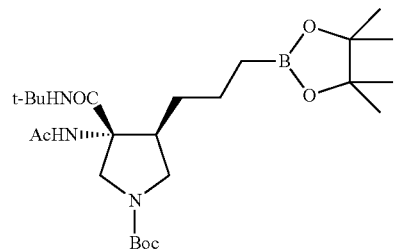

Step 3: (3R,4S)-tert-butyl 3-acetamido-3-(tert-butylcarbamoyl)-4-(3-(4,4,5,5-tetramethyl-1,3,2-dioxaborolan-2-yl)propyl)pyrrolidine-1-carboxylate A stirred solution of (3R,4S)-tert-butyl 3-acetamido-4-allyl-3-(tert-butylcarbamoyl)pyrrolidine-1-carboxylate (5.51 g, 15 mmol) in anhydrous methylene chloride (80 mL) under nitrogen was treated with chloro-1,5-cyclooctadiene iridium dimer (0.252 g, 0.375 mmol) and 1,2-bis(diphenylphosphino)ethane (0.299 g, 0.75 mmol), stirred for 30 min, and cooled (−20° C.). 4,4,5,5-Tetramethyl-1,3,2-dioxaborolane (3.30 mL, 22.5 mmol) was added dropwise, and the solution was placed in an ice bath and allowed to reach room temperature overnight (18 h). The mixture was quenched with water (75 mL), stirred 15 min, and extracted with ethyl acetate (400 mL, then 2×100 mL). The combined organic solution was washed with saturated aqueous sodium chloride (150 mL), dried (MgSO$_4$), and concentrated. The solid was recrystallized (2 crops) from acetonitrile to afford (3R,4S)-tert-butyl 3-acetamido-3-(tert-butylcarbamoyl)-4-(3-(4,4,5,5-tetramethyl-1,3,2-dioxaborolan-2-yl)propyl)pyrrolidine-1-carboxylate (6.13 g, 82%) as a white solid. NMR (CDCl$_3$) δ 6.40-6.60 (m, 1H), 6.23 (s, 1H), 3.95-4.05 (m, 1H), 3.65-3.75 (m, 2H), 2.90-3.20 (m, 2H), 2.00 (s, 3H), 1.45 (s, 9H), 1.30-1.45 (m, 4H), 1.33 (s, 9H), 1.22 (s, 12H), 0.70-0.80 (m, 2H). MS (m+1): 496.4.

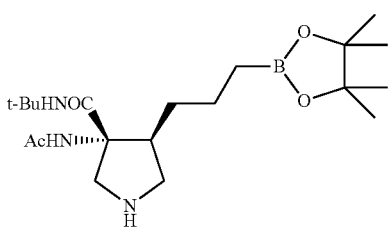

Step 4: (3R,4S)-3-acetamido-N-tert-butyl-4-(3-(4,4,5,5-tetramethyl-1,3,2-dioxaborolan-2-yl)propyl)pyrrolidine-3-carboxamide A 250 mL 3-neck round bottom flask was charged with (3R,4S)-tert-butyl 3-acetamido-3-(tert-butylcarbamoyl)-4-(3-(4,4,5,5-tetramethyl-1,3,2-dioxaborolan-2-yl)propyl)pyrrolidine-1-carboxylate (4.95 g, 10 mmol) and 4 N HCl/dioxane (50 mL). After stirring for 3 h the solution was diluted with ether (125 mL), stirred a few minutes, filtered, and the solid rinsed with ether, collected, and dried in vacuo to afford an HCl salt of the title compound. This was dissolved in water (30 mL) and treated with sodium hydroxide (0.5 g, 12.5 mmol). The aqueous solution was treated with sufficient potassium carbonate to render the free base product insoluble. The mixture was extracted with methylene chloride (75 mL, then 3×50 mL) and the combined organic solution was washed with saturated aqueous sodium chloride (30 mL), dried ($Na_2SO_4$), and concentrated to afford (3R,4S)-3-acetamido-N-tert-butyl-4-(3-(4,4,5,5-tetramethyl-1,3,2-dioxaborolan-2-yl)propyl)pyrrolidine-3-carboxamide (3.40 g, 86%) as a white solid. NMR ($CDCl_3$) δ 8.26 (br s, 1H), 7.25 (s, 1H), 3.86 (d, J=9.5 Hz, 1H), 3.53 (t, J=9.5 Hz, 1H), 3.20 (d, J=10 Hz, 1H), 2.98 (m, 1H), 2.74 (dd, $J_r$=10 Hz, $J_2$=7.5 Hz, 1H), 2.02 (s, 3H), 1.50 (m, 1H), 1.33 (s, 9H), 1.20-1.40 (m, 3H), 1.22 (s, 12H), 0.70-0.80 (m, 2H). MS (m+1): 396.0.

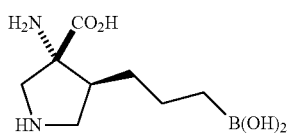 [SMILES: N[C@@]1(C(=O)O)CNC[C@@H]1CCCB(O)O]

Step 5: (3R,4S)-3-amino-4-(3-boronopropyl)pyrrolidine-3-carboxylic acid

A solution of (3R,4S)-3-acetamido-N-tert-butyl-4-(3-(4,4,5,5-tetramethyl-1,3,2-dioxaborolan-2-yl)propyl)pyrrolidine-3-carboxamide (198 mg, 0.5 mmol) in 2:1:1 concentrated HCl:glacial acetic acid:water (8 mL) in a pressure bottle was stirred for 2 h at 60° C., then capped and stirred for 18 h at 130° C., cooled to room temperature, and uncapped. The solution was diluted with water (20 mL), then extracted with methylene chloride (20 mL) and concentrated. The residue was treated with water (20 mL) and concentrated three times to remove excess HCl, then dissolved in water (40 mL) and treated with DOWEX® 550A-OH resin (3 g) which had been rinsed with methanol. The mixture was stirred for 40 min, then filtered and the resin washed successively with water, methanol, methylene chloride, water, methanol, and methylene chloride. The resin was then stirred four times with 1N HCl (15 mL) and filtered, and the combined filtrates were concentrated. The residue was treated with water (20 mL) and concentrated three times to remove excess HCl, then dissolved in 1.5-2.0 mL water and subjected to HPLC gradient purification as follows: 0-25% B with A=0.1% trifluoroacetic acid/water and B=0.1% trifluoroacetic acid/acetonitrile. The appropriate fractions were concentrated, treated three times with 1 N HCl (10 mL) and concentrated, treated three times with water (10 mL) and concentrated, then dissolved in water (10 mL), frozen, and lyophilized overnight to afford (3R,4S)-3-amino-4-(3-boronopropyl)pyrrolidine-3-carboxylic acid (114 mg, 79%) as a pale amber glass. NMR ($D_2O$) δ 3.90 (d, J=13 Hz, 1H), 3.71 (dd, J=11.5 Hz, $J_2$=8.5 Hz, 1H), 3.46 (d, J=13 Hz, 1H), 3.21 (t, J=12 Hz, 1H), 2.50-2.65 (m, 1H), 1.5-1.65 (m, 1H), 1.10-1.40 (m, 3H), 0.60-0.75 (m, 2H). MS (m+1): 217.3; MS (m−$H_2O$+1): 199.1.

Example 9: (3R,4R)-3-amino-4-(3-boronopropyl)pyrrolidine-3-carboxylic acid

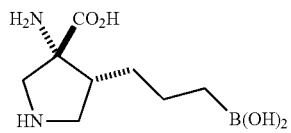 [SMILES: N[C@@]1(C(=O)O)CNC[C@H]1CCCB(O)O]

(3R,4R)-3-Amino-4-(3-boronopropyl)pyrrolidine-3-carboxylic acid was prepared in a manner analogous to that set forth in Example 8 except (3R,4R)-tert-butyl 3-acetamido-4-allyl-3-(tert-butylcarbamoyl)pyrrolidine-1-carboxylate from step 2 (minor isomer) was used. MS (+CI): m/z for $C_8H_{17}BN_2O_4$: expected 216.1; found 217.3 (M+H), 199.1 (M−$H_2O$+H)⁺.

Example 10: (3R,34R)-3-amino-4-(3-boronopropyl)pyrrolidine-3-carboxylic acid

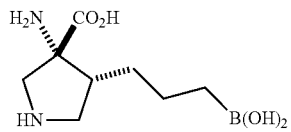 [SMILES: N[C@@]1(C(=O)O)CNC[C@H]1CCCB(O)O]

(3R,4R)-3-amino-4-(3-boronopropyl)pyrrolidine-3-carboxylic acid was prepared in a manner analogous to that set forth in Example 8 except that tert-butyl 2-allyl 3-oxopyrrolidine-1-carboxylate was used instead of tert-butyl 3-allyl-4-oxopyrrolidine-1-carboxylate in step 2. MS (+CI): m/z for $C_8H_{17}BN_2O_4$: expected 216.1; found 217.3 (M+H), 199.1 (M−$H_2O$+H)⁺.

Example 11: Preparation of (3R,4S)-3-amino-4-(3-boronopropyl)-1-isobutylpyrrolidine-3-carboxylic acid

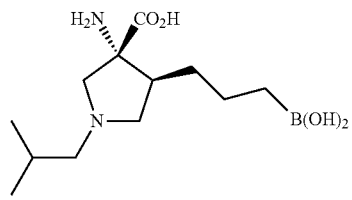 [SMILES: CC(C)CN1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and isobutyraldehyde (0.060 mL, 0.65 mmol), stirred for 2.5 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-isobutylpyrrolidine-3-carboxylic acid (44 mg, 26%) as a white semisolid. NMR (D$_2$O) δ 3.90 (m, 1H), 3.50 (m, 1H), 2.90-3.20 (m, 4H), 2.50 (m, 1H), 1.90 (m, 1H), 1.50 (m, 1H), 0.80-1.30 (m, 9H), 0.65 (m, 2H). MS (m+1): 273.2; MS (m−H$_2$O+1): 255.2; MS (m−2H$_2$O+1): 237.2.

Example 12: preparation of (3R,4S)-3-amino-1-benzyl-4-(3-boronopropyl)pyrrolidine-3-carboxylic acid

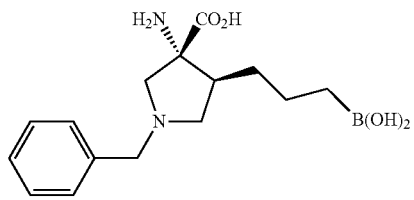 [SMILES: N[C@@]1(C(=O)O)CN(Cc2ccccc2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4)(166 mg, 0.42 mmol) in anhydrous 1,2-dichloroethane (5 mL) was treated with anhydrous sodium sulfate (2 g) and benzaldehyde (69 mg, 0.65 mmol), stirred for 2.5 h, then treated with sodium triacetoxyborohydride (212 mg, 1.0 mmol) and glacial acetic acid (2 drops) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-1-benzyl-4-(3-boronopropyl)pyrrolidine-3-carboxylic acid (70 mg, 44%) as a white semisolid. NMR (d6-DMSO) δ 7.62 (br s, 2H), 7.44 (br s, 3H), 4.30-4.60 (m, 2H), 3.60-3.90 (m, 2H), 3.35-3.50 (m, 2H), 2.85 (m, 1H), 2.50 (m, 1H), 1.20-1.80 (m, 3H), 0.60-0.80 (m, 2H). MS (m+1): 307.3; MS (m−H$_2$O+1): 289.2.

Example 13: preparation of (3R,4S)-3-amino-4-(3-boronopropyl)-1-(pyridin-3-ylmethyl)pyrrolidine-3-carboxylic acid

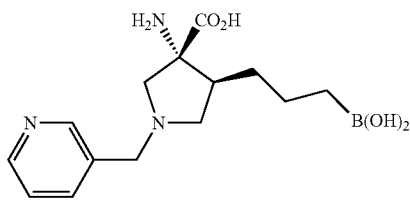 [SMILES: N[C@@]1(C(=O)O)CN(Cc2cccnc2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (175 mg, 0.443 mmol) in anhydrous 1,2-dichloroethane (5 mL) was treated with anhydrous sodium sulfate (1 g) and pyridine-3-carboxaldehyde (75 mg, 0.70 mmol), stirred for 2 h, then treated with sodium triacetoxyborohydride (212 mg, 1.0 mmol) and glacial acetic acid (2 drops) and stirred for 20 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(pyridin-3-ylmethyl)pyrrolidine-3-carboxylic acid (115 mg, 68%) as a white semisolid. NMR (d6-DMSO) δ 8.90 (m, 1H), 8.74 (m, 1H), 8.00 (m, 1H), 7.12 (m, 1H), 4.55-4.85 (m, 2H), 3.10-4.00 (m, 3H), 2.70-3.00 (m, 1H), 1.70 (m, 2H), 0.90-1.50 (m, 3H), 0.55-0.70 (m, 2H). MS (m+1): 308.4; MS (m−H$_2$O+1): 290.4.

Example 14: preparation of (3R,4S)-3-amino-1-(2-aminocyclopentyl)-4-(3-boronopropyl)pyrrolidine-3-carboxylic acid

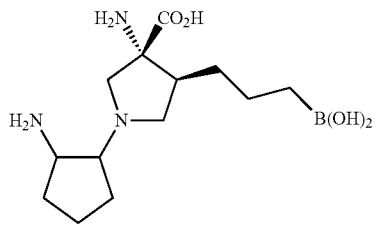 [SMILES: NC1CCCC1N1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and 2-(N-BOC-amino)cyclopentane-1-one (0.199 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 1.5 h, then cooled to room temperature and treated with sodium triacetoxyborohydride (276 mg, 1.3 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried (MgSO$_4$), and concentrated in vacuo. The crude material was deprotected and isolated using the method described for example 8, step 5 to afford (3R,4S)-3-amino-1-(2-aminocyclopentyl)-4-(3-boronopropyl)pyrrolidine-3-carboxylic acid (116 mg, 57%) as a white powder. NMR (D$_2$O) δ 3.85-4.05 (m, 4H), 3.77 (d, J=12.5 Hz, 1H), 3.42 (dt, J$_1$=11.5 Hz, J$_2$=4 Hz, 1H), 2.50-2.65 (m, 1H), 2.10-2.35 (m, 2H), 1.75-1.95 (m, 4H), 1.55-1.65 (m, 1H), 1.15-1.40 (m, 3H), 0.63-0.73 (m, 2H). MS (m+1): 300.0; MS (m−H$_2$O+1): 281.9.

Example 15: preparation of (3R,4S)-3-amino-4-(3-boronopropyl)-1-(piperidin-4-ylmethyl)pyrrolidine-3-carboxylic acid

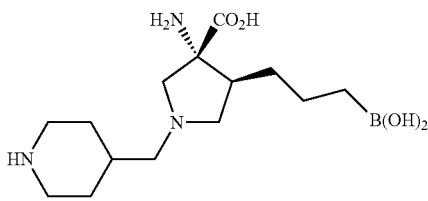 [SMILES: N[C@@]1(C(=O)O)CN(CC2CCNCC2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and N-boc-piperidine-4-carboxaldehyde (149 mg, 0.7 mmol), stirred for 2 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(piperidin-4-ylmethyl)pyrrolidine-3-carboxylic acid (66 mg, 31%) as a granular amber solid. NMR (D$_2$O) δ 3.70-4.00 (m, 2H), 3.30-3.45 (m, 4H), 3.25 (d, J=7 Hz, 2H), 2.92 (br t, J=13 Hz, 2H), 2.50-2.65 (m, 1H), 2.00-2.15 (m, 1H), 1.85-2.00 (m, 2H), 1.50-1.65 (m, 1H), 1.35-1.50 (m, 2H), 1.15-1.35 (m, 3H), 0.65-0.75 (m, 2H). MS (m−H$_2$O+1): 296.3; MS (m−2H$_2$O+1): 278.1.

Example 16: preparation of (3R,4S)-3-amino-4-(3-boronopropyl)-1-(3-(4-carboxyphenyl)propyl)pyrrolidine-3-carboxylic acid

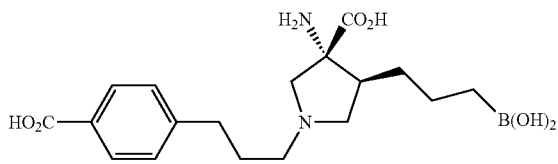 [SMILES: N[C@@]1(C(=O)O)CN(CCCc2ccc(C(=O)O)cc2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and 3-(4-(trifluoromethyl)phenyl)propionaldehyde (142 mg, 0.7 mmol), stirred for 2 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(3-(4-carboxyphenyl)propyl)pyrrolidine-3-carboxylic acid (12 mg, 5%) as a voluminous white powder. NMR (D$_2$O) δ 7.86 (d, J=8 Hz, 2H), 7.29 (d, J=8 Hz, 2H), 3.70-4.00 (m, 2H), 3.50 (m, 1H), 3.10-3.30 (m, 3H), 2.70 (t, J=7.5 Hz, 2H), 2.40-2.60 (m, 1H), 2.00 (m, 2H), 1.55 (m, 1H), 1.10-1.35 (m, 3H), 0.65 (m, 2H). MS (m−H$_2$O+1): 361.0; MS (m−2H$_2$O+1): 343.0.

Example 17: preparation of (3R,4S)-3-amino-4-(3-boronopropyl)-1-(3-(dimethylamino)-2,2-dimethylpropyl)pyrrolidine-3-carboxylic acid

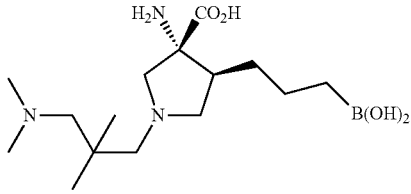 [SMILES: CN(C)CC(C)(C)CN1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and 3-dimethylamino-2,2-dimethylpropionaldehyde (91 mg, 0.7 mmol), stirred for 2 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(3-(dimethylamino)-2,2-dimethylpropyl)pyrrolidine-3-carboxylic acid (36 mg, 16%) as a white granular solid. NMR (D$_2$O) δ 3.80-4.00 (m, 2H), 3.35-3.50 (m, 3H), 3.20 (s, 2H), 2.89 (s, 6H), 2.50-2.65 (m, 1H), 1.50-1.65 (m, 1H), 1.25-1.35 (m, 2H), 1.21 (s, 6H), 0.65-0.75 (m, 2H). MS (m−H$_2$O+1): 312.0; MS (m−2H$_2$O+1): 294.4.

Example 18: preparation of (3R,4S)-3-amino-4-(3-boronopropyl)-1-(piperidin-3-ylmethyl)pyrrolidine-3-carboxylic acid

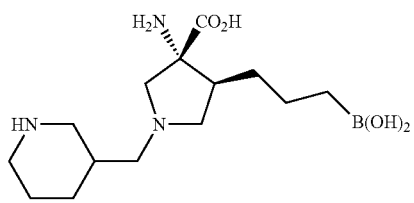 [SMILES: N[C@@]1(C(=O)O)CN(CC2CCCNC2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and N-boc-piperidine-3-carboxaldehyde (149 mg, 0.7 mmol), stirred for 2 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(piperidin-3-ylmethyl)pyrrolidine-3-carboxylic acid (62 mg, 29%) as a granular pale amber solid. NMR (D$_2$O) δ 3.70-4.00 (m, 2H), 3.20-3.45 (m, 5H), 2.65-2.90 (m, 2H), 2.50-2.65 (m, 2H), 2.15-2.30 (m, 1H), 1.75-2.00 (m, 2H), 1.50-1.75 (m, 2H), 1.10-1.40 (m, 4H), 0.65-0.75 (m, 2H). MS (m−H$_2$O+1): 296.3; MS (m−2H$_2$O+1): 278.1.

Example 19: preparation of (3R,4S)-3-amino-4-(3-boronopropyl)-1-(quinolin-4-ylmethyl)pyrrolidine-3-carboxylic acid

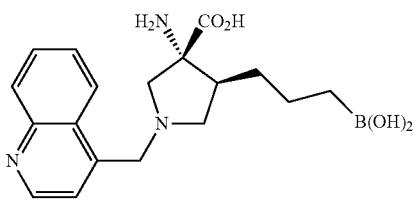 [SMILES: N[C@@]1(C(=O)O)CN(Cc2ccnc3ccccc23)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and quinoline-4-carboxaldehyde (110 mg, 0.7 mmol), stirred for 2 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(quinolin-4-ylmethyl)pyrrolidine-3-carboxylic acid (49 mg, 23%) as a pale amber solid. NMR (D$_2$O) δ 9.12 (d, J=5.5 Hz, 1H), 8.41 (d, J=8.5 Hz, 1H), 8.23 (d, J=8.5 Hz, 1H), 8.10-8.20 (m, 2H), 8.00 (t, J=8.5 Hz, 1H), 5.30 (m, 2H), 4.06 (d, J=12.5 Hz, 1H), 3.83 (m, 2H), 3.51 (t, J=11.5 Hz, 1H), 2.50-2.70 (m, 1H), 1.60 (m, 1H), 1.15-1.30 (m, 3H), 0.60-0.70 (m, 2H). MS (m−H$_2$O+1): 340.3; MS (m−2H$_2$O+1): 322.1.

Example 20: preparation of (3R,4S)-1-((1H-imidazol-4-yl)methyl)-3-amino-4-(3-boronopropyl)pyrrolidine-3-carboxylic acid

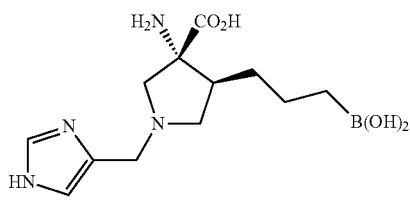 [SMILES: N[C@@]1(C(=O)O)CN(Cc2c[nH]cn2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and imidazole-4-carboxaldehyde (110 mg, 0.7 mmol), stirred for 2 h, then treated with sodium triacetoxyborohydride (212 mg, 1.0 mmol) and glacial acetic acid (2 drops) and stirred for 16 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-1-((1H-imidazol-4-yl)methyl)-3-amino-4-(3-boronopropyl)pyrrolidine-3-carboxylic acid (38 mg, 21%) as a pale yellow granular solid. NMR (D$_2$O) 8.74 (s, 1H), 7.71 (s, 1H), 4.60-4.80 (m, 2H), 3.96 (d, J=12.5 Hz, 1H), 3.80 (dd, J$_1$=11 Hz, J$_2$=8 Hz, 1H), 3.71 (d, J=12.5 Hz, 1H), 3.40 (t, J=11.5 Hz, 1H), 2.50-2.65 (m, 1H), 1.50-1.65 (m, 1H), 1.15-1.35 (m, 3H), 0.60-0.70 (m, 2H). MS (m−H$_2$O+1): 279.0; MS (m−2H$_2$O+1): 261.3.

Example 21: preparation of (3R,4S)-3-amino-4-(3-boronopropyl)-1-(piperidin-2-ylmethyl)pyrrolidine-3-carboxylic acid

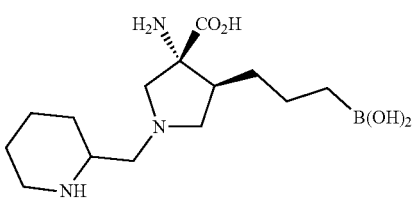 [SMILES: N[C@@]1(C(=O)O)CN(CC2CCCCN2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and cbz-piperidine-2-carboxaldehyde (173 mg, 0.7 mmol), stirred for 3 h, then treated with sodium triacetoxyborohydride (212 mg, 1.0 mmol) and glacial acetic acid (2 drops) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(piperidin-2-ylmethyl)pyrrolidine-3-carboxylic acid (156 mg, 74%) as a pale amber solid. NMR (D$_2$O) 3.85-4.05 (m, 2H), 3.76 (d, J=12.5 Hz, 1H), 3.50-3.65 (m, 3H), 3.39 (m, 2H), 2.95 (dt, J$_1$=12.5 Hz, J$_2$=3 Hz, 1H), 2.55-2.70 (m, 1H), 2.00 (m, 1H), 1.80 (m, 2H), 1.45-1.65 (m, 4H), 1.15-1.35 (m, 3H), 0.65-0.72 (m, 2H). MS (m+1): 314.1; MS (m−H$_2$O+1): 296.2.

Example 22: preparation of (3R,4S)-3-amino-4-(3-boronopropyl)-1-(3-(4-chlorophenyl)propyl)pyrrolidine-3-carboxylic acid

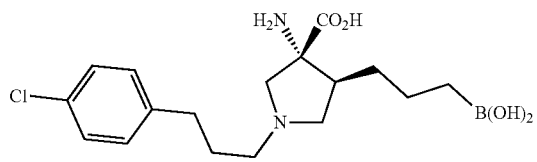 [SMILES: N[C@@]1(C(=O)O)CN(CCCc2ccc(Cl)cc2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and 3-(4-chlorophenyl)propionaldehyde (118 mg, 0.7 mmol), stirred for 2.5 h, then treated with sodium triacetoxyborohydride (212 mg, 1.0 mmol) and glacial acetic acid (2 drops) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(3-(4-chlorophenyl)propyl)pyrrolidine-3-carboxylic acid (84.3 mg, 38%) as a white powder. NMR (D$_2$O) 7.25 (d, J=8 Hz, 2H), 7.13 (d, J=8 Hz, 2H), 3.75-4.10 (m, 2H), 3.40-3.60 (m, 1H), 3.10-3.30 (m, 3H), 2.60 (t, J=7 Hz, 2H), 2.40-2.55 (m, 1H), 1.85-2.00 (m, 2H), 1.50-1.65 (m, 1H), 1.10-1.40 (m, 3H), 0.60-0.70 (m, 2H). MS (m+1): 369.1; MS (m−H$_2$O+1): 351.2.

Example 23: preparation of (3R,4S)-3-amino-4-(3-boronopropyl)-1-(7H-purin-6-yl)pyrrolidine-3-carboxylic acid

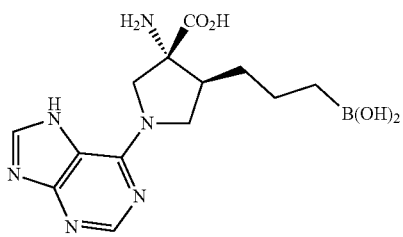 [SMILES: N[C@@]1(C(=O)O)CN(c2ncnc3nc[nH]c23)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 2-propanol (5 mL) was treated with 6-chloropurine (92 mg, 0.6 mmol) and diisopropylethylamine (0.174 mL, 1.0 mmol), heated to 80° C. for 18 h, then diluted with methylene chloride (20 mL). The mixture was filtered through Celite® and the filtrate concentrated. The crude material was deprotected and isolated using the method described for example 8, step 5 to afford (3R,4S)-3-amino-4-(3-boronopropyl)-1-(7H-purin-6-yl)pyrrolidine-3-carboxylic acid (41 mg, 20%) as a pale amber solid. NMR (D$_2$O) δ 8.20-8.45 (m, 2H), 4.20-4.60 (m, 2H), 3.50-4.00 (m, 2H), 2.60-2.80 (m, 2H), 1.65 (m, 1H), 1.20-1.55 (m, 3H), 0.65-0.75 (m, 2H). MS (m+1): 335.2; MS (m−H$_2$O+1): 317.1.

Example 24: preparation of (3R,4S)-3-amino-1-(2-aminoethyl)-4-(3-boronopropyl)pyrrolidine-3-carboxylic acid

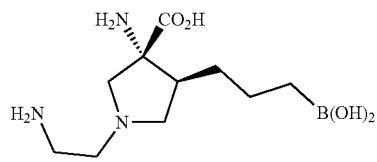 [SMILES: NCCN1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) in anhydrous 1,2-dichloroethane (5 mL) was treated with anhydrous sodium sulfate (1 g) and N-bocaminoacetaldehyde (111 mg, 0.7 mmol), stirred for 3 h, then treated with sodium triacetoxyborohydride (212 mg, 1.0 mmol) and glacial acetic acid (2 drops) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-1-(2-aminoethyl)-4-(3-boronopropyl)pyrrolidine-3-carboxylic acid (64 mg, 35%) as a yellow solid. NMR (D$_2$O) δ 3.60-4.00 (m, 4H), 3.15-3.50 (m, 4H), 2.60 (m, 1H), 1.40-1.65 (m, 1H), 1.10-1.35 (m, 3H), 0.63-0.73 (m, 2H). MS (m+1): 260.2; MS (m−H$_2$O+1): 242.3.

Example 25: preparation of 5-((3R,4S)-3-amino-4-(3-boronopropyl)-3-carboxypyrrolidin-1-yl)nicotinic acid

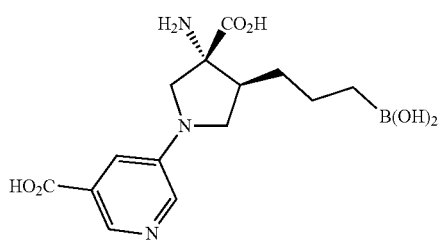 [SMILES: N[C@@]1(C(=O)O)CN(c2cncc(C(=O)O)c2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and ethyl 5-bromonicotinate (138 mg, 0.60 mmol) in anhydrous toluene (2.5 mL) was degassed under nitrogen for 15 min, then treated with palladium diacetate (14 mg, 0.06 mmol), rac-binap (75 mg, 0.12 mmol), and cesium carbonate (0.65 g, 2 mmol). The mixture was heated to 80° C. for 18 h, cooled to room temperature, diluted with methylene chloride (20 mL), filtered through Celite® and the filtrate concentrated. The crude material was deprotected and isolated using the method described for example 8, step 5 to afford 5-((3R,4S)-3-amino-4-(3-boronopropyl)-3-carboxypyrrolidin-1-yl)nicotinic acid (82 mg, 40%) as a yellow solid. NMR (D$_2$O) δ 8.37 (s, 1H), 8.00 (s, 2H), 3.99 (d, J=11 Hz, 1H), 3.88 (t, J=10 Hz, 1H), 3.68 (d, J=11 Hz, 1H), 3.26 (t, J=10 Hz, 1H), 2.60-2.75 (m, 1H), 1.60 (m, 1H), 1.20-1.50 (m, 3H), 0.65-0.75 (m, 2H). MS (m+1): 338.2; MS (m−H$_2$O+1): 320.1.

Example 26: preparation of (3R,4S)-3-amino-4-(3-boronopropyl)-1-(piperidin-4-yl)pyrrolidine-3-carboxylic acid

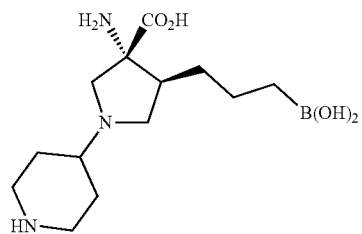 [SMILES: N[C@@]1(C(=O)O)CN(C2CCNCC2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-CBZ-piperidine-4-one (0.233 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 2.5 h, then cooled to room temperature and treated with sodium triacetoxyborohydride (265 mg, 1.25 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(piperidin-4-yl)pyrrolidine-3-carboxylic acid (146 mg, 71%) as a pale amber solid. NMR (D$_2$O) δ 4.02 (d, J=13 Hz, 1H), 3.90 (m, 1 H), 3.77 (m, 1H), 3.45-3.65 (m, 3H), 3.36 (m, 1H), 3.00 (m, 2H), 2.50-2.60 (m, 1H), 2.30-2.40 (m, 2H), 1.75-1.95 (m, 2H), 1.55-1.65 (m, 1H), 1.15-1.40 (m, 3H), 0.62-0.70 (m, 2H). MS (m+1): 300.0; MS (m−H$_2$O+1): 282.2.

Example 27: preparation of (3R,4S)-3-amino-4-(3-boronopropyl)-1,3'-bipyrrolidine-3-carboxylic acid

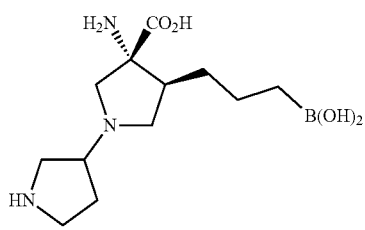 [SMILES: N[C@@]1(C(=O)O)CN(C2CCNC2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-BOC-pyrrolidine-3-one (0.185 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 2.5 h, then cooled to room temperature and treated with sodium triacetoxyborohydride (276 mg, 1.3 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1,3'-bipyrrolidine-3-carboxylic acid (160 mg, 81%) as an amber solid. NMR (D$_2$O) δ 4.25-4.35 (m, 1H), 4.00 (dd, J$_1$=12 Hz, J$_2$=5 Hz, 1H), 3.70-3.95 (m, 3H), 3.25-3.60 (m, 4H), 2.45-2.65 (m, 2H), 2.15-2.25 (m, 1H), 1.50-1.65 (m, 1H), 1.15-1.35 (m, 3H), 0.60-0.70 (m, 2H). MS (m+1): 286.1; MS (m−H$_2$O+1): 268.3.

Example 28: preparation of (3R,4S)-3-amino-4-(3-boronopropyl)-1-(piperidin-3-yl)pyrrolidine-3-carboxylic acid

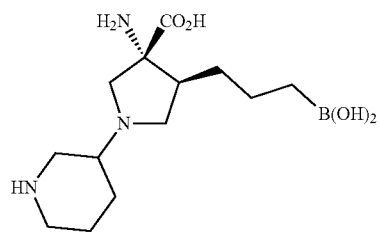 [SMILES: N[C@@]1(C(=O)O)CN(C2CCCNC2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-BOC-piperidine-3-one (0.199 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 3 h, then cooled to room temperature and treated with sodium triacetoxyborohydride (276 mg, 1.3 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(piperidin-3-yl)pyrrolidine-3-carboxylic acid (138 mg, 68%) as an amber solid. NMR (D$_2$O) δ 3.80-4.10 (m, 2H), 3.60-3.80 (m, 2H), 3.30-3.50 (m, 2H), 3.00-3.15 (m, 1H), 2.80-2.95 (m, 1H), 2.45-2.60 (m, 1H), 2.30 (m, 1H), 1.95-2.10 (m, 1H), 1.50-1.85 (m, 4H), 1.10-1.40 (m, 3H), 0.60-0.70 (m, 2H). MS (m+1): 300.1; MS (m−H$_2$O+1): 282.1.

Example 29: preparation of (3R,4S)-3-amino-4-(3-boronopropyl)-1-(pyridin-2-ylmethyl)pyrrolidine-3-carboxylic acid

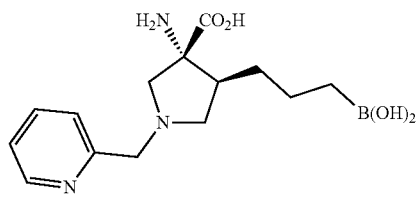 [SMILES: N[C@@]1(C(=O)O)CN(Cc2ccccn2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and pyridine-2-carboxaldehyde (0.199 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 3 h, then cooled to room temperature and treated with sodium triacetoxyborohydride (276 mg, 1.3 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(pyridin-2-ylmethyl)pyrrolidine-3-carboxylic acid (141 mg, 74%) as a white solid. NMR (D$_2$O) δ 8.63 (m, 1H), 8.20 (m, 1H), 7.65-7.85 (m, 2H), 4.50-4.65 (m, 2H), 3.86 (d, J=12.5 Hz, 1H), 3.70 (m, 2H), 3.22 (t, J=11 Hz, 1H), 2.55 (m, 1H), 1.55 (m, 1H), 1.15-1.35 (m, 3H), 0.60-0.70 (m, 2H). MS (m+1): 308.0; MS (m−H$_2$O+1): 290.2.

Example 30: preparation of (3R,4S)-3-amino-4-(3-boronopropyl)-1-(4-carboxycyclohexyl)pyrrolidine-3-carboxylic acid

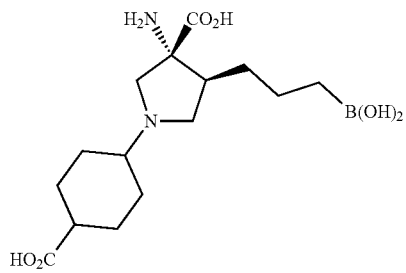 [SMILES: N[C@@]1(C(=O)O)CN(C2CCC(C(=O)O)CC2)C[C@@H]1CCCB(O)O]

A stirred solution of (3R,4S)-3-acctamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and 4-carbethoxycyclohexanone (0.170 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 3 h, then cooled to room temperature and treated with sodium triacetoxyborohydride (276 mg, 1.3 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO$_4$), and concentrated. The crude material was deprotected and isolated using the method described for example 8, step 5 to afford (3R,4S)-3-amino-4-(3-boronopropyl)-1-(4-carboxycyclohexyl)pyrrolidine-3-carboxylic acid (135 mg, 65%) as a white solid. NMR (D$_2$O) δ 3.97 (dd, J$_1$=13 Hz, J$_2$=7 Hz, 1H), 3.75-3.90 (m, 2H), 3.15-3.35 (m, 2H), 2.20-2.70 (m, 2H), 1.90-2.20 (m, 4H), 1.50-1.65 (m, 3H), 1.15-1.45 (m, 5H), 0.60-0.70 (m, 2H). MS (m+1): 343.1; MS (m−H$_2$O+1): 325.0.

Example 31: preparation of (3R,4S)-3-amino-4-(3-boronopropyl)-1-((1-methyl-1H-imidazol-2-yl)methyl)pyrrolidine-3-carboxylic acid

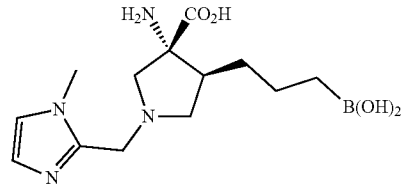 [SMILES: Cn1ccnc1CN1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and 1-methylimidazole-2-carboxaldehyde (83 mg, 0.75 mmol) in anhydrous 1,2-dichloroethane (5 mL) was treated with anhydrous sodium sulfate (1 g) and glacial acetic acid (30 mg, 0.5 mmol), stirred at room temperature for 3 h, then cooled to room temperature and treated with sodium triacetoxyborohydride (212 mg, 1.0 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and saturated aqueous sodium chloride (20 mL each), dried (MgSO₄), and concentrated. The crude material was deprotected and isolated using the method described for example 8, step 5 to afford (3R,4S)-3-amino-4-(3-boronopropyl)-1-((1-methyl-1H-imidazol-2-yl)methyl)pyrrolidine-3-carboxylic acid (140 mg, 67%) as a pale yellow solid. NMR (D₂O) δ 7.37 (s, 2H), 4.35-4.50 (m, 2H), 3.80 (s, 3H), 3.40-3.60 (m, 3H), 2.75-2.85 (m, 1H), 2.43 (m, 1H), 1.48 (s, 1H), 1.15-1.30 (3H), 0.60-0.70 (m, 2H). MS (m+1): 311.0; MS (m–H₂O+1): 293.1.

Example 32: preparation of (3R,4S)-3-amino-4-(3-boronopropyl)-1-(4-methylpyridin-3-yl)pyrrolidine-3-carboxylic acid

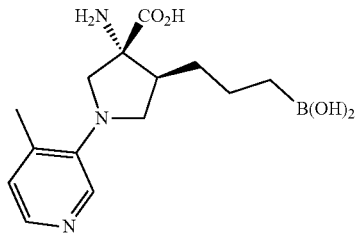 [SMILES: Cc1ccncc1N1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and 3-bromo-4-methylpyridine (0.258 g, 1.5 mmol) in anhydrous toluene (5 mL) was degassed under nitrogen for 15 min, then treated with Pd₂dba₃ (46 mg, 0.05 mmol), rac-binap (50 mg, 0.075 mmol), and sodium t-butoxide (0.18 g, 1.87 mmol). The mixture was heated to 70° C. for 18 h, cooled to room temperature, diluted with methylene chloride (20 mL), filtered through Celite® and the filtrate concentrated. The crude material was deprotected and isolated using the method described for example 8, step 5 to afford (3R,4S)-3-amino-4-(3-boronopropyl)-1-(4-methylpyridin-3-yl)pyrrolidine-3-carboxylic acid (22 mg, 12%) as a pale amber solid. NMR (D₂O) δ 7.99 (d, J=6 Hz, 1H), 7.95 (s, 1H), 7.57 (d, J=6 Hz, 1H), 3.80 (d, J=5 Hz, 2H), 3.72 (t, J=9.5 Hz, 1H), 3.25 (t, J=9.5 Hz, 1H), 2.49 (s, 3H), 2.40-2.60 (m, 1H), 1.50-1.60 (m, 1H), 1.20-1.45 (m, 3H), 0.65-0.75 (m, 2H). MS (m–H₂O+1): 290.0; MS (m–2H₂O+1): 271.9.

Example 33: preparation of (3R,4S)-3-amino-4-(3-boronopropyl)-1-(2-(piperidin-1-yl)ethyl)pyrrolidine-3-carboxylic acid

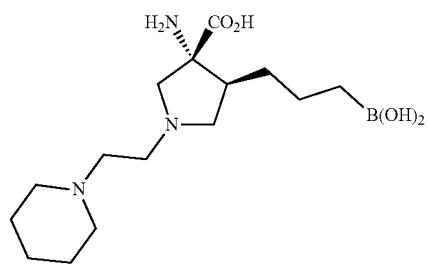 [SMILES: N[C@@]1(C(=O)O)CN(CCN2CCCCC2)C[C@@H]1CCCB(O)O]

A cooled (0° C.) solution of N-(2-hydroxyethyl)piperidine (90.5 mg, 0.70 mmol) and diisopropylethylamine (0.30 mL, 1.7 mmol) in anhydrous acetonitrile (12 mL) under nitrogen was treated with methanesulfonyl chloride (80.2 mg, 0.70 mmol), stirred 2 h, and treated with (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and heated to 60° C. for 15 h. The reaction mixture was concentrated, deprotected and isolated using the method described for example 8, step 5 to afford (3R,4S)-3-amino-4-(3-boronopropyl)-1-(2-(piperidin-1-yl)ethyl)pyrrolidine-3-carboxylic acid (140 mg, 64%) as a glassy colorless solid. NMR (D₂O) δ 3.85-4.05 (m, 2H), 3.65-3.80 (m, 3H), 3.35-3.55 (m, 5H), 2.85-3.00 (m, 2H), 2.60 (m, 1H), 1.80-1.95 (m, 2H), 1.55-1.75 (m, 4H), 1.10-1.50 (m, 4H), 0.63-0.73 (m, 2H). MS (m+1): 328.3; MS (m–H₂O+1): 310.0.

Example 34: preparation of (3R,4S)-3-amino-4-(3-boronopropyl)-1-(2-(diethylamino)ethyl)pyrrolidine-3-carboxylic acid

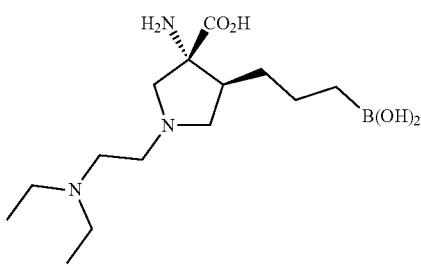 [SMILES: CCN(CC)CCN1C[C@H](CCCB(O)O)[C@](N)(C(=O)O)C1]

A cooled (0° C.) solution of N,N-diethylethanolamine (82 mg, 0.70 mmol) and diisopropylethylamine (0.30 mL, 1.7 mmol) in anhydrous acetonitrile (12 mL) under nitrogen was treated with methanesulfonyl chloride (80.2 mg, 0.70 mmol), stirred 2.5 h, and treated with (3R,4 S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and heated to 60° C. for 15 h. The reaction mixture was concentrated, deprotected and isolated using the method described for example 8, step 5 to afford (3R,4S)-3-amino-4-(3-boronopropyl)-1-(2-(diethylamino) ethyl)pyrrolidine-3-carboxylic acid (120 mg, 57%) as a white foam. NMR (D₂O) δ 3.97 (d, J=12.5 Hz, 1H), 3.87 (m, 1H), 3.65-3.80 (m, 3H), 3.35-3.55 (m, 3H), 3.19 (q, J=7.5 Hz, 4H), 2.55-2.65 (m, 1H), 1.50-1.65 (m, 1H), 1.20 (t, J=7.5 Hz, 6H), 1.15-1.35 (m, 3H), 0.63-0.73 (m, 2H). MS (m–H₂O+1): 298.3; MS (m–2H₂O+1): 280.1.

Example 35: Preparation of (3R,4S)-4-(3-boronopropyl)-3-(methylamino)pyrrolidine-3-carboxylic acid

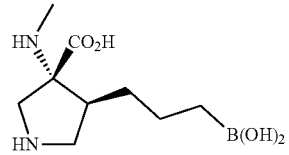 [SMILES: CN[C@@]1(C(=O)O)CNC[C@@H]1CCCB(O)O]

(3R,4S)-4-(3-boronopropyl)-3-(methylamino)pyrrolidine-3-carboxylic acid was prepared in a manner analogous to that set forth in Example 8, except methylamine and acetic acid were used in place of ammonium acetate in step 2. LC-MS ESI⁻ MS found for $C_9H_{19}BN_2O_4$ m/z 230.1: (m+1): 231.1; MS (m–$H_2O$+1): 213.1.

Example 36: preparation of (3R,4S)-3-amino-4-(3-boronopropyl)-1-((1-methylpiperidin-2-yl)methyl)pyrrolidine-3-carboxylic acid

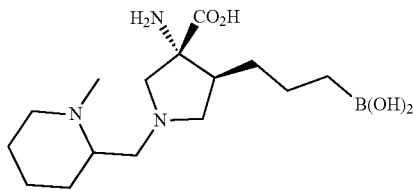 [SMILES: CN1CCCCC1CN1C[C@H](CCCB(O)O)[C@](N)(C(=O)O)C1]

A cooled (0° C.) solution of 1-methylpiperidine-2-methanol (97 mg, 0.75 mmol) and diisopropylethylamine (0.31 mL, 1.75 mmol) in anhydrous acetonitrile (12 mL) under nitrogen was treated with methanesulfonyl chloride (86 mg, 0.75 mmol), stirred 3 h, and treated with (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and heated to 60° C. for 15 h. The reaction mixture was concentrated, deprotected and isolated using the method described for example 8, step 5 to afford (3R,4S)-3-amino-4-(3-boronopropyl)-1-((1-methylpiperidin-2-yl)methyl)pyrrolidine-3-carboxylic acid (121 mg, 55%) as a white foam. NMR ($D_2O$) δ 3.60-4.00 (m, 4H), 3.15-3.55 (m, 3H), 2.90 (m, 2H), 2.67 (s, 3H), 2.50-2.80 (m, 2H), 2.00-2.30 (m, 1H), 1.45-1.95 (m, 5H), 1.10-1.40 (m, 3H), 0.63-0.73 (m, 2H). MS (m+1): 328.1; MS (m–$H_2O$+1): 310.1.

Example 37: preparation of (3R,4S)-3-amino-4-(3-boronopropyl)-1-(pyrrolidin-2-ylmethyl)pyrrolidine-3-carboxylic acid

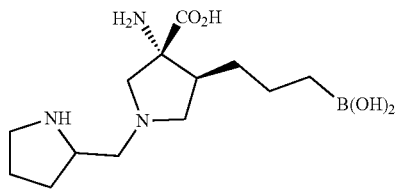 [SMILES: N[C@@]1(C(=O)O)CN(CC2CCCN2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-BOC-piperidine-2-carboxaldehyde (0.15 g, 0.75 mmol) in anhydrous 1,2-dichloroethane (5 mL) was treated with anhydrous sodium sulfate (1 g) and glacial acetic acid (30 mg, 0.5 mmol), stirred at room temperature for 3 h, then cooled to room temperature and treated with sodium triacetoxyborohydride (212 mg, 1.0 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried ($MgSO_4$), and concentrated in vacuo. The crude material was deprotected and isolated using the method described for example 8, step 5 to afford (3R,4S)-3-amino-4-(3-boronopropyl)-1-(pyrrolidin-2-ylmethyl)pyrrolidine-3-carboxylic acid (144 mg, 70%) as a white foam. NMR ($D_2O$) δ 3.85-4.05 (m, 3H), 3.60-3.80 (m, 3H), 3.40 (m, 1H), 3.30 (m, 2H), 2.55-2.70 (m, 1H), 2.20-2.35 (m, 1H), 1.85-2.10 (m, 2H), 1.75 (m, 1H), 1.60 (m, 1H), 1.15-1.40 (m, 3H), 0.63-0.73 (m, 2H). MS (m+1): 300.1; MS (m–$H_2O$+1): 282.1.

Example 38: preparation of (3R,4S)-3-amino-4-(3-boronopropyl)-1-(2-(pyrrolidin-1-yl)ethyl)pyrrolidine-3-carboxylic acid

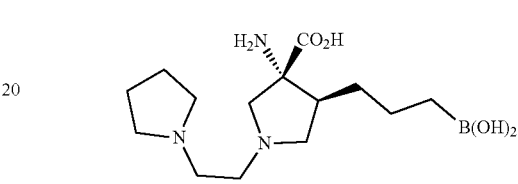

A cooled (0° C.) solution of N-(2-hydroxyethyl)pyrrolidine (92 mg, 0.80 mmol) and diisopropylethylamine (0.32 mL, 1.8 mmol) in anhydrous acetonitrile (12 mL) under nitrogen was treated with methanesulfonyl chloride (92 mg, 0.80 mmol), stirred 3 h, and treated with (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and heated to 60° C. for 15 h. The reaction mixture was concentrated, deprotected and isolated using the method described for example 8, step 5 to afford (3R,4S)-3-amino-4-(3-boronopropyl)-1-(2-(pyrrolidin-1-yl)ethyl)pyrrolidine-3-carboxylic acid (127 mg, 60%) as a white foam. NMR ($D_2O$) δ 3.80-4.00 (m, 2H), 3.50-3.80 (m, 4H), 3.40 (t, J=11 Hz, 1H), 3.05 (m, 2H), 2.55-2.75 (m, 4H), 2.05 (m, 2H), 1.90 (m, 2H), 1.60 (m, 1H), 1.10-1.40 (m, 3H), 0.63-0.73 (m, 2H). MS (m+1): 314.0; MS (m–$H_2O$+1): 296.2.

Example 39: preparation of (3R,4S)-3-amino-4-(3-boronopropyl)-1-(((S)-1,2,3,4-tetrahydroisoquinolin-3-yl)methyl)pyrrolidine-3-carboxylic acid

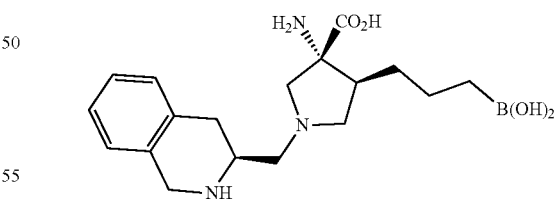

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-BOC-tetrahydroisoquinoline-3-carboxaldehyde (0.196 g, 0.75 mmol) in anhydrous 1,2-dichloroethane (5 mL) was treated with anhydrous sodium sulfate (1 g) and glacial acetic acid (30 mg, 0.5 mmol), stirred at room temperature for 3 h, then cooled to room temperature and treated with sodium triacetoxyborohydride (212 mg, 1.0 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried (MgSO$_4$), and concentrated in vacuo. The crude material was deprotected and isolated using the method described for example 8, step 5 to afford (3R,4S)-3-amino-4-(3-boronopropyl)-1-(((S)-1,2,3,4-tetrahydroisoquinolin-3-yl)methyl)pyrrolidine-3-carboxylic acid (146 mg, 62%) as a white solid. NMR (D$_2$O) δ 7.10-7.30 (m, 4H), 4.39 (br s, 2H), 3.85-4.10 (m, 3H), 3.60-3.80 (m, 3H), 3.20-3.50 (m, 2H), 2.90-3.10 (m, 1H), 2.62 (m, 1H), 1.60 (m, 1H), 1.15-1.30 (m, 3H), 0.63-0.73 (m, 2H). MS (m+1): 362.4; MS (m−H$_2$O+1): 344.0.

Example 40: preparation of (3R,4S)-3-amino-1-(2-(benzylamino)ethyl)-4-(3-boronopropyl)pyrrolidine-3-carboxylic acid

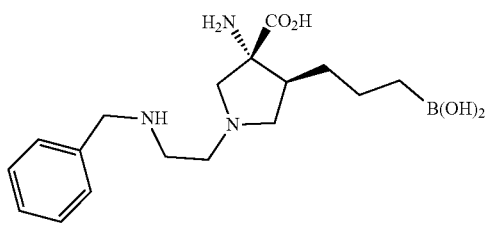 [SMILES: N[C@@]1(C(=O)O)CN(CCNCc2ccccc2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-benzyl-N-BOC-glycinaldehyde (0.187 g, 0.75 mmol) in anhydrous 1,2-dichloroethane (5 mL) was stirred at room temperature for 30 min, then cooled by ice bath and treated with sodium triacetoxyborohydride (212 mg, 1.0 mmol) and stirred for 3 h at room temperature. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried (MgSO$_4$), and concentrated in vacuo. The crude material was deprotected and isolated using the method described for example 8, step 5 to afford (3R,4S)-3-amino-1-(2-(benzylamino)ethyl)-4-(3-boronopropyl)pyrrolidine-3-carboxylic acid (112 mg, 49%) as a white solid. NMR (D$_2$O) δ 7.30-7.45 (m, 5H), 4.21 (s, 2H), 3.94 (d, 1H, J=12 Hz), 3.84 (t, J=9.5 Hz, 1 H), 3.60-3.75 (m, 3H), 3.30-3.50 (m, 3H), 2.50-2.65 (m, 1H), 1.50-1.65 (m, 1H), 1.10-1.35 (m, 3H), 0.63-0.73 (m, 2H). MS (m+1): 350.4; MS (m−H$_2$O+1): 332.1.

Example 41: preparation of (3R,4S)-3-amino-4-(3-boronopropyl)-1-(2-(3,4-dichlorobenzylamino)ethyl)pyrrolidine-3-carboxylic acid

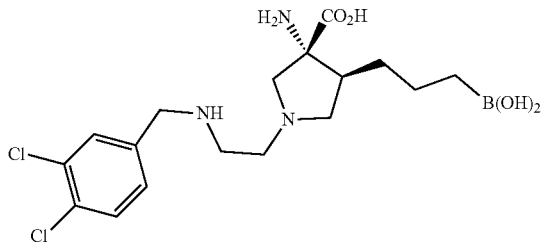 [SMILES: N[C@@]1(C(=O)O)CN(CCNCc2ccc(Cl)c(Cl)c2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and N-(3,4-dichlorobenzyl)-N-BOC-glycinaldehyde (0.240 g, 0.75 mmol) in anhydrous 1,2-dichloroethane (5 mL) was stirred at room temperature for 30 min, then cooled by ice bath and treated with sodium triacetoxyborohydride (212 mg, 1.0 mmol) and stirred for 3 h at room temperature. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried (MgSO$_4$), and concentrated in vacuo. The crude material was deprotected and isolated using the method described for example 8, step 5 to afford (3R,4S)-3-amino-4-(3-boronopropyl)-1-(2-(3,4-dichlorobenzylamino)ethyl)pyrrolidine-3-carboxylic acid (111 mg, 42%) as a white solid. NMR (D$_2$O) δ 7.50-7.60 (m, 2H), 7.28 (dd, J$_1$=8.5 Hz, J$_2$=2 Hz, 1H), 4.20 (s, 2H), 3.94 (d, J=12 Hz, 1H), 3.84 (dd, J$_1$=11.5 Hz, J$_2$=8 Hz, 1H), 3.60-3.75 (m, 3H), 3.30-3.45 (m, 3H), 2.50-2.65 (m, 1H), 1.50-1.65 (m, 1H), 1.10-1.35 (m, 3H), 0.62-0.72 (m, 2H). MS (m+1): 417.9; MS (m−H$_2$O+1): 400.3.

Example 42: preparation of (3R,4S)-3-amino-4-(3-boronopropyl)-1-(4-chlorophenylcarbamoyl)pyrrolidine-3-carboxylic acid

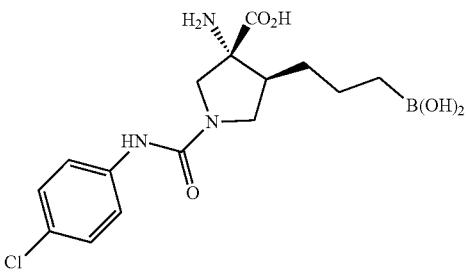 [SMILES: N[C@@]1(C(=O)O)CN(C(=O)Nc2ccc(Cl)cc2)C[C@@H]1CCCB(O)O]

(3R,4S)-3-amino-4-(3-boronopropyl)-1-(4-chlorophenylcarbamoyl)pyrrolidine-3-carboxylic acid was prepared in a manner analogous to that set forth in Example 46, except 1-chloro-4-isocyanatobenzene was used as the acylating agent in step 4. LC-MS ESI− MS found for C$_{15}$H$_{21}$BClN$_3$O$_5$ m/z 396.2: (m+1): 397.1; MS (m−H$_2$O+1): 379.0.

Example 43: preparation of (3R,4S)-3-amino-4-(3-boronopropyl)-1-((S)-pyrrolidine-2-carbonyl)pyrrolidine-3-carboxylic acid

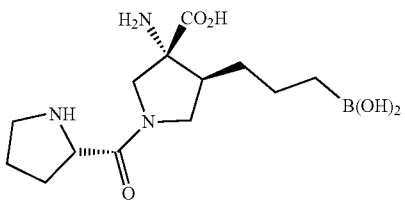

(3R,4S)-3-amino-4-(3-boronopropyl)-1-((S)-pyrrolidine-2-carbonyl)pyrrolidine-3-carboxylic acid was prepared in a manner analogous to that set forth in Example 46, except (S)-1-(tert-butoxycarbonyl)pyrrolidine-2-carboxylic acid was used as the acylating agent in step 4. LC-MS ESI⁻ MS found for $C_{13}H_{24}BN_3O_5$ m/z 313.2: (m+1): 314.1; MS (m–H₂O+1): 296.0.

Example 44: preparation of (3R,4S)-3-amino-1-(2-aminocyclohexyl)-4-(3-boronopropyl)pyrrolidine-3-carboxylic acid

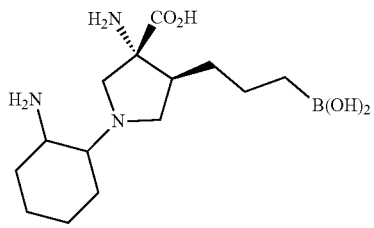 [SMILES: NC1CCCCC1N1C[C@H](CCCB(O)O)[C@](N)(C(=O)O)C1]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.5 mmol) and 2-(N-BOC-amino)cyclohexane-1-one (0.213 g, 1.0 mmol) in anhydrous 1,2-dichloroethane (5 mL) was treated with anhydrous sodium sulfate (1 g) and glacial acetic acid (30 mg, 0.5 mmol), stirred at 40° C. for 1 h, then cooled to room temperature and treated with sodium triacetoxyborohydride (276 mg, 1.3 mmol) and stirred for 18 h. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried (MgSO₄), and concentrated in vacuo. The crude material was deprotected and isolated using the method described for example 8, step 5 to afford (3R,4S)-3-amino-1-(2-aminocyclohexyl)-4-(3-boronopropyl)pyrrolidine-3-carboxylic acid (156 mg, 74%) as a white powder. NMR (D₂O) δ 3.65-4.05 (m, 3H), 3.05-3.60 (m, 3H), 2.90-3.10 (m, 1H), 1.95-2.10 (m, 2H), 1.45-1.75 (m, 5H), 1.15-1.40 (m, 5H), 0.62-0.72 (m, 2H). MS (m+1): 314.1; MS (m–H₂O+1): 296.1.

Example 45: preparation of (3R,4S)-3-amino-4-(3-boronopropyl)-1-(2-(4-chlorophenyl)acetyl)pyrrolidine-3-carboxylic acid

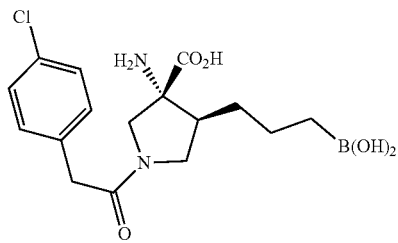 [SMILES: N[C@@]1(C(=O)O)CN(C(=O)Cc2ccc(Cl)cc2)C[C@@H]1CCCB(O)O]

(3R,4S)-3-amino-4-(3-boronopropyl)-1-(2-(4-chlorophenyl)acetyl)pyrrolidine-3-carboxylic acid was prepared in a manner analogous to that set forth in Example 46, except 2-(4-chlorophenyl)acetic acid was used as the acylating agent in step 4. LC-MS ESI⁻ MS found for $C_{16}H_{22}BClN_2O_5$ m/z 368.1: (m+1): 369.1; MS (m–H₂O+1): 352.1.

Example 46: preparation of (3R,4S)-3-amino-4-(3-boronopropyl)-1-(4-fluorobenzoyl)pyrrolidine-3-carboxylic acid

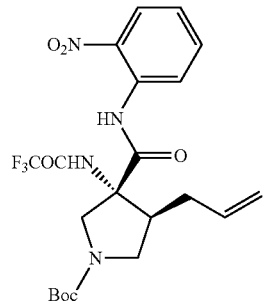

Step 1: tert-Butyl 4-allyl-3-[(2-nitrophenyl)carbamoyl]-3-[(trifluoroacetyl)amino]-pyrrolidine-1-carboxylate While under nitrogen, a stirred mixture of tert-butyl 3-allyl-4-oxopyrrolidine-1-carboxylate (600 mg, 2.66 mmol), ammonium trifluoroacetate (698 mg, 5.33 mmol) and 2-nitrophenyl isocyanide (690 mg, 4.6 mmol) in 2,2,2-trifluoroethanol (2.7 mL) was placed in a 60° C. oil bath and stirred overnight. After cooling to room temperature, the mixture was diluted with ethyl acetate (40 mL), washed with water (3×20 mL) and the combined aqueous phase was re-extracted with ethyl acetate (20 mL). The combined organic phase was washed with saturated aqueous sodium chloride (20 mL), dried over Na₂SO₄ and concentrated under reduced pressure. Purification by silica gel chromatography (90 g column, 0-5% ethyl acetate in methylene chloride) gave tert-butyl 4-allyl-3-[(2-nitrophenyl)carbamoyl]-3-[(trifluoroacetyl)amino]-pyrrolidine-1-carboxylate (665 mg, 51%, 3:2 mixture of diastereomers) as an amber gum. LC-MS ESI⁺ MS found for $C_{21}H_{25}F_3N_4O_6$ m/z 509.0 (M+Na). LC-MS ESI⁻ MS found for $C_{21}H_{25}F_3N_4O_6$ m/z 485.1 (M–H).

Step 2: tert-butyl 4-allyl-3-(1H-benzotriazol-1-ylcarbonyl)-3-[(trifluoroacetyl)amino]-pyrrolidine-1-carboxylate (Trans, Racemic)

A solution of tert-butyl 4-allyl-3-[(2-nitrophenyl)carbamoyl]-3-[(trifluoroacetyl)amino]pyrrolidine-1-carboxylate (0.816 g, 1.68 mmol) in methanol (30 mL) was treated with ammonium chloride (0.897 g, 16.8 mmol) and zinc (2.19 g, 33.5 mmol). After stirring at room temperature for 40 min, the mixture was diluted with ethyl acetate (30 mL) and filtered through a pad of Celite. The pad was washed with ethyl acetate and the filtrate was concentrated under reduced pressure. The residue was re-diluted with ethyl acetate (25 mL) and water (20 mL), and the layers were separated. The organic phase was washed with water (10 mL) and saturated aqueous sodium chloride (10 mL), dried over $Na_2SO_4$ and concentrated and dried under high vacuum for ~2 h to give the tert-butyl 4-allyl-3-[(2-aminophenyl)carbamoyl]-3-[(trifluoroacetyl)amino]pyrrolidine-1-carboxylate intermediate (760 mg, 3:2 mixture of diastereomers) as a off-white foam that was used without further purification.

While under nitrogen, the crude intermediate was dissolved in chloroform (30 mL) and treated with isoamyl nitrite (0.78 mL, 5.6 mmol). The homogeneous mixture was stirred at room temperature for 3 h, concentrated under reduced pressure and purified by silica gel chromatography (90 g column, 2.5-7% ethyl acetate in methylene chloride) to give tert-butyl 4-allyl-3-(1H-benzotriazol-1-ylcarbonyl)-3-[(trifluoroacetyl)amino]-pyrrolidine-1-carboxylate (347 mg, 44%, 95:5 trans/cis) as an off-white foam. For intermediate mixture of anilines (mix of diastereomers), LC-MS ESI$^-$ MS found for $C_{21}H_{27}F_3N_4O_4$ m/z 455.2 (M H). For benzotriazole (isolated as the diastereomer shown), LC-MS ESI$^+$ MS found for $C_{21}H_{24}F_3N_5O_4$ m/z 490.0 (M+Na). $^1$H NMR (CDCl$_3$, 400 MHz) δ 8.30 (m, 1H), 8.17 (m, 1H), 7.77 (m, 1H), 7.60 (m, 1H), 5.45 (m, 1H), 4.90 (m, 2H), 4.60-4.15 (m, 2H), 3.95-3.60 (m, 2H), 3.19 (m, 1H), 2.10 (m, 2H), 1.53 (s, 9H) (rotamers present).

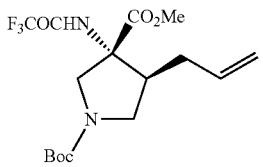

Step 3: 1-tert-Butyl 3-methyl (3R,4S)-4-allyl-3-[(trifluoroacetyl)amino]pyrrolidine-, 3-dicarboxylate (Racemic)

A solution of tert-butyl 4-allyl-3-(1H-benzotriazol-1-ylcarbonyl)-3-[(trifluoroacetyl)amino]pyrrolidine-1-carboxylate (340 mg, 0.727 mmol, 95:5 trans/cis) in methylene chloride (6 mL) and methanol (3 mL) was treated with Et$_3$N (0.0203 mL, 0.145 mmol) and stirred at room temperature for 45 min. The mixture was concentrated under reduced pressure and purified by silica gel chromatography (40 g column, 2-5% ethyl acetate/methylene chloride) to give 1-tert-butyl 3-methyl (3R,4S)-4-allyl-3-[(trifluoroacetyl)amino]pyrrolidine-1,3-dicarboxylate (racemic) (208 mg, 75%) as a partially crystalline film. LC-MS ESI$^-$ MS found for $C_{16}H_{23}F_3N_2O_5$ m/z 379.1 (M−H). $^1$H NMR (CDCl$_3$, 400 MHz) δ 7.20 (m, 1H), 5.73 (m, 1H), 5.13 (m, 2H), 4.02 (d, J=11.7 Hz, 1H), 3.88 (s, 3H), 3.80 (m, 2H), 3.25-2.85 (m, 2H), 2.18-1.93 (m, 2H), 1.49 (s, 9H) (rotamers present).

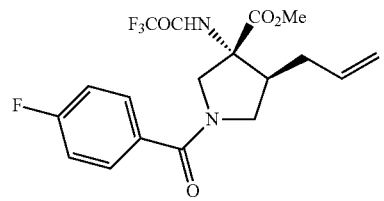

Step 4: Methyl (3R,4S)-4-allyl-1-(4-fluorobenzoyl)-3-[(trifluoroacetyl)amino]-pyrrolidine-3-carboxylate (Racemic)

While under nitrogen, a solution of racemic 1-tert-butyl 3-methyl (3R,4S)-4-allyl-3-[(trifluoroacetyl)amino]pyrrolidine-1,3-dicarboxylate (Step 3, 0.207 g, 0.544 mmol) in methylene chloride (11 mL) was treated with trifluoroacetic acid (838 uL, 10.9 mmol). After stirring for 2 h, the mixture was concentrated and dried under high vacuum overnight to give methyl (3R,4S)-4-allyl-3-[(trifluoroacetyl)amino]pyrrolidine-3-carboxylate trifluoroacetate as a faint yellow foam that was used without further purification. A stirred solution of this intermediate in dry methylene chloride (11 mL) under nitrogen was treated with Et$_3$N (0.341 mL, 2.45 mmol) followed by 4-fluorobenzoyl chloride (0.0979 mL, 0.816 mmol). After stirring at room temperature for 1.5 h, the solution was diluted with methylene chloride (15 mL), washed successively with water (10 mL), saturated aqueous NaHCO$_3$ (10 mL) and saturated aqueous sodium chloride (5 mL). The resulting organic phase was dried over Na$_2$SO$_4$ and concentrated, and purification by radial chromatography (2000 micron silica gel rotor, 40-75% ethyl acetate in hexanes) to give methyl (3R,4S)-4-allyl-1-(4-fluorobenzoyl)-3-[(trifluoroacetyl)amino]-pyrrolidine-3-carboxylate (racemic) (220 mg, 100%) as a faint yellow film. Rf=0.33 (50% Ethyl acetate in hexanes). For intermediate pyrrolidine trifluoroacetate, LC-MS ESI$^+$ MS found for $C_{11}H_{15}F_3N_2O_3$ m/z 281.1 (M+H). For amide product, LC-MS ESI$^-$ MS found for $C_{18}H_{18}F_4N_2O_4$ m/z 401.1 (M−H).

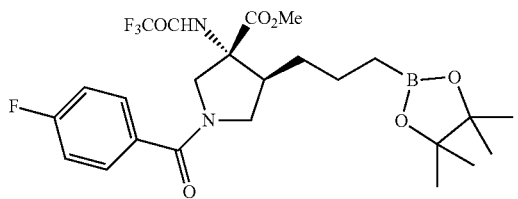

Step 5: Methyl (3R,4S)-1-(4-fluorobenzoyl)-4-[3-(4,4,5,5-tetramethyl-1,3,2-dioxaborolan-2-yl)propyl]-3-[(trifluoroacetyl)amino]pyrrolidine-3-carboxylate (Racemic)

Methyl (3R,4S)-1-(4-fluorobenzoyl)-4-[3-(4,4,5,5-tetramethyl-1,3,2-dioxaborolan-2-yl)propyl]-3-[(trifluoroacetyl)amino]pyrrolidine-3-carboxylate (racemic) is prepared in a manner analogous to that set forth in Example 1, step 3 except methyl (3R,4S)-4-allyl-1-(4-fluorobenzoyl)-3-[(trifluoroacetyl)amino]-pyrrolidine-3-carboxylate (racemic) is used as the substrate. ESI$^+$ MS found for $C_{24}H_{31}BF_4N_2O_6$ m/z 531.2 (M+H). R$_f$=0.28 (50% ethyl acetate in hexanes).

Step 6: (3R,4S)-3-Amino-4-[3-(dihydroxyboryl) propyl]-1-(4-fluorobenzoyl)pyrrolidine-3-carboxylic acid hydrochloride (Racemic)

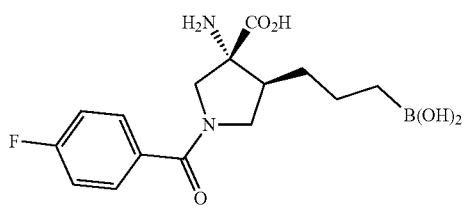

A stirred solution of racemic methyl (3R,4S)-1-(4-fluorobenzoyl)-4-[3-(4,4,5,5-tetramethyl-1,3,2-dioxaborolan-2-yl)propyl]-3-[(trifluoroacetyl)amino]pyrrolidine-3-carboxylate (200 mg, 0.377 mmol) in THF (4.2 mL) and water (3.7 mL) was sparged with nitrogen for 5 min. Lithium hydroxide monohydrate (33.2 mg, 0.792 mmol) was added, and the mixture was sparged with nitrogen for 10 min and stirred under nitrogen at room temperature for 4 days, during which additional lithium hydroxide monohydrate (39.6 mg, 0.943 mmol) was added. The mixture was diluted with water (5 mL) and acidified to pH<1 with 3 M aqueous HCl. The resulting solution was washed with ethyl acetate (2×20 mL) and methylene chloride (2×20 mL). The aqueous phase was concentrated under reduced pressure and purified by reverse phase HPLC. Product fractions were pooled, concentrated, re-dissolved in 1M aqueous HCl, concentrated and lyophilized to give racemic (3R,4S)-3-amino-4-[3-(dihydroxyboryl)propyl]-1-(4-fluorobenzoyl)pyrrolidine-3-carboxylic acid hydrochloride (42 mg, 30%) as a white amorphous solid. MS (ESI+) m/z 321 (M-$H_2O$+H+), 303 (M-$2H_2O$+H+) and MS (ESI-) m/z 319 (M-$H_2O$-H+).

Example 47: preparation of (3R,4S)-3-amino-4-(3-boronopropyl)-1-(4-methoxybenzoyl)pyrrolidine-3-carboxylic acid

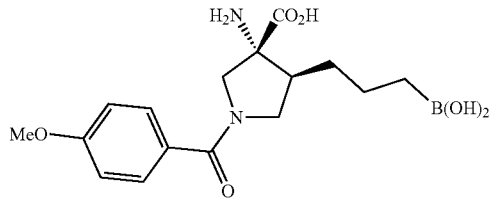 [SMILES: COc1ccc(C(=O)N2C[C@H](CCCB(O)O)[C@](N)(C(=O)O)C2)cc1]

(3R,4S)-3-amino-4-(3-boronopropyl)-1-(4-methoxybenzoyl)pyrrolidine-3-carboxylic acid was prepared in a manner analogous to that set forth in Example 46, except 4-methoxybenzoyl chloride was used as the acylating agent in step 4.

Example 48: preparation of (3R,4S)-3-amino-4-(3-boronopropyl)-1-(4-fluorophenylcarbamoyl)pyrrolidine-3-carboxylic acid

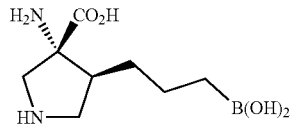

Step 1: (3R,4S)-3-Amino-4-[3-(dihydroxyboryl) propyl]pyrrolidine-3-carboxylic acid dihydrochloride (racemate)

tert-Butyl (3R,4S)-3-acctamido-3-(tert-butylcarbamoyl)-4-[3-(4,4,5,5-tetramethyl-1,3,2-dioxaborolan-2-yl)propyl] pyrrolidine-1-carboxylate (racemic) (1.60 g, 3.23 mmol) was placed in an Ace pressure tube, carefully treated with conc. HCl (22 mL) and heated to ~120° C. After 16 h, the mixture was cooled to room temperature, added slowly to ice water (45 mL) and washed with methylene chloride (3×40 mL). The aqueous phase was concentrated redissolved in deionized water and lyophilized to give racemic (3R,4S)-3-amino-4-[3-(dihydroxyboryl)propyl]pyrrolidine-3-carboxylic acid dihydrochloride as a off-white solid. The solid could be azeotroped from toluene several times to remove additional water. $^1$H NMR ($D_2O$, 400 MHz) δ 3.87 (d J=12.8 Hz, 1H), 3.72 (dd, J=11.7, 8.5 Hz, 1H), 3.44 (d, J=12.8 Hz, 1H), 3.23 (br t, J=11.7 Hz, 1H), 2.53 (m, 1H), 1.60 (m, 1H), 1.31 (m, 2H), 1.19 (m, 1H), 0.68 (m, 2H). ESI$^+$ MS found for $C_8H_{17}BN_2O_4$ m/z 199.1 (M-18+H), 181.8 (M-36+H); ESI$^-$ MS found for $C_8H_{17}BN_2O_4$ m/z 197.3 (M-18-H).

Step 2: (3R,4S)-3-amino-4-[3-(dihydroxyboryl)propyl]-1-[(4-fluorophenyl) carbamoyl]pyrrolidine-3-carboxylic acid hydrochloride (Racemate)

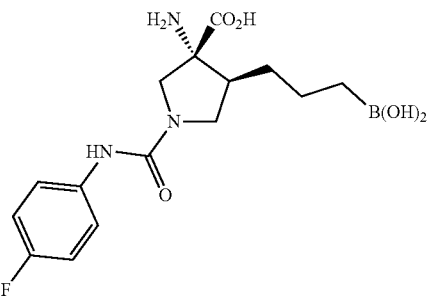 [SMILES: N[C@@]1(C(=O)O)CN(C(=O)Nc2ccc(F)cc2)C[C@@H]1CCCB(O)O]

While under nitrogen, a stirred mixture of (3R,4S)-3-amino-4-[3-(dihydroxyboryl)propyl]pyrrolidine-3-carboxylic acid dihydrochloride (0.225 g, 0.623 mmol) in dry DMF (9 mL) was treated with $Et_3N$ (0.521 mL, 3.74 mmol) and 4-fluorophenyl isocyanate (92.1 uL, 0.810 mmol). After stirring for 1.5 h, the reaction mixture was diluted with water (5 mL) and acidified to pH ~1 with 3M aqueous HCl (5 mL). The aqueous phase was washed with methylene chloride (2×25 mL) and ethyl acetate (25 mL), concentrated and purified by reverse phase HPLC. Product fractions were pooled, concentrated, re-dissolved in 1M aqueous HCl, concentrated and lyophilized to give (3R,4S)-3-amino-4-[3-

(dihydroxyboryl)propyl]-1-[(4-fluorophenyl)carbamoyl]pyrrolidine-3-carboxylic acid hydrochloride (racemate) (65 mg, 27%) as a white amorphous solid. MS (ESI+) m/z 336 (M−H$_2$O+H+), 318 (M−2H$_2$O+H$^+$) and MS (ESI−) m/z 334 (M−H$_2$O+H$^+$).

Example 49: preparation of (3R,4S)-3-amino-4-(3-boronopropyl)-1-((7-chloro-1,2,3,4-tetrahydroisoquinolin-3-yl)methyl)pyrrolidine-3-carboxylic acid (Mixture of Two Diastereomers; Each a Racemate)

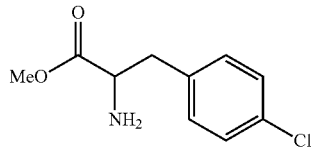 [SMILES: COC(=O)C(N)Cc1ccc(Cl)cc1]

Step 1: Methyl 2-amino-3-(4-chlorophenyl)propanoate hydrochloride

While under nitrogen, a stirred suspension of 4-chlorophenylalanine (2.50 g, 12.5 mmol) in anhydrous methanol (18 mL) was cooled in an ice-water bath and carefully treated with thionyl chloride (1.00 mL, 13.8 mmol). After stirring for 10 min, and the cooling bath was removed and the mixture was allowed to warm to room temperature. A reflux condenser was attached, and the slurry was warmed to 55° C. After stirring overnight, the mixture was cooled to room temperature, concentrated and dried under reduced pressure to give methyl 2-amino-3-(4-chlorophenyl)propanoate hydrochloride (3.13 g, 99%) as a white solid. ESI$^+$ MS found for C$_{10}$H$_{12}$ClNO$_2$ m/z 214.0 (M+H).

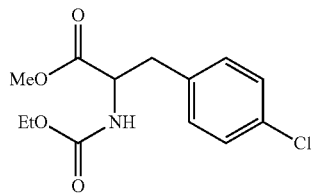 [SMILES: CCOC(=O)NC(Cc1ccc(Cl)cc1)C(=O)OC]

Step 2: Methyl 3-(4-chlorophenyl)-2-(ethoxycarbonylamino)propanoate

While under nitrogen, a stirred mixture of methyl 2-amino-3-(4-chlorophenyl)propanoate hydrochloride (3.13 g, 12.5 mmol) in methylene chloride (42 mL) was cooled in an ice-water bath and carefully treated with pyridine (2.23 mL, 27.5 mmol) and ethyl chloroformate (1.27 mL, 13.3 mmol). After stirring for 1 h, the solution was diluted with ethyl acetate (50 mL) and water (50 mL), and the layers were separated. The aqueous phase was re-extracted with ethyl acetate (2×25 mL), and the combined organic phase was washed with saturated aqueous sodium chloride (25 mL), dried over Na$_2$SO$_4$ and concentrated under reduced pressure to give methyl 3-(4-chlorophenyl)-2-(ethoxycarbonylamino)propanoate (3.56 g, 99%) as a white solid. $^1$H NMR (CDCl$_3$, 400 MHz) δ 7.28 (m, 2H), 7.08 (m, 2H), 5.12 (m, 1H), 4.65 (m, 1H), 4.13 (q, J=8 Hz, 2H), 3.74 (s, 3H), 3.10 (qd, J=16, 4.0 Hz, 2H), 1.25 (t, J=8 Hz, 3H). LC-MS gives ESI$^+$ MS found for C$_{13}$H$_{16}$ClNO$_4$ nm/z 308.0 (M+Na), 286.0 (M+H).

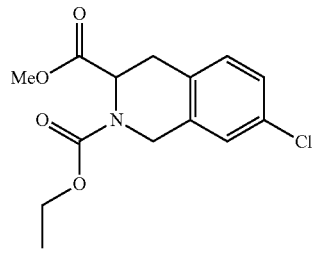 [SMILES: CCOC(=O)N1Cc2cc(Cl)ccc2CC1C(=O)OC]

Step 3: 2-Ethyl 3-methyl 7-chloro-3,4-dihydroisoquinoline-2,3(1H)-dicarboxylate

A mixture of methyl 3-(4-chlorophenyl)-2-(ethoxycarbonylamino)propanoate (3.55 g, 12.4 mmol) in acetic acid (12 mL) and sulfuric acid (4 mL) was treated with paraformaldehyde (0.392 g, 13.0 mmol). After stirring at room temperature overnight, the mixture was added to ice (50-60 g), diluted with water (30 mL) and extracted with ethyl acetate (3× ~50 mL). The combined organic phase was washed with saturated aqueous sodium chloride (25 mL), dried over MgSO$_4$ and concentrated. Purification by silica gel chromatography (90 g column, 25-50% ethyl acetate in hexanes) gave 2-ethyl 3-methyl 7-chloro-3,4-dihydroisoquinoline-2,3(1H)-dicarboxylate (2.19 g, 59%) as a clear, viscous oil. $^1$H NMR (CDCl$_3$, 400 MHz) δ 7.12 (m, 3H), 5.20 (m, ~0.6H), 4.98 (m, ~0.4H), 4.76 (m, 1H), 4.53 (m, 1H), 4.25 (m, 2H), 3.65 (s, 3H), 3.20 (m, 2H), 1.35 (t, J=7 Hz, ~1.8H), 1.28 (t, J=7 Hz, ~1.2 H) (mixture of rotamers). ESI$^+$ MS found for C$_{14}$H$_{16}$ClNO$_4$ m/z 298.0 (M+H, weak).

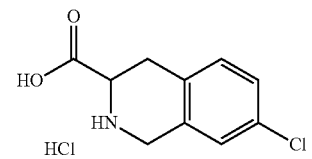 [SMILES: O=C(O)C1Cc2ccc(Cl)cc2CN1 ; Cl]

Step 4: 7-chloro-1,2,3,4-tetrahydroisoquinoline-3-carboxylic acid hydrochloride

A mixture of 2-ethyl 3-methyl 7-chloro-3,4-dihydroisoquinoline-2,3(1H)-dicarboxylate (2.19 g, 7.36 mmol) in 6 M aqueous HCl (30 mL) was heated to 100-105° C. for 2 days. The resulting mixture was concentrated under reduced pressure and triturated with toluene (2×100 mL). Once the supernatant was removed, the solid residue was dried under high vacuum to give 7-chloro-1,2,3,4-tetrahydroisoquinoline-3-carboxylic acid hydrochloride (1.71 g, 94%) as a faint yellow solid which was used in the next step without further purification. $^1$H NMR (DMSO-d$_6$, 400 MHz) δ 14.2 (bs, ~1H), 10.0 (bs, ~2H), 7.41 (s, 1H), 7.32 (m, 2H), 4.40 (m, 1H), 4.32 (m, 2H), 3.32 (dd, J=17, 4.9 Hz, 1H), 3.10 (dd, J=17, 11 Hz). LC-MS gives ESI$^+$ MS found for C$_{10}$H$_{10}$ClNO$_2$ m/z 212.1 (M+H).

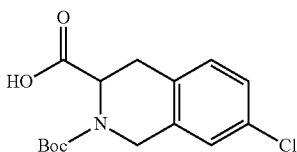 [SMILES: CC(C)(C)OC(=O)N1Cc2cc(Cl)ccc2CC1C(=O)O]

Step 5: 2-(tert-Butoxycarbonyl)-7-chloro-1,2,3,4-tetrahydroisoquinoline-3-carboxylic acid A solution of 7-chloro-1,2,3,4-tetrahydroisoquinoline-3-carboxylic acid hydrochloride (1.70 g, 6.85 mmol) in 1,4-dioxane (11 mL) and 1 M aqueous NaOH (22.3 mL, 22.3 mmol) was cooled in an ice-water bath and treated with a second solution of di-tert-butyldicarbonate (1.87 g, 8.56 mmol) in 1,4-dioxane (11 mL). After 15 min and the cooling bath was removed and stirring was continued for 2 h. The resulting mixture was diluted with water (25 mL) and washed with ethyl acetate (50 mL). The aqueous phase was adjusted to pH ~3 with 1M citric acid and extracted with ethyl acetate (2×75 mL). The combined organic phase was washed with saturated aqueous sodium chloride (50 mL), dried over MgSO$_4$ and concentrated under reduced pressure. The residue was purified by silica gel chromatography (90 g column, 25-75% ethyl acetate in hexanes) to give 2-(tert-butoxycarbonyl)-7-chloro-1,2,3,4-tetrahydroisoquinoline-3-carboxylic acid (1.61 g, 79%) as a white solid. $^1$H NMR (DMSO-d$_6$, 400 MHz) δ 12.8 (s, 1H), 7.34 (m, 1H), 7.24 (m, 2H), 4.88 (m, ~0.5H), 4.67 (m, ~0.5H), 4.50 (m, 2H), 3.10 (m, 2H), 1.46 (s, ~4.5H), 1.40 (s, ~4.5H) (mixture of rotamers). LC-MS gives ESI$^-$ MS found for C$_{15}$H$_{18}$ClNO$_4$ m/z 310.1 (M–H).

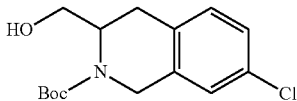

Step 6: tert-Butyl 7-chloro-3-(hydroxymethyl)-3,4-dihydroisoquinoline-2(1H)-carboxylate While under nitrogen, a flame-dried flask was charged with 2-(tert-butoxycarbonyl)-7-chloro-1,2,3,4-tetrahydroisoquinoline-3-carboxylic acid (400 mg, 1.28 mmol) and anhydrous THF (2.5 mL), cooled in an ice-saturated aqueous sodium chloride bath and carefully treated with a solution of borane in THF (1 M, 2.63 mL, 2.63 mmol). The resulting mixture was stirred at 0° C. for ~1.5 h and then at room temperature overnight. The mixture was then cooled in an ice-water bath, quenched slowly by the dropwise addition of water until most gas evolution ceased, diluted with additional water (15 mL) and extracted with ethyl acetate (2×25 mL). The combined organic phase was washed with saturated aqueous NaHCO$_3$ (10 mL), water (10 mL) and saturated aqueous sodium chloride (10 mL), dried over Na$_2$SO$_4$ and concentrated under reduced. Purification by silica gel chromatography (40 g column, 10-20% ethyl acetate in methylene chloride) gave tert-butyl 7-chloro-3-(hydroxymethyl)-3,4-dihydroisoquinoline-2(1H)-carboxylate (292 mg, 76%) as a clear gum. $^1$H NMR (DMSO-d$_6$, 400 MHz) δ 7.29 (m, 1H), 7.20 (m, 1H), 4.81 (m, 1H), 4.64 (d, J=17 Hz, 1H), 4.20 (bm, 2H), 3.30 (m, 1H), 3.12 (m, 1H), 2.84 (m, 2H), 1.43 (s, 9H).

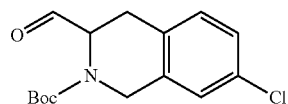 [SMILES: CC(C)(C)OC(=O)N1Cc2cc(Cl)ccc2CC1C=O]

Step 7: tert-Butyl 7-chloro-3-formyl-3,4-dihydroisoquinoline-2(1H)-carboxylate While under nitrogen, a stirred solution of tert-butyl 7-chloro-3-(hydroxymethyl)-3,4-dihydroisoquinoline-2(1H)-carboxylate (Step 6, 270 mg, 0.907 mmol) in methylene chloride (11 mL) was cooled in an ice-water bath and treated dropwise with a solution of Dess-Martin periodinane (461 mg, 1.09 mmol) in methylene chloride (3 mL) over several minutes. The cooling bath was removed, and the resulting clear mixture was stirred at room temperature for 1.5 h. Once complete, the mixture was re-cooled in an ice-water bath, quenched portionwise with a 1:1 mixture of saturated aqueous Na$_2$S$_2$O$_3$ and saturated aqueous NaHCO$_3$ (20 mL total) and stirred for 10 min at room temperature. The layers were separated, the aqueous phase was re-extracted with methylene chloride (20 mL), and the combined organic phase was washed with saturated aqueous sodium chloride (10 mL), dried over Na$_2$SO$_4$ and concentrated under reduced pressure. Purification by silica gel chromatography (40 g column, 10-30% ethyl acetate in hexanes) gave tert-butyl 7-chloro-3-formyl-3,4-dihydroisoquinoline-2(1H)-carboxylate (162 mg, 60%) as a clear gum. 1H NMR (DMSO-d$_6$, 400 MHz) δ 9.45 (bs, 1H), 7.34 (m, 1H), 7.26 (m, 2H), 4.78 (m, ~0.5H), 4.64 (m, ~0.5H), 4.50 (m, 2H), 3.21 (m, 1H), 3.05 (m, 1H), 1.46 (s, ~4.5H), 1.38 (s, ~4.5H) (mixture of rotamers).

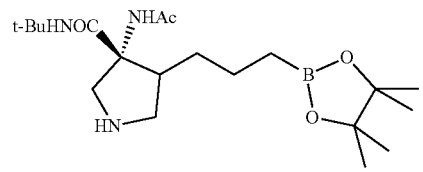

Step 8: (3R,4S)-3-Acetamido-N-tert-butyl-4-[3-(4,4,5,5-tetramethyl-1,3,2-dioxaborolan-2-yl)propyl]pyrrolidine-3-carboxamide hydrochloride (Racemate)

While under nitrogen, a stirred solution of tert-butyl (3R,4S)-3-acetamido-3-(tert-butylcarbamoyl)-4-[3-(4,4,5,5-tetramethyl-1,3,2-dioxaborolan-2-yl)propyl]pyrrolidine-1-carboxylate (400 mg, 0.807 mmol) in anhydrous THF (5 mL) was treated with 4 M HCl in 1,4-dioxane (3.03 mL, 12.1 mmol). After 2.5 h, the mixture was diluted with diethyl ether (15 mL) and filtered, washed with additional ether and concentrated to give (3R,4S)-3-acetamido-N-tert-butyl-4-[3-(4,4,5,5-tetramethyl-1,3,2-dioxaborolan-2-yl)propyl]pyrrolidine-3-carboxamide hydrochloride (340 mg, 97%) as a white solid. $^1$H NMR (D$_2$O, 400 MHz) δ 4.11 (d, J=12 Hz, 1H), 3.58 (dd, J=11.5, 7.7 Hz, 1H), 3.19 (d, J=12 Hz, 1H), 3.01 (t, J=11.5, 1H), 2.42 (m, 1H), 1.92 (s, 3H), 1.52 (m, 1H), 1.30 (m, 2H), 1.19 (s, 9H), 1.16 (s, 12H), 1.08 (m, 1H), 0.75 (m, 2H). LC-MS gives ESI+ MS found for C$_{20}$H$_{38}$BN$_3$O$_4$ m/z 396.1 (M+H).

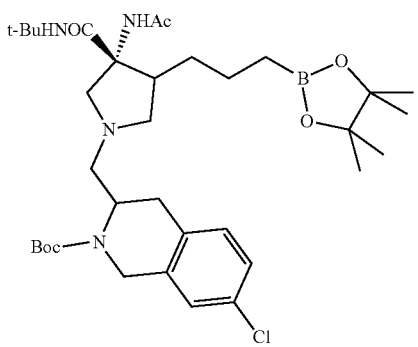

Step 9: tert-Butyl 3-({(3R,4S)-3-acetamido-3-(tert-butylcarbamoyl)-4-[3-(4,4,5,5-tetramethyl-1,3,2-dioxaborolan-2-yl)propyl]pyrrolidin-1-yl}methyl)-7-chloro-3,4-dihydroisoquinoline-2 (1H)-carboxylate A stirred mixture of (3R,4S)-3-acetamido-N-tert-butyl-4-[3-(4,4,5,5-tetramethyl-1,3,2-dioxaborolan-2-yl)propyl]pyrrolidine-3-carboxamide hydrochloride (226 mg, 0.524 mmol) and Et₃N (0.110 mL, 0.786 mmol) in methylene chloride (2.5 mL) was treated with a solution of tert-butyl 7-chloro-3-formyl-3,4-dihydroisoquinoline-2(1H)-carboxylate (155 mg, 0.524 mmol) in methylene chloride (2.5 mL). After stirring for 20 min, sodium triacetoxyborohydride (233 mg, 1.10 mmol) was added and stirring was continued for 1 h. The resulting mixture was carefully quenched with saturated aqueous NaHCO₃ (5 mL), diluted with saturated aqueous sodium chloride (15 mL) and extracted with methylene chloride (4×15 mL). The combined organic phase was dried over Na₂SO₄ and concentrated. Purification by silica gel chromatography (40 g column, 2-4% MeOH in ethyl acetate) gave tert-butyl 3-({(3R,4S)-3-acetamido-3-(tert-butylcarbamoyl)-4-[3-(4,4,5,5-tetramethyl-1,3,2-dioxaborolan-2-yl)propyl]pyrrolidin-1-yl}methyl)-7-chloro-3,4-dihydroisoquinoline-2(1H)-carboxylate (296 mg, 84%, mixture of diastereomers) as a clear gum. LC-MS gives ESI⁺ MS found for $C_{35}H_{56}BClN_4O_6$ m/z 675.4 (M+H).

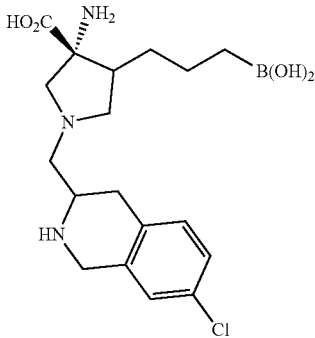 [SMILES: N[C@@]1(C(=O)O)CN(CC2Cc3ccc(Cl)cc3CN2)CC1CCCB(O)O]

Step 10: (3R,4S)-3-Amino-1-[(7-chloro-1,2,3,4-tetrahydroisoquinolin-3-yl)methyl]-4-[3-(dihydroxyboryl)propyl]pyrrolidine-3-carboxylic acid trihydrochloride (Mixture of 2 Diastereomers, Each a Racemate)

In an Ace pressure tube, a solution of tert-butyl 3-({(3R,4S)-3-acetamido-3-(tert-butylcarbamoyl)-4-[3-(4,4,5,5-te-tramethyl-1,3,2-dioxaborolan-2-yl)propyl]pyrrolidin-1-yl}methyl)-7-chloro-3,4-dihydroisoquinoline-2(1H)-carboxylate (280 mg, 0.415 mmol) was treated with concentrated HCl (8 mL) and stirred at room temperature. After 10 min the tube was sealed, and the mixture was heated to ~118° C. for 16 h. After cooling to room temperature, the solution was carefully diluted with water (20 mL) and washed with methylene chloride (2×15 mL). The aqueous phase was concentrated under reduced pressure, and the resulting residue purified by reverse phase HPLC. Product fractions (mixture of diastereomers) were pooled and concentrated. The residue was reconstituted in 1 M HCl and re-concentrated. The resulting residue was diluted with deionized water and lyophilized to give (3R,4 S)-3-amino-1-[(7-chloro-1,2,3,4-tetrahydroisoquinolin-3-yl)methyl]-4-[3-(dihydroxyboryl)propyl]-pyrrolidine-3-carboxylic acid trihydrochloride (mixture of 2 diastereomers, each a racamate) (102 mg, 49%) as a faint yellow amorphous solid. ¹H NMR (0.1M DCl in D₂O, 400 MHz) δ 7.23 (m, 1H), 7.15 (m, 2H), 4.37 (s, 2H), 4.00 (m, 3H), 3.84 (m, 2H), 3.69 (m, 1H), 3.43 (m, 1H), 3.22 (m, 1H), 2.98 (m, 1H), 2.68 (m, 1H), 1.60 (m, 1H), 1.25 (m, 3H), 0.64 (m, 2H). ESI⁺ MS found for $C_{18}H_{27}BClN_3O_4$ m/z 378.1 (M 18+H), 360.1 (M−36+H); ESI⁻ MS m/z 376.2 (M−18−H).

Example 50: preparation of (3R,4S)-3-amino-1-(2-aminophenylsulfonyl)-4-(3-boronopropyl)pyrrolidine-3-carboxylic acid

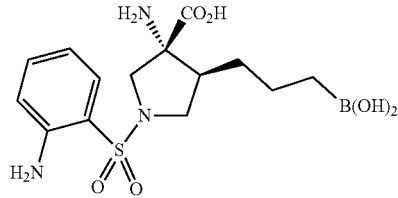 [SMILES: Nc1ccccc1S(=O)(=O)N1C[C@H](CCCB(O)O)[C@](N)(C(=O)O)C1]

(3R,4S)-3-amino-1-(2-aminophenylsulfonyl)-4-(3-boronopropyl)pyrrolidine-3-carboxylic acid was prepared in a manner analogous to that set fourth in Example 46 except 2-nitrobenzene-1-sulfonyl chloride was used as the acylating agent in step 4. LC-MS ESI⁻ MS found for $C_{14}H_{20}BN_3O_8S$ m/z 400.1 (M−H).

Example 51: preparation of (3R,4S)-3-amino-4-(3-boronopropyl)-1-((6-chloro-1,2,3,4-tetrahydroisoquinolin-3-yl)methyl)pyrrolidine-3-carboxylic acid

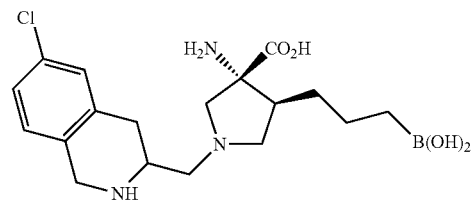 [SMILES: N[C@@]1(C(=O)O)CN(CC2Cc3cc(Cl)ccc3CN2)C[C@@H]1CCCB(O)O]

(3R,4S)-3-amino-4-(3-boronopropyl)-1-((6-chloro-1,2,3,4-tetrahydroisoquinolin-3-yl)methyl)pyrrolidine-3-carboxylic acid trihydrochloride (mixture of two diastereomers, each a racemate) is prepared in a manner analogous to that set forth in Example 49, except 3-chlorophenylalanine is used in place of 4-chlorophenylalanine in Step 1. ¹H NMR (0.1M DCl in D₂O, 400 MHz) δ 7.23 (m, 2H), 7.09 (m, 1H), 4.37 (s, 2H), 4.00 (m, 3H), 3.82 (m, 2H), 3.69 (m, 1H), 3.43 (m, 1H), 3.22 (m, 1H), 3.00 (m, 1H), 2.68 (m, 1H), 1.60 (m, 1H), 1.26 (m, 3H), 0.66 (m, 2H). ESI+ MS found for $C_{18}H_{27}BClN_3O_4$ m/z 378.1 (M−18+H), 360.0 (M−36+H); ESI⁻ MS m/z 376.1 (M−18−H).

Example 52: preparation of (3R,4S)-3-amino-1-(2-(biphenyl-4-ylamino)ethyl)-4-(3-boronopropyl)pyrrolidine-3-carboxylic acid

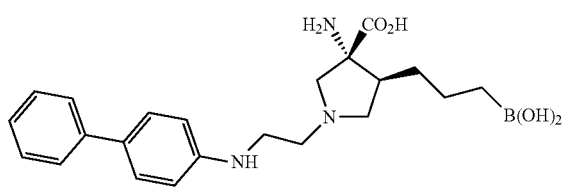 [SMILES: N[C@@]1(C(=O)O)CN(CCNc2ccc(-c3ccccc3)cc2)C[C@@H]1CCCB(O)O]

A stirred solution of (3R,4S)-3-acetamido-N-tert-butyl-4-(3-(4,4,5,5-tetramethyl-1,3,2-dioxaborolan-2-yl)propyl)pyrrolidine-3-carboxamide (Example 8, step 4) (198 mg, 0.50 mmol) and N-(4-phenyl)benzyl-N-BOC-glycinaldehyde (244 mg, 0.75 mmol) in anhydrous 1,2-dichloroethane (5 mL) was stirred at room temperature for 1 h, then cooled by ice bath and treated with sodium triacetoxyborohydride (212 mg, 1.0 mmol) and stirred for 18h at room temperature. Aqueous sodium carbonate (10%, 5 mL) was added and the mixture stirred for a few minutes and extracted with ethyl acetate (30 mL, then 2×10 mL). The combined organic solution was washed with water and brine (20 mL each), dried (MgSO₄), and concentrated in vacuo. The crude material was deprotected and isolated using the method described for example 8, step 5 to afford (3R,4S)-3-amino-1-(2-(biphenyl-4-ylamino)ethyl)-4-(3-boronopropyl)pyrrolidine-3-carboxylic acid (72 mg, 27%) as a voluminous white solid. NMR (D₂O) δ 7.60-7.75 (m, 4H), 7.30-7.55 (m, 5H), 4.27 (s, 2H), 3.94 (d, J=12.5 Hz, 1H), 3.82 (dt, J₁=11 Hz, J₂=8 Hz, 1H), 3.60-3.75 (m, 3H), 3.45 (m, 2H), 3.37 (t, J=11 Hz, 1H), 2.50-2.65 (m, 1H), 1.50-1.65 (m, 1H), 1.10-1.35 (m, 3H), 0.60-0.70 (m, 2H). MS (m+1): 426.1; MS (m−H₂O+1): 408.1.

Example 53: preparation of (3R,4S)-3-amino-4-(3-boronopropyl)-1-(1,2,3,4-tetrahydroisoquinoline-3-carbonyl)pyrrolidine-3-carboxylic acid

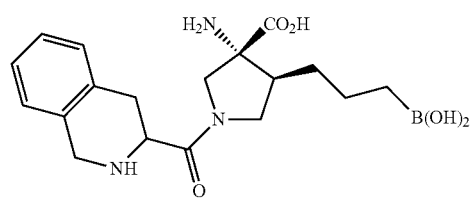 [SMILES: N[C@@]1(C(=O)O)CN(C(=O)C2Cc3ccccc3CN2)C[C@@H]1CCCB(O)O]

(3R,4S)-3-amino-4-(3-boronopropyl)-1-(1,2,3,4-tetrahydroisoquinoline-3-carbonyl)pyrrolidine-3-carboxylic acid was prepared in a manner analogous to that set forth in Example 46, except 2-(tert-butoxycarbonyl)-1,2,3,4-tetrahydroisoquinoline-3-carboxylic acid was used as the acylating agent in step 4. omers, each a racemate) (43 mg, 12% overall for 3 steps) as a pale yellow amorphous solid. MS (ESI+) m/z 375 (M−H₂O+H+), 392.

Example 54: preparation of (3R,4S)-3-amino-4-[3-(dihydroxyboryl)propyl]-1 [4-(trifluoromethyl)phenylalanyl]pyrrolidine-3-carboxylic acid dihydrochloride (Mixture of Two Diastereomers; Each a Racemate)

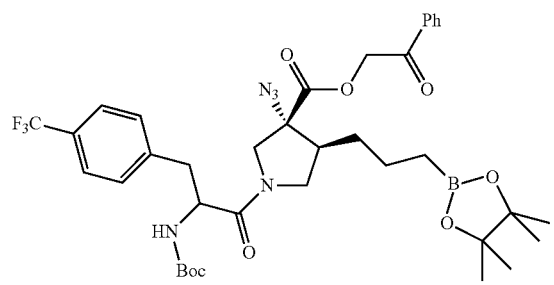 [SMILES: CC(C)(C)OC(=O)NC(Cc1ccc(C(F)(F)F)cc1)C(=O)N1C[C@H](CCCB2OC(C)(C)C(C)(C)O2)[C@](N=[N+]=[N-])(C(=O)OCC(=O)c2ccccc2)C1]

Step 1: 2-Oxo-2-phenylethyl (3R,4S)-3-azido-1-[N-(tert-butoxycarbonyl)-4-(trifluoromethyl)phenylalanyl]-4-[3-(4,4,5,5-tetramethyl-1,3,2-dioxaborolan-2-yl)propyl]pyrrolidine-3-carboxylate A mixture of N-(tert-butoxycarbonyl)-4-(trifluoromethyl)phenylalanine (268 mg, 0.804 mmol), 1-hydroxybenzotriazole hydrate (123 mg, 0.804 mmol) and N-(3-dimethylaminopropyl)-N'-ethylcarbodiimide hydrochloride (154 mg, 0.804 mmol) in dry methylene chloride (10 mL) and DMF (3 mL) was stirred at room temperature. After 1 h, a second solution of racemic 2-oxo-2-phenylethyl (3R,4S)-3-azido-4-[3-(4,4,5,5-tetramethyl-1,3,2-dioxaborolan-2-yl)propyl]pyrrolidine-3-carboxylate hydrochloride (350 mg, 0.73 mmol) in methylene chloride (3.5 mL) was added, followed immediately by Et₃N (204 uL, 1.46 mmol), and the resulting homogeneous mixture was stirred at room temperature for 3.5 h. Once complete, the mixture was diluted with dichloromethane (8 mL), washed successively with water (2×20 mL), saturated aqueous NaHCO₃ (2×20 mL) and saturated aqueous sodium chloride, dried over Na₂SO₄ and concentrated. Purification by silica gel chromatography (90 g column, 15-35% ethyl acetate in hexanes) gave 2-oxo-2-phenylethyl (3R,4S)-3-azido-1-[N-(tert-butoxycarbonyl)-4-(trifluoromethyl)phenylalanyl]-4-[3-(4,4,5,5-tetramethyl-1,3,2-dioxaborolan-2-yl)propyl]pyrrolidine-3-carboxylate (233 mg, ~60% purity) as a white foam which was used without further purification. LC-MS ESI+ MS found for $C_{37}H_{47}BF_3N_5O_8$ m/z 758.3 (M+H), 780.3 (M+Na); ESI⁺ MS m/z 756.5 (M−H).

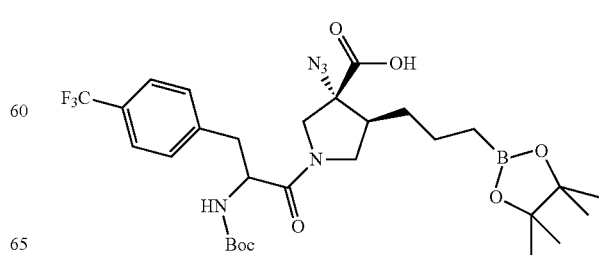

Step 2: (3R,4S)-3-Amino-1-[N-(tert-butoxycarbonyl)-4-(trifluoromethyl)phenylalanyl]-4-[3-(4,4,5,5-tetramethyl-1,3,2-dioxaborolan-2-yl)propyl]pyrrolidine-3-carboxylic acid A stirred solution of 2-oxo-2-phenylethyl (3R,4S)-3-azido-1-[N-(tert-butoxycarbonyl)-4-(trifluoromethyl)phenylalanyl]-4-[3-(4,4,5,5-tetramethyl-1,3,2-dioxaborolan-2-yl)propyl]pyrrolidine-3-carboxylate (Step 1) in acetic acid (9 mL) was treated with zinc (201 mg, 3.08 mmol, 10 equiv), and the heterogeneous mixture was stirred at room temperature. After 1.25 h, the reaction was filtered, the filter pad was washed with acetic acid and ethyl acetate, and the filtrate was concentrated and dried under reduced pressure to give the crude (3R,4S)-3-amino-1-[N-(tert-butoxycarbonyl)-4-(trifluoromethyl)phenylalanyl]-4-[3-(4,4,5,5-tetramethyl-1,3,2-dioxaborolan-2-yl)propyl]pyrrolidine-3-carboxylic acid (242 mg) as a clear film which was used without further purification. LC-MS ESI$^+$ MS found for $C_{29}H_{43}BF_3N_3O_7$ m/z 614.3 (M+H); ESI$^+$ MS m/z 612.3 (M–H).

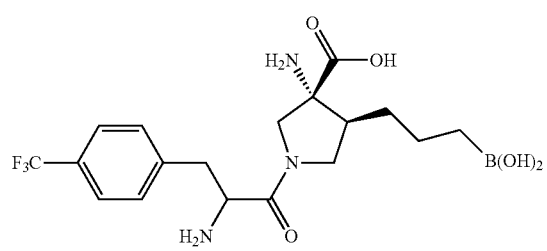 [SMILES: NC(Cc1ccc(C(F)(F)F)cc1)C(=O)N1C[C@H](CCCB(O)O)[C@](N)(C(=O)O)C1]

Step 3: (3R,4S)-3-amino-4-[3-(dihydroxyboryl)propyl]-1-[4-(trifluoromethyl)phenylalanyl]pyrrolidine-3-carboxylic acid dihydrochloride (Mixture of Two Diastereomers; Each a Racemate)

A solution of the crude (3R,4S)-3-amino-1-[N-(tert-butoxycarbonyl)-4-(trifluoromethyl)phenylalanyl]-4-[3-(4,4,5,5-tetramethyl-1,3,2-dioxaborolan-2-yl)propyl]pyrrolidine-3-carboxylic acid (Step 2, 242 mg) in anhydrous THF (6 mL) under nitrogen was treated with 4 N HCl in 1,4-dioxane (6 mL). After stirring for 2 h at room temperature, 1M aqueous HCl (6 mL) was added and stirring was contained for an additional 1.5 h. The reaction mixture was diluted with water (15 mL) and washed successively with ethyl acetate (25 mL) and methylene chloride (25 mL). The aqueous phase was concentrated and the residue was purified by reverse phase HPLC. Product fractions (mixture of diastereomers) were pooled and concentrated. The residue was reconstituted in 1 M HCl and re-concentrated. The resulting residue was diluted with deionized water and lyophilized to give give (3R,4S)-3-amino-4-[3-(dihydroxyboryl)propyl]-1-[4-(trifluoromethyl)phenylalanyl]-pyrrolidine-3-carboxylic acid dihydrochloride (mixture of two diastereomers, each a racemate) (43 mg, 12% overall for 3 steps) as a pale yellow amorphous solid. MS (ESI+) m/z 414 (M–H$_2$O+H+), 396 (M–2H$_2$O+H+); MS (ESI–) m/z 412 (M–H$_2$O–H+).

Example 55: preparation of (3R,4S)-3-amino-4-(3-boronopropyl)-1-((7-(trifluoromethyl)-1,2,3,4-tetrahydroisoquinolin-3-yl)methyl)pyrrolidine-3-carboxylic acid (Mixture of Two Diastereomers; Each a Racemate)

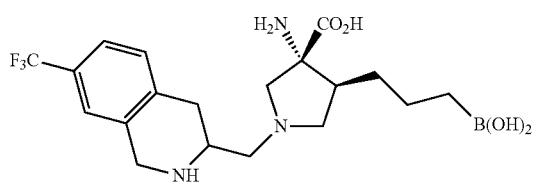 [SMILES: N[C@@]1(C(=O)O)CN(CC2Cc3ccc(C(F)(F)F)cc3CN2)C[C@@H]1CCCB(O)O]

(3R,4S)-3-Amino-4-(3-boronopropyl)-1-((7-(trifluoromethyl)-1,2,3,4-tetrahydroisoquinolin-3-yl)methyl)pyrrolidine-3-carboxylic acid is prepared in a manner analogous to that set forth in Example 51, except 4-(trifluoromethyl)-phenylalanine is used in place of 4-chlorophenylalanine in Step 1. $^1$H NMR (0.1M DCl in D$_2$O, 400 MHz) δ 7.53 (d, J=8.0 Hz, 1H), 7.49 (s, 1H), 7.34 (d, J=8.3 Hz, 1H), 4.46 (s, 2H), 4.08 (m, 2H), 3.97 (m, 1H), 3.83 (m, 2H), 3.71 (m, 1H), 3.44 (m, 1H), 3.34 (m, 1H), 3.07 (m, 1H), 2.69 (m, 1 H), 1.60 (m, 1H), 1.26 (m, 3H), 0.66 (m, 2H). ESI$^-$ MS found for $C_{19}H_{27}BF_3N_3O_4$ m/z 412.1 (M–18+H), 394.1 (M–36+H); ESI$^-$ MS m/z 410.2 (M–18–H).

Example 56: preparation of (3R,4S)-3-amino-4-(3-boronopropyl)-1-(7-chloro-1,2,3,4-tetrahydroisoquinoline-3-carbonyl)pyrrolidine-3-carboxylic acid

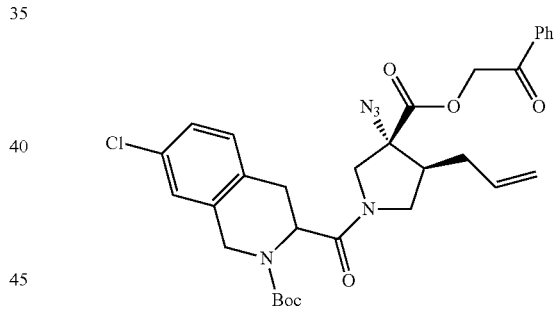

Step 1: tert-butyl 3-((3R,4S)-4-allyl-3-azido-3-((2-oxo-2-phenylethoxy)carbonyl)pyrrolidine-1-carbonyl)-7-chloro-3,4-dihydroisoquinoline-2 (1H)-carboxylate A stirred mixture of racemic 2-oxo-2-phenylethyl (3R,4S)-4-allyl-3-azidopyrrolidine-3-carboxylate hydrochloride (228 mg, 0.650 mmol) and 2-(tert-butoxycarbonyl)-7-chloro-1,2,3,4-tetrahydroisoquinoline-3-carboxylic acid (258 mg, 0.826 mmol) in methylene chloride (6 mL) was treated with Et$_3$N (0.272 mL, 1.95 mmol) followed by N,N,N',N'-tetramethyl-O-(7-azabenzotriazol-1-yl)uronium hexafluorophosphate (HATU, 321 mg, 0.845 mmol), and the resulting nearly homogeneous mixture was stirred at room temperature. After 1 h, the reaction was diluted with methylene chloride (20 mL), washed successively with water (20 mL), 1 N aqueous HCl (20 mL), saturated aqueous NaHCO$_3$ (20 mL) and saturated aqueous sodium chloride (10 mL), dried over Na$_2$SO$_4$, and concentrated. Purification by silica gel chromatography (40 g column, 15-25% ethyl acetate in hexanes) gave tert-butyl 3-({(3R,4S)-4-allyl-3-azido-3-[(2-oxo-2-phenylethoxy)carbonyl]pyrrolidin-1-yl}carbonyl)-7-chloro-3,4-dihydroisoquinoline-2(1H)-carboxylate (214 mg, 54%) as a pale amber film which was used without further purification. LC-MS ESI+ MS found for $C_{31}H_{34}ClN_5O_6$ m/z 608.2 (M+H), 630.3 (M+Na); ESI− MS m/z 606.3 (M−H).

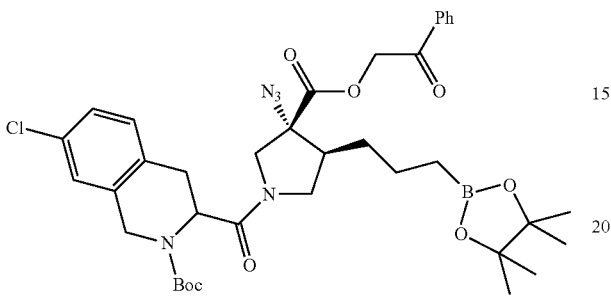

Step 2: tert-butyl 3-((3R,4S)-3-azido-3-((2-oxo-2-phenylethoxy)carbonyl)-4-(3-(4,4,5,5-tetramethyl-1,3,2-dioxaborolan-2-yl)propyl)pyrrolidine-1-carbonyl)-7-chloro-3,4-dihydroisoquinoline-2 (1H)-carboxylate tert-Butyl 3-((3R,4S)-3-azido-3-((2-oxo-2-phenylethoxy)carbonyl)-4-(3-(4,4,5,5-tetramethyl-1,3,2-dioxaborolan-2-yl)propyl)pyrrolidine-1-carbonyl)-7-chloro-3,4-dihydroisoquinolinc-2(1H)-carboxylate is prepared in a manner analogous to that set forth in Example 1, step 3 except tert-butyl 3-({(3R,4S)-4-allyl-3-azido-3-[(2-oxo-2-phenylethoxy)carbonyl]pyrrolidin-1-yl}carbonyl)-7-chloro-3,4-dihydroisoquinoline-2(1H)-carboxylate is used as the substrate. Following chromatography, the slightly impure material was used without further purification. LC-MS ESI+ MS found for $C_{37}H_{47}BClN_5O_8$ m/z 736.3 (M+H).

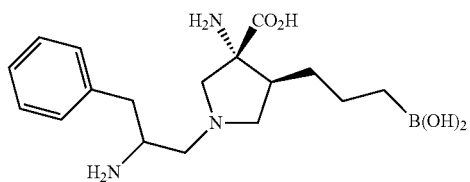 [SMILES: NC(Cc1ccccc1)CN1C[C@H](CCCB(O)O)[C@](N)(C(=O)O)C1]

Step 3: (3R,4S)-3-Amino-1-[(7-chloro-1,2,3,4-tetrahydroisoquinolin-3-yl) carbonyl]-4-[3-(dihydroxyboryl)propyl]pyrrolidine-3-carboxylic acid dihydrochloride (mixture of two diastereomers; each a racemate)

(3R,4S)-3-Amino-1-[(7-chloro-1,2,3,4-tetrahydroisoquinolin-3-yl)carbonyl]-4-[3-(dihydroxyboryl)propyl]pyrrolidine-3-carboxylic acid dihydrochloride (mixture of two diastereomers; each a racemate) is prepared in a manner analogous to that set forth in Example 54, Steps 2-3, except tert-butyl 3-({(3R,4S)-3-azido-3-[(2-oxo-2-phenylethoxy)carbonyl]-4-[3-(4,4,5,5-tetramethyl-1,3,2-dioxaborolan-2-yl)propyl]pyrrolidin-1-yl}carbonyl)-7-chloro-3,4-dihydroisoquinoline-2(1H)-carboxylate (Step 2) is used as the substrate.

Example 57: preparation of (3R,4S)-3-amino-1-(2-amino-3-phenylpropyl)-4-(3-boronopropyl)pyrrolidine-3-carboxylic acid (mixture of two diastereomers; each a racemate)

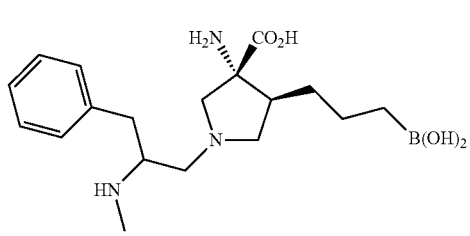 [SMILES: CNC(Cc1ccccc1)CN1C[C@H](CCCB(O)O)[C@](N)(C(=O)O)C1]

(3R,4S)-3-Amino-1-(2-amino-3-phenylpropyl)-4-[3-(dihydroxyboryl)propyl]pyrrolidine-3-carboxylic acid trihydrochloride (mixture of two diastereomers; each a racemate) is prepared in a manner analogous to that set forth in Example 54, Steps 1-3 except commercial N-(tert-butoxycarbonylamino)-phenylalanine is used in place of tert-butyl 7-chloro-3-(hydroxymethyl)-3,4-dihydroisoquinoline-2 (1H)-carboxylate. $^1$H NMR (0.1M DCl in $D_2O$, 400 MHz) δ 7.30 (m, 5H), 4.41 (s, 2H), 4.00 (m, 3H), 3.85 (m, 2H), 3.75 (m, 1H), 3.41 (m, 2H), 2.86 (m, 1H), 2.69 (m, 1H), 1.60 (m, 1H), 1.27 (m, 3H), 0.67 (m, 2H). ESI− MS found for $C_{17}H_{28}BN_3O_4$ m/z 332.2 (M−18+H), 314.2 (M−36 $(2H_2O)^+$ H); ESI− MS m/z 330.2 (M−18 ($H_2O$)−H).

Example 58: preparation of (3R,4S)-3-amino-4-(3-boronopropyl)-1-(2-(methylamino)-3-phenylpropanoyl)pyrrolidine-3-carboxylic acid (3R,4S)-3-amino-4-(3-boronopropyl)-1-(2-(methylamino)-3-phenylpropanoyl)pyrrolidine-3-carboxylic acid was prepared in a manner analogous to that set forth in Example 46, except 2-(tert-butoxycarbonyl(methyl)amino)-3-phenylpropanoic acid was used as the acylating agent in step 4. MS (ESI+) m/z 378 (M−H$_2$O+H+), 395.

Example 59: preparation of (3R,4S)-3-amino-1-[(5,7-dichloro-1,2,3,4-tetrahydroisoquinolin-3-yl)methyl]-4-[3-(dihydroxyboryl)propyl]pyrrolidine-3-carboxylic acid trihydrochloride (mixture of two diastereomers; each a racemate)

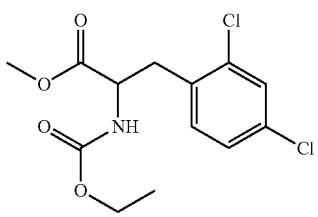 [SMILES: CCOC(=O)NC(Cc1ccc(Cl)cc1Cl)C(=O)OC]

Step 1: Methyl 2,4-dichloro-N-(ethoxycarbonyl)phenylalaninate

Methyl 2,4-dichloro-N-(ethoxycarbonyl)phenylalaninate is prepared in a manner analogous to that set forth in Example 51, Steps 1-2, except 2,4-dichlorophenylalanine is used in place of 4-chlorophenylalanine in Step 1. $^1$H NMR (DMSO-$d_6$, 400 MHz) δ 7.71 (d, J=8.4 Hz, 1H), 7.61 (s, 1H), 7.38 (m, 1H), 4.30 (m, 1H), 3.92 (m, 2H), 3.64 (s, 3H), 3.19 (m, 1H), 2.93 (m, 1H), 1.10 (t, J=7.1 Hz, 3H). LC-MS gives ESI$^+$ MS found for $C_{13}H_{15}Cl_2NO_4$ m/z 320.0 (M+H).

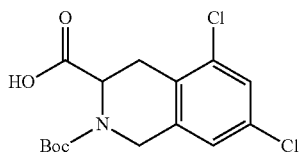 [SMILES: CC(C)(C)OC(=O)N1Cc2cc(Cl)cc(Cl)c2CC1C(=O)O]

Step 2: 2-(tert-Butoxycarbonyl)-5,7-dichloro-1,2,3,4-tetrahydroisoquinoline-3-carboxylic acid A mixture of methyl 2,4-dichloro-N-(ethoxycarbonyl)phenylalaninate (100 mg, 0.312 mmol) and paraformaldehyde (10.3 mg, 0.344 mmol) in acetic acid (0.90 mL) in a microwave tube was treated with conc. sulfuric acid (0.30 mL) (slight exotherm on mixing). The mixture was heated at 80° C. in the microwave for a total of 8 h, during which aliquots were checked by HPLC. The reaction mixture was then added to water (8 mL), and this aqueous phase was washed with methylene chloride (2×20 mL) and concentrated to give a ~4:1 mixture of the desired 5,7-dichloro-1,2,3,4-tetrahydroisoquinoline-3-carboxylic acid product and the 2,4-dichlorophenylalanine by-product in residual sulfuric acid.

A slurry of the crude 5,7-dichloro-1,2,3,4-tetrahydroisoquinoline-3-carboxylic acid in water (15 mL) was cooled in an ice bath, adjusted to pH ~8.5 with 50% aqueous NaOH, diluted with 1,4-dioxane (10 mL) and treated with a solution of di-tert-butyldicarbonate (530 mg, 2.43 mmol) in 1,4-dioxane (8 mL) quickly dropwise. The heterogeneous mixture was stirred at 0° C. for 10 min and then at room temperature overnight, giving a thick white mixture. HPLC indicated remaining starting material, so the reaction was treated with 2 N aqueous NaOH (0.48 mL, 0.96 mmol) and additional di-tert-butyldicarbonate (204 mg, 0.935 mmol). After stirring for 4 h, the mixture was diluted with water (25 mL) and washed with Et$_2$O (2×25 mL). The aqueous phase was adjusted to pH ~3 with 1 M aqueous citric acid and extracted with ethyl acetate (2×40 mL). The combined organic phase (Et$_2$O/ethyl acetate) was washed with saturated aqueous sodium chloride (10 mL), dried over MgSO$_4$ and concentrated. Purification by silica gel chromatography (40 g column, 15-45% ethyl acetate in hexanes) gave 2-(tert-butoxycarbonyl)-5,7-dichloro-1,2,3,4-tetrahydroisoquinoline-3-carboxylic acid (265 mg, 41%) as a white, partially crystalline solid. $^1$H NMR (DMSO-$d_6$, 400 MHz) δ 12.9 (s, 1H), 7.51 (m, 1H), 7.41 (m, 1H), 4.98 (m, ~0.5H), 4.80 (m, ~0.5H), 4.50 (m, 2H), 3.29 (m, 1H), 2.98 (m, 1H), 1.46 (s, ~4.5H), 1.41 (s, ~4.5H) (mixture of rotamers). LC-MS gives ESI$^-$ MS found for $C_{15}H_{17}Cl_2NO_4$ m/z 344.1 (M−H).

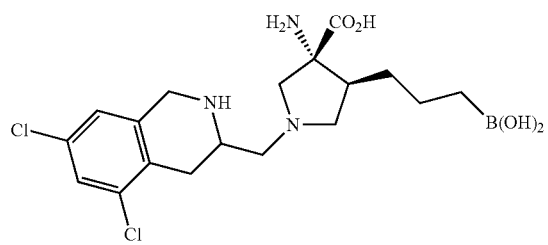 [SMILES: N[C@@]1(C(=O)O)CN(CC2Cc3c(Cl)cc(Cl)cc3CN2)C[C@@H]1CCCB(O)O]

Step 3: (3R,4S)-3-Amino-1-[(5,7-dichloro-1,2,3,4-tetrahydroisoquinolin-3-yl)methyl]-4-[3-(dihydroxyboryl)propyl]pyrrolidine-3-carboxylic acid trihydrochloride (mixture of two diastereomers; each a racemate)

(3R,4S)-3-amino-1-[(5,7-dichloro-1,2,3,4-tetrahydroisoquinolin-3-yl)methyl]-4-[3-(dihydroxyboryl)propyl]pyrrolidine-3-carboxylic acid trihydrochloride (mixture of two diastereomers, each a racemate) is prepared in a manner analogous to that set forth in Example 49, steps. $^1$H NMR (0.1M DCl in $D_2O$, 400 MHz) δ 7.43 (m, 1H), 7.17 (m, 1H), 4.41 (s, 2H), 4.00 (m, 3H), 3.85 (m, 2H), 3.75 (m, 1H), 3.41 (m, 2H), 2.86 (m, 1H), 2.69 (m, 1H), 1.60 (m, 1H), 1.27 (m, 3H), 0.67 (m, 2H). ESI$^+$ MS found for $C_{18}H_{26}BCl_2N_3O_4$ m/z 412.2 (M−18+H), 394.2 (M−36+H); ESI$^-$ MS m/z 410.3 (M−18−H).

Example 60: preparation of (3aR,4S,5S,6aR)-5-amino-4-(3-boronopropyl)octahydrocyclopenta[c]pyrrole-5-carboxylic acid

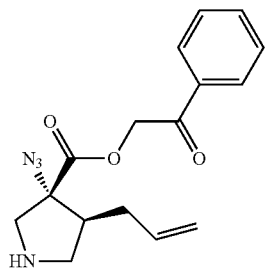 [SMILES: C=CC[C@H]1CNC[C@@]1(N=[N+]=[N-])C(=O)OCC(=O)c1ccccc1]

Step 1: 2-Oxo-2-phenylethyl (3R,4S)-4-allyl-3-azidopyrrolidine-3-carboxylate trifluoroacetate (racemic)

While under nitrogen, a solution of racemic 1-tert-butyl 3-(2-oxo-2-phenylethyl) (3R,4S)-4-allyl-3-azidopyrrolidine-1,3-dicarboxylate (0.425 g, 1.02 mmol) in methylene chloride (4 mL) was treated with trifluoroacetic acid (1.2 mL, 15 mmol) quickly dropwise, and the resulting homogeneous mixture was stirred at room temperature. After 40 min, the mixture was concentrated under reduced pressure and dried under high vacuum for several hours to give crude racemic 2-oxo-2-phenylethyl (3R,4S)-4-allyl-3-azidopyrrolidine-3-carboxylate trifluoroacetate as a dark amber viscous oil which was used immediately in the next step. LC-MS ESI+ MS found for $C_{16}H_{18}N_4O_3$ m/z 315.2 (M+H). $^1$H NMR (CDCl$_3$, 400 MHz) δ 7.92 (m, 2H), 7.69 (m, 1H), 7.55 (m, 2H), 5.75 (m, 1H), 5.62 (m, 2H), 5.24 (d, J=17 Hz, 1H), 5.20 (d, J=10.2 Hz, 1H), 4.08 (m, 1H), 3.80 (m, 1H), 3.55 (m, 2H), 2.80 (m, 1H), 2.63 (m, 1H), 2.27 (m, 1H).

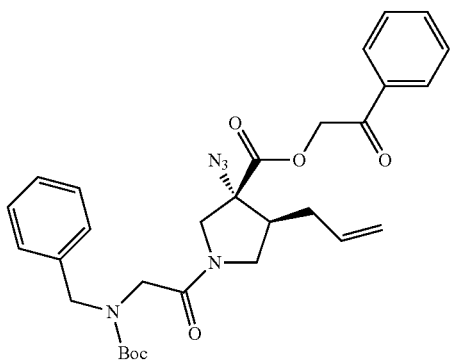 [SMILES: C=CC[C@H]1CN(C(=O)CN(Cc2ccccc2)C(=O)OC(C)(C)C)C[C@@]1(N=[N+]=[N-])C(=O)OCC(=O)c1ccccc1]

Step 2: 2-Oxo-2-phenylethyl (3R,4S)-4-allyl-3-azido-1-[N-benzyl-N-(tert-butoxycarbonyl)glycyl]pyrrolidine-3-carboxylate A stirred mixture of the crude racemic 2-oxo-2-phenylethyl (3R,4S)-4-allyl-3-azidopyrrolidine-3-carboxylate trifluoroacetate (Step 1, ~1 mmol) and N-benzyl-N-(tert-butoxycarbonyl)glycine (337 mg, 1.27 mmol) in methylene chloride (9 mL) was treated with Et$_3$N (0.495 mL, 3.55 mmol) followed by N,N,N',N'-tetramethyl-O-(7-azabenzotriazol-1-yl)uronium hexafluorophosphate (HATU, 502 mg, 1.32 mmol), and the resulting mixture was stirred at room temperature and monitored by HPLC. At 1 h, the reaction was diluted with methylene chloride (20 mL), washed with water (20 mL), 1N aqueous HCl (10 mL), saturated aqueous NaHCO$_3$ (20 mL) and saturated aqueous sodium chloride (10 mL), dried over Na$_2$SO$_4$, and concentrated under reduced pressure. Purification by silica gel chromatography (40 g column, 15-30% ethyl acetate in hexanes) gave 2-oxo-2-phenylethyl (3R,4S)-4-allyl-3-azido-1-[N-benzyl-N-(tert-butoxycarbonyl)glycyl]pyrrolidine-3-carboxylate (365 mg, 64%) as an amber gum which was used as is in the next step. LC-MS ESI+ MS found for $C_{30}H_{35}N_5O_6$ m/z 562.3 (M+H), 584.3 (M+Na). $^1$H NMR (CDCl$_3$, 400 MHz) δ 7.92 (m, 2H), 7.66 (m, 1H), 7.53 (m, 2H), 7.30 (m, 5H), 5.75 (m, 1H), 5.52 (m, 2H), 5.12 (m, 2H), 4.58 (m, 2H), 4.22-3.42 (m, 6H), 2.60 (m, 1H), 2.50 (m, 1H), 2.12 (m, 1H), 1.48 (s, 9H).

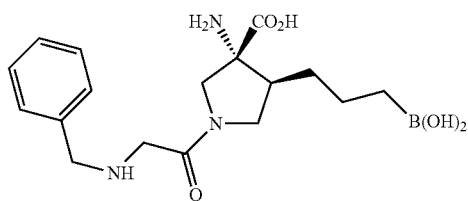 [SMILES: N[C@@]1(C(=O)O)CN(C(=O)CNCc2ccccc2)C[C@@H]1CCCB(O)O]

Step 3: (3R,4S)-3-Amino-1-(N-benzylglycyl)-4-[3-(dihydroxyboryl)propyl]pyrrolidine-3-carboxylic acid dihydrochloride (mixture of two diastereomers; each a racemate)

(3R,4S)-3-Amino-1-(N-benzylglycyl)-4-[3-(dihydroxyboryl)propyl]pyrrolidine-3-carboxylic acid dihydrochloride (mixture of two diastereomers; each a racemate) is prepared in a manner analogous to that set forth in Example 23, Steps 2-3, except 2-oxo-2-phenylethyl (3R,4S)-4-allyl-3-azido-1-[N-benzyl-N-(tert-butoxycarbonyl)glycyl]pyrrolidine-3-carboxylate (Step 2) is used in place of tert-butyl 3-({(3R,4S)-4-allyl-3-azido-3-[(2-oxo-2-phenylethoxy)carbonyl]pyrrolidin-1-yl}carbonyl)-7-chloro-3,4-dihydroisoquinoline-2(1H)-carboxylate. MS (ESI+) m/z 346 (M−H$_2$O+H+), 328 (M−2H$_2$O+H+); MS (ESI−) m/z 344 (M−H$_2$O−H+).

Example 61: preparation of (1S,2S,4S)-1,4-diamino-2-(3-boronopropyl) cyclopentanecarboxylic acid (racemic)

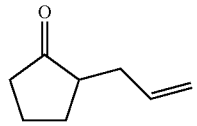

Step 1: 2-allylcyclopentanone

A stirred solution of methyl 2-carboxycyclopentanone (35.5 g, 250 mmol) in acetone (500 mL) was treated with anhydrous potassium carbonate (138 g, 1.0 mol) and allyl bromide (100 mL, 1.15 mol) and refluxed for 5 h. The mixture was cooled and filtered through Celite® (rinse filter cake with acetone), and the filtrate was concentrated in vacuo. The residual oil was dissolved in methanol (450 mL), treated with 6 N HCl (250 mL), and refluxed for 40 h. The solution was cooled to room temperature, concentrated in vacuo to remove most methanol, and diluted with water (200 mL). The aqueous solution was extracted with dichloromethane (3×250 mL), and the combined organic solution was washed with water, saturated aqueous sodium bicarbonate, and saturated aqueous sodium chloride (200 mL each), dried (Na$_2$SO$_4$), and gently (volatile product) concentrated in vacuo to 75 mL volume. This solution was loaded onto a silica gel column (~500 cc) and eluted with dichloromethane to afford (after gentle concentration of fractions) 2-allylcyclopentanone (27.3 g, 88%) as a colorless oil. NMR (CDCl$_3$): δ 5.65-5.75 (m, 1H), 4.90-5.05 (m, 2H), 2.40-2.50 (m, 1H), 2.20-2.30 (m, 1H), 1.85-2.15 (m, 5H), 1.65-1.75 (m, 1H), 1.45-1.55 (m, 1H).

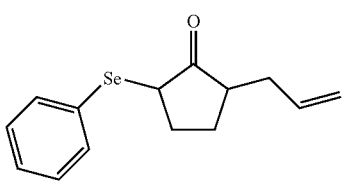 [SMILES: C=CCC1CCC([Se]c2ccccc2)C1=O]

Step 2: 2-allyl-5-(phenylselanyl)cyclopentanone

While under a nitrogen, a solution of 2-allylcyclopentanone (12.4 g, 100 mmol) in anhydrous tetrahydrofuran (100 mL) was cooled to −70° C. and treated with 1 N lithium bis(tri-methylsilyl)amide/tetrahydrofuran (200 mL, 200 mmol) at a rate to keep pot temperature below −55° C. Once the addition was complete, the mixture was stirred at −60 to −70° C. for one additional hour. A second solution of phenylselenyl chloride (19.5 g, 102 mmol) in anhydrous tetrahydrofuran (50 mL) was added dropwise and the mixture stirred at −60 to −70° C. for 30 min, then allowed to warm to 0° C. The reaction was quenched by addition of the solution to a rapidly stirred mixture of ethyl acetate (500 mL) and 5% aqueous citric acid (200 mL), and the organic layer was separated. The aqueous solution was extracted with ethyl acetate (2×100 mL) and the combined organic solution was washed with saturated aqueous sodium chloride (200 mL), dried (MgSO$_4$), and concentrated in vacuo. The residue was dissolved in heptane and loaded onto a silica gel column (~600 cc) and eluted with 2:1 heptane/dichloromethane, then with 1:1 heptane/dichloromethane to afford 2-allyl-5-(phenylselanyl)cyclopentanone (19.7 g, 71%) as a pale yellow oil. NMR (CDCl$_3$): δ 7.40-7.50 (m, 2H), 7.05-7.25 (m, 3H), 5.50-5.70 (m, 1H), 4.80-4.95 (m, 2H), 3.45-3.75 (m, 1H), 2.30-2.50 (m, 1H), 1.80-2.25 (m, 5H), 1.50-1.75 (m, 1H). MS (M+1): 279.1/280.9 (for 2 major isotopes of Se).

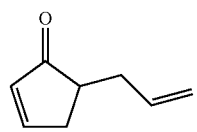

Step 3: 5-allylcyclopent-2-enone

A stirred, ice cold (3° C.) solution of 2-allyl-5-(phenylselanyl)cyclopentanone, mixture of isomers (12.0 g, 43 mmol) in dichloromethane (200 mL) in a 1 L round bottomed-flask equipped for boil-over containment was treated with saturated aqueous ammonium chloride (45 mL), then dropwise with 30% aqueous hydrogen peroxide (22 mL), and slowly carefully warmed to room temperature. At approximately 20° C. a vigorous exotherm started, and the ice bath was re-applied. The mixture was cooled to room temperature and stirred for 1 h, then the solution was washed with water (100 mL), stirred with 10% aqueous sodium thiosulfate pentahydrate (75 mL) for 10 min, and separated. The organic solution was washed with saturated aqueous sodium bicarbonate and saturated aqueous sodium chloride (75 mL each), dried (Na$_2$SO$_4$), and concentrated to 30 mL volume. The solution was added to a silica gel column (~400 cc) and eluted with dichloromethane to afford (after very gentle concentration of appropriate fractions) 5-allylcyclopent-2-enone (3.95 g, 75%) as a very pale yellow oil. NMR (CDCl$_3$): δ 7.61 (m, 1H), 6.12 (m, 1H), 5.60-5.75 (m, 1H), 4.90-5.05 (m, 2H), 2.70-2.80 (m, 1H), 2.45-2.55 (m, 1H), 2.30-2.40 (m, 2H), 2.05-2.15 (m, 1H).

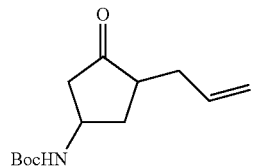 [SMILES: C=CCC1CC(NC(=O)OC(C)(C)C)CC1=O]

Step 4: tert-butyl 3-allyl-4-oxocyclopentylcarbamate

A stirred solution of 5-allylcyclopent-2-enone (2.20 g, 18 mmol), t-butyl carbamate (4.70 g, 40 mmol), and tetra-n-butylammonium bromide (6.45 g, 20 mmol) in anhydrous dichloromethane (40 mL) under nitrogen was cooled in an ice bath (3° C.) and treated dropwise with boron trifluoride etherate (2.22 mL, 18 mmol). The reaction mixture was allowed to warm to room temperature and stirred for 18 h. Saturated aqueous sodium bicarbonate (40 mL) was added and then mixture stirred for 15 min and separated. The aqueous solution was extracted with dichloromethane (2×20 mL) and the combined organic solution was washed with water and saturated aqueous sodium chloride (20 mL each), dried (Na$_2$SO$_4$), and concentrated in vacuo. The residue was dissolved in minimum dichloromethane and added to a column of silica gel (~300 cc) and eluted first with 85:15 heptane/ethyl acetate to afford recovered starting material (0.3 5 g), then with 4:1 heptane/ethyl acetate to afford a mixture of t-butyl carbamate and subject compound. This mixture was warmed in heptane and filtered to remove most of the t-butyl carbamate, then the filtrate was added to a column of silica gel (~300 cc) and eluted with 6:3:1 heptane/dichloromethane/ethyl acetate to afford tert-butyl 3-allyl-4-oxocyclopentylcarbamate 1.17 g (27%) as a pale amber solid. NMR (CDCl$_3$): δ 5.60-5.75 (m, 1H), 4.90-5.05 (m, 2H), 4.50 (br s, 1H), 4.00-4.25 (m, 1H), 2.30-2.80 (m, 3H), 2.20-2.30 (m, 1H), 1.85-2.15 (m, 3H), 1.38 (s, 9H). MS (M+1): 240.1.

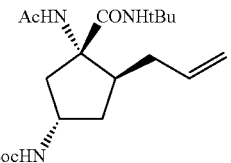

Step 5: tert-butyl (1S,3S,4S)-3-acetamido-4-allyl-3-(tert-butylcarbamoyl) cyclopentylcarbamate While under nitrogen, a mixture of tert-butyl 3-allyl-4-oxocyclopentylcarbamate, mixture of isomers (1.08 g, 4.5 mmol) and ammonium acetate (1.39 g, 18 mmol) in 2,2,2-trifluoroethanol (5 mL) was treated with t-butylisonitrile (1.53 mL, 13.5 mmol) and stirred at room temperature for 3 days. The reaction mixture was concentrated in vacuo and dissolved in dichloromethane (50 mL). The solution was washed with water (25 mL), dried (Na$_2$SO$_4$), and added to a silica gel column (~250 cc). This was eluted successively with 50%, 65%, 70%, and 75% ethyl acetate in heptane to afford tert-butyl (1S,3S,4S)-3-acetamido-4-allyl-3-(tert-butylcarbamoyl) cyclopentylcarbamate (0.99 g, 58%) as a white solid. NMR (CDCl$_3$): δ 7.72 and 7.04 (br s, 1H combined), 7.27 and 6.35 (br s, 1H combined), 5.84 and 5.06 (br s, 1H combined), 5.55-5.70 (m, 1H), 4.85-4.95 (m, 2H), 3.90-4.15 (m, 1H), 2.10-2.90 (m, 4H), 1.70-2.00 (m, 6H), 1.20-1.40 (m, 18H). MS (M+1): 382.2.

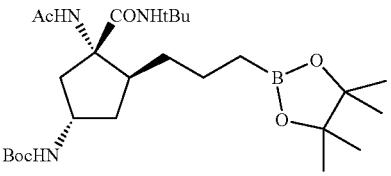

Step 6: tert-butyl (1S,3S,4S)-3-acetamido-3-(tert-butylcarbamoyl)-4-(3-(4,4,5,5-tetramethyl-1,3,2-dioxaborolan-2-yl)propyl)cyclopentylcarbamate A stirred solution of tert-butyl (1S,3 S,4S)-3-acetamido-4-allyl-3-(tert-butylcarbamoyl) cyclopentylcarbamate, mixture of isomers (0.954 g, 2.50 mmol) in anhydrous dichloromethane (25 mL) under nitrogen was treated with chloro-1,5-cyclooctadiene iridium dimer (54 mg, 0.08 mmol) and Diphos® (64 mg, 0.16 mmol), and cooled (−25° C.). After stirring 30 min, pinacolborane (0.55 mL, 3.8 mmol) was added dropwise via syringe, and the pot temperature allowed to warm to ice bath temperature and gradually warmed to room temperature overnight (18 h). Water (10 mL) was added and the mixture was stirred 20 min, and then extracted with ethyl acetate (100 mL). The organic solution was washed with saturated aqueous sodium chloride (50 mL), dried (MgSO$_4$) and concentrated in vacuo. The residual solid was recrystallized several times from acetonitrile to afford tert-butyl (1S,3 S,4S)-3-acetamido-3-(tert-butylcarbamoyl)-4-(3-(4,4,5,5-tetramethyl-1,3,2-dioxaborolan-2-yl)propyl) cyclopentylcarbamate, and the concentrated mother liquor was chromatographed on silica gel (eluted with 3:2, then 4:1 ethyl acetate/heptane) and recrystallized several times from acetonitrile to afford additional subject compound. The total yield was 0.52 g (41%) as a white solid. NMR (CDCl$_3$): δ 7.26 (br s, 1H), 6.56 (br s, 1H), 5.48 (br s, 1H), 4.13 (m, 1H), 2.65-2.80 (m, 1H), 2.40-2.60 (m, 1H), 2.15-2.25 (m, 1H), 1.90-2.05 (m, 1H), 1.93 (s, 3H), 1.40-1.55 (m, 1H), 1.00-1.40 (m, 4H), 1.38 (s, 9H), 1.28 (s, 9H), 1.16 (s, 12H), 0.60-0.75 (m, 2H). MS (M+1): 510.6.

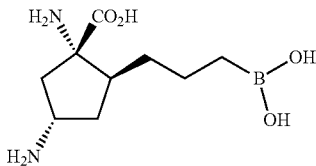 [SMILES: N[C@H]1C[C@H](CCCB(O)O)[C@](N)(C(=O)O)C1]

Step 7: (1S,2S,4S)-1,4-diamino-2-(3-boronopropyl) cyclopentanecarboxylic acid (racemic)

A solution of tert-butyl (1 S,3S,4S)-3-acetamido-3-(tert-butylcarbamoyl)-4-(3-(4,4,5,5-tetramethyl-1,3,2-dioxaborolan-2-yl)propyl)cyclopentylcarbamate (0.204 g, 0.40 mmol) in 2:1:1 concentrated HCl:glacial acetic acid:water (8 mL) in a pressure bottle was stirred for 2 h at 60° C., then capped and stirred for 18 h at 130° C., cooled to room temperature, and uncapped. The solution was diluted with water (20 mL), extracted with dichloromethane (20 mL) and concentrated in vacuo. The resulting residue was treated with water (20 mL) and concentrated three times to remove excess HCl, then dissolved in water (40 mL) and treated with DOWEX® 550A-OH resin (3 g) which had been rinsed with methanol. The mixture was stirred for 40 min, then filtered and the resin washed successively with water, methanol, dichloromethane, water, methanol, and dichloromethane. The resin was stirred four times with 1N HCl (15 mL) and filtered, and the combined filtrates were concentrated in vacuo. The residue was treated with water (20 mL) and concentrated three times to remove excess HCl, then dissolved in 1.5-2.0 mL water. After purification by HPLC, the appropriate fractions were concentrated in vacuo, treated three times with 1N HCl (10 mL) and concentrated, treated three times with water (10 mL) and concentrated, then dissolved in water (10 mL), frozen, and lyophilized overnight to afford the subject compound (98 mg, 81%) as a white foam. NMR (D$_2$O) δ 4.00-4.10 (m, 1H), 2.82 (dd, J$_1$=10.5 Hz, J$_2$=6 Hz, 1H), 2.35-2.45 (m, 1H), 2.05-2.15 (m, 2H), 1.90-2.00 (m, 1H), 1.52 (m, 1H), 1.40 (m, 1H), 1.27 (m, 1H), 1.09 (m, 1H), 0.65-0.75 (m, 2H). MS (M+1): 230.9; MS (M−H$_2$O+1): 213.1.

Example 62: preparation of (1S,2S,4S)-1-amino-4-(benzylamino)-2-(3-boronopropyl)cyclopentanecarboxylic acid (racemic)

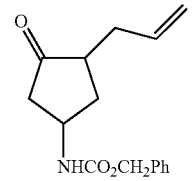

Step 1: benzyl 3-allyl-4-oxocyclopentylcarbamate

A solution of 5-(propene-3-yl)cyclopent-2-enone (4.28 g, 35 mmol) in dichloromethane (15 mL) was treated with benzyl carbamate (10.6 g, 70 mmol) and bismuth trinitrate pentahydrate (2.2 g, 4.5 mmol), stirred rapidly for 18 h, then diluted with dichloromethane (50 mL). The mixture was filtered through Celite® (rinse with dichloromethane) and the filtrate added directly to a silica gel column (~550 cc). Elution first with 3:2 petroleum ether/dichloromethane afforded recovered starting material (1.01 g), then 4:1 heptane/ethyl acetate gave the subject compound (4.54 g, 47.5% uncorrected yield) as a pale yellow oil. NMR (CDCl$_3$): δ 7.28 (br s, 5H), 5.55-5.70 (m, 1H), 5.03 (br s, 2H), 4.90-5.10 (m, 2H), 4.75-4.90 (m, 1H), 4.10-4.30 (m, 1H), 2.40-2.80 (m, 2H), 2.15-2.40 (m, 2H), 1.85-2.15 (m, 3H). MS (M+Na): 296.0; MS (M−H$_2$O+1): 256.0 (no M+1 visible).

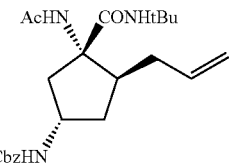

Step 2: benzyl (1S,3S,4S)-3-acetamido-4-allyl-3-(tert-butylcarbamoyl) cyclopentylcarbamate A stirred mixture of benzyl 3-allyl-4-oxocyclopentylcarbamate, mixture of isomers (5.19 g, 19 mmol) and ammonium acetate (5.86 g, 76 mmol) in 2,2,2-trifluoroethanol (20 mL) under nitrogen was treated with t-butylisonitrile (6.50 mL, 57 mmol) and stirred at room temperature for 3 days. The reaction mixture was concentrated in vacuo, dissolved in dichloromethane and added to a silica gel column (~550 cc). Successive elution with 60%, 70%, and 80% ethyl acetate/heptane afforded the subject compound together with an undesired isomer (total 3.48 g). Recrystallization (2 crops) from minimum acetonitrile/ether gave the subject compound (1.83 g, 23%) as a white solid. NMR (CDCl$_3$): δ 7.38 (br s, 5H), 7.10 (br s, 1H), 5.65-5.80 (m, 1H), 5.67 (br s, 1H), 4.95-5.15 (m, 4H), 4.25-4.35 (m, 1H), 2.85-3.00 (m, 1H), 2.60-2.70 (m, 1H), 2.20-2.35 (m, 2H), 1.85-2.15 (m, 3H), 2.03 (s, 3H), 1.40 (s, 9H). MS (M+1): 416.1.

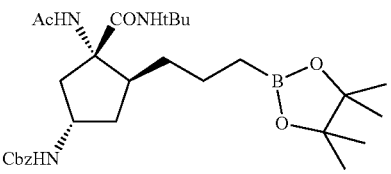

Step 3: benzyl (1S,3S,4S)-3-acetamido-3-(tert-butylcarbamoyl)-4-(3-(4,4,5,5-tetramethyl-1,3,2-dioxaborolan-2-yl)propyl)cyclopentylcarbamate While under nitrogen, a stirred solution of benzyl (1S,3S,4S)-3-acetamido-4-allyl-3-(tert-butylcarbamoyl) cyclopentylcarbamate (1.25 g, 3.00 mmol) in anhydrous dichloromethane (30 mL) was treated with chloro-1,5-cyclooctadiene iridium dimer (70.5 mg, 0.105 mmol) and Diphos® (83.7 mg, 0.21 mmol) and cooled (−25° C.). After stirring 30 min, pinacolborane (0.65 mL, 4.5 mmol) was added dropwise via syringe, and the pot temperature allowed to warm to ice bath temperature and gradually warmed to room temperature overnight (18 h). Water (5 mL) was added, the mixture stirred 20 min, and then extracted with ethyl acetate (2×30 mL). The organic solution was washed with water and saturated aqueous sodium chloride (25 mL each), dried (MgSO$_4$) and concentrated in vacuo. The residue was dissolved in minimum dichloromethane and loaded onto a silica gel column (~250 cc) and eluted with 2:1 ethyl acetate/heptane to afford the subject compound (0.75 g, 46%) as a white solid. NMR (CDCl$_3$): δ 7.20-7.35 (m, 6H), 5.30 (br s, 1H), 4.95-5.10 (m, 2H), 4.20 (m, 1H), 2.73 (m, 1H), 2.46 (m, 1H), 2.23 (d, J=12 Hz, 1H), 2.05 (m, 1H), 1.93 (s, 3H), 1.45 (m, 1H), 1.05-1.35 (m, 4H), 1.28 (s, 9H), 1.15 (s, 12H), 0.60-0.75 (m, 2H). MS (M+1): 544.0.

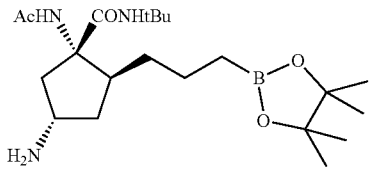

Step 4: (1S,2S,4S)-1-acetamido-4-amino-N-tert-butyl-2-(3-(4,4,5,5-tetramethyl-1,3,2-dioxaborolan-2-yl)propyl)cyclopentanecarboxamide While under nitrogen, a stirred solution of benzyl (1S,3S,4S)-3-acetamido-3-(tert-butylcarbamoyl)-4-(3-(4,4,5,5-tetramethyl-1,3,2-dioxaborolan-2-yl)propyl)cyclopentylcarbamate (0.544 g, 1.00 mmol) in 4:1 ethyl acetate/methanol (20 mL) was treated with 20% Pd(OH)$_2$/C (0.30 g), purged with hydrogen, and stirred under a balloon for 18 h. The mixture was purged with nitrogen and carefully filtered through a pad of Celite® (without letting filter pad dry) and the filtrate concentrated in vacuo to afford 0.409 g (100%) of the subject compound as a white solid. NMR (CDCl$_3$): δ 6.72 (br s, 1H), 6.67 (br s, 1H), 3.63 (m, 1H), 2.80 (m, 1H), 2.57 (m, 1H), 1.75-2.00 (m, 4H), 1.93 (s, 3H), 1.00-1.50 (m, 3H), 1.25 (s, 9H), 1.17 (s, 12H), 0.60-0.75 (m, 2H). MS (M+1): 410.5.

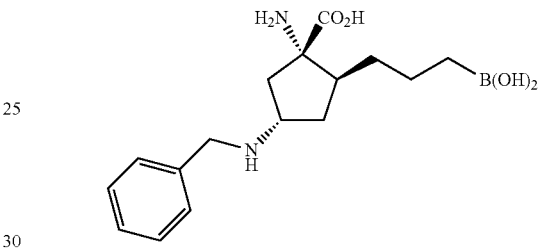

Step 5: (1S,2S,4S)-1-amino-4-(benzylamino)-2-(3-boronopropyl)cyclopentanecarboxylic acid (racemic)

A stirred solution of benzaldehyde (32 mg, 0.30 mmol) in methanol (2.5 mL) was treated with (1S,2S,4S)-1-acetamido-4-amino-N-tert-butyl-2-(3-(4,4,5,5-tetramethyl-1,3,2-dioxaborolan-2-yl)propyl)cyclopentanecarboxamide (102.4 mg, 0.25 mmol) and stirred for 1 h at 50° C., then cooled on an ice bath. Sodium borohydride (12 mg, 0.32 mmol) was added, and the mixture was stirred for h at 3° C., warmed to room temperature, stirred for 30 min, and quenched with water (1 mL). The crude product, in a pressure bottle, was dissolved in 2:1:1 concentrated HCl: glacial acetic acid:water (8 mL) and stirred for 2 h at 60° C., then capped and stirred for 18 h at 130° C., cooled to room temperature, and uncapped. The solution was diluted with water (20 mL), extracted with dichloromethane (20 mL) and concentrated in vacuo. The resulting residue was treated with water (20 mL) and concentrated three times to remove excess HCl, then dissolved in water (40 mL) and treated with DOWEX® 550A-OH resin (3 g) which had been rinsed with methanol. The mixture was stirred for 40 min, then filtered and the resin washed successively with water, methanol, dichloromethane, water, methanol, and dichloromethane. The resin was stirred four times with 1N HCl (15 mL) and filtered, and the combined filtrates were concentrated in vacuo. The residue was treated with water (20 mL) and concentrated three times to remove excess HCl, then dissolved in 1.5-2.0 mL water. After purification by HPLC, the appropriate fractions were concentrated in vacuo, treated three times with 1N HCl (10 mL) and concentrated, treated three times with water (10 mL) and concentrated, then dissolved in water (10 mL), frozen, and lyophilized overnight to afford the subject compound (30.7 mg, 31%) as a white foam. NMR (D₂O) δ 7.40 (br s, 5H), 4.17 (br s, 2H), 4.00-4.10 (m, 1H), 2.78 (m, 1H), 2.34 (m, 1H), 2.20 (m, 1H), 1.95-2.15 (m, 2H), 1.50 (m, 1H), 1.39 (m, 1H), 1.25 (m, 1H), 1.06 (m, 1H), 0.60-0.75 (m, 2H). MS (M+1): 321.1; MS (M−H₂O+1): 303.3; MS (M−2H₂O+1): 285.4.

Example 63: preparation of (1S,2S,4S)-1-amino-2-(3-boronopropyl)-4-(dimethylamino)cyclopentanecarboxylic acid (racemic)

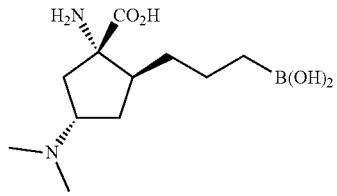 [SMILES: CN(C)[C@H]1C[C@H](CCCB(O)O)[C@](N)(C(=O)O)C1]

A stirred mixture of (1S,2S,4S)-1-acetamido-4-amino-N-tert-butyl-2-(3-(4,4,5,5-tetramethyl-1,3,2-dioxaborolan-2-yl)propyl)cyclopentanecarboxamide (102.4 mg, 0.25 mmol) and 37% aqueous formaldehyde (0.07 mL, 0.94 mmol) in 1,2-dichloroethane (2 mL) was treated with triethylamine (one drop), then with sodium triacetoxyborohydride (0.20 g, 0.94 mmol) and stirred at room temperature for 2 days, then quenched with saturated aqueous sodium bicarbonate (1 mL). The mixture was extracted with dichloromethane (2×10 mL) and the combined organic extracts were washed with water and saturated aqueous sodium chloride (5 mL each), dried (Na₂SO₄), and concentrated in vacuo. The crude product, in a pressure bottle, was dissolved in 2:1:1 concentrated HCl:glacial acetic acid:water (8 mL) and stirred for 2 h at 60° C., then capped and stirred for 18 h at 130° C., cooled to room temperature, and uncapped. The solution was diluted with water (20 mL), extracted with dichloromethane (20 mL) and concentrated in vacuo. The resulting residue was treated with water (20 mL) and concentrated three times to remove excess HCl, then dissolved in water (40 mL) and treated with DOWEX® 550A-OH resin (3 g) which had been rinsed with methanol. The mixture was stirred for 40 min, then filtered and the resin washed successively with water, methanol, dichloromethane, water, methanol, and dichloromethane. The resin was stirred four times with 1N HCl (15 mL) and filtered, and the combined filtrates were concentrated in vacuo. The residue was treated with water (20 mL) and concentrated three times to remove excess HCl, then dissolved in 1.5-2.0 mL water. After purification by HPLC, the appropriate fractions were concentrated in vacuo, treated three times with 1N HCl (10 mL) and concentrated, treated three times with water (10 mL) and concentrated, then dissolved in water (10 mL), frozen, and lyophilized overnight to afford the subject compound (24.5 mg, 30%) as a white foam. NMR (D₂O) δ 4.00-4.10 (m, 1H), 2.81 (s, 3H), 2.79 (s, 3H), 2.70 (dd, J₁=11 Hz, J₂=7 Hz, 1H), 2.20-2.35 (m, 2H), 2.00-2.15 (m, 2H), 1.50 (m, 1H), 1.38 (m, 1H), 1.25 (m, 1H), 1.06 (m, 1H), 0.60-0.75 (m, 2H). MS (M+1): 259.3; MS (M−H₂O+1): 241.5; MS (M−2H₂O+1): 223.4.

Example 64: preparation of (1S,2S,4R)-1-amino-4-(aminomethyl)-2-(3-boronopropyl)cyclopentanecarboxylic acid

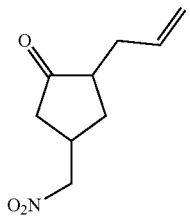

Step 1: 2-allyl-4-(nitromethyl)cyclopentanone

A stirred solution of 5-(propene-3-yl)cyclopent-2-enone (0.428, 3.5 mmol) in nitromethane (2 mL) under nitrogen was treated with DOWEX® 550A-OH resin (0.80 g, rinsed with methanol and partially air dried), and heated to 60° C. for 2 h. The mixture was cooled to room temperature, diluted with dichloromethane (20 mL), and filtered. The filtrate was concentrated in vacuo, redissolved in minimum dichloromethane, and added to a silica gel column (~100 cc) and eluted with dichloromethane to afford the subject compound (0.368 g, 57%) as a colorless oil. NMR (CDCl₃): δ 5.65-5.80 (m, 1H), 5.00-5.15 (m, 2H), 4.40-4.50 (m, 2H), 2.85-3.15 (m, 1H), 2.30-2.70 (m, 4H), 1.90-2.20 (m, 3H). MS (M+1): 183.9.

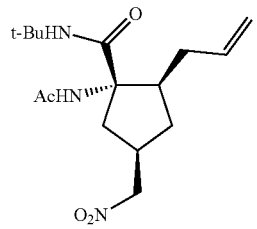
isomer A

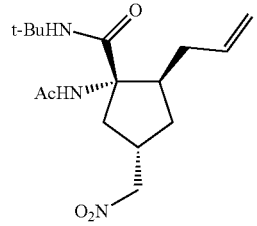
isomer B

Step 2: (1S,2S)-1-acetamido-2-allyl-N-tert-butyl-4-(nitromethyl) cyclopentanecarboxamide, Isomers A and B A stirred solution of 2-allyl-4-(nitromethyl)cyclopentanone, mixture of isomers (0.366 g, 2.0 mmol) in 2,2,2-trifluoroethanol (1.5 mL) under nitrogen was treated with ammonium acetate (0.617 g, 8 mmol) and t-butylisonitrile (0.68 mL, 6.0 mmol) and stirred at room temperature for 2 days. The mixture was diluted with dichloromethane (20 mL) and added directly to a silica gel column (~250 cc) and eluted with 7:3 dichloromethane/ethyl acetate to afford first the two isomers with acetamino and allyl substituents in syn relative geometry, then isomer A (122 mg, 19%) as a white solid, then isomer B (195 mg, 30%) as a white solid. For isomer A: NMR (CDCl₃): δ 6.12 (br s, 2H), 5.65-5.80 (m, 1H), 5.00-5.15 (m, 2H), 4.53 (d, J=7 Hz, 1H), 4.35-4.50 (m, 1H), 2.80-3.00 (m, 1H), 2.45-2.60 (m, 1H), 2.25-2.35 (m, 2H), 1.90-2.20 (m, 2H), 2.00 (s, 3H), 1.20-1.60 (m, 2H), 1.34 (s, 9H). MS (M+1): 326.0. For isomer B: NMR (CDCl₃): δ 6.05-6.15 (m, 2H), 5.65-5.80 (m, 1H), 5.00-5.15 (m, 2H), 4.43 (d, J=6.5 Hz, 2H), 2.90-3.10 (m, 2H), 2.40-2.50 (m, 1H), 2.20-2.30 (m, 1H), 2.00 (s, 3H), 1.70-2.00 (m, 4H), 1.35 (s, 9H). MS (M+1): 326.0.

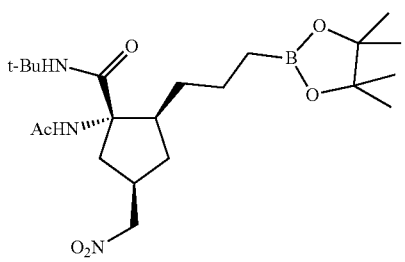

Step 3: (1S,2S,4R)-1-acetamido-N-tert-butyl-4-(nitromethyl)-2-(3-(4,4,5,5-tetramethyl-1,3,2-dioxaborolan-2-yl)propyl)cyclopentanecarboxamide (racemic)

While under nitrogen, a stirred solution of (1S,2S)-1-acetamido-2-allyl-N-tert-butyl-4-(nitromethyl) cyclopentanecarboxamide, isomer A (0.180 g, 0.553 mmol) in anhydrous dichloromethane (5 mL) was treated with chloro-1,5-cyclooctadiene iridium dimer (12 mg, 0.018 mmol) and Diphos® (14 mg, 0.035 mmol) and cooled (−25° C.). After stirring for 30 min, pinacolborane (0.123 mL, 0.85 mmol) was added dropwise via syringe, and the pot temperature allowed to warm to ice bath temperature and gradually warmed to room temperature overnight (18 h). Water (3 mL) was added, the mixture stirred 20 min, and then extracted with ethyl acetate (25 mL, then 10 mL). The combined organic solution was washed with water and saturated aqueous sodium chloride (20 mL each), dried (MgSO₄) and concentrated in vacuo. Recrystallization from acetonitrile (2 crops) afforded 0.170 g (68%) of the subject compound as a white solid. NMR (CDCl₃): δ 6.08 (br s, 1H), 5.92 (br s, 1H), 4.46 (d, J=5 Hz, 2H), 2.75-2.90 (m, 1H), 2.49 (dd, J₁=11 Hz, J₂=6 Hz, 1H), 2.00-2.15 (m, 3H), 1.95 (s, 3H), 1.20-1.50 (m, 5H), 1.25 (s, 9H), 1.17 (s, 12H), 0.65-0.85 (m, 2H). MS (M+1): 454.5.

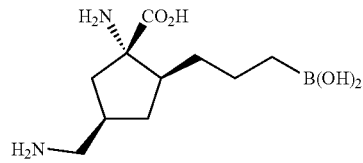 [SMILES: NC[C@@H]1C[C@H](CCCB(O)O)[C@](N)(C(=O)O)C1]

Step 4: (1S,2S,4R)-1-amino-4-(aminomethyl)-2-(3-boronopropyl) cyclopentanecarboxylic acid (racemic)

A stirred solution of (1S,2S,4R)-1-acetamido-N-tert-butyl-4-(nitromethyl)-2-(3-(4,4,5,5-tetramethyl-1,3,2-dioxaborolan-2-yl)propyl)cyclopentanecarboxamide (racemic), isomer A (0.167 g, 0.368 mmol) in ethanol (5 mL) and tetrahydrofuran (2 mL) under nitrogen was treated with Rancy nickel (0.30 g), purged with hydrogen, and stirred under a balloon for 20 h. The flask was purged with nitrogen and the mixture filtered through Celite® (carefully, do not let filter cake dry), and the filtrate concentrated in vacuo. The crude product, in a pressure bottle, was dissolved in 2:1:1 concentrated HCl:glacial acetic acid:water (8 mL) and stirred for 2 h at 60° C., then capped and stirred for 18 h at 130° C., cooled to room temperature, and uncapped. The solution was diluted with water (20 mL), extracted with dichloromethane (20 mL) and concentrated in vacuo. The resulting residue was treated with water (20 mL) and concentrated three times to remove excess HCl, then dissolved in water (40 mL) and treated with DOWEX® 550A-OH resin (3 g) which had been rinsed with methanol. The mixture was stirred for 40 min, then filtered and the resin washed successively with water, methanol, dichloromethane, water, methanol, and dichloromethane. The resin was stirred four times with 1N HCl (15 mL) and filtered, and the combined filtrates were concentrated in vacuo. The residue was treated with water (20 mL) and concentrated three times to remove excess HCl, then dissolved in 1.5-2.0 mL water. After purification by HPLC, the appropriate fractions were concentrated in vacuo, treated three times with 1N HCl (10 mL) and concentrated, treated three times with water (10 mL) and concentrated, then dissolved in water (10 mL), frozen, and lyophilized overnight to afford the subject compound (62 mg, 53%) as a white foam. NMR (D₂O) δ 2.95-3.10 (m, 2H), 2.50 (m, 1H), 2.10-2.30 (m, 4H), 1.35-1.55 (m, 2H), 1.10-1.35 (m, 3H), 0.65-0.75 (m, 2H). MS (M+1): 245.2; MS (M−H₂O+1): 227.2.

Example 65: preparation of (1S,2S,4S)-1-amino-4-(aminomethyl)-2-(3-boronopropyl) cyclopentanecarboxylic acid (racemic)

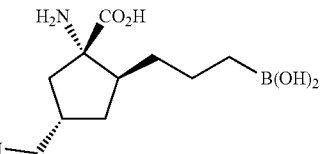

(1S,2S,4S)-1-amino-4-(aminomethyl)-2-(3-boronopropyl) cyclopentanecarboxylic acid (racemic) was prepared in a manner analogus to Example 64 except isomer B was used in the hydroboration step. NMR (D₂O) δ 2.85-3.15 (m, 2H), 2.45-2.80 (m, 2H), 2.15-2.35 (m, 1H), 1.75-2.00 (m, 2H), 1.10-1.75 (m, 5H), 0.65-0.80 (m, 2H). MS (M+1): 245.2; MS (M−H₂O+1): 227.1.

Example 66: preparation of (1S,2S,4R)-1-amino-4-(2-aminoethyl)-2-(3-boronopropyl)cyclopentanecarboxylic acid (racemic)

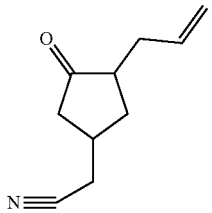

Step 1: 2-(3-allyl-4-oxocyclopentyl)acetonitrile

While under nitrogen, a cooled (−70° C.) solution of trimethylsilylacetonitrile (1.83 g, 15 mmol) in anhydrous tetrahydrofuran (180 mL) was treated dropwise via syringe with 2.3N n-butyllithium/hexane (7.4 mL, 17 mmol), stirred for 30 min, then treated with DMPU (9 mL). After 30 min more at −70° C., a solution of 5-(propene-3-yl)cyclopent-2-enone (1.83 g, 15 mmol) in anhydrous tetrahydrofuran (20 mL) was added dropwise, and the temperature maintained at −70° C. for 30 min, warmed slowly to −35° C., and the mixture quenched with 5% aqueous citric acid (90 mL). The reaction mixture was extracted with ethyl acetate (500 mL, then 2×75 mL), and the combined organic solution washed with water, saturated aqueous sodium bicarbonate, and brine (150 mL each), dried (MgSO$_4$), and concentrated in vacuo. The residue was dissolved in acetonitrile (162 mL) and treated with a solution of potassium fluoride (1.05 g, 18 mmol) in water (18 mL), and stirred for one hour. The solution was concentrated in vacuo to remove most acetonitrile, diluted with water (150 mL), and the aqueous mixture extracted with ether (150 mL, then 3×75 mL). The combined organic solution washed with water, saturated aqueous sodium bicarbonate, and brine (100 mL each), dried (MgSO$_4$), and concentrated in vacuo. The residual oil was dissolved in minimal methylene chloride, loaded onto a silica gel column (~225 cc), and eluted with methylene chloride to afford 1.64 g (67%) of 3-cyanomethyl-5-(propene-3-yl)cyclopentanone, mixture of isomers, as a pale yellow oil. NMR (CDCl$_3$): δ 5.65-5.80 (m, 1H), 5.05-5.15 (m, 2H), 2.60-2.70 (m, 1H), 2.40-2.60 (m, 5H), 2.10-2.25 (m, 2H), 1.95-2.10 (m, 2H). MS (M+1): 164.3.

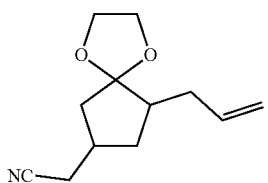

Step 2: 2-(9-allyl-1,4-dioxaspiro[4.4]nonan-7-yl)acetonitrile

A stirred solution of 2-(3-allyl-4-oxocyclopentyl)acetonitrile, mixture of isomers (0.816 g, 5 mmol) in anhydrous toluene (40 mL) under nitrogen was treated with ethylene glycol (0.56 mL, 10 mmol) and toluenesulfonic acid hydrate (40 mg, 0.21 mmol), refluxed under a Dean-Stark trap for 8 h, concentrated in vacuo, and the residue dissolved in ether (100 mL). The organic solution was washed with water, saturated aqueous sodium bicarbonate, and brine (50 mL each), dried (MgSO$_4$), and concentrated in vacuo. The residual oil was dissolved in minimal methylene chloride, loaded onto a silica gel column (~200 cc) and eluted with 30% ethyl acetate/heptane to afford 0.875 g (84%) of 3-cyanomethyl-5-(propene-3-yl)cyclopentanone, ketal with ethylene glycol, as a pale yellow oil. NMR (CDCl$_3$): δ 5.70-5.85 (m, 1H), 4.95-5.10 (m, 2H), 3.85-4.00 (m, 4H), 2.40 (m, 2H), 2.25-2.35 (m, 2H), 1.90-2.20 (m, 4H), 1.65-1.80 (m, 1H), 1.60 (m, 1H). MS (M+1): 208.0.

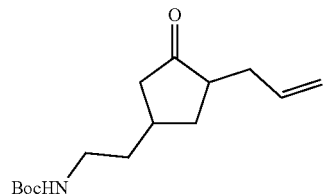 [SMILES: C=CCC1CC(CCNC(=O)OC(C)(C)C)CC1=O]

Step 3: tert-butyl 2-(3-allyl-4-oxocyclopentyl)ethylcarbamate

An ice-cooled (3° C.) stirred solution of 2-(9-allyl-1,4-dioxaspiro[4.4]nonan-7-yl)acetonitrile with ethylene glycol (0.829 g, 4.0 mmol) in anhydrous tetrahydrofuran (30 mL) was treated via syringe with 2N lithium aluminum hydride/tetrahydrofuran (6 mL, 12 mmol) and refluxed for 4h (precipitate formed). The mixture was cooled on an ice bath and treated successively and carefully with water (0.5 mL), 15% aqueous sodium hydroxide (0.5 mL), and water (1.5 mL), filtered, and the filtrate concentrated in vacuo. The residual oil was dissolved in methylene chloride (20 mL), treated with di-t-butyldicarbonate (1.09 g, 5 mmol), stirred for 3h, and concentrated in vacuo. The residue was dissolved in 5:1 acetone/water (30 mL), treated with Montmorillonite K-10 clay (5 g), refluxed for 6 h, cooled to room temperature, and filtered through Celite. The filtrate was concentrated in vacuo, the residue was diluted with water (20 mL), and the aqueous solution extracted with methylene chloride (2×30 mL). The combined organic solution was washed with water (25 mL), dried (Na$_2$SO$_4$), and concentrated in vacuo. The residue was dissolved in minimal methylene chloride, added to a silica gel column (~150 cc) and eluted with 5% ethyl acetate/methylene chloride to afford 0.5 g (48%) of the subject compound as a colorless oil. NMR (CDCl$_3$): δ 5.60-5.75 (m, 1H), 4.90-5.05 (m, 2H), 4.47 (m, 1H), 3.10 (m, 2H), 2.40-2.50 (m, 1H), 2.20-2.40 (m, 2H), 2.10-2.20 (m, 1H), 1.90-2.10 (m, 2H), 1.65-1.90 (m, 2H), 1.45-1.60 (m, 2H), 1.37 (s, 9H). MS (M+1): 268.2; MS (M+Na): 290.1.

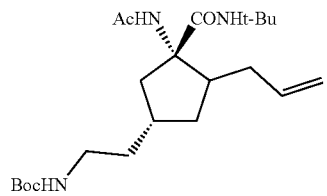

Step 4: tert-butyl 2-((R,3S)-3-acetamido-4-allyl-3-(tert-butylcarbamoyl) cyclopentyl) ethylcarbamate A stirred solution of tert-butyl 2-(3-allyl-4-oxocyclopentyl)ethylcarbamate, mixture of isomers (0.50 g, 1.87 mmol) in 2,2,2-trifluoroethanol (2 mL) under nitrogen was treated with ammonium acetate (0.62 g, 8 mmol) and t-butylisonitrile (0.68 mL, 6.0 mmol) and stirred at room temperature for 3 days. The mixture was diluted with methylene chloride (20 mL) and added directly to a silica gel column (~250 cc) and eluted with 1:1 ethyl acetate/heptane, then 2:1 ethyl acetate/heptane to afford tert-butyl 2-((1R,3S)-3-acetamido-4-allyl-3-(tert-butylcarbamoyl) cyclopentyl) ethylcarbamate (260 mg, 34%) as a white solid. NMR (CDCl$_3$): δ 6.25 (br s, 1H), 6.00 (br s, 1H), 5.55-5.70 (m, 1H), 4.90-5.00 (m, 2H), 4.48 (m, 1H), 3.03 (m, 2H), 2.35-2.80 (m, 1H), 2.27 (m, 1H), 2.00-2.20 (m, 2H), 1.70-2.00 (m, 2H), 1.93 (s, 3H), 1.45-1.65 (m, 4H), 1.36 (s, 9H), 1.27 (s, 9H). MS (M+1): 410.3; MS (M+Na): 432.4.

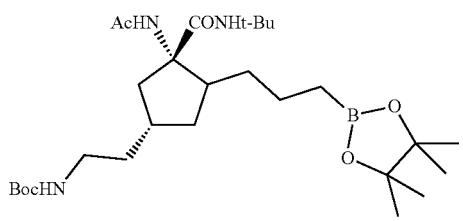

Step 5: tert-butyl 2-((1R,3S)-3-acetamido-3-(tert-butylcarbamoyl)-4-(3-(4,4,5,5-tetramethyl-1,3,2-dioxaborolan-2-yl)propyl)cyclopentyl)ethylcarbamate While under nitrogen, a stirred solution of tert-butyl 2-((1R,3S)-3-acetamido-4-allyl-3-(tert-butylcarbamoyl) cyclopentyl) ethylcarbamate (0.25 g, 0.61 mmol) in anhydrous methylene chloride (6 mL) was treated with chloro-1,5-cyclooctadiene iridium dimer (14.5 mg, 0.021 mmol) and Diphos® (17 mg, 0.042 mmol) and cooled (−25° C.). After stirring for 30 min, pinacolborane (0.134 mL, 0.92 mmol) was added dropwise via syringe, and the pot temperature allowed to warm to ice bath temperature and gradually warmed to room temperature overnight (18 h). Water (4 mL) was added, the mixture stirred 20 min, and then extracted with ethyl acetate (30 mL, then 20 mL). The combined organic solution was washed with water and brine (20 mL each), dried (MgSO$_4$) and concentrated in vacuo. Recrystallization from acetonitrile (2 crops) afforded 0.136 g of the subject compound as a white solid. Silica gel chromatography (eluted with 70:30 ethyl acetate/heptane) of the concentrated mother liquor afforded an additional 0.102 g of the subject compound. The total yield was 0.238 g (73%). NMR (CDCl$_3$): δ 5.95-6.10 (m, 2H), 4.50 (m, 1H), 3.03 (m, 2H), 2.00-2.85 (m, 4H), 1.92 (s, 3H), 1.00-1.70 (m, 8H), 1.37 (s, 9H), 1.25 (s, 9H), 1.17 (s, 12H), 0.60-0.75 (m, 2H). MS (M+1): 538.1; MS (M+Na): 560.4.

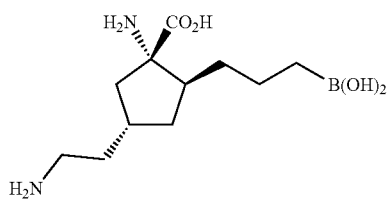 [SMILES: NCC[C@H]1C[C@H](CCCB(O)O)[C@](N)(C(=O)O)C1]

Step 6: (1S,2S,4R)-1-amino-4-(2-aminoethyl)-2-(3-boronopropyl) cyclopentanecarboxylic acid tert-butyl 2-((1R,3S)-3-acetamido-3-(tert-butylcarbamoyl)-4-(3-(4,4,5,5-tetramethyl-1,3,2-dioxaborolan-2-yl)propyl)cyclopentyl)ethylcarbamate (0.226 g, 0.42 mmol), in a pressure bottle, was dissolved in 2:1:1 concentrated HCl: glacial acetic acid:water (8 mL) and stirred for 2 h at 60° C., then capped and stirred for 18 h at 130° C., cooled to room temperature, and uncapped. The solution was diluted with water (20 mL), extracted with dichloromethane (20 mL) and concentrated in vacuo. The resulting residue was treated with water (20 mL) and concentrated three times to remove excess HCl, then dissolved in water (40 mL) and treated with DOWEX® 550A-OH resin (3 g) which had been rinsed with methanol. The mixture was stirred for 40 min, then filtered and the resin washed successively with water, methanol, dichloromethane, water, methanol, and dichloromethane. The resin was stirred four times with 1N HCl (15 mL) and filtered, and the combined filtrates were concentrated in vacuo. The residue was treated with water (20 mL) and concentrated three times to remove excess HCl, then dissolved in 1.5-2.0 mL water. After purification by HPLC, the appropriate fractions were concentrated in vacuo, treated three times with 1N HCl (10 mL) and concentrated, treated three times with water (10 mL) and concentrated, then dissolved in water (10 mL), frozen, and lyophilized overnight to afford the subject compound (85 mg, 61%) as a white foam. NMR (D$_2$O) δ 2.85-3.00 (m, 2H), 2.64 (br s, 1H), 2.35-2.60 (m, 1H), 2.05-2.25 (m, 2H), 1.65-1.85 (m, 3H), 1.35-1.55 (m, 2H), 1.10-1.30 (m, 3H), 0.65-0.80 (m, 2H). MS (M+1): 259.0; MS (M−H$_2$O+1): 241.2.

Methods and Uses

The inventive compounds are useful for inhibiting the expression or activity of arginase I, arginase II or a combination of these enzymes. The enzymes of the arginase family play an important role in regulating the physiological levels of L-arginine, a precursor of the signaling molecule nitric oxide (NO), as well as in regulating levels of certain polyamines that are important physiological signal transducers.

More specifically, the invention provides methods and uses for inhibiting arginase I, arginase II, or a combination thereof in a cell, comprising contacting the cell with at least one compound according to Formula I or Formula II, or composition thereof as described herein. In some embodiments, the invention provides a method for the treatment or prevention of a disease or condition associated with expression or activity of arginase I, arginase II, or a combination thereof in a subject.

For instance, the disease or condition is selected from the group consisting of heart disease, heart disease, hypertension, sexual disorders, gastric disorders, autoimmune disorders, parasitic infections, pulmonary disorders, smooth muscle relaxation disorders and hemolytic disorders.

More specifically, hypertension includes systemic hypertension, pulmonary arterial hypertension (PAH), and pulmonary arterial hypertension in high altitude.

Exemplary sexual disorders are disease or conditions selected from the group consisting of Peyronie's Disease and erectile dysfunction (ED).

In one embodiment an arginase inhibitor in accordance with the present invention is suitable for treating a pulmonary disorder selected from the group consisting of chemically-induced lung fibrosis, idiopathic pulmonary fibrosis, cystic fibrosis, chronic obstructive pulmonary disease (COPD.

Compounds in accordance with the present invention are also useful for treating gastrointestinal disorders, such as diseases or conditions selected from the group consisting of gastrointestinal motility disorders, gastric cancers, reduced hepatic blood flow disorders, inflammatory bowel disease, Crohn's disease, ulcerative colitis, and gastric ulcers.

The transport of organs increases the risk of ischemia reperfusion (IR) injury, such as liver IR, kidney IR, and myocardial IR. Formula I or Formula II compounds in accordance with the present invention are useful in protecting organs during organ transport.

In another embodiment, inhibitors of arginase in accordance with the present invention are used to treat hemolytic disorders selected from the group consisting of paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, cardiopulmonary bypass, mechanical heart valve-induced anemia and chemical induced anemia. In addition, the compounds described herein are useful in the treatment of malaria.

The inventive compounds are useful in the treatment of autoimmune diseases selected from the group consisting of encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes and ankylosing spondylitis. In another embodiment, Formulae I or II compounds are useful for treating immune disorders selected from the group consisting of immune-response, T-cell dysfunction, such as myeloid-derived suppressor cell (MDSC) mediated T-cell dysfunction, human immunodeficiency virus (HIV) and autoimmune encephalomyelitis.

Other exemplary disease conditions for which compounds described herein are candidate therapeutics are African sleeping sickness, Chagas' disease, smooth muscle relaxation disorders, for example, disorders of smooth muscle selected from the group consisting of a gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle disorder.

The increased levels of arginase in certain cancer patients implicates a therapeutic role for the inventive arginase inhibitors in the treatment of certain cancers, for example, renal cell carcinoma, prostate cancer, colorectal cancer, breast cancer, skin cancer, lung cancer, ovarian cancer, gastric cancer.

Advantageously, the compounds of the invention are especially useful in treating conditions or disorders selected from the group consisting of arthritis, myocardial infarction and atherosclerosis, renal disease, asthma, inflammation, psoriasis, leishmaniasis, sickle cell disease (SCD), neurodegenerative diseases, wound healing, such as infected and uninfected wound healing, hepatitis B virus (HBV), *H. pylori* infections, fibrotic diseases such as cystic fibrosis, candidiasis, periodontal disease, keloids, adenotonsilar disease, cerebral vasospasm, and Goodpasture's syndrome.

More specific descriptions of diseases and conditions follow below.

Erectile Dysfunction

The observation that there are differences in the activity of arginase in the penis of young mice versus older mice led to the conclusion that arginase may play a role in erectile dysfunction (ED). In this context, Champion et. al., (Am. J. Physiol. Heart Circ. Physiol. 292:340-351, (2006) and Biochem. and Biophys. Research Communications, 283: 923-27, (2001)), observed an increase of mRNA expression levels and arginase protein in aged mice along with a reduction in the activity of constitutively active NOS.

Nitric oxide is implicated in nonadrenergic, noncholinergic neurotransmission that leads to smooth-muscle relaxation in the corpus cavernosum enabling penile erection (New England Journal of Medicine, 326, (1992)). Hence, erectile dysfunction can often be treated by elevating penile tissue nitric oxide (NO) levels. Such an elevation in tissue nitric oxide (NO) levels can be achieved by inhibiting arginase activity in penile tissue of aged subjects. Stated differently, arginase has been postulated to deplete the pool of free L-arginine available to NOS in cells which results in lower levels of nitric oxide (NO) and erectile dysfunction. See Christianson et. al., Ace. Chem. Res., 38:191-201, (2005), and Nature Structural Biol., 6(11):1043-1047, (1999). Inhibitors of arginase, therefore, can play a role in the treatment of erectile dysfunction.

In addition to its role in male sexual function, Christianson et. al., (Biochemistry, 42:8445-51, (2003), have proposed a role for ARG II in female sexual arousal. The underlying mechanism by which inhibition of ARGII promotes arousal, however, appears to be the same as that for promoting male arousal. That is, inhibition of ARGII increases the level of free L-arginine available as a substrate for NOS. This causes higher NO levels in clitoral corpus cavernosum and thereby leads to enhanced sexual arousal.

Pulmonary Hypertension

It has been proposed that alterations in arginine metabolism are involved in the pathogenesis of pulmonary hypertension (Xu et al., FASEB J., 18:1746-48, 2004). The proposition is based in part on the finding that arginase II expression and arginase activity are significantly elevated in pulmonary artery endothelial cells derived from lung explants of patients with class I pulmonary hypertension.

Additionally, secondary pulmonary hypertension is emerging as one of the leading causes of mortality and morbidity in patients suffering from hemolytic anemias, such as thalassemia and sickle cell disease. The underlying cause for secondary pulmonary hypertension is impaired nitric oxide bioavailability due to release of arginase following hemolysis which decreases the pool of free arinine that is required for nitric oxide (NO) synthesis. Accordingly, inhibition of arginase activity can provide a potential therapeutic avenue for treating pulmonary hypertension.

Hypertension

Xu et al. (*FASEB* 2004, 14, 1746-8), proposed a fundamental role of arginase II in blood pressure regulation. In this context, high levels of vascular arginase are correlated to concomitant reduction of vascular nitric oxide (NO) in hypertensive animals. For instance, up-regulation of arginase activity precedes rise in blood pressure in rats that were genetically predisposed to hypertension (i.e., spontaneously hypertensive rats), but administration of the anti-hypertensive agent hydralazine lowered blood pressure with a decrease in the expression levels of vascular arginase, thereby indicating a strong correlation between the arginase activity and blood pressure (Berthelot et al. Life Sciences, 80:1128-34, (2008). Similar administration of the known arginase inhibitor $N^{\omega}$-hydroxy-nor-L-arginine (nor-NOHA) lowered blood pressure and improved the vascular response of resistance vessels to blood flow and pressure in spontaneously hypertensive animals, thereby highlighting inhibitors of arginase as candidate therapeutics for treating hypertension (Demougeot et al., (J. Hypertension, 26:1110-18, (2008).

Arginase also plays a role in reflex cutaneous hypertension by lowering the cellular levels of nitric oxide (NO). Nitric oxide causes vasodilation and levels of nitric oxide (NO) are normally elevated or lowered to maintain blood pressure at physiologically acceptable levels. Kenny et al., (J. of Physiology 581 (2007) 863-872), hypothesized that reflex vasodilation in hypertensive subjects can attenuate arginase inhibition, thereby implicating a role for arginase inhibitors for the treatment of hypertension.

Asthma

Arginase activity is also associated with airway hyperresponsiveness in asthma. For example, arginase I is upregulated in human asthmatics and in mice suffering from acute and chronic asthma, whilst levels of arginase II and NOS isoforms remain unchanged (Scott et al., (Am. J. Physiol. Lung Cell Mol. Physiol. 296:911-920 (2009)). Furthermore, methacholine induced responsiveness of the central airways in the murine chronic model attenuated upon the administration of the arginase inhibitor S-(2-boronoethyl)-L-cysteine. The similarity between the expression profiles of ARG I in humans and in mice having chronic asthma indicates that compounds capable of inhibiting arginase activity are candidate therapeutics for treating asthma.

Other lines of evidence reveal further correlations between increased activity of arginase in asthmatic lung tissue and disease progression, such as an upregulation for genes related to the metabolism of cationic amino acids, including Arginase I and II in mice having asthma (Rothenberg et al., (J. Clin. Invest., 111:1863-74 (2003), and Mcurs et. al., (Expert Opin. Investig Drugs, 14(10: 12211231, (2005)).

Further, levels of all amino acids are lower in the plasma of asthmatics, but the levels of arginine are significantly lower in plasma compared to that of a normal subject (Morris et al., (Am. J. Respir. Crit Care Med., 170:148-154, (2004)). Thus, arginase activity is significantly increased in the plasma from an asthmatic, in which elevated levels of arginase activity may contribute to the lower bioavailability of plasma arginine that creates an nitric oxide (NO) deficiency, which is responsible for promoting hyperreactive airways in asthmatics.

Inflammation

Arginase activity also is associated with autoimmune inflammation (Chen et al., Immunology, 110:141-148, (2003)), The authors identified upregulation in the expression levels of the ARG I gene in murine spinal cells from animals undergoing experimental autoimmune encephalomyelitis (EAE). Administration of the arginase inhibitor amino-6-boronohexanoic acid (ABH), however, resulted in the animals developing a much milder form of EAE than in control animals. These results implicate inhibitors of arginase in a therapeutic role for treating autoimmune encephalomyelitis.

Moreover, Horowitz et al., (American J. Physiol Gastrointestinal Liver Physiol., 292:G1323-36, (2007)), suggest a role for arginase enzymes in vascular pathophysiology. For example, these authors indicate a loss of nitric oxide (NO) production in chronically inflamed gut blood vessels in patients suffering from irritable bowel disease (IBD), Crohn's disease and ulcerative colitis. The loss in nitric oxide (NO) production correlated with an upregulation of arginase expression and activity that reduced levels of arginine preventing nitric oxide synthase (NOS), from synthesizing nitric oxide (NO). Inhibitors of arginase activity, therefore, may be candidate therapeutics for treating vascular pathophysiology.

Ischaemia Reperfusion

Arginase inhibition is also suggested to play a cardioprotective role during ischaemia reperfusion. More specifically, inhibition of arginase protects against myocardial infarction by a mechanism that may be dependent on NOS activity and the consequent bioavailability of nitric oxide (NO) (Pernow et al., (Cardiovascular Research, 85:147-154 (2010)).

Myocardial Infarction and Artherosclerosis

Arginase I polymorphism is associated with myocardial infarction along with an increased risk of developing carotid artery intima media thickness that is considered to be a reliable indicator of arthrosclerosis as well as of other coronary arterial diseases (Brousseau et al., (J. Med Genetics, 44:526-531, (2007)). Increased arginase activity elevates levels of ornithine that is biochemically involved in promoting the formation of the matrix and cellular components of artherosclerotic plaque. Id. Thus, arginase inhibitors may serve as candidate therapeutics for treating artheroscleosis. Berkowitz et al., (Circulation Res. 102, (2008)), implicated a role for ARGII in the formation of plaque and artherosclerosis. Oxidation of LDLP that accompanies plaque formation increases arginase activity and lower nitric oxide (NO) levels in endothelial cells. In particular, levels of ARGII are elevated in artherosclerotic mice, indicating a role for inhibitors of arginase as candidate therapeutics for treating artherosclerosis.

Additionally, studies by Ming et. al., (Current Hypertension Reports., 54:54-59, (2006)), indicate that an upregulation of arginase rather than endothelial nitric oxide (NO) dysfunction plays an important role in cardiovascular disorders, including artherosclerosis. That arginase is involved in cardiovascular diseases is further supported by the observation ARGI and ARGII activity is upregulated in cardiac myocytes which in turn negatively impacts NOS activity and myocardial contractility. (See, Margulics et. al., Am. J. Physiol. Heart Circ. Physiol., 290:1756-62, (2006)).

Immune Response

The arginine/nitric oxide (NO) pathway may also play a role in immune response, such as after organ transplants. For instance, it was postulated that reperfusion of an orthotopic liver transplant graft caused a significant increase in ornithine levels due to upregulation of arginase activity in the graft (Tsikas et al., (Nitric oxide, 20:61-67, (2009)). The elevated levels of hydrolytic and proteolytic enzymes in the graft may result in a less favorable outcome for the grafted organ. Thus, inhibiting the arginase enzymes may present an alternate therapeutic avenue for improving the outcome of a transplant.

Psoriasis

Arginase has been implicated to play a role in the pathogenesis of psoriasis. For example, ARG I is highly expressed in hyperproliferative psoriasis, and in fact, is responsible for down regulation of nitric oxide (NO) an inhibitor of cell proliferation by competing for the common substrate L-arginine as postulated by D. Bruch-Gerharz et al., American Journal of Pathology 162(1) (2003) 203-211. More recent work by Abeyakirthi et al. (British J. Dermatology, (2010)), and Berkowitz et al, (WO/2007/005620) support the finding of low nitric oxide (NO) levels in psoriatic keratinocytes. Abeyakirthi et al, found that psoriatic keratinocytes were poorly differentiated and hyperproliferative. The poor differentiation was postulated to result from low levels of nitric oxide (NO), not because of poor expression of NOS, but rather the over expression of arginase that competes with NOS for substrate L-arginine. Thus, inhibition of arginase may provide therapeutic relief from psoriasis.

Wound Healing

Under normal physiological conditions, nitric oxide (NO) plays an important role in promoting wound healing. For example, Hulst et al., (Nitric Oxide, 21:175-183, (2009)), studied the role of ARGI and ARG II in wound healing. Immediately following injury, it is desirable to elevate tissue levels of nitric oxide (NO) so as to promote angiogenesis and cell proliferation that are important for healing. Inhibitors of arginase may therefore find use as therapeutics to treat wounds because such compounds would elevate tissue levels of nitric oxide (NO). Further support for the use of arginase inhibitors as candidate therapeutics for treating wounds was provided by South et al. (Experimental Dermatology, 29:664-668 (2004)), who found a 5-fold increase in Arginase I in chronic wounds such as skin erosions and blisters.

Cystic Fibrosis

Cystic fibrosis (CF) is a multisystem disorder caused by mutations of the cystic fibrosis transmembrane conductance regulator (CFTR) gene. The common symptoms of CF are persistent pulmonary infection, difficulty in breathing, pancreatic insufficiency, and elevated sweat chloride levels. CF can be fatal if untreated, with pulmonary diseases, resulting from mucus build-up and decreased mucociliary clearance, being the leading cause of morbidity and mortality.

It has been asserted that patients with cystic fibrosis (CF) have increased plasma and sputum arginase activity, with an accompanying decrease in the levels of plasma 1-arginine (H. Grasemann et al., Am. J. Respir. Crit. Care Med. 172(12) (2005) 1523-1528. The increased arginase activity, however, results in lower physiological levels of nitric oxide (NO) that can cause airway obstruction decreased pulmonary function in patients suffering from cystic fibrosis (CF).

Impaired electrical field induced-stimulation of smooth muscle relaxation in the airway of a mouse model of CF and the administration of 1-arginine and NO reversed this effect as proposed by M. Mhanna et al. Am. J. Respir. Cell Mol. Biol. 24(5) (200)1 621-626. Graesmann et al., found a positive correlation exists between pulmonary function and exhaled NO and NO metabolite concentrations in the sputum of CF patients (Grasemann et al. 1997, 1998).

Taken together, theses results indicate that increased Arginase activity in CF contributes to the NO deficiency and pulmonary obstruction in CF by limiting the availability of 1-arginine to NOS. Thus, inhibitors of arginase activity are candidate therapeutics for treating cystic fibrosis (CF)

Organ Protection

Another therapeutic avenue for compounds in accordance with the present invention is protecting organs during transport from donor to a site where they will be transplanted into a recipient. Ischemic reperfusion injury (IR) due to exposure of the transplant organs to a period of warm ischemia (time from donor until flushed with preservation media), and cold ischemia (hypothermic preservation) is frequently observed in patients undergoing transplant surgery. Ischemic reperfusion injury (IR) and accompanying primary graft dysfunction and/or acute or chronic rejection results due to alteration in the cellular activity of the L-Arginine/NO pathway.

It was proposed that Arginase 1 and arginase 2 are released from apoptotic endothelial cells and kidney cells within the first 24 hours of organ removal from the body. To counteract the released arginase, L-Arginine is added to preservation media. Results with canine kidney transplants indicate that addition of L-arginine reduced the incidence and severity of ischemia, resulted in post-transplant with lower MDA levels at 1 hour, and lowered BUN & Serum creatinine levels during the first 72 hrs. See Erkasap, 2000.

Similar results were observed for canine lung grafts over a 24 hour period when lungs were preserved in the University of Wisconsin solution supplemented with L-Arginine. Yen et al., observed that the addition of L-arginine to the preservation medium increased pulmonary endothelial protection and lowered the incidence of ischemia when compared to a control that is preserved in medium that does not contain L-arginine (Yen Chu, 2004).

Koch et al. stated that improved myocardial contractility and relaxation in heart muscle of rats following transplantation when hearts were preserved in HTK solution having L-Arginine and N-alpha-acetyl-histidine (Koch, 2009).

Addition of an arginase inhibitor, therefore, can be a candidate therapeutic for preventing and/or reducing the incidence and risk of ischemic reperfusion injury by a synergistically increasing the organ protective effect of the preservation media. Given the low number of available organs that are suitable for transplant and the loss and injury of organs due to the onset of ischemia, arginase inhibitors in accordance with the present invention can find use as therapeutics for preserving organs, increasing organ availability by reducing the amount of ischemic reperfusion injury during organ transport.

Leishmaniasis

Leishmaniasis is caused by a protozoan and manifests as cutaneous leishmaniasis (i.e., skin infection causing hypopigmented nodules) and visceral lieshmaniasis (more severe affecting internal organs). Arginase it postulated to play a role in disease progression since the parasite relies on arginase for the synthesis of cellular polyamines that are essential for pathogenesis. Inhibition of arginase, therefore, would reduce cellular parasitic burden and promote increased nitric oxide (NO) levels enhancing parasitic clearance. See Liew F Y et al. Eur J Immunol 21 (1991) 2489, Iniesta V et al. Parasite Immunol. 24 (2002) 113-118, and Kane M M et al. J. J Immunol. 166 (2001) 1141-1147. Compounds according to Formula I or Formula II, therefore can be used as therapeutics for treating liesmaniasis.

Myeloid Derived Suppressor Cells (MDSC)

MDSC's are potent immune modulators that limit immune responses through several pathways, such as, L-arginine depletion via arginase 1 release into the microenvironment (Rodriguez 2009 Cancer Res), MHC restricted suppression (Nagaraj 2007 Nat Med), induction of T regulatory cells (Serafini 2008 Cancer Res), and production of IL10 (Rodrigues 2010 Neuro Oncol) (Sinha 2007 J Immunol), for instance.

It is postulated that tumor development is accompanied by an increase in the number of MDSC's both peripherally and infiltrated within tumors. See Almand 2001 J Immunol and Gabrilovich 2004 Nat Rev Immunol. Treatment of tumor bearing mice with established chemotherapeutics such as gemcitabine and 5-Fluorouracil eliminates MDSC immune-suppression and results in delayed tumor growth. See Le 2009 Int Immunopharmacol . . . and Vincent 2010 Cancer Res., . . . respectively. Moreover, inhibition of arginase 1 enhanced antitumor immunity by reducing MDSC function. Thus, inhibitors of arginase, such as compounds in accordance with the present invention reduce or delay tumor growth and can be used in combination with established anti-cancer agents in the treatment of cancer.

Helicobacter pylori (H. pylori)

Helicobacter pylori (H. pylori) is a Gram-negative bacterium that colonizes the human gastric mucosa. Bacterial colonization can lead to acute or chronic gastritis and is highly associated with peptic ulcer disease and stomach cancer. The observation that the addition of L-arginine to co-culture of H. pylori and macrophages increased nitric oxide (NO) mediated killing of the H. pylori (Chaturvedi 2007), supports the hypothesis that bacterial arginase competes with macrophage arginase for free arginine that is required for nitric oxide (NO) synthesis. See Gobert A P 2001. L-arginine is required for T-cell activation and for the rapid clearance of bacteria from infected cells. By depleting the pools of free L-arginine in vivo, H. pyroli reduces arginine-induced CD3zeta expression on T-cells and prevents T-cell activation and proliferation. See Zabaleta J, 2004.

The inhibition of bacterial arginase using the known inhibitor NOHA, however, reestablished CD3 expression on T-cells and (Zabaleta J 2004), and enhanced production of NO by macrophages, thus, promoting macrophage mediated clearance of bacteria from infected cells. See Chaturvedi 2007.

Furthermore, Lewis et al., have suggested a role for arginase II in H. pyroli infection. For example, these authors indicate that argII−/− primary macrophages incubated with H. pylori extracts showed enhanced NO production and correspondingly an increased (~15%) NO-mediated killing of bacterial cells (Lewis N D 2010). Inhibitors of arginase activity, therefore, may be candidate therapeutics for treating vascular pathophysiology. Inhibitors of arginase activity, therefore, may be candidate therapeutics for treating H. pyroli infections and for treating gastric ulcers, peptic ulcers and cancer.

Sickle Cell Disease (SCD)

Sickle-cell disease (SCD), or sickle-cell anaemia, or drepanocytosis, is a genetic blood disorder, characterized by red blood cells that assume an abnormal, rigid, sickle shape. Sickling decreases the cells' flexibility and increases the risk of complications. An increase in the concentration of reactive oxygen species (ROS) in circulation causes adherence of blood cells and consumption of NO that results in poor vasodilation or the inability of blood vessels to vasodilate. The inability to vasodilate along with the increased adherence of blood cells in SCD results in vaso occlusive crisis and pain.

Low levels of plasma L-arginine are normally detected in patients with SCD (Morris 2005 JAMA) According to these authors, lysis of red blood cells (RBC's) in patients suffering from SCD causes the release of arginase and a subsequent lowering of physiological L-Arginine levels. This sequence of biological events lowers physiological concentrations of nitric oxide (NO), a signaling molecule that plays a role in vasodilation. Other biological events also limit NO bioavailabilty. These include, for example, the uncoupling of nitric oxide synthase (NOS), and the subsequent decrease in physiological NO levels, as well as the reaction of superoxide ($O^{-2}$) reactive oxygen species with NO to sequester the latter as $ONOO^-$.

Based on these observations, inhibitors of arginase, especially arginase I inhibitors are being proposed by the present inventors as candidate therapeutics for patients with sickle cell disease. As stated above, SCD causes the uncoupling of eNOS due to low physiological levels L-arginine. Inhibition of arginase present in the blood circulation, however, may address this problem by increasing the physiological levels L-arginine, the substrate of endothelial nitric oxide synthase (eNOS). This sequence of events, importantly, are proposed by the present inventors to enhance endothelial function and relieve vasoconstriction associated with SCD.

Human Immunodeficiency Virus (HIV)

HIV is caused by virus that infects CD4+ helper T cells and causes severe lymphopacnia that predisposes the infected individuals to opportunistic infection. Although, anti-retroviral therapy (ART) is extensively used to combat HIV infection, the wide spread use of anti-retroviral drugs has resulted in the generation of resistant strains of HIV.

A correlation exists between the activity of arginase in patients suffering from HIV and the severity of HIV disease. That is increased arginase activity has been correlated to increased viral titres in HIV patients. These patients also show decrease serum arginine levels as well as decreased levels of CD4+/CD8+ cells.

Taken together, these observations suggest a role for arginase inhibitors, such as compounds according to Formulae I or II as candidate therapeutics in the treatment of HIV infection.

Chronic Hepatitis B Virus (HBV)

Chronic hepatitis B infection is a viral disease that is transmitted by contact with infected body fluids. Chronic HBV infections are characterized by inflammation of the liver and jaundice and if left untreated can cause cirrhosis of the liver that can progresses to form hepatocellular carcinomas. Anti-viral drugs currently used, however, have low efficacy against chronic HBV infections. Serum and liver homogenates of patients with chronic HBV infections show reduced levels of arginine and increased arginase activity. For infected patients moreover, the increased arginase activity is correlated to an impaired cytotoxic T-lymphocytes (CTL) response with reduced IL-2 production and CD3z expression.

Replenishing serum arginine to physiologically acceptable levels, however, reconstituted CD3z and IL-2 expression, implicating a role for arginase inhibitors as potential therapeutics in the treatment of chronic HBV infections.

Routes of Administration and Dosing Regimen

Despite ample evidence associating arginase inhibition with therapies of various diseases and conditions, only a limited number of compounds are known that are capable of inhibiting arginase activity. The present invention therefore provides compounds and their pharmaceutical compositions that are useful in treating a subject suffering from such a disease or condition, as more generally set forth above.

In one embodiment, the subject receiving treatment is a mammal. For instance, the methods and uses described herein are suitable for medical use in humans. Alternatively, the methods and uses are also suitable in a veterinary context, wherein the subject includes but is not limited to a dog, cat, horse, cow, sheep and lamb.

The compound or composition of the invention can be formulated as described hereinabove and is suitable for administration in a therapeutically effective amount to the subject in any number of ways. The therapeutically effective amount of a Formula I or Formula II compound can depend upon the amounts and types of excipients used, the amounts and specific types of active ingredients in a dosage form and the route by which the compound is to be administered to patients. However, typical dosage forms of the invention comprise a compound, or a pharmaceutically acceptable salt, solvate, hydrate, isomer, or prodrug thereof.

Typical dosage levels for Formula I or Formula II compounds generally range from about 0.001 to about 100 mg per kg of the patient's body weight per day which can be administered in single or multiple doses. An exemplary dosage is about 0.01 to about 25 mg/kg per day or about 0.05 to about 10 mg/kg per day. In other embodiments, the dosage level is from about 0.01 to about 25 mg/kg per day, about 0.05 to about 10 mg/kg per day, or about 0.1 to about 5 mg/kg per day.

A dose typically ranges from about 0.1 mg to about 2000 mg per day, given as a single once-a-day dose or, alternatively, as divided doses throughout the day, optionally taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary up to from about 200 mg per day to about 2000 mg per day, administered as either a single dose or divided into multiple doses, depending on the patient's global response.

Depending on the disease to be treated and the subject's condition, the compounds according to Formula I or Formula II may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration. The compounds can be formulated, alone or together, in suitable dosage unit formulations containing conventional non-toxic pharmaceutically acceptable carriers, adjuvants and vehicles, as described above, that are appropriate for each route of administration. The invention also contemplates administration of the compounds of the invention in a depot formulation, in which the active ingredient is released over a defined time period.

Inhibition of Arginase

The inventive compounds inhibit human arginase I (ARG I) and arginase II (ARG II) as evidenced by an ex vivo assay set forth by a published protocol (Baggio et al. *J. Pharmacol. Exp. Ther.* 1999, 290, 1409-1416). The assay established the concentration of inhibitor that is required to reduce arginase activity by 50% ($IC_{50}$), as shown in Table 2 below.

Assay Protocol

Inhibition of arginase I (ARG I) and arginase II (ARG II) by Formula I or Formula II compounds is followed spectrophotometrically at 530 nm. The compound to be tested was dissolved in DMSO at an initial concentration 50-fold greater than its final concentration in the cuvette. 10 μl of the stock solution was diluted in 90 μl of the assay buffer that comprises 0.1M sodium phosphate buffer containing 130 mM NaCl, pH 7.4, to which is added ovalbumin (OVA) at a concentration of 1 mg/ml. Solutions of arginase I and II were prepared in 100 mM sodium phosphate buffer, pH 7.4 containing 1 mg/ml of OVA to give an arginase stock solution at a final concentration of 100 ng/ml.

To each well of a 96-well microtiter plate was added 40 μl of enzyme, 10 μl of an inventive compound and 10 μl of enzyme substrate (L-arginine+manganese sulfate). For wells that were used as positive controls, only the enzyme and its substrate were added, while wells used as negative controls contained only manganese sulfate.

After incubating the microtiter plate at 37° C. for 60 minutes, 150 μl of a urea reagent obtained by combining equal proportions (1:1) of reagents A and B is added to each well of the microtiter plate to stop the reaction. The urea reagent is made just before use by combining Reagent A (10 mM o-phthaldialdehyde, and 0.4% polyoxyethylene (23) lauryl ether (w/v) in 1.8 M sulfuric acid) with Reagent B (1.3 mM primaquine diphosphate, 0.4% polyoxyethylene (23) lauryl ether (w/v), 130 mM boric acid in 3.6 mM sulfuric acid). After quenching the reaction mixture, the microtiter plate is allowed to stand for an additional 10 minutes at room temperature to allow the color to develop. The inhibition of arginase was computed by measuring the optical density (OD) of the reaction mixture at 530 nm and normalizing the OD value to percent inhibition observed in the control. The normalized OD is then used to generate a dose-response curve by plotting the the normalized OD values against log [concentration] and using regression analysis to compute the $IC_{50}$ values.

Table 2 below ranks the potency of Formula I compounds on a scale from 1 through 5, that is, the most potent compounds are designated as 1 and the least potent compounds being designated as 5. Thus, a potency value of 1 refers to inventive compounds with $IC_{50}$ values in the range from 0.1 nM to 250 nM; a potency value of 2 refers to inventive compounds with $IC_{50}$ values in the range from 251 nM to 1000 nM; compounds having a potency value of 3 exhibit $IC_{50}$ values in the range from 1001 nM to 2000 nM; inventive compounds with $IC_{50}$ values in the range from 2001 nM to 5000 nM are assigned a potency value of 4, and compounds with $IC_{50}$ values above 5001 nM are assigned a potency value of 5.

TABLE 2

Exemplary Arginase Inhibitors

| Ex. # | Structure* | Name | Arg I $IC_{50}$ | Arg II $IC_{50}$ |
|---|---|---|---|---|
| 1 | 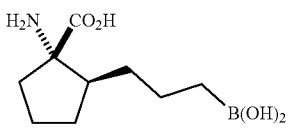 [SMILES: N[C@@]1(C(=O)O)CCC[C@@H]1CCCB(O)O] | (1S,2S)-1-amino-2-(3-boronopropyl)cyclopentanecarboxylic acid | 2 | 2 |

TABLE 2-continued

Exemplary Arginase Inhibitors

| Ex. # | Structure* | Name | Arg I IC$_{50}$ | Arg II IC$_{50}$ |
|---|---|---|---|---|
| 2 | 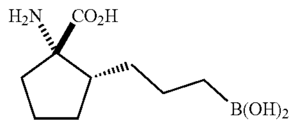 [SMILES: N[C@@]1(C(=O)O)CCC[C@H]1CCCB(O)O] | (1S,2R)-1-amino-2-(3-boronopropyl)cyclopentanecarboxylic acid | 5 | 5 |
| 3 | 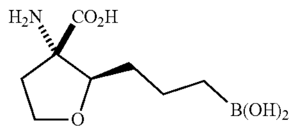 [SMILES: N[C@@]1(C(=O)O)CCO[C@@H]1CCCB(O)O] | (2R,3S)-3-amino-2-(3-boronopropyl)tetrahydrofuran-3-carboxylic acid | 3 | 4 |
| 4 | 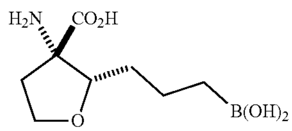 [SMILES: N[C@@]1(C(=O)O)CCO[C@H]1CCCB(O)O] | (2S,3S)-3-amino-2-(3-boronopropyl)tetrahydrofuran-3-carboxylic acid | 1 | 1 |
| 5 | 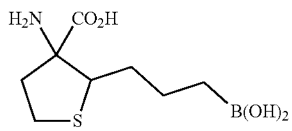 [SMILES: NC1(C(=O)O)CCSC1CCCB(O)O] | 3-amino-2-(3-boronopropyl)tetrahydrothiophene-3-carboxylic acid | 3 | 4 |
| 6 | 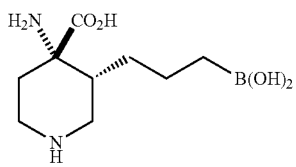 [SMILES: N[C@@]1(C(=O)O)CCNC[C@H]1CCCB(O)O] | (3R,4S)-4-amino-3-(3-boronopropyl)piperidine-4-carboxylic acid | 2 | 4 |
| 7 | 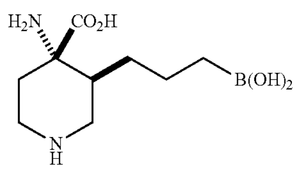 [SMILES: N[C@@]1(C(=O)O)CCNC[C@@H]1CCCB(O)O] | (3S,4S)-4-amino-3-(3-boronopropyl)piperidine-4-carboxylic acid | 2 | 2 |
| 8 | 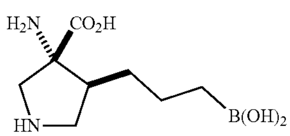 [SMILES: N[C@@]1(C(=O)O)CNC[C@@H]1CCCB(O)O] | (3R,4S)-3-amino-4-(3-boronopropyl)pyrrolidine-3-carboxylic acid | 2 | 2 |
| 9 | 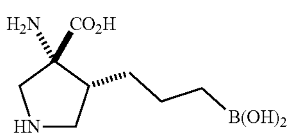 [SMILES: N[C@@]1(C(=O)O)CNC[C@H]1CCCB(O)O] | (3R,4R)-3-amino-4-(3-boronopropyl)pyrrolidine-3-carboxylic acid | 3 | 3 |
| 10 | 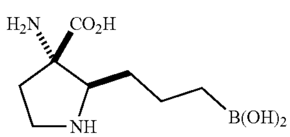 [SMILES: N[C@@]1(C(=O)O)CCN[C@@H]1CCCB(O)O] | (2R,3S)-3-amino-2-(3-boronopropyl)pyrrolidine-3-carboxylic acid | 5 | 5 |
| 11 | 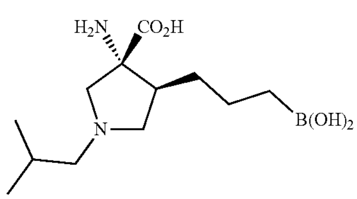 [SMILES: CC(C)CN1C[C@H](CCCB(O)O)[C@](N)(C(=O)O)C1] | (3R,4S)-3-amino-4-(3-boronopropyl)-1-isobutylpyrrolidine-3-carboxylic acid | 2 | 3 |

TABLE 2-continued

Exemplary Arginase Inhibitors

| Ex. # | Structure* | Name | Arg I IC$_{50}$ | Arg II IC$_{50}$ |
|---|---|---|---|---|
| 12 | 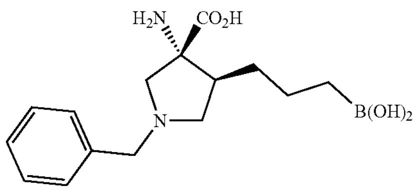 [SMILES: N[C@@]1(C(=O)O)CN(Cc2ccccc2)C[C@@H]1CCCB(O)O] | (3R,4S)-3-amino-1-benzyl-4-(3-boronopropyl)pyrrolidine-3-carboxylic acid | 2 | 3 |
| 13 | 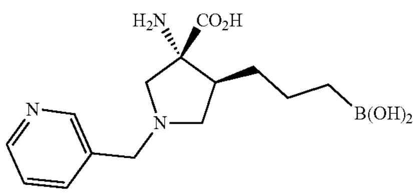 [SMILES: N[C@@]1(C(=O)O)CN(Cc2cccnc2)C[C@@H]1CCCB(O)O] | (3R,4S)-3-amino-4-(3-boronopropyl)-1-(pyridin-3-ylmethyl)pyrrolidine-3-carboxylic acid | 2 | 3 |
| 14 | 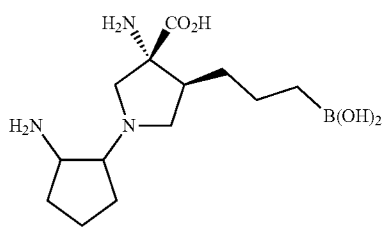 [SMILES: NC1CCCC1N1C[C@H](CCCB(O)O)[C@](N)(C(=O)O)C1] | (3R,4S)-3-amino-1-(2-aminocyclopentyl)-4-(3-boronopropyl)pyrrolidine-3-carboxylic acid | 1 | 1 |
| 15 | 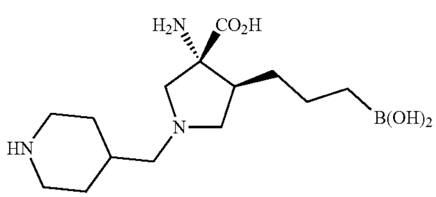 [SMILES: N[C@@]1(C(=O)O)CN(CC2CCNCC2)C[C@@H]1CCCB(O)O] | (3R,4S)-3-amino-4-(3-boronopropyl)-1-(piperidin-4-ylmethyl)pyrrolidine-3-carboxylic acid | 2 | 3 |
| 16 | 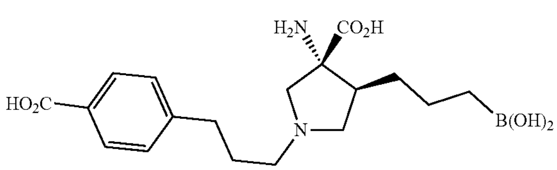 [SMILES: N[C@@]1(C(=O)O)CN(CCCc2ccc(C(=O)O)cc2)C[C@@H]1CCCB(O)O] | (3R,4S)-3-amino-4-(3-boronopropyl)-1-(3-(4-carboxyphenyl)propyl)pyrrolidine-3-carboxylic acid | 1 | 1 |
| 17 | 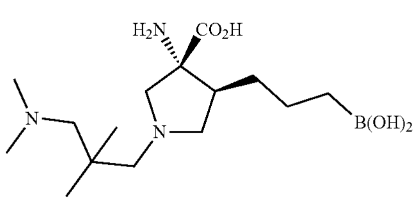 [SMILES: CN(C)CC(C)(C)CN1C[C@H](CCCB(O)O)[C@](N)(C(=O)O)C1] | (3R,4S)-3-amino-4-(3-boronopropyl)-1-(3-(dimethylamino)-2,2-dimethylpropyl)pyrrolidine-3-carboxylic acid | 4 | n.d. |
| 18 | 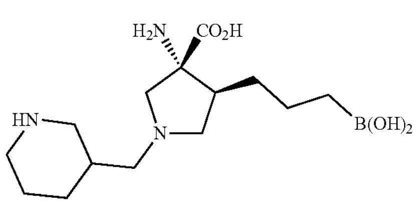 [SMILES: N[C@@]1(C(=O)O)CN(CC2CCCNC2)C[C@@H]1CCCB(O)O] | (3R,4S)-3-amino-4-(3-boronopropyl)-1-(piperidin-3-ylmethyl)pyrrolidine-3-carboxylic acid | 1 | 2 |

TABLE 2-continued

Exemplary Arginase Inhibitors

| Ex. # | Structure* | Name | Arg I IC$_{50}$ | Arg II IC$_{50}$ |
|---|---|---|---|---|
| 19 | 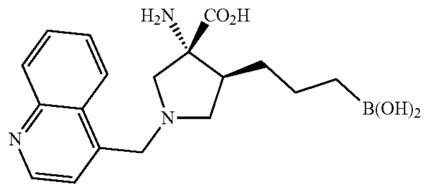 [SMILES: N[C@@]1(C(=O)O)CN(Cc2ccnc3ccccc23)C[C@@H]1CCCB(O)O] | (3R,4S)-3-amino-4-(3-boronopropyl)-1-(quinolin-4-ylmethyl)pyrrolidine-3-carboxylic acid | 2 | 2 |
| 20 | 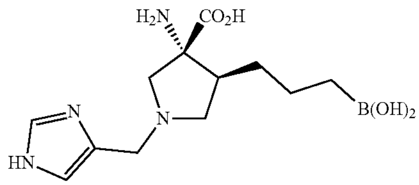 [SMILES: N[C@@]1(C(=O)O)CN(Cc2c[nH]cn2)C[C@@H]1CCCB(O)O] | (3R,4S)-1-((1H-imidazol-4-yl)methyl)-3-amino-4-(3-boronopropyl)pyrrolidine-3-carboxylic acid | 1 | 2 |
| 21 | 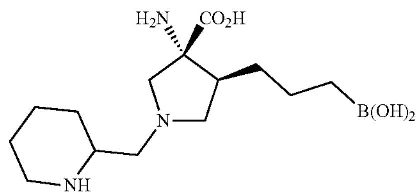 [SMILES: N[C@@]1(C(=O)O)CN(CC2CCCCN2)C[C@@H]1CCCB(O)O] | (3R,4S)-3-amino-4-(3-boronopropyl)-1-(piperidin-2-ylmethyl)pyrrolidine-3-carboxylic acid | 1 | 1 |
| 22 | 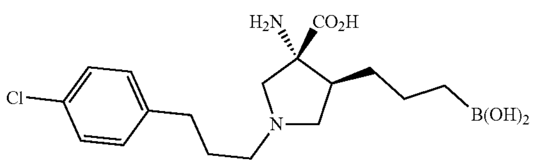 [SMILES: N[C@@]1(C(=O)O)CN(CCCc2ccc(Cl)cc2)C[C@@H]1CCCB(O)O] | (3R,4S)-3-amino-4-(3-boronopropyl)-1-(3-(4-chlorophenyl)propyl)pyrrolidine-3-carboxylic acid | 2 | 2 |
| 23 | 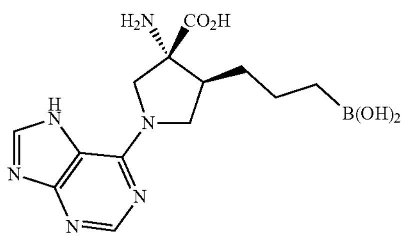 [SMILES: N[C@@]1(C(=O)O)CN(c2ncnc3nc[nH]c23)C[C@@H]1CCCB(O)O] | (3R,4S)-3-amino-4-(3-boronopropyl)-1-(7H-purin-6-yl)pyrrolidine-3-carboxylic acid | 2 | 3 |
| 24 | 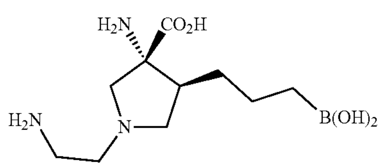 [SMILES: NCCN1C[C@H](CCCB(O)O)[C@](N)(C(=O)O)C1] | (3R,4S)-3-amino-1-(2-aminoethyl)-4-(3-boronopropyl)pyrrolidine-3-carboxylic acid | 1 | 1 |
| 25 | 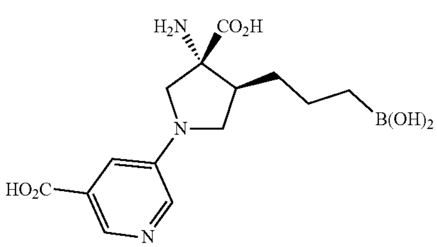 [SMILES: N[C@@]1(C(=O)O)CN(c2cncc(C(=O)O)c2)C[C@@H]1CCCB(O)O] | 5-((3R,4S)-3-amino-4-(3-boronopropyl)-3-carboxypyrrolidin-1-yl)nicotinic acid | 2 | 2 |

TABLE 2-continued

Exemplary Arginase Inhibitors

| Ex. # | Structure* | Name | Arg I IC$_{50}$ | Arg II IC$_{50}$ |
|---|---|---|---|---|
| 26 | 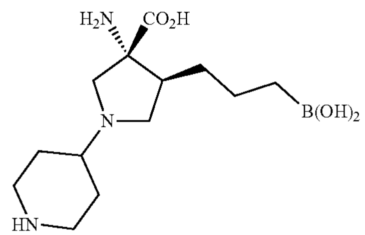 [SMILES: N[C@@]1(C(=O)O)CN(C2CCNCC2)C[C@@H]1CCCB(O)O] | (3R,4S)-3-amino-4-(3-boronopropyl)-1-(piperidin-4-yl)pyrrolidine-3-carboxylic acid | 2 | 2 |
| 27 | 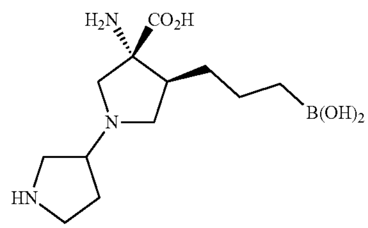 [SMILES: N[C@@]1(C(=O)O)CN(C2CCNC2)C[C@@H]1CCCB(O)O] | (3R,4S)-3-amino-4-(3-boronopropyl)-1,3'-bipyrrolidine-3-carboxylic acid | 1 | 1 |
| 28 | 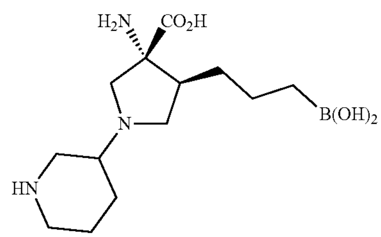 [SMILES: N[C@@]1(C(=O)O)CN(C2CCCNC2)C[C@@H]1CCCB(O)O] | (3R,4S)-3-amino-4-(3-boronopropyl)-1-(piperidin-3-yl)pyrrolidine-3-carboxylic acid | 1 | 2 |
| 29 | 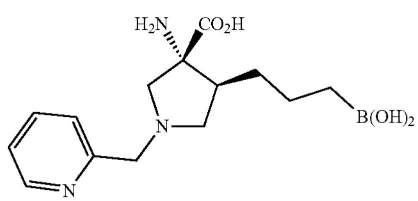 [SMILES: N[C@@]1(C(=O)O)CN(Cc2ccccn2)C[C@@H]1CCCB(O)O] | (3R,4S)-3-amino-4-(3-boronopropyl)-1-(pyridin-2-ylmethyl)pyrrolidine-3-carboxylic acid | 3 | 3 |
| 30 | 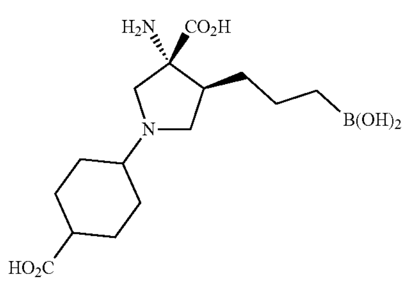 [SMILES: N[C@@]1(C(=O)O)CN(C2CCC(C(=O)O)CC2)C[C@@H]1CCCB(O)O] | (3R,4S)-3-amino-4-(3-boronopropyl)-1-(4-carboxycyclohexyl)pyrrolidine-3-carboxylic acid | 2 | 3 |
| 31 | 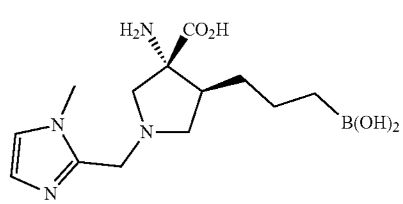 [SMILES: Cn1ccnc1CN1C[C@H](CCCB(O)O)[C@](N)(C(=O)O)C1] | (3R,4S)-3-amino-4-(3-boronopropyl)-1-((1-methyl-1H-imidazol-2-yl)methyl)pyrrolidine-3-carboxylic acid | 1 | 2 |

TABLE 2-continued

Exemplary Arginase Inhibitors

| Ex. # | Structure* | Name | Arg I IC$_{50}$ | Arg II IC$_{50}$ |
|---|---|---|---|---|
| 32 | 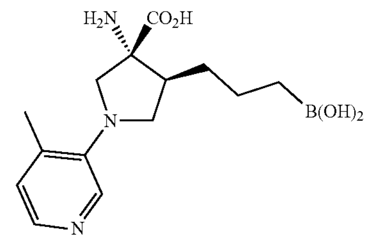 [SMILES: Cc1ccncc1N1C[C@H](CCCB(O)O)[C@](N)(C(=O)O)C1] | (3R,4S)-3-amino-4-(3-boronopropyl)-1-(4-methylpyridin-3-yl)pyrrolidine-3-carboxylic acid | 3 | 3 |
| 33 | 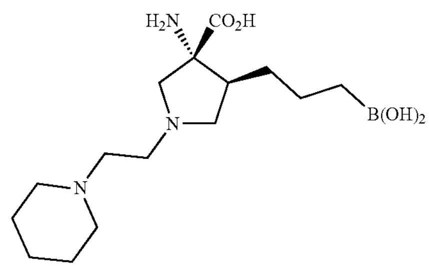 [SMILES: N[C@@]1(C(=O)O)CN(CCN2CCCCC2)C[C@@H]1CCCB(O)O] | (3R,4S)-3-amino-4-(3-boronopropyl)-1-(2-(piperidin-1-yl)ethyl)pyrrolidine-3-carboxylic acid | 1 | 2 |
| 34 | 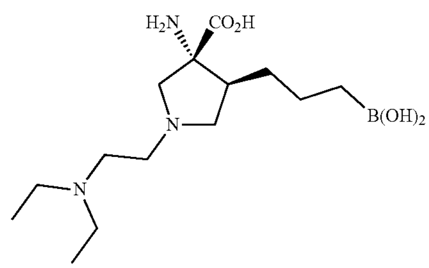 [SMILES: CCN(CC)CCN1C[C@H](CCCB(O)O)[C@](N)(C(=O)O)C1] | (3R,4S)-3-amino-4-(3-boronopropyl)-1-(2-(diethylamino)ethyl)pyrrolidine-3-carboxylic acid | 1 | 2 |
| 35 | 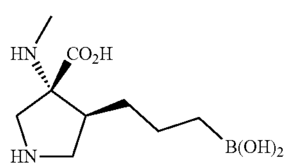 [SMILES: CN[C@@]1(C(=O)O)CNC[C@@H]1CCCB(O)O] | (3R,4S)-4-(3-boronopropyl)-3-(methylamino)pyrrolidine-3-carboxylic acid | 2 | 2 |
| 36 | 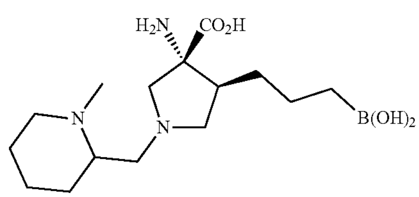 [SMILES: CN1CCCCC1CN1C[C@H](CCCB(O)O)[C@](N)(C(=O)O)C1] | (3R,4S)-3-amino-4-(3-boronopropyl)-1-((1-methylpiperidin-2-yl)methyl)pyrrolidine-3-carboxylic acid | 1 | 2 |
| 37 | 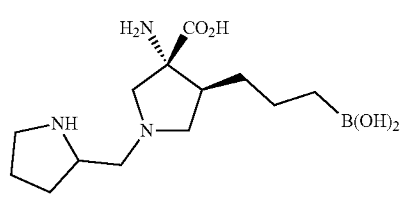 [SMILES: N[C@@]1(C(=O)O)CN(CC2CCCN2)C[C@@H]1CCCB(O)O] | (3R,4S)-3-amino-4-(3-boronopropyl)-1-(pyrrolidin-2-ylmethyl)pyrrolidine-3-carboxylic acid | 1 | 2 |
| 38 | 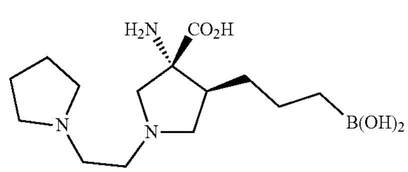 [SMILES: N[C@@]1(C(=O)O)CN(CCN2CCCC2)C[C@@H]1CCCB(O)O] | (3R,4S)-3-amino-4-(3-boronopropyl)-1-(2-(pyrrolidin-1-yl)ethyl)pyrrolidine-3-carboxylic acid | 1 | 1 |

TABLE 2-continued

Exemplary Arginase Inhibitors

| Ex. # | Structure* | Name | Arg I IC$_{50}$ | Arg II IC$_{50}$ |
|---|---|---|---|---|
| 39 | 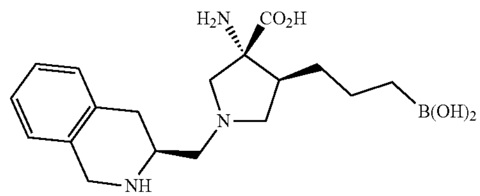 [SMILES: N[C@@]1(C(=O)O)CN(C[C@@H]2Cc3ccccc3CN2)C[C@@H]1CCCB(O)O] | (3R,4S)-3-amino-4-(3-boronopropyl)-1-(((S)-1,2,3,4-tetrahydroisoquinolin-3-yl)methyl)pyrrolidine-3-carboxylic acid | 1 | 1 |
| 40 | 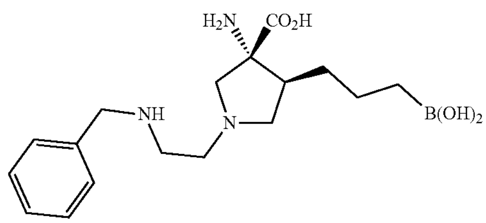 [SMILES: N[C@@]1(C(=O)O)CN(CCNCc2ccccc2)C[C@@H]1CCCB(O)O] | (3R,4S)-3-amino-1-(2-(benzylamino)ethyl)-4-(3-boronopropyl)pyrrolidine-3-carboxylic acid | 1 | 1 |
| 41 | 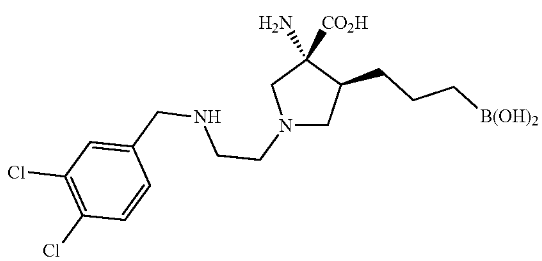 [SMILES: N[C@@]1(C(=O)O)CN(CCNCc2ccc(Cl)c(Cl)c2)C[C@@H]1CCCB(O)O] | (3R,4S)-3-amino-4-(3-boronopropyl)-1-(2-(3,4-dichlorobenzylamino)ethyl)pyrrolidine-3-carboxylic acid | 1 | 1 |
| 42 | 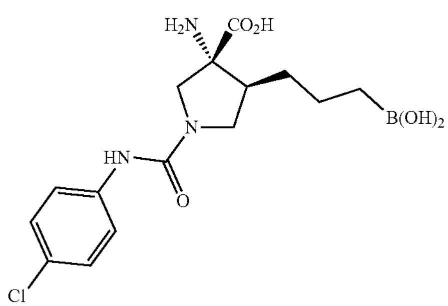 [SMILES: N[C@@]1(C(=O)O)CN(C(=O)Nc2ccc(Cl)cc2)C[C@@H]1CCCB(O)O] | (3R,4S)-3-amino-4-(3-boronopropyl)-1-(4-chlorophenylcarbamoyl)pyrrolidine-3-carboxylic acid | 2 | 2 |
| 43 | 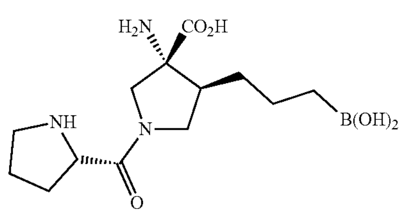 | (3R,4S)-3-amino-4-(3-boronopropyl)-1-((S)-pyrrolidine-2-carbonyl)pyrrolidine-3-carboxylic acid | 1 | 2 |
| 44 | 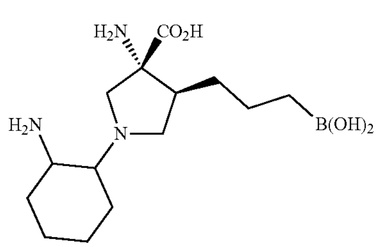 [SMILES: NC1CCCCC1N1C[C@H](CCCB(O)O)[C@](N)(C(=O)O)C1] | (3R,4S)-3-amino-1-(2-aminocyclohexyl)-4-(3-boronopropyl)pyrrolidine-3-carboxylic acid | 1 | 1 |

TABLE 2-continued

Exemplary Arginase Inhibitors

| Ex. # | Structure* | Name | Arg I IC$_{50}$ | Arg II IC$_{50}$ |
|---|---|---|---|---|
| 45 | 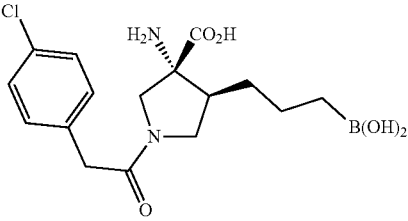 [SMILES: N[C@@]1(C(=O)O)CN(C(=O)Cc2ccc(Cl)cc2)C[C@@H]1CCCB(O)O] | (3R,4S)-3-amino-4-(3-boronopropyl)-1-(2-(4-chlorophenyl)acetyl)pyrrolidine-3-carboxylic acid | 2 | 2 |
| 46 | 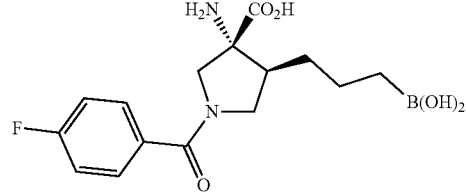 [SMILES: N[C@@]1(C(=O)O)CN(C(=O)c2ccc(F)cc2)C[C@@H]1CCCB(O)O] | (3R,4S)-3-amino-4-(3-boronopropyl)-1-(4-fluorobenzoyl)pyrrolidine-3-carboxylic acid | 2 | 2 |
| 47 | 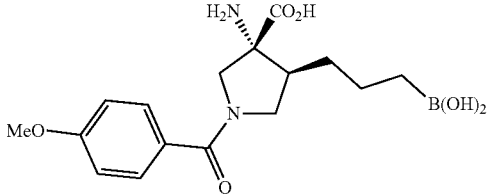 [SMILES: COc1ccc(C(=O)N2C[C@H](CCCB(O)O)[C@](N)(C(=O)O)C2)cc1] | (3R,4S)-3-amino-4-(3-boronopropyl)-1-(4-methoxybenzoyl)pyrrolidine-3-carboxylic acid | 2 | 2 |
| 48 | 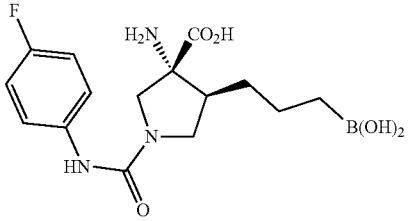 [SMILES: N[C@@]1(C(=O)O)CN(C(=O)Nc2ccc(F)cc2)C[C@@H]1CCCB(O)O] | (3R,4S)-3-amino-4-(3-boronopropyl)-1-(4-fluorophenylcarbamoyl)pyrrolidine-3-carboxylic acid | 2 | 2 |
| 49 | 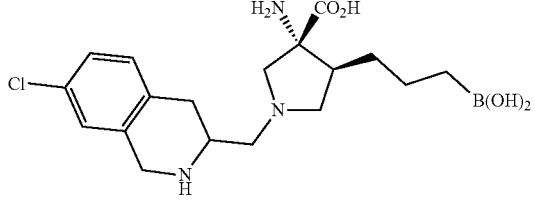 [SMILES: N[C@@]1(C(=O)O)CN(CC2Cc3ccc(Cl)cc3CN2)C[C@@H]1CCCB(O)O] | (3R,4S)-3-amino-4-(3-boronopropyl)-1-((7-chloro-1,2,3,4-tetrahydroisoquinolin-3-yl)methyl)pyrrolidine-3-carboxylic acid | 1 | 1 |
| 50 | 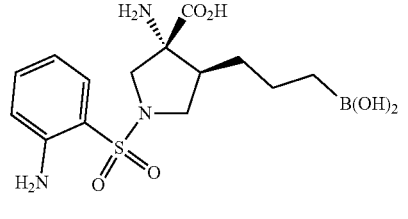 [SMILES: Nc1ccccc1S(=O)(=O)N1C[C@H](CCCB(O)O)[C@](N)(C(=O)O)C1] | (3R,4S)-3-amino-1-(2-aminophenylsulfonyl)-4-(3-boronopropyl)pyrrolidine-3-carboxylic acid | 2 | 3 |
| 51 | 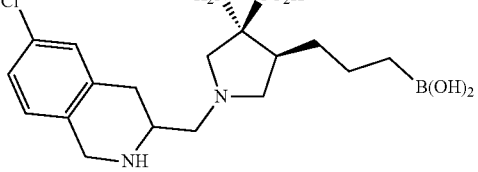 | (3R,4S)-3-amino-4-(3-boronopropyl)-1-((6-chloro-1,2,3,4-tetrahydroisoquinolin-3-yl)methyl)pyrrolidine-3-carboxylic acid | 1 | 1 |

TABLE 2-continued

Exemplary Arginase Inhibitors

| Ex. # | Structure* | Name | Arg I IC$_{50}$ | Arg II IC$_{50}$ |
|---|---|---|---|---|
| 52 | 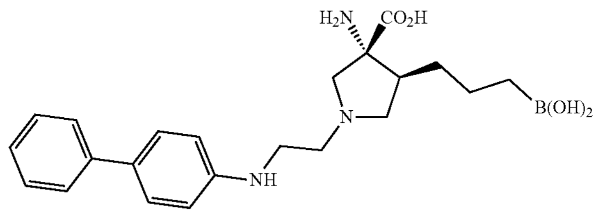 [SMILES: N[C@@]1(C(=O)O)CN(CCNc2ccc(-c3ccccc3)cc2)C[C@@H]1CCCB(O)O] | (3R,4S)-3-amino-1-(2-(biphenyl-4-ylamino)ethyl)-4-(3-boronopropyl)pyrrolidine-3-carboxylic acid | 1 | 1 |
| 53 | 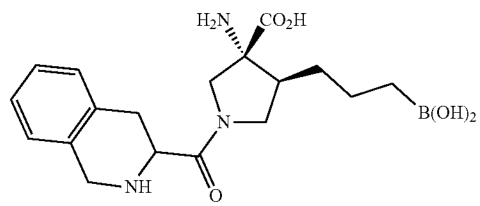 [SMILES: N[C@@]1(C(=O)O)CN(C(=O)C2Cc3ccccc3CN2)C[C@@H]1CCCB(O)O] | (3R,4S)-3-amino-4-(3-boronopropyl)-1-(1,2,3,4-tetrahydroisoquinoline-3-carbonyl)pyrrolidine-3-carboxylic acid | 1 | 2 |
| 54 | 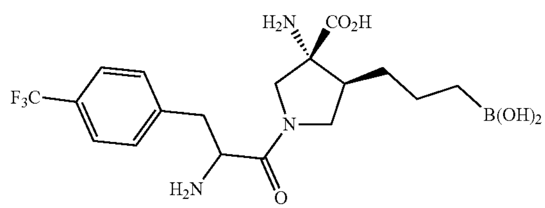 [SMILES: NC(Cc1ccc(C(F)(F)F)cc1)C(=O)N1C[C@H](CCCB(O)O)[C@](N)(C(=O)O)C1] | (3R,4S)-3-amino-1-(2-amino-3-(4-(trifluoromethyl)phenyl)propanoyl)-4-(3-boronopropyl)pyrrolidine-3-carboxylic acid | 2 | 3 |
| 55 | 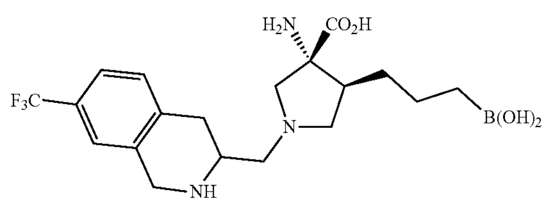 [SMILES: N[C@@]1(C(=O)O)CN(CC2Cc3ccc(C(F)(F)F)cc3CN2)C[C@@H]1CCCB(O)O] | (3R,4S)-3-amino-4-(3-boronopropyl)-1-((7-(trifluoromethyl)-1,2,3,4-tetrahydroisoquinolin-3-yl)methyl)pyrrolidine-3-carboxylic acid | 1 | 1 |
| 56 | 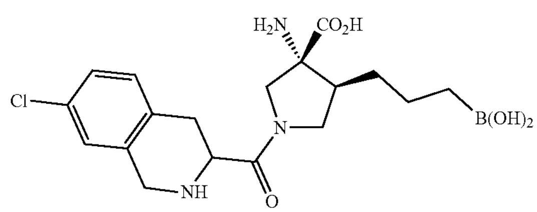 [SMILES: N[C@@]1(C(=O)O)CN(C(=O)C2Cc3ccc(Cl)cc3CN2)C[C@@H]1CCCB(O)O] | (3R,4S)-3-amino-4-(3-boronopropyl)-1-(7-chloro-1,2,3,4-tetrahydroisoquinoline-3-carbonyl)pyrrolidine-3-carboxylic acid | 1 | 1 |
| 57 | 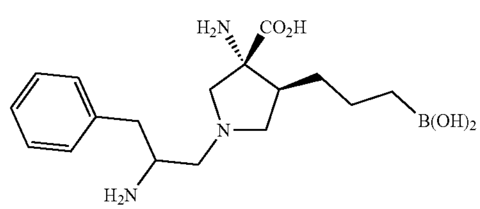 [SMILES: NC(Cc1ccccc1)CN1C[C@H](CCCB(O)O)[C@](N)(C(=O)O)C1] | (3R,4S)-3-amino-1-(2-amino-3-phenylpropyl)-4-(3-boronopropyl)pyrrolidine-3-carboxylic acid | 1 | 1 |
| 58 | 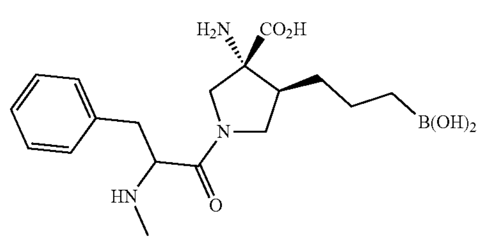 [SMILES: CNC(Cc1ccccc1)C(=O)N1C[C@H](CCCB(O)O)[C@](N)(C(=O)O)C1] | (3R,4S)-3-amino-4-(3-boronopropyl)-1-(2-(methylamino)-3-phenylpropanoyl)pyrrolidine-3-carboxylic acid | 3 | 3 |

TABLE 2-continued

Exemplary Arginase Inhibitors

| Ex. # | Structure* | Name | Arg I IC$_{50}$ | Arg II IC$_{50}$ |
|---|---|---|---|---|
| 59 | 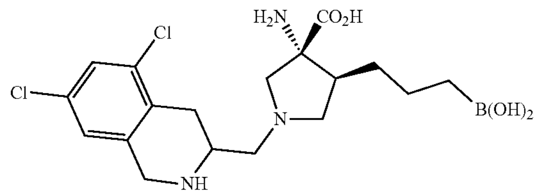 [SMILES: N[C@@]1(C(=O)O)CN(CC2Cc3c(Cl)cc(Cl)cc3CN2)C[C@@H]1CCCB(O)O] | (3R,4S)-3-amino-4-(3-boronopropyl)-1-((5,7-dichloro-1,2,3,4-tetrahydroisoquinolin-3-yl)methyl)pyrrolidine-3-carboxylic acid | 1 | 1 |
| 60 | 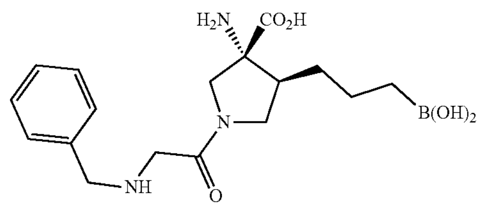 [SMILES: N[C@@]1(C(=O)O)CN(C(=O)CNCc2ccccc2)C[C@@H]1CCCB(O)O] | (3R,4S)-3-amino-1-(2-(benzylamino)acetyl)-4-(3-boronopropyl)pyrrolidine-3-carboxylic acid | 2 | 3 |
| 61 | 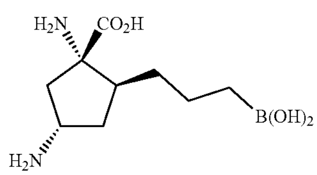 [SMILES: N[C@H]1C[C@H](CCCB(O)O)[C@](N)(C(=O)O)C1] | (1S,2S,4S)-1,4-diamino-2-(3-boronopropyl)cyclopentanecarboxylic acid | 2 | 2 |
| 62 | 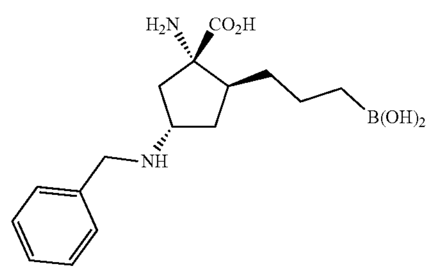 [SMILES: N[C@@]1(C(=O)O)C[C@@H](NCc2ccccc2)C[C@@H]1CCCB(O)O] | (1S,2S,4S)-1-amino-4-(benzylamino)-2-(3-boronopropyl)cyclopentanecarboxylic acid | 1 | 1 |
| 63 | 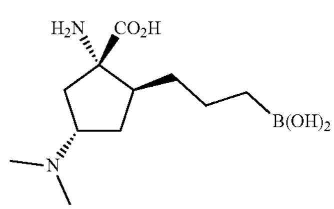 [SMILES: CN(C)[C@H]1C[C@H](CCCB(O)O)[C@](N)(C(=O)O)C1] | (1S,2S,4S)-1-amino-2-(3-boronopropyl)-4-(dimethylamino)cyclopentanecarboxylic acid | 1 | 1 |
| 64 | 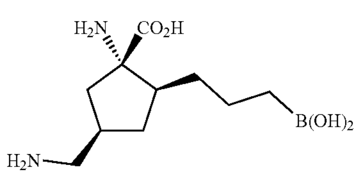 [SMILES: NC[C@@H]1C[C@H](CCCB(O)O)[C@](N)(C(=O)O)C1] | (1S,2S,4R)-1-amino-4-(aminomethyl)-2-(3-boronopropyl)cyclopentanecarboxylic acid | 1 | 1 |
| 65 | 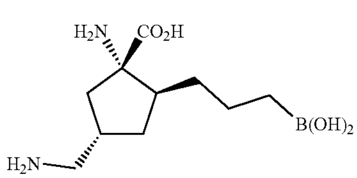 [SMILES: NC[C@H]1C[C@H](CCCB(O)O)[C@](N)(C(=O)O)C1] | (1S,2S,4S)-1-amino-4-(aminomethyl)-2-(3-boronopropyl)cyclopentanecarboxylic acid | 2 | 3 |

TABLE 2-continued

Exemplary Arginase Inhibitors

| Ex. # | Structure* | Name | Arg I IC$_{50}$ | Arg II IC$_{50}$ |
|---|---|---|---|---|
| 66 | 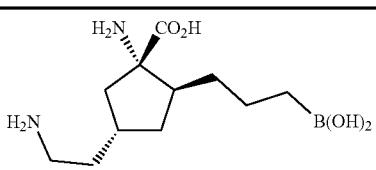 | (1S,2S,4R)-1-amino-4-(2-aminoethyl)-2-(3-boronopropyl)cyclopentanecarboxylic acid | 1 | 1 |

$^a$Order of Potency (highest-lowest): 1 = 0.1 nM 250 nM; 2 = 251 nM 1000 nM; 3 = 1001 nM 2000 nM; 4 = 2001 nM 5000 nM; 5 = 5001 nM greater and n.d. = not determined.

Arterial Ring Relaxation

The purpose of this example is to demonstrate that arginase inhibitor compounds according to the invention show efficacy of treating pulmonary hypertension in an ex vivo model of the disease. Thus, arginase inhibitors in accordance with the present invention are evaluated for their effectiveness at enhancing acetylcholine induced relaxation of pre-contracted arterial tissue obtained from mice.

In this study, mice are divided randomly into two groups. A first group of mice that serve as control and a second group of mice that are injected with a solution of monocrotaline, an agent that is experimentally used to induce increased blood pressure in the pulmonary artery and vein of the heart.

Both groups of mice are caged for 3-4 weeks to establish pulmonary hypertension in the monocrotaline treated group. At the end of this period and prior to sacrifice, mice from the control and monocrotaline groups are divided into two sub-groups. After euthanization, the main pulmonary artery, its left and right branches are excised from each animal, cleaned and maintained in a physiologically acceptable solution prior to their use in the relaxation study.

The obtained arterial tissue is first sliced to obtain arterial ring segments approximately 1.5-2 mm in length. Ring segments from each individual animal are then mounted in independent chambers of a myograph (Danish MyoTechnology) using a 200 jam stainless steel wire. After bathing the arterial ring segments in Kreb's buffer, each ring segment is set to a predetermined optimum passive tension (i.e., length/tension ratio) and allowed to acclimatize for at least 1 hour prior to determining the tissue viability using KCl (60 mM).

Arterial tissue from mice in one of two sub-groups within the control and monocrotaline groups are then allowed to incubate with an appropriate arginase inhibitor for 30 minutes at a molar concentration of 100 μM prior to addition of phenylephrine (PE), an agent known to cause muscle contraction.

Arterial tissue belonging to the second sub-group within the control and monocrotaline groups, however, is induced to contract by directly exposing the tissue to a 1 μM solution of phenylephrine. To calculate the effectiveness of the inventive arginase inhibitors to enhance acetylcholine induced relaxation of pre-contracted arterial tissue, a myograph is used to measure the change in tension for each tissue segment exposed or unexposed to an inventive compound in the control and monocrotaline groups.

For the inventive compounds, the arterial ring relaxation study indicates that for mice belonging to the control group (i.e., for mice that were not administered monocrotalin), there is no difference in the percent increase in relaxation of precontracted arterial tissue segments exposed to an arginase inhibitor or exposed to vehicle (buffer), prior to the addition of acetylcholine (AC) to induce relaxation.

In contrast, for mice belonging to the monocrotaline group, exposure of arterial tissue to an arginase inhibitor at a concentration of 100 μM prior to inducing contraction using phenylephrine, enhances tissue relaxation by about 75%. For tissue from monocrotaline treated mice that was exposed to vehicle (buffer), prior to contraction, addition of acetylcholine causes a smaller increase in relaxation of about 40% to 45%.

Without ascribing to any specific hypothesis, that the inventors believe that the inventive compounds inhibit arginase causing an increase in the intracellular pool of arginine which is then available as substrate for cellular nitric oxide synthases (NOS). NOS converts arginine to nitric oxide (NO) and important physiological signaling molecule implicated to play a role in muscle relaxation. Accordingly, arginase inhibitors of the present invention are suitable as therapeutics for the treatment of diseases such as hypertension, and erectile dysfunction.

We claim:

1. A compound according to Formula I,

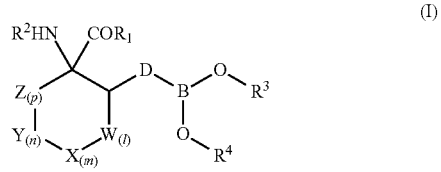

wherein

R$^1$ is selected from —OH, OR$^a$, and NR$^b$R$^c$;

R$^a$ is selected from hydrogen, straight or branched chain (C$_1$-C$_6$)alkyl, (C$_3$-C$_8$)cycloalkyl, (C$_3$-C$_{14}$)aryl, (C$_3$-C$_{14}$)heterocycloalkyl-(C$_1$-C$_6$)alkylene-, (C$_3$-C$_{14}$)heteroaryl-(C$_1$-C$_6$)alkylene-, and (C$_3$-C$_{14}$)aryl (C$_1$-C$_6$)alkylene-;

R$^b$ and R$^c$ are each independently selected from H, —OH, straight or branched (C$_1$-C$_6$)alkyl, —SO$_2$-(C$_1$-C$_6$)alkyl, (C$_3$-C$_{14}$)aryl-SO$_2$—, (C$_3$-C$_{14}$)heterocycloalkyl-(C$_1$-C$_6$)alkylene-, and (C$_3$-C$_{14}$)heteroaryl-(C$_1$-C$_6$)alkylene-;

R$^2$ is selected from H, straight or branched (C$_1$-C$_6$) alkyl, and (C$_1$-C$_6$)alkyl-C(O)—;

W, X, Y, and Z are each independently selected from —C(R''')$_2$—, —NR'''—, —O—, and S; and wherein W, X, Y, and Z taken together with the carbon atoms to which they are bonded form a tetrahydrofuran, tetrahydrothiophene, or pyrrolidine ring;

l, m, n and p independently are integers between 0 and 2 inclusive, and wherein at least one of l, m, n, or p is not 0;

$R^3$ and $R^4$ are each independently selected from hydrogen, straight or branched $(C_1-C_6)$alkyl, and C(O)—R', or $R^3$ and $R^4$ together with the boron atom to which they are bound form a 5- or 6-membered ring that is fully saturated, or partially saturated;

D is propylene;

R' and R''' are each independently selected from H, OH, $(C_1-C_8)$alkyl, $(C_3-C_6)$aryl, —$NH_2$, —$NH(C_1-C_6)$alkyl, —$N[(C_1-C_6)$alkyl$]2$, —$C(O)(C_1-C_6)$alkyl, —$C(O)(C_3-C_{14})$aryl, —$C(O)O(C_1-C_6)$alkyl, —$C(O)O(C_3-C_{14})$aryl, $(C_3-C_6)$cycloalkyl, $(C_3-C_{14})$heterocycloalkyl, $(C_3-C_{14})$heteroaryl, $(C_3-C_{14})$aryl-$(C_1-C_6)$alkylene-, $(C_3-C_6)$cycloalkyl-$(C_1-C_6)$alkylene-, $(C_3-C_{14})$heteroaryl-$(C_1-C_6)$alkylene-, and$(C_3-C_{14})$heterocycle-$(C_1-C_6)$alkylene-; and wherein any alkyl, alkylene, aryl, heteroaryl, cycloalkyl, or heterocycloalkyl is optionally substituted with one or more members selected from halogen, oxo, —COOH, —CN, —$NO_2$, —OH, —$NR^gR^e$, —$NR^gS(O)_2R^h$, $(C_1-C_6)$alkoxy, and $(C_3-C_{14})$aryloxy;

wherein $R^d$, $R^e$, $R^g$, and $R^h$ are each independently selected from H, straight or branched $(C_1-C_6)$alkyl, $(C_3-C_{14})$aryl$(C_1-C_6)$alkylene-, $(C_3-C_{14})$aryl, $(C_1-C_6)$hydroxyalkyl, $(C_1-C_6)$aminoalkyl, $H_2N(C_1-C_6)$alkylene-, $(C_3-C_6)$cycloalkyl, $(C_3-C_{14})$heterocycloalkyl, $(C_3-C_{14})$heteroaryl, $(C_3-C_{14})$aryl-$(C_1-C_6)$alkylene-, and $(C_3-C_6)$aryl-$(C_3-C_{14})$-cycloalkylene-, or a pharmaceutically acceptable salt thereof.

2. The compound of claim 1, wherein $R^1$ is —OH.

3. The compound of claim 2, wherein each of $R^2$, $R^3$, and $R^4$ is hydrogen.

4. The compound of claim 3, wherein, W, X, Y, and Z taken together with the carbon atoms to which they are bonded form a pyrrolidine ring.

5. The compound of claim 4, having the following structure:

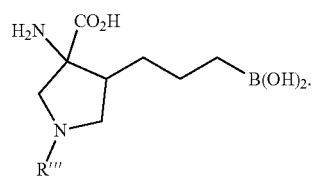

6. The compound of claim 4, having the following structure:

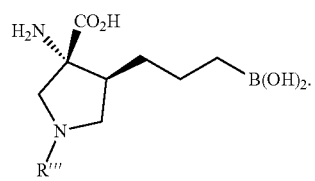

7. The compound of claim 6, wherein R''' is selected from —$C(O)(C_1-C_6)$alkyl, —$C(O)(C_3-C_{14})$aryl, —$C(O)(C_3-C_{14})$heterocycloalkyl, —$C(O)O(C_1-C_6)$alkyl, and —$C(O)O(C_3-C_{14})$aryl;

wherein any alkyl, aryl, or heterocycloalkyl is optionally substituted with one or more members selected from halogen, oxo, —COOH, —CN, —$NO_2$, —OH, —$NR^dR^e$, —$NR^gS(O)_2R^h$, $(C_1-C_6)$alkoxy, and $(C_3-C_{14})$aryloxy;

wherein $R^d$, $R^e$, $R^g$, and $R^h$ are each independently selected from H, straight or branched $(C_1-C_6)$alkyl, $(C_3-C14)$aryl$(C_1-C_6)$alkylene-, $(C_3-C14)$aryl, $(C_1-C_6)$hydroxyalkyl, $(C_1-C_6)$aminoalkyl, $H_2N(C_1-C_6)$alkylene-, $(C_3-C_6)$cycloalkyl, $(C_3-C_{14})$heterocycloalkyl, $(C_3-C_{14})$heteroaryl, $(C_3-C_{14})$aryl-$(C_1-C_6)$alkylene-, and $(C_3-C_6)$aryl-$(C_3-C_{14})$-cycloalkylene-;

or a pharmaceutically acceptable salt thereof.

8. A pharmaceutical composition comprising a compound of claim 1.

9. A pharmaceutical composition comprising a compound of claim 7.

* * * * *